US012808877B2

(12) United States Patent
Dubach

(10) Patent No.: US 12,808,877 B2
(45) Date of Patent: Nov. 24, 2026

(54) METHODS OF DETECTING MOLECULAR AGGREGATES USING IMAGE CORRELATION SPECTROSCOPY (ICS)

(71) Applicant: The General Hospital Corporation, Boston, MA (US)

(72) Inventor: John M. Dubach, Concord, MA (US)

(73) Assignee: The General Hospital Corporation, Boston, MA (US)

( * ) Notice: Subject to any disclaimer, the term of this patent is extended or adjusted under 35 U.S.C. 154(b) by 214 days.

(21) Appl. No.: 18/855,111

(22) PCT Filed: Apr. 7, 2023

(86) PCT No.: PCT/US2023/017926
§ 371 (c)(1),
(2) Date: Oct. 8, 2024

(87) PCT Pub. No.: WO2023/196621
PCT Pub. Date: Oct. 12, 2023

(65) Prior Publication Data

US 2025/0251402 A1 Aug. 7, 2025

Related U.S. Application Data

(60) Provisional application No. 63/328,820, filed on Apr. 8, 2022.

(51) Int. Cl.

| | |
|---|---|
| ***G01N 33/58*** | (2006.01) |
| ***G01N 21/64*** | (2006.01) |
| ***G06T 7/00*** | (2017.01) |
| ***G06V 10/26*** | (2022.01) |

(52) U.S. Cl.
CPC ....... *G01N 33/582* (2013.01); *G01N 21/6458* (2013.01); *G06T 7/0012* (2013.01); *G06V 10/26* (2022.01); *G01N 2223/401* (2013.01)

(58) Field of Classification Search
None
See application file for complete search history.

(56) References Cited

U.S. PATENT DOCUMENTS

| | | | |
|---|---|---|---|
| 9,738,937 B1 * | 8/2017 | Hsieh | C12Q 1/6886 |
| 11,300,564 B2 * | 4/2022 | Holmes | G01N 33/56966 |
| 2004/0122706 A1 | 6/2004 | Walker et al. | |
| 2018/0306813 A1 | 10/2018 | Dobson et al. | |
| 2024/0159675 A1 * | 5/2024 | Baaske | G01N 21/6428 |

OTHER PUBLICATIONS

Alberti et al., "Biomolecular condensates at the nexus of cellular stress, protein aggregation disease and ageing," Nature Reviews Molecular Cell Biology, Jan. 2021, 22:196-213.
Aleksandrov et al., "Protein Dynamics in Complex DNA Lesions," Molecular Cell, Mar. 2018, 69(6):1046-1061.e5.
Alemasova et al., "Poly(ADP-ribosyl)ation by PARP1: reaction mechanism and regulatory proteins," Nucleic Acids Research, May 2019, 47(8):3811-3827.

(Continued)

*Primary Examiner* — Vikkram Bali
(74) *Attorney, Agent, or Firm* — Fish & Richardson P.C.

(57) ABSTRACT

Methods of detecting a molecular aggregate in a biological sample using image correlation spectroscopy (ICS) are disclosed herein.

24 Claims, 105 Drawing Sheets

(56) References Cited

OTHER PUBLICATIONS

Altmeyer et al., "Liquid demixing of intrinsically disordered proteins is seeded by poly (ADP-ribose)," Nature Communications, Aug. 2015, 6:8088, 12 pages.
Alvarez-Gonzalez et al., "Characterization of polymers of adenosine diphosphate ribose generated in vitro and in vivo," Biochemistry, Jun. 1987, 26(11):3218-3224.
Ame et al., "The PARP superfamily," Bioessays, Aug. 2004, 26(8):882-893.
Ayyappan et al., "ADPriboDB 2.0: an updated database of ADP-ribosylated proteins," Nucleic Acids Research, Jan. 2021, Published online on Nov. 2020, 49(D1):D261-D265.
Böcker et al., "Computational Methods for analysis of foci: validation for radiation-induced gamma-H2AX foci in human cells," Radiation Research, Jan. 2006, 165(1):113-24.
Botuyan et al., "Structural basis for the methylation state-specific recognition of histone H4-K20 by 53BP1 and Crb2 in DNA repair," Cell, Dec. 2006, 127(7):1361-1373.
Brady et al., "Increased error-prone NHEJ activity in myeloid leukemias is associated with DNA damage at sites that recruit key nonhomologous end-joining proteins," Cancer Research, Apr. 2003, 63(8):1798-1805.
Bray et al., "A dataset of images and morphological profiles of 30 000 small-molecule treatments using the Cell Painting assay," Gigascience, Dec. 2017, 6(12):1-5.
Bray et al., "Cell Painting, a high-content image-based assay for morphological profiling using multiplexed fluorescent dyes," Nature Protocols, Sep. 2016, 11(9):1757-1774.
Brem et al., "XRCC1 is required for DNA single-strand break repair in human cells," Nucleic Acids Research, May 2005, 33(8):2512-2520.
Bryant et al., "Specific killing of BRCA2-deficient tumours with inhibitors of poly(ADP-ribose) polymerase," Nature, Apr. 2005, 434(7035):913-917.
Caicedo et al., "Applications in image-based profiling of perturbations," Current Opinion in Biotechnology, Jun. 2016, 39:134-142.
Cambronne et al., "Biosensor reveals multiple sources for mitochondrial NAD+," Science, Jun. 2016, 352(6292):1474-1477.
Celeste et al., "Histone H2AX phosphorylation is dispensable for the initial recognition of DNA breaks," Nature Cell Biology, Jul. 2003, 5(7):675-679.
Chapman et al., "Playing the end game: DNA double-strand break repair pathway choice," Molecular Cell, Aug. 2012, 47(4):497-510.
Chaudhuri et al., "Replication fork stability confers chemoresistance in BRCA- deficient cells," Nature, Jul. 2016, 535(7612):382-387.
Cortes-Gutierrez et al., "Use of DBD-FISH for the study of cervical cancer progression," Methods in Molecular Biology, 2015, 1249:291-301.
Cox et al., "Tales of 1,008 small molecules: phenomic profiling through live-cell imaging in a panel of reporter cell lines," Scientific Reports, Aug. 2020, 10(1):13262, 14 pages.
Demin et al., "XRCC1 prevents toxic PARP1 trapping during DNA base excision repair," Molecular Cell, Jul. 2021, 81(14):3018-3030.
Dias et al., "Understanding and overcoming resistance to PARP inhibitors in cancer therapy," Nature Reviews Clinical Oncology, Dec. 2021, 18(12):773-791.
Dimitrova et al., "53BP1 promotes non-homologous end joining of telomeres by increasing chromatin mobility," Nature, Nov. 2008, 456(7221):524-528, 27 pages.
DiTullio, Jr. et al., "53BP1 functions in an ATM-dependent checkpoint pathway that is constitutively activated in human cancer," Nature Cell Biology, Dec. 2002, 4(12):998-1002.
Dubach et al., "Autocorrelation analysis of a phenotypic screen reveals hidden drug activity," bioRxiv, posted on Mar. 15, 2023, 8 pages.
Dubach et al., "In vivo imaging of specific drug-target binding at subcellular resolution," Nature Communications, May 2014, 5:3946, 9 pages.
Dubach et al., "Quantitating drug-target engagement in single cells in vitro and in vivo," Nature Chemical Biology, Feb. 2017, 13(2):168-173.
Dueva et al., "Replication protein A: a multifunctional protein with roles in DNA replication, repair and beyond," NAR Cancer, Sep. 2020, 2(3):zcaa022, 24 pages.
Escribano-Díaz et al., "A Cell Cycle-Dependent Regulatory Circuit Composed of 53BP1-RIF1 and BRCA1-CtIP Controls DNA Repair Pathway Choice," Molecular Cell, Mar. 2013, 49(5):872-883.
Farmer et al., "Targeting the DNA repair defect in BRCA mutant cells as a therapeutic strategy," Nature, Apr. 2005, 434(7035):917-721.
Featherstone et al., "Ku, a DNA repair protein with multiple cellular functions?," Mutation Research, May 1999, 434(1):3-15.
Figueroa-Gonzalez et al., "Strategies for the evaluation of DNA damage and repair mechanisms in cancer," Oncology Letters, Jun. 2017, 13(6):3982-3988.
Fjeld et al., "Differential binding of $NAD^+$ and NADH allows the transcriptional corepressor carboxyl-terminal binding protein to serve as a metabolic sensor," The Proceedings of the National Academy of Sciences (PNAS) USA, Jul. 2003, 100(16):9202-9207.
Fradet-Turcotte et al., "53BP1 is a reader of the DNA-damage-induced H2A Lys 15 ubiquitin mark," Nature, Jul. 2013, 499(7456):50-54.
Fu et al., "Balancing repair and tolerance of DNA damage caused by alkylating agents," Nature Reviews Cancer, Jan. 2012, 12(2):104-20.
Fugger et al., "Tackling PARP inhibitor resistance," Trends in Cancer, Dec. 2021, 7(12):1102-1118.
Giglia-Mari et al., "DNA damage response," Cold Spring Harbor Perspectives in Biology, Jan. 2011, 3(1):a000745, 19 pages.
Gillespie, "Exact stochastic simulation of coupled chemical reactions," The Journal of Physical Chemistry, Dec. 1977, 81(25):2340-2361.
Gopal et al., "Biomolecular condensates govern PARP inhibitor trapping and present mechanisms of resistance," bioRxiv preprint, posted on Apr. 27, 2022, 33 pages.
Gopal et al., "Netrin-1-Regulated Distribution of UNC5B and DCC in Live Cells Revealed by TICCS," Biophysical Journal, Feb. 2016, 110(3):623-634.
Gopal et al., "Spatially Selective Dissection of Signal Transduction in Neurons Grown on Netrin-1 Printed Nanoarrays via Segmented Fluorescence Fluctuation Analysis," ACS Nano, Aug. 2017, 11(8):8131-8143.
Grimaldi et al., "PCR-Based Methods for Detecting DNA Damage and its Repair at the Sub-gene and Single Nucleotide Levels in Cells," Molecular Biotechnology, Feb. 2002, 20(2):181-196.
Haghighi et al., "High-dimensional gene expression and morphology profiles of cells across 28,000 genetic and chemical perturbations," HHS Public Access Author Manuscript, doi: 10.1038/s41592-022-01667-0, published online Jun. 1, 2023; published in final edited form as: Nature Methods, Dec. 2022, 19(12):1550-1557, 28 pages.
Haince et al., "PARP1-dependent kinetics of recruitment of MRE11 and NBS1 proteins to multiple DNA damage sites," The Journal of Biological Chemistry, Jan. 2008, 283(2):1197-1208.
Hass et al., "Repair-specific functions of replication protein A," The Journal of Biological Chemistry, Feb. 2012, 287(6):3908-3918.
Helleday, "The underlying mechanism for the PARP and BRCA synthetic lethality: clearing up the misunderstandings," Molecular Oncology, Aug. 2011, 5(4):387-393.
Her et al., "53BP1 Mediates ATR-Chk1 Signaling and Protects Replication Forks under Conditions of Replication Stress," Molecular and Cellular Biology, Mar. 2018, 38(8):e00472-17, 17 pages.
Hernandez et al., "Highly sensitive automated method for DNA damage assessment: gamma-H2AX foci counting and cell cycle sorting," International Journal of Molecular Sciences, Jul. 2013, 14(8):15810-15826.
Hey et al., "Binding of XPA and RPA to Damaged DNA Investigated by Fluorescence Anisotropy," Biochemistry, Mar. 2001, 40(9):2901-2910.

(56) References Cited

OTHER PUBLICATIONS

Hoch et al., "XRCC1 mutation is associated with PARP1 hyperactivation and cerebellar ataxia," Nature, Jan. 2017, 541(7635):87-91, 5 pages.
Hoeijmakers, "DNA damage, aging, and cancer," The New England Journal of Medicine, Oct. 2009, 361(15):1475-1485.
Hoeijmakers, "Genome maintenance mechanisms for preventing cancer," Nature, May 2001, 411(6835):366-374.
Hopkins et al., "Mechanistic Dissection of PARP1 Trapping and the Impact on In Vivo Tolerability and Efficacy of PARP Inhibitors," Molecular Cancer Research, Nov. 2015, 13(11):1465-1477.
Hottiger et al., "Toward a unified nomenclature for mammalian ADP-ribosyltransferases," Trends in Biochemical Sciences, Apr. 2010, 35(4):208-219.
ImageJ.net [online], "ImageJ User Guide—Section 29: Process," Jun. 27, 2012, retrieved on Dec. 30, 2024, retrieved from URL<https://imagej.net/ij/docs/guide/146-29.html>, 17 pages.
International Preliminary Report on Patentability in International Appln. No. PCT/US2023/017926, mailed on Oct. 17, 2024, 9 pages.
International Search Report and Written Opinion in International Appln. No. PCT/US2023/017926, mailed on Jul. 20, 2023, 12 pages.
Izhar et al,. "A Systematic Analysis of Factors Localized to Damaged Chromatin Reveals PARP-Dependent Recruitment of Transcription Factors" Cell Reports, Jun. 2015, 11(9):1486-1500.
Jackson et al., "The DNA-damage response in human biology and disease," Nature, Oct. 2009, 461(7267):1071-1078.
Jaspers et al., "Loss of 53BP1 causes PARP inhibitor resistance in Brca1-mutated mouse mammary tumors," Cancer Discovery, Jan. 2013, 3(1):68-81.
Jayakumar et al., "Nrf2 facilitates repair of radiation induced DNA damage through homologous recombination repair pathway in a ROS independent manner in cancer cells," Mutation Research, Sep. 2015, 779:33-45.
Jucha et al., "FociCounter: a freely available PC programme for quantitative and qualitative analysis of gamma-H2AX foci," Mutation Research, Feb. 2010, 696(1):16-20.
Kilic et al., "Phase separation of 53BP1 determines liquid-like behavior of DNA repair compartments," The EMBO Journal, Aug. 2019, 38(16):e101379, 17 pages.
Koury et al., "Differential RPA-1 and RAD-51 recruitment in vivo throughout the C. elegans germline, as revealed by laser microirradiation," Nucleic Acids Research, Jan. 2018, 46(2):748-764.
Kraus et al., "PARP goes transcription," Cell, Jun. 2003, 113:677-683.
Langelier et al., "$NAD^+$ analog reveals PARP-1 substrate-blocking mechanism and allosteric communication from catalytic center to DNA-binding domains," Nat Commun., 2018, 9:844, 13 pages.
Langelier et al., "Structural basis for DNA damage-dependent poly(ADP-ribosyl)ation by human PARP-1," Science, May 2012, 336(6082):728-732.
Langelier et al., "The Zn3 Domain of Human Poly(ADP-ribose) Polymerase-1 (PARP-1) Functions in Both DNA-dependent Poly(ADP-ribose) Synthesis Activity and Chromatin Compaction," The Journal of Biological Chemistry, Jun. 2010, 285(24):18877-18887.
Lapytsko et al., "FoCo: a simple and robust quantification algorithm of nuclear foci," BMC Bioinformatics, Nov. 2015, 16:392, 13 pages.
Larsen et al., "Systems-wide Analysis of Serine ADP-Ribosylation Reveals Widespread Occurrence and Site-Specific Overlap with Phosphorylation," Cell Reports, Aug. 2018, 24(9):2493-2505.e4, 27 pages.
Leung, "Poly(ADP-ribose): A Dynamic Trigger for Biomolecular Condensate Formation," Trends in Cell Biology, May 2020, 30(5):370-383, 14 pages.
Li et al., "BRD4 Promotes DNA Repair and Mediates the Formation of TMPRSS2-ERG Gene Rearrangements in Prostate Cancer," Cell Reports, Jan. 2018, 22(3):796-808.
Li et al., "Tumor Cell Death Induced by Topoisomerase-Targeting Drugs," Annual Review of Pharmacology and Toxicology, Apr. 2001, 41:53-77.
Linsenmeier et al., "Analysis of biomolecular condensates and protein phase separation with microfluidic technology," Biochimica et Biophysica Acta (BBA)—Molecular Cell Research, Jan. 2021, 1868(1):118823, 13 pages.
Loo, "TUNEL assay. An overview of techniques," Methods in Molecular Biology, 2002, 203:21-30.
Lord et al., "BRCAness revisited," Nature Reviews Cancer, Feb. 2016, 16(2):110-120.
Lord et al., "PARP inhibitors: Synthetic lethality in the clinic," Science, Mar. 2017, 355(6330):1152-1158.
Ludwig et al., "Immunoquantitation and size determination of intrinsic poly (ADP-ribose) polymerase from acid precipitates. An analysis of the in vivo status in mammalian species and in lower eukaryotes," The Journal of Biological Chemistry, May 1988, 263(15):6993-6999.
Lundin et al., "Methyl methanesulfonate (MMS) produces heat-labile DNA damage but no detectable in vivo DNA double-strand breaks," Nucleic Acids Research, Jul. 2005, 33(12):3799-3811.
Marsischky et al., "Role of glutamic acid 988 of human poly-ADP-ribose polymerase in polymer formation. Evidence for active site similarities to the ADP-ribosylating toxins," The Journal of Biological Chemistry, Feb. 1995, 270(7):3247-3254.
Mateo et al., "Appraising iniparib, the PARP inhibitor that never was-what must we learn?," Nature Reviews Clinical Oncology, Dec. 2013, 10:688-696.
Maynard et al., "DNA Damage, DNA Repair, Aging, and Neurodegeneration," Cold Spring Harbor Perspectives Medicine, Sep. 2015, 5(10):a025130, 18 pages.
Melan et al., "Redistribution and differential extraction of soluble proteins in permeabilized cultured cells. Implications for immunofluorescence microscopy," Journal of Cell Science, Apr. 1992, 101(Pt4):731-743.
Menissier de Murcia et al., "Functional interaction between PARP-1 and PARP-2 in chromosome stability and embryonic development in mouse," The EMBO Journal, May 2003, 22(9):2255-2263.
Meyer et al., "Particle counting by fluorescence correlation spectroscopy. Simultaneous measurement of aggregation and diffusion of molecules in solutions and in membranes," Biophysical Journal, Dec. 1988, 54(6):983-993.
Mir et al., "The efficacy of image correlation spectroscopy for characterization of the extracellular matrix," Biomedical Optics Express, Feb. 2012, 3(2):215-224.
Mistrik et al., "Cells and Stripes: A novel quantitative photo-manipulation technique," Scientific Reports, Jan. 2016, 6:19567, 9 pages.
Mitchell et al., "Quantification of photoproducts in mammalian cell DNA using radioimmunoassay," Methods in Molecular Biology, 1999, 113:165-173.
Moffat et al., "Opportunities and challenges in phenotypic drug discovery: an industry perspective," Nature Reviews Drug Discovery, Aug. 2017, 16(8):531-543.
Moore et al., "The CHD6 chromatin remodeler is an oxidative DNA damage response factor," Nature Communications, Jan. 2019, 10(1):241, 16 pages.
Murai et al., "Stereospecific PARP trapping by BMN 673 and comparison with olaparib and rucaparib," Molecular Cancer Therapeutics, Feb. 2014, 13(2):433-443.
Murai et al., "Trapping of PARP1 and PARP2 by Clinical PARP Inhibitors," Cancer Research, Nov. 2012, 72(21):5588-5599.
Natale et al., "Identification of the elementary structural units of the DNA damage response," Nature Communications, Jan. 2017, 8:15760, 18 pages.
Nicolai et al., "ZNF281 is recruited on DNA breaks to facilitate DNA repair by non-homologous end joining," Oncogene, Jan. 2020, 39(4):754-766.
Nohe et al., "Image correlation spectroscopy," Sci STKE, Dec. 2007, 2007(417):p17, 17 pages.
Oeck et al., "The Focinator—a new open-source tool for high-throughput foci evaluation of DNA damage," Radiation Oncology, Aug. 2015, 10:163, 11 pages.

(56) References Cited

OTHER PUBLICATIONS

Olive et al., "Heterogeneity in DNA damage using the comet assay," Cytometry Part A, Jul. 2005, 66A(1):1-8.
Oshidari et al., "DNA repair by Rad52 liquid droplets," Nature Communications, Feb. 2020, 11(1):695, 8 pages.
Padella et al., "Targeting PARP proteins in acute leukemia: DNA damage response inhibition and therapeutic strategies," Journal of Hematology & Oncology, Jan. 2022, 15(1):10, 21 pages.
Palmer et al., "Fluorescence correlation spectroscopy for detecting submicroscopic clusters of fluorescent molecules in membranes," Chemistry and Physics of Lipids, Jun. 1989, 50(3-4):253-270.
Panier et al., "Double-strand break repair: 53BP1 comes into focus," Nature Reviews Molecular Cell Biology, Jan. 2014, 15(1):7-18.
Pascal, "The comings and goings of PARP-1 in response to DNA damage," HHS Public Access Author Manuscript, doi: 10.1016/j.dnarep.2018.08.022, published online Nov. 1, 2019; published in final edited form as: DNA Repair (Amst), Nov. 2018, 71:177-182, 6 pages.
Patel et al., "A Liquid-to-Solid Phase Transition of the ALS Protein FUS Accelerated by Disease Mutation," Cell, Aug. 2015, 162(5):1066-1077.
Paull et al., "A critical role for histone H2AX in recruitment of repair factors to nuclear foci after DNA damage," Current Biology, Aug. 2000, 10(15):886-895.
Pessina et al., "Functional transcription promoters at DNA double-strand breaks mediate RNA-driven phase separation of damage-response factors," Nature Cell Biology, Oct. 2019, 21(10):1286-1299.
Petersen et al., "Quantitation of membrane receptor distributions by image correlation spectroscopy: concept and application," Biophysical Journal, Sep. 1993, 65(3):1135-1146.
Pilch et al., "Characteristics of gamma-H2AX foci at DNA double-strand breaks sites," Biochemistry and Cell Biology, Jun. 2003, 81(3):123-129.
Pommier et al., "Laying a trap to kill cancer cells: PARP inhibitors and their mechanisms of action," Science Translational Medicine, Oct. 2016, 8(362):362ps17, 8 pages.
Prokhorova et al., "Serine-linked PARP1 auto-modification controls PARP inhibitor response," Nature Communications, Jul. 2021, 12(1):4055, 12 pages.
Reardon et al., "Comparative analysis of binding of human damaged DNA-binding protein (XPE) and *Escherichia coli* damage recognition protein (UvrA) to the major ultraviolet photoproducts: T[c,s]T, T[t,s]T, T[6-4]T, and T[Dewar]T," The Journal of Biological Chemistry, Oct. 1993, 268(28):21301-21308.
Rona et al., "PARP1-dependent recruitment of the FBXL10-RNF68-RNF2 ubiquitin ligase to sites of DNA damage controls H2A.Z loading," eLife, Jul. 2018, 7:e38771, 31 pages.
Rudolph et al., "Poly(ADP-ribose) polymerase 1 searches DNA via a 'monkey bar' mechanism," eLife, Aug. 2018, 7:e37818, 23 pages.
Sanjana et al., "Improved vectors and genome-wide libraries for CRISPR screening," Nature Methods, Aug. 2014, 11(8):783-784.
Schmidt et al., "Cell Detection with Star-Convex Polygons," [Lecture Notes in Computer Science] Medical Image Computing and Computer Assisted Intervention, Sep. 2018, 11071:265-273.
Schnell et al., "Immunolabeling artifacts and the need for live-cell imaging," Nature Methods, Feb. 2012, 9(2):152-158.
Schultz et al., "p53 Binding Protein 1 (53bp1) Is an Early Participant in the Cellular Response to DNA Double-Strand Breaks," Journal of Cell Biology, Dec. 2000, 151(7):1381-1390.
Shao et al., "Clinical PARP inhibitors do not abrogate PARP1 exchange at DNA damage sites in vivo," Nucleic Acids Research, Sep. 2020, 48(17):9694-9709.
Shearer et al., "Internalization of a-synuclein oligomers into SH-SY5Y cells," Biophysical Journal, Mar. 2021, 120(5):877-885.
Shen et al., "BMN 673, a novel and highly potent PARP1/2 inhibitor for the treatment of human cancers with DNA repair deficiency," Clinical Cancer Research, Sep. 2013, 19(18):5003-5015.
Shen et al., "Trapping Poly(ADP-Ribose) Polymerase," The Journal of Pharmacology and Experimental Therapeutics, Jun. 2015, 353(3):446-457.
Singatulina et al., "PARP-1 Activation Directs FUS to DNA Damage Sites to Form PARG-Reversible Compartments Enriched in Damaged DNA," Cell Reports, May 2019, 27(6):1809-1821.
Smith-Clerc et al., "Immunofluorescence detection of the cytoskeleton and extracellular matrix in tissue and cultured cells," Methods in Molecular Biology, Jan. 2010, 611:43-57.
Spegg et al., "Biomolecular condensates at sites of DNA damage: More than just a phase," DNA Repair (Amst), Oct. 2021, 106:103179, 13 pages.
Sukhodolets et al., "The 32-kilodalton subunit of replication protein A interacts with menin, the product of the MEN1 tumor suppressor gene," Molecular and Cellular Biology, Jan. 2003, 23(2):493-509.
Sun et al., "NRF2 preserves genomic integrity by facilitating ATR activation and G2 cell cycle arrest," Nucleic Acids Research, Sep. 2020, 48(16):9109-9123.
Suskiewicz et al., "HPF1 completes the PARP active site for DNA damage-induced ADP-ribosylation," Nature, Mar. 2020, 579(7800):598-602.
Sutherland et al., "Quantifying clustered DNA damage induction and repair by gel electrophoresis, electronic imaging and number average length analysis," Mutation Research, Oct. 2003, 531(1-2):93-107.
Swinney et al., "How were new medicines discovered?," Nature Reviews Drug Discovery, Jul. 2011, 10(7):507-519.
Thompson et al., "Fluorescence Correlation Spectroscopy," Topics in Fluorescence Spectroscopy, vol. I: Techniques, Springer, 1999, Chapter 6, pp. 337-378.
Varma et al., "GPI-anchored proteins are organized in submicron domains at the cell surface," Nature, Aug. 1998, 394(6695):798-801.
Vincent et al., "Phenotypic drug discovery: recent successes, lessons learned and new directions," HHS Public Access Author Manuscript, doi: 10.1038/s41573-022-00472-w, published online Jun. 1, 2023; published in final edited form as: Nature Reviews Drug Discovery, Dec. 2022, 21(12):899-914, 39 pages.
Vyas et al., "A systematic analysis of the PARP protein family identifies new functions critical for cell physiology," Nature Communications, Aug. 2013, 4:2240, 13 pages.
Williams et al., "Image Data Resource: a bioimage data integration and publication platform," Nature Methods, Aug. 2017, 14(8):775-781.
Wiseman et al., "Counting dendritic spines in brain tissue slices by image correlation spectroscopy analysis," Journal of Microscopy, Feb. 2002, 205(Pt 2):177-186.
Wiseman et al., "Image correlation spectroscopy. II. Optimization for ultrasensitive detection of preexisting platelet-derived growth factor-β receptor oligomers on intact cells," Biophysical Journal, Feb. 1999, 76(2):963-977.
Wiseman, "Image correlation spectroscopy: principles and applications," Cold Spring Harbor Protocols, Apr. 2015, 2015(4):336-348.
Wu et al., "Usnic Acid Inhibits Proliferation and Migration through ATM Mediated DNA Damage Response in RKO Colorectal Cancer Cell," Current Pharmaceutical Biotechnology, Jul. 2021, 22(8):1129-1138.
Xue et al., "A two-step mechanism governing PARP1-DNA retention by PARP inhibitors," Science Advances, Sep. 2022, 8(36):eabq0414, 11 pages.
Yang et al., "Single cell resolution in vivo imaging of DNA damage following PARP inhibition," Scientific Reports, May 2015, 5:10129, 13 pages.
Yang et al., "The lipogenic LXR-SREBF1 signaling pathway controls cancer cell DNA repair and apoptosis and is a vulnerable point of malignant tumors for cancer therapy," Cell Death & Differentiation, Aug. 2020, 27(8):2433-2450.
Zandarashvili et al., "Structural basis for allosteric PARP-1 retention on DNA breaks," HHS Public Access Author Manuscript, doi: 10.1126/science.aax6367, published online Apr. 3, 2021; published in final edited form as: Science, Apr. 2020, 368(6486):eaax6367, 24 pages.

(56) References Cited

OTHER PUBLICATIONS

Zhang et al., "53BP1 regulates heterochromatin through liquid phase separation," Nature Communications, Jan. 2022, 13(1):360, 16 pages.
Zhou et al., "The DNA damage response: putting checkpoints in perspective," Nature, Nov. 2000, 408(6811):433-439.
Zhou et al., "The roles of nuclear focal adhesion kinase (FAK) on Cancer: a focused review," Journal of Experimental & Clinical Cancer Research, Jun. 2019, 38(1):250, 11 pages.

* cited by examiner

FIG. 9G
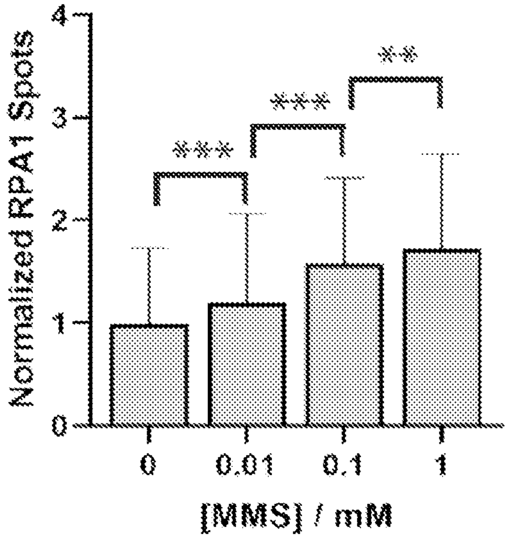
FIG. 9H
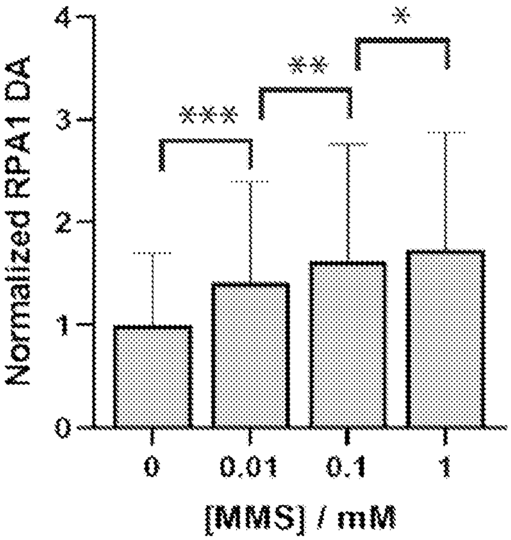
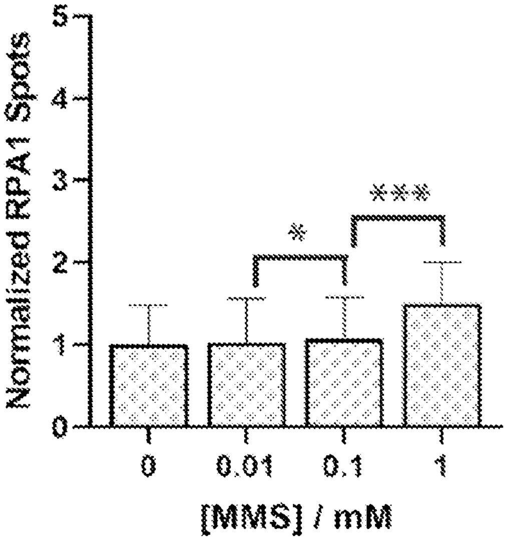
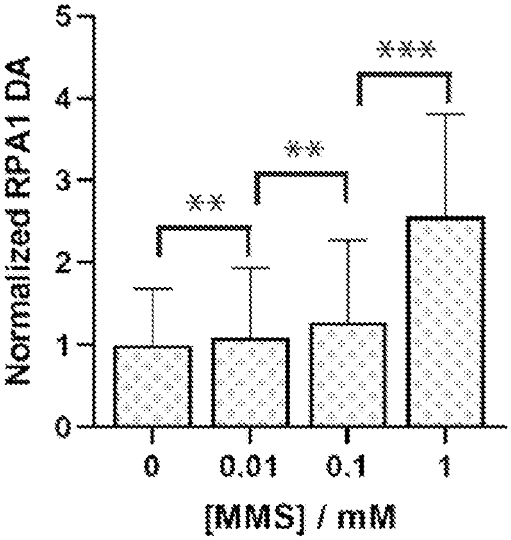
FIG. 9I
FIG. 9J FIG. 10G
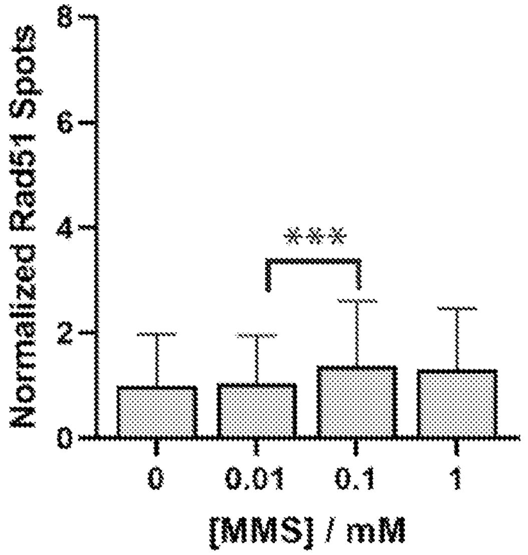
FIG. 10H
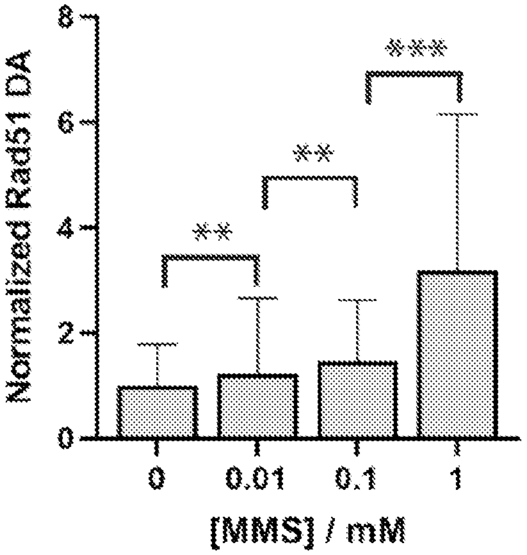
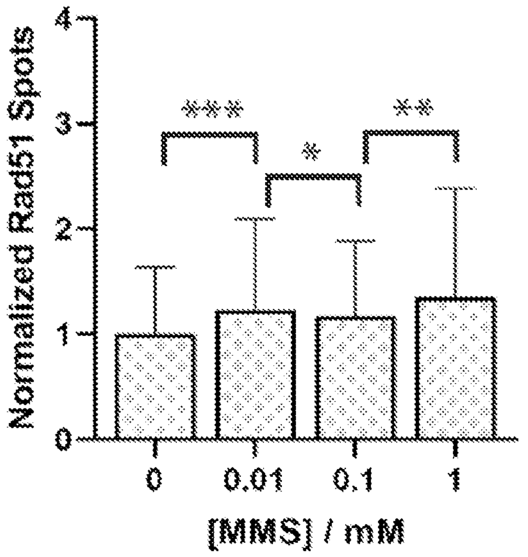
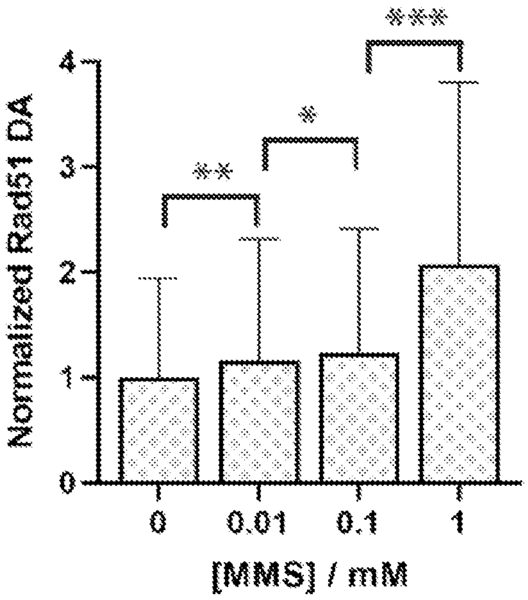
FIG. 10I
FIG. 10J $$\left( \begin{array}{l} \frac{d(PARP_{DNA})_{PARn}}{dt} = k_{a(PAR)}.[NAD+].(PARP_{DNA})_{PARn-1} - \gamma.k_{d(rel)}.(PARP_{DNA})_{PARn} - k_{a(trap)}[PARPi].(PARP_{DNA})_{PARn} + \\ \quad k_{d(trap)}(PARP_{trap})_{PARn} - k_{a(PAR)}.[NAD+].(PARP_{DNA})_{PARn} \\ \frac{d(PARP_{trap})_{PARn}}{dt} = k_{a(trap)}.[PARPi].(PARP_{DNA})_{PARn} - k_{d(trap)}(PARP_{trap})_{PAR\,n} - \gamma.k_{d(rel\text{-}PARPi)}.(PARP_{trap})_{PARn} \\ \frac{d(PARP_{rel\text{-}PARPi})_{PARn}}{dt} = \gamma.k_{d(rel\text{-}PARPi)}.(PARP_{trap})_{PARn} \\ \frac{d(PARP_{rel})_{PARn}}{dt} = \gamma.k_{d(rel)}.(PARP_{DNA})_{PARn} \end{array} \right)_{n=0 \ldots PAR_{release}}$$

FIG. 18B

Rate in a two state system $$k_{off_{obs}} = \eta_{rest} k_{off_{rest}} + \eta_{active} k_{off_{active}}$$

METHODS OF DETECTING MOLECULAR AGGREGATES USING IMAGE CORRELATION SPECTROSCOPY (ICS)

CROSS-REFERENCE TO RELATED APPLICATIONS

This application is the U.S. National Phase Application under 35 U.S.C. § 371 of International Patent Application No. PCT/US2023/017926, filed on Apr. 7, 2023, which claims the benefit of U.S. Provisional Patent Application Ser. No. 63/328,820, filed on Apr. 8, 2022, the entire contents of each of the foregoing are hereby incorporated by reference herein.

CLAIM OF PRIORITY

This application claims the benefit of U.S. Provisional Application Ser. No. 63/328,820, filed on Apr. 8, 2022, which is incorporated by reference herein in its entirety.

FEDERALLY SPONSORED RESEARCH OR DEVELOPMENT

This invention was made with Government support under Grant No. CA241179 awarded by the National Institutes of Health. The government has certain rights in the invention.

FIELD

The present invention is directed to detecting molecular aggregates in a biological sample.

BACKGROUND

Molecular aggregation plays a role in many biological processes (e.g., formation of transcription complexes, recruitment of DNA damage response factors to sites of DNA damage) and diseases (e.g., protein aggregation in Alzheimer's or Huntington's diseases). Detecting and quantifying molecular aggregates can be useful for understanding cellular mechanisms and identifying therapies and therapeutic targets. Thus, there is a need for methods for detecting molecular aggregates.

SUMMARY

The present disclosure is based, at least in part, on the finding that the degree of aggregation (DA) calculated from an image correlation spectroscopy (ICS) analysis of a fluorescent image provided a more reliable measure of dose dependent DNA damage than conventional foci counting and captured the dose dependent clustering of two proteins, RPA1 and RAD51, which do not form foci resolvable by conventional foci counting. It was also shown that the ICS calculated DA revealed compound activity that was not detectable by conventional foci counting.

Accordingly, aspects of the present disclosure provide a method of detecting a molecular aggregate in a biological sample, the method comprising:

- directing an excitation beam to a biological sample, wherein the biological sample comprises a plurality of molecules, each of which comprises a fluorescent label, and wherein the biological sample comprises a region of interest (ROI);

- acquiring an image of the biological sample, wherein the image comprises a plurality of pixels, each of which has a size that is smaller than a size of the excitation beam;
- segmenting the ROI;
- performing an image correlation spectroscopy (ICS) analysis of the ROI using a signal from the fluorescent label;
- calculating a degree of aggregation (DA) of $$DA = \frac{\langle i \rangle}{\langle n \rangle} = c\frac{\langle n_f \rangle}{\langle n \rangle}$$

from the ICS analysis of the ROI, wherein $\langle i \rangle$ comprises an average intensity of the signal from the fluorescent label; $\langle n \rangle$ comprises a mean number of molecules in the plurality of molecules; $\langle n_f \rangle$ comprises a total number of the fluorescent label; and c comprises a constant relating signal intensity to number of signals; and

- determining an absence or a presence of a molecular aggregate based on the calculated DA, wherein a deviation of the calculated DA from a control value indicates the presence of the molecular aggregate.

In some embodiments, calculating the DA comprises calculating a spatial correlation $$r(\xi, \eta) = \frac{\langle \delta i(x, y)\delta i(x+\xi, y+\eta)\rangle}{\langle i \rangle^2},$$

function of wherein $\xi$ and $\eta$ comprise discrete pixel shifts in an x and a y direction, respectively, in the image of the biological sample.

In some embodiments, the spatial correlation function is calculated using a Fourier method of $$r(\xi, \eta) = \frac{F^{-1}[F(i(x, y))F^*(i(x, y))]}{\langle i \rangle^2} - 1,$$

wherein F comprises a discrete 2D spatial fast Fourier transform of the ROI, F* comprises a complex conjugate, and $F^{-1}$ comprises an inverse Fourier transform.

In some embodiments, methods described herein further comprise fitting the spatial correlation function to a two-dimensional (2-D) Gaussian function of $$r(\xi, \eta) = g(0, 0)\exp\left[-\frac{\xi^2 + \eta^2}{\omega_0^2}\right] + g_\infty,$$

wherein g(0, 0) comprises a zero-lags amplitude, wo comprises an $e^{-2}$ Gaussian correlation radius, and $g^\infty$ comprises a long spatial lag offset.

In some embodiments, directing the excitation beam comprises scanning the excitation beam over the biological sample. In some embodiments, directing the excitation beam comprises widefield illumination.

In some embodiments, segmenting the ROI comprises using differential interference contrast (DIC). In some embodiments, segmenting the ROI comprises labeling the ROI with an additional fluorescent label and detecting a signal from the additional fluorescent label.

In some embodiments, directing the excitation beam and acquiring the image comprises using a low magnification objective. In some embodiments, the low magnification objective comprises a magnification between 4× and 20×.

In some embodiments, the size of each pixel is between 200 to 500 nm. In some embodiments, the size of each pixel is between 300 to 350 nm.

In some embodiments, the size of the excitation beam is between 500 to 1000 nm. In some embodiments, the size of the excitation beam is between 700 to 800 nm.

In some embodiments, the control value is a calculated DA from a control sample. In some embodiments, the control sample is an untreated biological sample. In some embodiments, the control value is a predetermined threshold value. In some embodiments, the biological sample comprises a cellular sample, a tissue sample, or a whole animal.

In some embodiments, the fluorescent label and/or the additional fluorescent label comprises a fluorescent protein. In some embodiments, the fluorescent protein comprises a green fluorescent protein (GFP) or a red fluorescent protein (RFP). In some embodiments, the fluorescent label and/or the additional fluorescent label comprises a fluorescent dye. In some embodiments, the fluorescent dye comprises 4',6-diamidino-2-phenylindole (DAPI), fluorescein isothiocyanate (FITC), tetramethylrhodamine isothiocyanate (TRITC), or aniline blue. In some embodiments, the fluorescent dye comprises an Alexa fluor dye, a Cy3 dye, or a Cy5 dye. In some embodiments, the fluorescent label and/or the additional fluorescent label is conjugated to an antibody.

In some embodiments, the ROI comprises a nucleus of a cell and the second fluorescent label comprises 4',6-diamidino-2-phenylindole (DAPI). In some embodiments, the ROI comprises an extracellular matrix of a cell and the second fluorescent label comprises aniline blue.

In some embodiments, the molecular aggregate is extracellular or intracellular. In some embodiments, the molecular aggregate comprises proteins and/or nucleic acids. In some embodiments, the molecular aggregate comprises a stress granule, a DNA repair foci, a transcription complex, an immune signaling complex, a nucleolus, a P body, a chromatin complex, or a membrane signaling complex. In some embodiments, the molecular aggregate comprises 53BP1, γH2AX, RPA1, RAD51, LIG3, KU80, PCGF1, VCP/P97, RPA32, TOPBP1, FEN1, RFWD3, SUMO-2, SUMO-3, APLF, or combinations thereof. In some embodiments, the molecular aggregate comprises α-synuclein, FUS, TDP-43, tau, β-amyloid, huntingtin, or combinations thereof.

In some embodiments, the plurality of molecules comprises proteins and/or nucleic acids. In some embodiments, the plurality of molecules comprises 53BP1, γH2AX, RPA1, RAD51, LIG3, KU80, PCGF1, VCP/P97, RPA32, TOPBP1, FEN1, RFWD3, SUMO-2, SUMO-3, APLF, or combinations thereof. In some embodiments, the plurality of molecules comprises α-synuclein, FUS, TDP-43, tau, β-amyloid, huntingtin, or combinations thereof.

Aspects of the present disclosure provide a method of detecting a molecular aggregate in a biological sample, the method comprising:

- providing an image of a biological sample comprising a plurality of molecules, each of which comprises a fluorescent label, wherein the biological sample comprises a region of interest (ROI) comprising a second fluorescent label;
- segmenting the ROI using a signal from the second fluorescent label;
- performing an image correlation spectroscopy (ICS) analysis of the ROI using a signal from the fluorescent label;
- calculating a degree of aggregation (DA) of $$DA = \frac{\langle i \rangle}{\langle n \rangle} = c\frac{\langle n_f \rangle}{\langle n \rangle}$$

from the ICS analysis of the ROI, wherein $\langle i \rangle$ comprises an average intensity of the signal from the fluorescent label; $\langle n \rangle$ comprises a mean number of molecules in the plurality of molecules; $\langle n_f \rangle$ comprises a total number of the fluorescent label; and c comprises a constant relating signal intensity to number of signals; and

- determining an absence or a presence of a molecular aggregate based on the calculated DA, wherein a deviation of the calculated DA from a control value indicates the presence of the molecular aggregate.

In some embodiments, the image of the biological sample is obtained from a publically available database. In some embodiments, the publically available database is available from Image Data Resource (IDR).

Aspects of the present disclosure provide a method comprising:

- providing a plurality of images of a biological sample; wherein each biological sample comprises a plurality of molecules, each of which comprises a fluorescent label;
- wherein each biological sample comprises a region of interest (ROI) comprising a second fluorescent label; and wherein each image comprises the biological sample in a presence of a different amount of a test compound;
- segmenting the ROI for each image using a signal from the second fluorescent label;
- performing an image correlation spectroscopy (ICS) analysis of the ROI for each image using a signal from the fluorescent label;
- calculating a degree of aggregation (DA) of $$DA = \frac{\langle i \rangle}{\langle n \rangle} = c\frac{\langle n_f \rangle}{\langle n \rangle}$$

from the IC'S analysis of the ROI for each image, wherein $\langle i \rangle$ comprises an average intensity of the signal from the fluorescent label; $\langle n \rangle$ comprises a mean number of molecules in the plurality of molecules; $\langle n_f \rangle$ comprises a total number of the fluorescent label; and c comprises a constant relating signal intensity to number of signals; and

- determining an absence or a presence of a molecular aggregate based on the calculated DA, wherein a deviation of the calculated DA from a control value indicates the presence of the molecular aggregate.

In some embodiments, methods described herein further comprise plotting the calculated DA for each image against the concentration of the test compound in the image.

In some embodiments, the control value is a calculated DA from the biological sample in an absence of the test compound. In some embodiments, the control value is a predetermined threshold value.

In some embodiments, the test compound is an antibody. In some embodiments, the test compound is a small molecule. In some embodiments, the test compound is olaparib, talazoparib, veliparib, GMX1778, mirin, PFI-1, PF CBP1, A66, thiotepa, or SAHA.

DESCRIPTION OF DRAWINGS

(FIG. 2A) Schematic depiction of showing how higher concentrations of DNA damaging agent will induce more DNA damage and allow recruitment patterns to be quantified and statistically tested. (FIG. 2B) Representative IF images of, left, APLF in HCC1395 cells treated with control or 10 μM olaparib, and right, KU80 in UWB cells treated with control or 10 μM olaparib. (FIG. 2C) Graphs showing recruitment of 10 different DDR proteins in response to the PARP inhibitor olaparib in 4 cell lines. (FIG. 2D) Schematic depictions of recruitment patters.

(FIG. 3A) Schematic depiction showing ICS autocorrelation directly quantifying cluster colocalization of two proteins to determine the degree of co-recruitment to DNA damage. (FIG. 3B) Representative IF images from HCC1937 cells labeled with DAPI to identify the nucleus for segmentation and immuno-labelled for SUMO 2/3 and TOPBP1 using two different fluorophores for simultaneous imaging. (FIG. 3C) Graphs showing SUMO 2/3 recruitment to DNA damage dependency on temozolomide (TMZ) dose for three different cell lines. Graphs showing protein recruitment of 5 different proteins to TMZ induced DNA damage (FIG. 3D). (FIG. 3E) Graphs showing cluster colocalization of each protein with SUMO 2/3 dependent on TMZ induced DNA damage. (FIG. 3F) Representative images of UWB1.289 cells labeled for γH2AX and SUMO 2/3, with merge. (FIG. 3G) Schematic depiction of differences in cluster colocalization from recruitment into different spaces or recruitment at different times.

(FIG. 5A) DAPI channel with 5 μm scale bar, (FIG. 5B) γH2AX channel, (FIG. 5C) Composite of (FIG. 5A) and (FIG. 5B). (FIGS. 5D-5E) Foci counting with Find Maxima tool in ImageJ with a threshold of (FIG. 5D) 600 and (FIG. 5E) 300. (FIG. 5F) Foci counting using Imaris Spots with an automatic threshold and an expected spot size of 1 μm. (FIG. 5G) Number of maxima per nucleus from different thresholds using ImageJ for the same cell. (FIG. 5H) Foci counting comparison between a user defined threshold in ImageJ and automatic threshold in Imaris on the same cell. (FIG. 5I) Intensity adjusted γH2AX channel showing lower intensity foci (white arrows), larger foci (gray arrows) and higher background intensities (gray arrows with white dots arrows).

(FIG. 6A) Schematic population of monomeric fluorescent particles where emitting particles (black) are in a diffraction limited excitation focus (gray)—not to scale. (FIG. 6B) Schematic showing increase in particle density from (FIG. 6A) which results in an increase in average fluorescence intensity. (FIG. 6C) Schematic showing clustering of fluorescent particles where the total number of independent particle clusters is the same as (FIG. 6A). Spatial ICS measures the average number of independent fluorescent units per area which, along with the average fluorescence intensity, is used to calculate the average degree of aggregation of the particles. (FIG. 6D) Intensity-based segmentation of the DAPI channel with an automatic threshold using the MATLAB function imbinarize to create a mask of the nucleus. The mask specifies the ROI for ICS analysis of the γH2AX channel, outputting mean number of independent fluorescent particles per focal spot area (inverse of the intensity normalized spatial correlation function amplitude). (FIGS. 6E-6F) Comparison of the ICS parameter TNOP with FIG. 6E ImageJ Find Maxima tool with a user defined threshold and FIG. 6F Imaris Spots with an automatic threshold for the same nuclei. A linear line of best fit is shown on each graph with the resulting $R^2$.

FIGS. 7A-7O: Imaris Spots and ICS capture dose dependent DNA damage through γH2AX foci in SKOV3 cells. (FIGS. 7A-7C) SKOV3 cells treated with 0.1 mM MMS; (FIG. 7A) DAPI channel with 10 μm scale bar, (FIG. 7B) γH2AX channel, (FIG. 7C) γH2AX channel with intensity-adjustment.

FIGS. 8A-8O: Imaris Spots and ICS DA capture dose dependent DNA damage through γH2AX in OVCA429 cells. (FIGS. 8A-8C) OVCA429 cells treated with 0.1 mM MMS; (FIG. 8A) DAPI channel with 10 μm scale bar, (FIG. 8B) γH2AX channel, (FIG. 8C) γH2AX channel with intensity-adjustment. (FIG. 8G, FIG. 8K, and FIG. 8O) Normalized ICS DA of γH2AX signal across different MMS (FIGS. 8D-8G), veliparib (FIGS. 8H-8K) and olaparib (FIGS. 8L-8O) in OVCA429 cells. Results are pooled from 3 independent experiments where each set of concentrations were normalized to the relevant control. MMS; N=1194-2068, veliparib; N=1256-1997, olaparib; N=1445-2334. * indicates $p<0.05$,  indicates $p<0.001$, * indicates $p<1\times10^{-10}$ via one-way ANOVA significance testing. Error bars are standard deviations.

FIGS. 9A-9J: Measuring dose-dependent DNA damage through RPA1. (FIGS. 9A-9C) Control SKOV3 cells, (FIGS. 9D-9F) SKOV3 cells treated with 1 mM MMS; (FIG. 9A and FIG. 9D) DAPI channel with 10 μm scale bar, (FIG. 9B and FIG. 9E) RPA1 channel, (FIG. 9C and FIG. 9F) RPA1 channel with intensity-adjustment, (FIG. 9G) Normalized RPA1 Imaris Spots analysis in SKOV3, (FIG. 9H) Normalized RPA1 DA in SKOV3, (FIG. 9I) Normalized RPA1 Imaris Spots analysis in OVCA429, (FIG. 9J) Normalized RPA1 DA in OVCA429 across different MMS concentrations. Results are pooled from 3 independent experiments where each set of concentrations were normalized to the relevant control. N=1600-1872 for SKOV3 and N=1320-2198 for OVCA429. * indicates $p<0.05$,  indicates $p<0.001$, * indicates $p<1\times10^{-10}$ via one-way ANOVA significance testing. Error bars are standard deviations.

FIGS. 10A-10J: Measuring dose-dependent DNA damage through RAD51. (FIGS. 10A-10C) Control SKOV3 cells, (FIGS. 10D-10F) SKOV3 cells treated with 1 mM MMS; (FIG. 10A and FIG. 10D) DAPI channel with 10 μm scale bar, (FIG. 10B and FIG. 10E) RAD51 channel, (FIG. 10C and FIG. 10F) RAD51 channel with intensity-adjustment, (FIG. 10G) Normalized RAD51 Imaris Spots analysis in SKOV3, (FIG. 10H) Normalized RAD51 DA in SKOV3, (FIG. 10I) Normalized RAD51 Imaris Spots analysis in OVCA429, (FIG. 10J) Normalized RAD51 DA in OVCA429 across different MMS concetrations. Results are pooled from 3 independent experiments where each set of concentrations were normalized to the relevant control. N=1597-2241 for SKOV3 and N=1822-2311 for OVCA429. * indicates $p<0.05$,  indicates $p<0.001$, * indicates $p<1\times10^{-10}$ via one-way ANOVA significance testing. Error bars are standard deviations.

FIG. 11B, WPMY-1; FIG. 11C, HepG2). Above the black line (p=0.05) are compounds with significant activity. Identified compounds are known to impact the DNA damage response.

FIGS. 12A-121: PARP trapping is not driven by the physical engagement of PARP1 to DNA. (FIG. 12A) Normalized PARP1 trapping in HT1080 cells treated with PARPi (1 μM overnight) versus IC50 with linear fit (gray line), individual measurements, n=5 with average (black line). (FIGS. 12F-121) ODE solution for the amount of trapped PARP1 (FIG. 12F) in the presence of PARPi, (FIG. 12G) with different veliparib concentrations, (FIG. 12H) with synthetically altered olaparib binding constants or absence of NAD+, and (FIG. 12I) with olaparib under synthetically altered PARPi bound PARP1-DNA binding constants. All data, * $p<0.005$,  $p<0.001$, * $p<0.0001$ vs. control (Student's t test).

(FIG. 13A) An assay to measure dissociation of bound drug from cellular PARP. Excess PARPi occupies PARP target inside cells, fluorescently labeled olaparib (olap, BFL=BODIPY FL) is then added and PARPi is removed. The binding rate of fluorescent drug represents the dissociation ($k_{off}$) of PARPi. (FIG. 13B) Representative anisotropy images of fluorescent olaparib in HT1080 cells during dissociation measurements, PARPi is removed at t=0, scale bar=5 μM. (FIG. 13C) ΔrINT measurements of fluorescent olaparib binding in the dissociation assay for 3 different PARPi, shown are fitted one phase association curves for single cells. (FIG. 13D) Single cell apparent dissociation constants ($k_{off}$) for 3 different PARPi, shown are individual cells with average and st. dev., n=30-57 cells, >=4 biological repeats, * $p<1\times10^{-16}$ (Student's t test). (FIG. 13E) Apparent $k_{off}$ as a function of relative PARP activity for 3 PARPi, data are average with st. dev., n>=6 cells, and fitted one phase dissociation curve, * $p<5\times10^{-4}$ (Student's t test) between control and maximum PARP activity for each PARPi.

(FIG. 14A) PAR is produced when PARP1 is activated upon binding DNA, which helps to establish a biomolecular condensate at the site of DNA damage by recruiting proteins. Other signaling also occurs, such as H2AX phosphorylation and protein recruitment in a PAR independent pathway. Under PARP inhibition, PAR-recruited proteins will be reduced and the relative density of other components will be higher. (FIG. 14B) Expected dependency of condensate density on PAR production and correlation to PARP trapping. (FIG. 14C) Representative $\gamma H_2AX$ immunofluorescence images of HT1080 cell nuclei treated with 1 μM PARPi or control. (FIG. 14D) ICS DA (degree of aggregation) of γH2AX IF in HT1080 cells treated with 1 μM PARPi overnight versus PARP1 trapping, with linear fit (gray line), shown are average with SEM, trapping-n=5, DA-n>=536 cells, 3 biological repeats. (FIG. 14E) ICS DA of γH2AX IF in HT1080 cells treated with veliparib versus PARP1 trapping, with linear fit (gray line), shown are average with SEM, trapping-n=5, DA-n>=1165 cells, 3 biological repeats, * $p=7\times10^{-18}$, ** $p=4\times10^{-16}$, Student's t test. (FIG. 14F) ICS DA of $\gamma H_2AX$ IF in HT1080 cells treated with 10 nM GMX1778 for 24 hours or control versus PARP1 trapping, shown are average with SEM, trapping-n=5, DA-n>=1285 cells, 3 biological repeats, * $p=1\times10^{-18}$, Student's t test. (FIG. 14G) ICS DA of $\gamma H_2AX$ IF labeled cells treated with 1 μM PARPi overnight versus cell line $EC_{50}$ cell viability, shown are average with SEM, n>=536 cells, 3 biological repeats, with linear fit (gray line), Pearson correlation coefficient=−0.81, $p<0.0001$. (FIG. 14H) ICS DA of $\gamma H_2AX$ IF labeled cells treated with 1 μM PARPi overnight versus cell line $IC_{50}$ cell viability for 3 UWB1.289 cell lines, shown are average with SEM, n>=539 cells, 3 biological repeats, with linear fit (gray line), Pearson correlation coefficient=−0.87, $p<0.005$.

(FIG. 15A) Model of PARP1 activity during biomolecular condensate formation in response to DNA damage. PARP1, PARPi, DNA, and DDR (other DNA binding proteins in the DDR pathway) can bind to and dissociate from their targets. When DNA-bound PARP1 binds $NAD^+$ a random protein is PARylated. PARylated PARP1 can exchange with unPARylated PARP1 outside the condensate and DDR proteins are recruited to condensates in a PAR-dependent manner. Histones represent PAR targets that cannot leave the condensate. (FIG. 15B) ICS DA of PARP1 IF in HT1080 cells treated overnight with 100 μM TMZ or control, shown are single cell values with average (black bar), n>=1202 cells, 2 biological repeats. (FIGS. 15C-15D) Stochastic simulation results of (FIG. 15C) trapped PARP1 on DNA and (FIG. 15D) condensate PAR levels as a function of time in the absence or presence of 1 μM PARPi. (FIG. 15E) Representative image of 10 μM PAR binding peptide uptake in an HT1080 cell after 1 hour incubation. (FIG. 15F) ICS DA of $\gamma H_2AX$ IF in HT1080 cells treated with 1 μM veliparib, 10 μM PAR binding peptide or the combination overnight versus PARP1 trapping, with linear fit (gray line), shown are average with SEM, trapping-n=5, DA-n>=917 cells, 3 biological repeats, * $p<0.0005$ (Student's t test). (FIG. 15G) single nuclei ICS $\gamma H_2AX$ DA of HT1080 cells versus PAR binding peptide nuclear intensity for cells treated with 10 μM PAR binding peptide (light gray) or 10 μM PAR binding peptide plus 1 μM veliparib (dark gray) overnight, with linear fit, n>=917 cells, 3 biological repeats. (FIG. 15H) Stochastic simulation results of trapped PARP1 on DNA as a function of time for veliparib, talazoparib, an artificial PARPi with veliparib PARP1 binding constants and the talazoparib allosteric PARP1-DNA binding constants, and an artificial PARPi with talazoparib PARP1 binding constants and the veliparib allosteric PARP1-DNA binding constants. All simulation data are an average of 1000 simulations.

(FIG. 16A) RPA1 DA in untreated cells or cells treated with 100 μM TMZ overnight, shown are average with SEM, n>=680 cells, 3 biological repeats, all cell lines except OVCA429 p<0.05 for control vs. TMZ (Student's t test). And, western blot RPA1 expression levels for each cell line. (FIG. 16B) RPA1 DA in cells treated with 1 μM PARPi overnight, shown are average, normalized to untreated control, with SEM, n>=350 cells, 2 biological repeats. (FIG. 16C) The linear fit slope of RPA DA vs. cell line IC50 as a function of average PARPi z-score for each cell line. Shown are slope fit with SEM and average z-score over three PARPi with st. dev. (FIG. 16D) RPA1 DA as a function of olaparib concentration for HT1080 and HCC1937 cells, shown are average with SEM, n>=504 cells, 3 biological repeats, and linear fit. (FIG. 16E) PARP1 trapping in UWB1.289 and UWB1.289+BRCA1 cells treated with 1 μM talazoparib overnight, n=5, * p<0.05, Student's t test. (FIG. 16F) Model of PARPi efficacy. DDR proteins are recruited by DNA damage condensates through PAR (left bars) or PAR-independent mechanisms (right bars). The presence of DNA binding DDR proteins in the condensate results in increased competition for binding DNA which outcompetes PARP1. In the absence of DNA binding DDR proteins PARP1 remains "trapped" preventing progression of DNA damage repair.

(FIG. 17A) Representative western blot of HT1080 cells treated with PARPi or GMX1778, H3-histone H3. Shown are chromatin, nuclear soluble and cytoplasmic fractions. (FIG. 17B) Merged results from FIG. 12A and FIG. 12C, n=5 with average and st. dev., * 100 μM veliparib vs. 1 μM talazoparib p<0.005 (Student's t test), normalized to DMSO control. (FIG. 17C) Western blot of PARP1 expression in normal (con) of PARP1 knockout (KO) cells, non-specific (NS) bands were used as a loading control. (FIG. 17D) Dose response of HT1080 cells to treatment with either talazoparib or veliparib. (FIG. 17E) Dose response of HT1080 cells with PARP1 knocked out through CRISPR/CAS9 to talazoparib or veliparib. Dose response data average±st. dev., n=3 biological repeats, with fitted sigmoidal curve. (FIG. 17F) PAR western blot and (FIG. 17G) quantification of HT1080 cells treated with GMX1778 at varying concentrations for 24 hours followed by treatment with 1 μM $H_2O_2$ for 10 minutes, shown is normalized signal quantification and sigmoidal response curve fit.

FIGS. 18A-18B: The ODE model of PARP1-DNA engagement. (FIG. 18A) Model of PARPi induced trapping of PARP1 to damaged DNA. Governed by rate constants, DNA-bound PARP1 either dissociates from DNA, binds NAD" to undergo ADP-ribosylation, or engages PARPi. PARPi engaged PARP1 bound to DNA can dissociate from DNA or the PARPi can dissociate. Upon ADP-ribosylation PARP1 is self-PARylated and the model proceeds to $PAR_{n+1}$. At $PAR_n$=release PARP1 loses all affinity for DNA, by default release=500. Here, $\gamma_n$ is a correction factor that decreases PARP1 affinity for DNA as a function of PAR level. (FIG. 18B) The core differential equations used in the model.

(FIG. 19A) Solution results of species levels in the presence (orange) or absence (gray) of 1 μM olaparib. Trapping (solid line), release (dashed line) and full PARylation (PARylated, dotted line) show the fate of PARP1. In the presence of olaparib all release occurred before full PARylation (500 events) was reached. (FIG. 19B) The impact of the number of rounds on the results from the ODE solution shown in the absence (top) and presence (bottom) of 1 μM olaparib. Solid lines are the default value (500). The values in the legend correspond to curves from right to left (high trapping to lower trapping). (FIG. 19C) The impact of the NAD" concentration on the results from the ODE solution shown in the absence (top) and presence (bottom) of 1 μM olaparib. Solid lines are the default value (100 μM). The values in the legend correspond to curves from right to left (high trapping to lower trapping). A lower NAD" concentration increases trapping by limiting PARylation. (FIG. 19D) The impact of the association constant of NAD" binding to DNA on the results from the ODE solution shown in the absence (top) and presence (bottom) of 1 μM olaparib. Solid lines are the default value ($5\times10^5\ M^{-1}s^{-1}$). The values in the legend correspond to curves from right to left (high trapping to lower trapping). These results share the same impact as NAD" concentration. (FIG. 19E) The impact of γ on the results from the ODE solution shown in the absence (top) and presence (bottom) of 1 μM olaparib. Solid lines are the default value (2). The values in the legend correspond to curves from right to left (high trapping to lower trapping). Lower values decrease trapping by lowering the impact of PARylation induced release. (FIG. 19F) The impact of the dissociation constant of uninhibited PARP1 from DNA on the results from the ODE solution shown in the absence (top) and presence (bottom) of 1 μM olaparib. Solid lines are the default value ($3.36\times10^{-3}\ s^{-1}$). The values in the legend correspond to curves from right to left (high trapping to lower trapping). Lower values increase trapping for only control by increasing the affinity of PARP1 for DNA.

(FIG. 20A) Comparison of fluorescent olaparib binding to PARP1 as PARPi dissociates as approximated by our model (black dashed line) and the ODE solution. Shown are the bound PARPi (black), free PARP1 (light gray) and bound fluorescent olaparib (dark gray) as determined by the ODE solution. (FIG. 20B) The fitted rate using our model versus actual rate as solved by the ODE equations (black curve) for the rates under consideration (gray box). At higher dissociation rates the model becomes less accurate as fluorescent drug binding becomes the limiting rate. (FIG. 20C) Extended measurements of olaparib dissociation from PARP in HT1080 cells, n=45 cells, 3 biological repeats. Shown are single cell fitted fluorescent drug association curves demonstrating that shorter experimental times enable accurate rate fitting. (FIG. 20D) Binding of fluorescent olaparib in the absence of PARPi in HT1080 cells. Shown are fitted curves for individual cells, n=32 cell, 3 biological repeats.

(FIG. 21A) Apparent $k_{off}$ of olaparib in three different cell lines. Shown are single cell values with average and st. dev., n>=28 cells, over 3 experiments for each cell line, *p<0.001, Student's t test. (FIG. 21B). Basal level PAR expression western blot with GAPDH loading controls (top) and quantification (bottom) in HT1080, HCC1937 and MHH-ESI cell lines. Shown are representative western blot with average and SEM, n=4, *p<0.05 versus HT1080, Student's t test. (FIG. 21C) TMZ induced cellular PAR production in HT1080 cells analyzed by western blot, with PARP1 and GAPDH loading controls (top) and quantification (bottom) with one phase association fit curve (black line). Shown are representative western blot with average and SEM, n=2. (FIG. 21D) Depiction of apparent $k_{off}$ in a two-state system, where n is the number of molecules in each state. (FIG. 21E and FIG. 21F) Modeled impact of two $k_{off}$ states on the apparent rate as a function of distribution among states and relative $k_{off}$ values.

(FIG. 22A) The apparent $k_{on}$ of fluorescent olaparib in in the presence or absence of 100 μM TMZ, shown are single cells with average and st. dev., n>=17 cells, 3 biological repeats, * $p<1\times10^{-12}$ (Student's t test). (FIG. 22B) ODE solved impact of active PARP $k_{on}$ on fitted $k_{off}$ values (gray bars) and the impact of 100 μM TMZ on apparent $k_{off}$ (white bars). (FIG. 22C) Binding of fluorescent olaparib in the absence of PARPi in untreated HT1080 cells (gray) or cells treated with 100 μM TMZ. Shown are fitted curves for individual cells, n>=17 cells, 3 biological repeats. (FIG. 22D) ODE solution of fluorescent olaparib association to PARP1 in the presence of 1 μM PARPi with $k_{on}$ values measured in control cells (solid line) or cells treated with 100 μM TMZ (dashed lines).

(FIG. 23A) Nuclear intensity of $\gamma H_2AX$ IF in HT1080 cells treated with 1 μM PARPi overnight versus PARPi induced PARP trapping, shown are average with SEM and linear correlation, trapping-n=5, DA-n>=536 cells, 3 biological repeats. (FIG. 23B) Nuclear intensity of $\gamma H_2AX$ IF in HT1080 cells treated with veliparib overnight versus PARP1 trapping, with linear fit (gray line), shown are average with SEM, trapping-n=5, DA-n>=1165 cells, 3 biological repeats, * $p=3\times10^{-3}$, ** $p=2\times10^{-8}$ (Student's t test). (FIG. 23C) Representative $\gamma H_2AX$ IF images in HT1080 cells untreated or treated with 10 nM GMX1778 for 24 hours (FIG. 23D) Nuclear intensity of $\gamma H_2AX$ IF in HT1080 cells treated with 10 nM GMX1778 for 24 hours or control, shown are average with SEM, trapping-n=5, DA-n>=1285 cells, 3 biological repeats. (FIG. 23E) Representative intensity (left) and anisotropy (right) images of an HCC1937 cell nucleus expressing 53BP1-mApple. (FIG. 23F) Anisotropy of 53BP1-mApple in nuclei excluding condensates (nuc) and condensates in HCC1937 cells treated with 1 μM PARPi or control, and 100 μM TMZ for 1 hour, shown are single cell or condensate values with average (black bar), n=116 nuclei and n>=335 condensates, 3 biological repeats, * p<0.05,  p<0.001, * p<0.0001 (Student's t test). (FIG. 23G) Intensity values of the data in (FIG. 23F). Shown are single condensate values with average (black bar), n>=335, 3 biological repeats. (FIGS. 23H-231) Anisotropy (FIG. 23H) and intensity (FIG. 23I) of 53BP1-mApple condensates in HCC1937 cells treated with 10 nM GMX1778 for 24 hours or control, followed by 100 μM TMZ for 1 hour, shown are single condensate values with average (black bar), n>=405 condensates, 3 biological repeats, * $p<7\times10^{-13}$ (Student's t test). (FIG. 23J) Anisotropy and (FIG. 23K) intensity values of 53BP1-mApple condensates in HT1080 cells treated with veliparib at difference concentrations or control. Data are single condensates with average, n>=311 condensates, 3 biological repeats, *p<0.005, ** p=0.0001 (Student's t test). All scale bars=2 μM.

(FIGS. 24A-24B) PARPi specific $\gamma H_2AX$ DA (FIG. 24A) and intensity (FIG. 24B) normalized to control, shown is average with SEM, n>=536 cells, 3 biological repeats, * increase with p<0.05 Student's t test vs. cell line control (FIG. 24C) Measured binding property or DA and the number of cell lines with significant correlation, p<0.05 F-test, to the PARPi $EC_{50}$ cell viability for talazoparib, olaparib and veliparib. (FIG. 24D) BRCA1 expression in UWB1.289, UWB1.289 resistant to olaparib, and UWB1.289+BRCA1 cells, with GAPDH loading control. (FIGS. 24E-24F) PARPi specific $\gamma H_2AX$ DA (FIG. 24E) and intensity (FIG. 24F) normalized to control, shown is average with SEM, n>=539 cells, 3 biological repeats, * p<0.05 Student's t test vs. UWB1.289 treated with the same PARPi.

(FIG. 25A) Heatmap plots of PARP1 PARylation as a function of time. Shown is relative concentration of PARylated PARP1 under normal model conditions (left), in the absence of PARP1 exchange (middle), and in the absence of PARP1 exchange, γ, and histones (right). (FIG. 25B) Corresponding trapped PARP1 (left), PAR levels (middle) and protein recruitment (right) to the heatmaps in (FIG. 25A). Shown are simulation results under normal conditions (black), in the absence of PARP1 exchange (dark gray), and in the absence of PARP1 exchange, γ, and histones (light gray). (FIG. 25C) Heatmap of PARP1 PARylation in the presence of 1 μM olaparib as a function of time (left) and corresponding protein recruitment (right). (FIG. 25D) The equilibrium PAR/protein recruited ratio is dependent on the PARPi.

(FIG. 26A) The impact of histone concentration in a biomolecular condensate on the simulation results in the absence (top) and presence (bottom) of 1 μM olaparib. Gray lines are the default value (5). (FIG. 26B) The impact of the ratio of PARP1 to initial other DNA damage binding proteins in a biomolecular condensate on the simulation results in the absence (top) and presence (bottom) of 1 μM olaparib. Gray lines are the default value (10:1). (FIG. 26C) The impact of the PARP1 DNA affinity PARylation dependence factor γ on the simulation results in the absence (top) and presence (bottom) of 1 μM olaparib. Gray lines are the default value (2). (FIG. 26D) The impact of the exchange rate of PARylated PARP1 in a biomolecular condensate exchange with unPARylated PARP1 on the simulation results in the absence (top) and presence (bottom) of 1 μM olaparib. Gray lines are the default value (0.2/p.PARP0). (FIG. 26E) The impact of the DNA binding protein recruitment threshold value on the simulation results in the absence (top) and presence (bottom) of 1 μM olaparib. Gray lines are the default value (2). (FIGS. 26F-26H) Single simulation values of recruited protein as a function of time in the presences of 1 μM (FIG. 26F) veliparib, (FIG. 26G) olaparib, and (FIG. 26H) talazoparib. (FIG. 26I) Stochastic simulation results of protein recruited to levels greater than PARP1 in the presence or absence of 1 μM PARPi. All tracings (except FIGS. 26F-26H) are an average of 1000 simulations.

(FIG. 27A) $\gamma H_2AX$ DA in HT1080 cells treated in the absence of PARPi (control), or with 1 μM veliparib or 1 μM talazoparib with or without 100 nM PDD00017273 overnight, shown are average with SEM, n>=378 cells. There were no significant differences between cells with and without PDD00017273, Student's t test. (FIG. 27B) Dose response of HT1080 cells to veliparib in the absence (closed circles-solid line) or presence (open circles-dashed line) of 100 nM PDD00017273, shown are average with standard deviation of two experiments, n=3 for each experiment, and sigmoidal curve fit (prism) to the average of the two experiments. (FIG. 27C) Nuclear intensity of $\gamma H_2AX$ IF in HT1080 cells treated with 1 μM veliparib, 10 μM PAR binding peptide or the combination overnight versus PARPi induced PARP trapping, shown are average with SEM normalized to control, trapping-n=5, DA-n>=917 cells, 3 biological repeats, no condition showed a significant increase over control (Student's t test). (FIG. 27D) Representative images of HT1080 cells treated overnight with 10 μM of PAR binding peptide, fixed and immunolabeled for $\gamma H_2AX$ and stained with DAPI, scale bar=5 μm. (FIG. 27E) Dose response of HT1080 cells to veliparib in the absence or presence of 10 μM PDD00017273.

(FIGS. 28A-28B) Stochastic simulation results of trapped PARP1 on DNA (FIG. 28A) and condensate recruited DDR protein levels (FIG. 28B) as a function of time at decreasing nuclear NAD" concentration levels, shown are the percentage of baseline NAD" concentration. (FIGS. 28C-28D) Stochastic simulation results of trapped PARP1 on DNA (FIG. 28C) and condensate recruited DDR protein levels (FIG. 28D) as a function of time at 3 different veliparib concentrations. (FIG. 28E) The impact of synthetic PARPi dissociation constant (p.kd_trap) values on trapping within a biomolecular condensate. Shown are simulation results with the labeled $k_d$ value and default olaparib values for other binding constants and 1 μM olaparib. The measured value used in normal conditions is $3\times10^{-4}$ $s^{-1}$. (FIG. 28F) The impact of synthetic olaparib bound PARP1 dissociation from DNA constant (p.kd_relD0) values on trapping within a biomolecular condensate. Shown are simulation results with the labeled $k_d$ values and default olaparib values for other binding constants and 1 μM olaparib. The measured value used in normal conditions is $2.31\times10^{-3}$ $s^{-1}$. (FIG. 28G) The impact of synthetic veliparib at 1 μM. Shown are normal (0 shift) and shifts in both $k_a$ and $k_d$ (the equilibrium binding constant $k_D$ remains the same). (FIG. 28H) The impact of synthetic talazoparib at 1 μM. Shown are normal (0 shift) and shifts in both $k_a$ and $k_d$ (the equilibrium binding constant $k_D$ remains the same). (FIG. 28I) The impact of synthetic talazoparib at 1 μM. Shown are normal (0 shift) and shifts in only $k_a$, which alters the equilibrium binding constant $k_D$ by the same degree. (FIG. 28J) The impact of synthetic talazoparib at 1 μM. Shown are normal (0 shift) and shifts in only $k_d$, which alters the equilibrium binding constant $k_D$ by the same degree. All tracings are an average of 1000 simulations.

(FIG. 29A) RPA1 nuclear intensity in cells untreated or treated with 100 μM TMZ overnight, shown are average with SEM, n>=680 cells, 3 biological repeats, normalized to control for each cell line. (FIG. 29B) Western blot RPA1 expression levels for each cell line in (FIG. 29A) along with GAPDH loading controls. (FIG. 29C) RPA1 nuclear intensity in cells treated with 1 μM PARPi overnight, shown are average, normalized to untreated control, with SEM, n>=350 cells, 2 biological repeats. (FIG. 29D) RPA1 DA as a function of cell line IC50 for each cell line and PARPi shown in FIG. 16B. Shown are average, normalized to untreated control, with SEM, n>=350 cells, 2 biological repeats and linear fit (prism) for each cell line.

DETAILED DESCRIPTION

Image correlation spectroscopy (ICS) is a powerful technique for detecting an arrangement of fluorophores in images. ICS has been used to distinguish images with a homogeneous fluorophore distribution from those with a tightly clustered fluorophore distribution, e.g., a tightly clustered fluorophore distribution indicative of a static molecular aggregate such as a membrane receptor aggregate.

However, conventional ICS methods are unable to distinguish images with a homogeneous fluorophore distribution from those with a loosely clustered fluorophore distribution, e.g., a loosely clustered fluorophore distribution indicative of a dynamic molecular aggregate such as a DNA damage foci.

Figure 1:
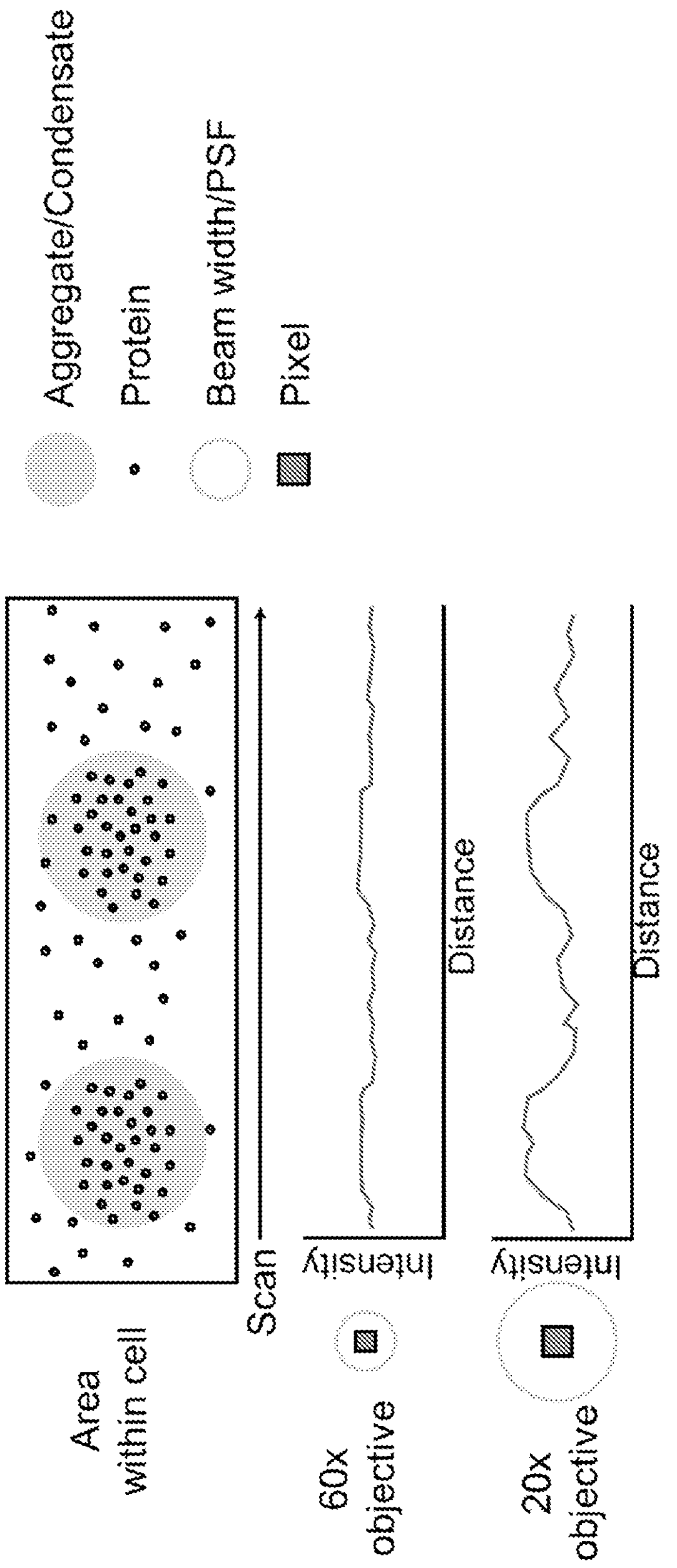
FIG. 1: Schematic depiction of impact of objective and pixel size on measuring aggregation within larger structures. In the 60× image, the intensity difference between adjacent pixels is too low because the beam width (also defined as the point spread function (PSF)) is too small to capture multiple proteins at once.

As shown in FIG. 1, traditional ICS microscope settings use a high magnification objective (e.g., between 60× to 100× magnification) and small pixel sizes (e.g., <100 nm) to create an imaging configuration in which the signal intensity from areas with dynamic molecular aggregates is indistinguishable from the signal produced by non-aggregated molecules.

By contrast, methods described herein involve use of a low magnification objective (e.g., between 5× to 20× magnification) and a large pixel size (e.g., between 200 to 500 nm) to create an imaging configuration in which the signal intensity from areas with dynamic molecular aggregates is distinguishable from the signal produced by non-aggregated molecules (FIG. 1).

Thus, the present disclosure provides, in some embodiments, methods for detecting dynamic molecular aggregates comprising acquiring images using a low magnification objective and a large pixel size, and calculating a degree of aggregation (DA) based on an ICS analysis of the image.

Methods of Detecting Molecular Aggregates

To detect a molecular aggregate (also referred to as condensates) using the methods described herein, an ICS analysis of an image of a biological sample is performed, a DA is calculated based on the ICS analysis, and an absence or presence of a molecular aggregate is determined by comparing the calculated DA to a control value. A deviation of the calculated DA from the control value indicates the presence of the molecular aggregate.

Images of biological samples for use in methods described herein can be acquired using a fluorescent microscope or obtained from other sources such as a publically available database (e.g., Image Data Resource (IDR)).

When using a fluorescent microscope, methods described herein comprise directing an excitation beam to a biological sample and acquiring an image of the biological sample. The excitation beam can be scanned over the biological sample, e.g., using scanning fluorescence microscopy. Alternatively, or in addition to, the excitation beam can be directed over a single area of the biological sample, e.g., using widefield illumination. The excitation beam can be produced by a laser in a fluorescence microscope, and the image of can be acquired using a camera in the fluorescence microscope. In such instances, the image comprises a plurality of pixels, each of which has a size that is smaller than a size of the excitation beam.

In some embodiments, the size of each pixel is between 200 to 500 nm, e.g., between 250 to 500 nm, between 300 to 500 nm, between 350 to 500 nm, between 400 to 500 nm, between 450 to 500 nm, between 200 to 450 nm, between 200 to 400 nm, between 200 to 350 nm, between 200 to 300 nm, or between 200 to 250 nm.

In some embodiments, the size of the excitation beam is between 500 to 1000 nm, e.g., between 600 to 1000 nm, between 700 to 1000 nm, between 800 to 1000 nm, between 900 to 1000 nm, between 500 to 900 nm, between 500 to 800 nm, between 500 to 700 nm, or between 500 to 600 nm. In some embodiments, the size of the excitation beam is between 600 to 700 nm, between 700 to 800 nm, between 800 to 900 nm, or between 900 to 1000 nm. In some embodiments, the size of the excitation beam is between 700 to 900 nm. In some embodiments, the size of the excitation beam is 700 nm, 710 nm, 720 nm, 730 nm, 740 nm, 750 nm, 760 nm, 770 nm, 780 nm, 790 nm, 800 nm, 810 nm, 820 nm, 830 nm, 840 nm, 850 nm, 860 nm, 870 nm, 880 nm, 890 nm, or 900 nm.

In some embodiments, methods described herein involve low magnification objectives, large pixel sizes, or both low magnification objectives and large pixel sizes. In some embodiments, the low magnification objective is between 4× and 20×, e.g., between 10× and 20×, between 15× and 20×, between 4× and 15×, or between 4× and 10×.

Methods described herein can be used to detect molecular aggregates in any biological sample suitable for fluorescent imaging. Non-limiting examples of biological samples include a cellular sample, a blood sample, a tissue sample, and a whole animal. In some examples, the biological sample comprises one or more cells, a piece of tissue, or some or all of an organ. The biological sample can be from a healthy subject or from a subject having a disease such as cancer.

Any region of interest (ROI) in the biological sample can be segmented and used in methods described herein. The ROI can be segmented using any means suitable for identifying the ROI from a region of non-interest in the biological sample. For examples, the RIO can be segmented using differential interference contrast (DIC). Alternatively, or in addition to, the RIO can be segmented by labeling the ROI with a fluorescent label and detecting a signal from the fluorescent label. In such instances, the fluorescent label used for labeling the ROI is different from the fluorescent label used for labeling the molecule of interest.

In some embodiments, the ROI is intracellular, e.g., a nucleus of a cell. In such instances, the nucleus can be fluorescently labeled with a conventional fluorescent label such as DAPI. Alternatively, or in addition to, the ROI is extracellular, e.g., an extracellular matrix (ECM) of a cell. In such instances, the ECM can be fluorescently labeled with a conventional fluorescent label such as aniline blue.

Any molecule that can be fluorescently labeled and detected can be used in methods described herein. In some embodiments, the molecule comprises protein and/or nucleic acid (e.g., DNA, RNA, or both DNA and RNA). Methods described herein encompass detection and analysis of one or more molecules of interest (e.g., 1, 2, 3, or more). A molecule of interest can be labeled with one or more fluorescent labels (e.g., 1, 2, 3, or more).

In some embodiments, the fluorescently labeled molecule can comprise a protein such as a DNA damage factor. Non-limiting examples of DNA damage factors that can be fluorescently labeled for detection of molecular aggregates include 53BP1, γH2AX, RPA1, RAD51, LIG3, KU80, PCGF1, VCP/P97, RPA32, TOPBP1, FEN1, RFWD3, SUMO-2, SUMO-3, or APLF. In another example, the fluorescently labeled molecule can comprise a pathological protein such as α-synuclein, FUS, TDP-43, tau, β-amyloid, or huntingtin.

As used herein, the term "fluorescent label" (also referred to as "fluorophore" or "fluorescent dye") refers to moieties that absorb light energy at a defined excitation wavelength and emit light energy at a different wavelength. The fluorescent label can be a small molecule such as a fluorescent dye, a fluorescent protein such as GFP or a quantum dot nanoparticle. In some embodiments, the fluorescent label is attached to a protein such as an antibody that binds to the molecule of interest or to the ROI. Any method suitable for conjugating a fluorescent label to a molecule of interest or to the ROI can be used in methods described herein, e.g., NHS ester labeling of the amino groups of molecules.

Non-limiting examples of fluorescent dyes for use in methods described herein include Alexa Fluor® dyes (e.g., Alexa Fluor® 488, Alexa Fluor® 594, Alexa Fluor® 647), cyanine derivatives (e.g., Cy® dyes (e.g., Cy3®, Cy5®), cyanine, indocarbocyanine, oxacarbocyanine, thiacarbocyanine, merocyanine), xanthene derivatives (e.g., fluorescein, rhodamine, Oregon green, eosin, Texas Red®), naphthalene derivatives (e.g., dansyl, prodan derivatives), pyrene derivatives (e.g., cascade blue), oxadiazole derivatives (e.g., pyridyloxazole, nitrobenzoxadiazole and benzoxadiazole), oxazine derivatives (e.g., Nile red, Nile blue, cresyl violet and oxazine 70), acridine derivatives (e.g., proflavin, acridine orange, acridine yellow), arylmethine derivatives (e.g., auramine, crystal violet, malachite green), tetrapyrrole derivatives (e.g., porphin, phthalocyanine, bilirubin), coumarin derivatives, fluorescent proteins (e.g., green fluorescent protein (GFP), red fluorescent protein (RFP)), 4',6-diamidino-2-phenylindole (DAPI), fluorescein isothiocyanate (FITC), tetramethylrhodamine isothiocyanate (TRITC), or aniline blue.

Methods described herein can be used to detect any molecular aggregate suitable for fluorescent detection via a fluorescently labeled molecule in the molecular aggregate. The molecular aggregate can be extracellular or intracellular. The molecular aggregate can comprise protein and/or nucleic acids (e.g., DNA, RNA, or both DNA and RNA). Non-limiting examples of molecular aggregates that can be detected using methods described herein include stress granules, DNA repair foci, transcription complexes, immune signaling complexes, nucleoli, P bodies, chromatin complexes, membrane signaling complexes, and combinations thereof.

In some embodiments, the molecular aggregate comprises a DNA damage foci. In such instances, the molecular aggregate can comprise one or more DNA damage factors. In some embodiments, one or more DNA damage factors comprises a fluorescent label. Non-limiting examples of DNA damage factors include 53BP1, γH2AX, RPA1, RAD51, LIG3, KU80, PCGF1, VCP/P97, RPA32, TOPBP1, FEN1, RFWD3, SUMO-2, SUMO-3, and APLF.

In some embodiments, the molecular aggregate comprises a pathological protein aggregate. In some embodiments, the pathological protein comprises a fluorescent label. Non-limiting examples of proteins found in a pathological protein aggregate include α-synuclein, FUS, TDP-43, tau, β-amyloid, huntingtin, or combinations thereof.

Methods described herein can involve any type of fluorescence microscopy suitable for obtaining a fluorescent image. Non-limiting examples of fluorescence microscopy for use in methods described herein include wide-field fluorescence microscopy, confocal fluorescence microscopy, total internal refraction microscopy, and combinations thereof.

Screening

Methods of detecting a molecular aggregate as described herein can be used to identify a compound that promotes or inhibits aggregation. In some instances, the identified compound is selected for further studies based on whether the compound promotes or inhibits molecular aggregation.

Accordingly, methods described herein can comprise calculating a DA from an image of a biological sample in an absence of the compound, calculating a DA from an image of the biological sample in a presence of the compound, and comparing the calculated DA values to identify the compound as promoting or inhibiting aggregation. In some embodiments, methods described herein can further comprise plotting the calculated DA for each image against the concentration of the test compound in the image.

Any compound can be screened in methods described herein. The compound can be an antibody or a small molecule. Non-limiting examples of compounds include olaparib, talazoparib, veliparib, GMX1778, mirin, PFI-1, PF CBP1, A66, thiotepa, or SAHA.

Image Correlation Spectroscopy (ICS) Analysis

ICS is based on the analysis of fluorescence intensity fluctuations arising from variations in the number of fluorescent particles within focal spots imaged in space and/or time using a fluorescence microscope. ICS analysis for use in methods described herein involve calculating the image autocorrelation and fitting of the autocorrelation function to a two-dimensional (2-D) Gaussian function to calculate the DA.

Methods described herein can involve any type of ICS suitable for calculating DA. Non-limiting examples of image correlation spectroscopy include image cross-correlation spectroscopy, dynamic image correlation spectroscopy, raster image correlation spectroscopy, and combinations thereof. In some embodiments, methods described herein can comprise spatial ICS and/or temporal ICS.

In principle, aggregation could be directly measured from the intensity information encoded in the pixels as the variance to mean intensity ratio in Eq. 1, but only if there is no white noise present, and all signal fluctuations were due to particle number variations.

$$\frac{\langle(\delta i)^2\rangle}{\langle i\rangle^2} = \frac{1}{\langle n\rangle} \tag{1}$$

In Eq. 1, $\delta i = i - \langle i\rangle$ is the intensity fluctuation, where $\langle i\rangle$ is the mean intensity and $\langle n\rangle$ is the mean number of independent fluorescent particles per focal spot area. Thus, the square relative intensity fluctuation (intensity variance/mean intensity, Eq. 1) is the mean number of detected independent fluorescent particles per focal spot, since ideal behavior entails that the molecules obey Poisson statistics within the volume.

However, in practice, white noise (e.g., shot noise) will always be present. The ICS methods described herein employ correlation function analysis as a filter for white noise. The zero lags amplitude is extrapolated from an autocorrelation function fit since white noise will only correlate at zero lags in a correlation function. The goal of the correlation analysis described herein is to obtain the molecule number/aggregation information from the extrapolated amplitudes of correlation functions.

Accordingly, ICS methods described herein calculate the mean intensity normalized spatial autocorrelation function of fluorescence intensity fluctuations (Eq. 2) of a region of interest (ROI) to obtain molecule number/aggregation information independent of white noise sources.

$$r(\xi, \eta) = \frac{\langle \delta i(x, y)\delta i(x+\xi, y+\eta)\rangle}{\langle i\rangle^2} \tag{2}$$

The orthogonal spatial lag variables $\xi$ and $\eta$ represent discrete pixel shifts in x and y directions in an image at which the spatial correlation is calculated. The zero spatial lags value of the spatial autocorrelation function is the square relative intensity and hence the particle number density. For computational speed, the spatial correlation function is calculated using Fourier methods (Eq. 3), where F is the discrete 2D spatial fast Fourier transform of the ROI, F* is the complex conjugate and $F^{-1}$ is the inverse Fourier transform.

$$r(\xi, \eta) = \frac{F^{-1}[F(i(x, y))F^*(i(x, y))]}{\langle i\rangle^2} - 1 \tag{3}$$

The calculated spatial intensity fluctuation correlation functions are then each fit to a 2D Gaussian (Eq. 4) using a non-linear least-squares algorithm, where the zero lags point is not weighted due to white noise contributions. Output fit parameters are g(0, 0), the zero-lags amplitude, $\omega_0$, the $e^{-2}$ Gaussian correlation radius, and $g_\infty$, the long spatial lag offset.

$$r(\xi, \eta) = g(0, 0)\exp\left[-\frac{\xi^2+\eta^2}{\omega_0^2}\right] + g_\infty \tag{4}$$

The best fit zero lags amplitude of the correlation function is an estimate of the square relative fluctuation from Eq. 1, with an inverse that is the mean number of independent fluorescent particles per focal spot area, $\langle n\rangle$ (Eq. 5). The total number of particles (TNoP) in the ROI can be calculated using the image area and $\omega_0$ (Eq. 6).

$$\langle n\rangle = \frac{1}{g(0, 0)} \tag{5}$$

$$TNoP = \frac{\text{Image Area}}{g(0, 0)\cdot\pi\omega_0^2} \tag{6}$$

When fluorescent molecules undergo clustering/aggregation, the clusters/aggregates are not resolvable using diffraction limited optical microscopy (e.g., confocal microscopy) unless large aggregates are present (such as individually distinguishable foci). However, aggregation manifests in the ROI as larger relative intensity fluctuations from a smaller number of brighter fluorescent particles per focal spot. If the number of overall fluorophores does not change, the mean fluorescent intensity should be constant, but the number of independent fluorescent particles (formed of one or more fluorophores) should decrease after clustering. Since the average intensity of the ROI is proportional to the total number of fluorophores $\langle n_f\rangle$ after background correction and a constant (c) relating intensity to fluorophore count, a degree of aggregation (DA) measurement can be calculated using the average intensity, $\langle i\rangle$, and the mean number of fluorescent particles, $\langle n\rangle$;

$$DA = \frac{\langle i\rangle}{\langle n\rangle} = c\frac{\langle n_f\rangle}{\langle n\rangle} \tag{7}$$

To first order, the degree of aggregation is proportional to the mean number of fluorophores per aggregate if the variance of the aggregate distribution is small.

Controls

Methods described herein involve determining an absence or a presence of a molecular aggregate based on a degree of aggregation (DA) calculated from an ICS image analysis, wherein a deviation of the DA compared to a control value indicates the presence of the molecular aggregate. In some embodiments, the control value is a DA calculated from a control sample. In some embodiments, a control sample is a biological sample that has not been treated (also referred to as an untreated biological sample). In some embodiments, an untreated biological sample comprises a biological sample that has not been treated with a drug or an agent (e.g., a DNA damaging agent such as a chemical treatment such as camptothecin or a radiation treatment such as ionizing radiation). In some embodiments, a control sample is obtained from a healthy tissue in the same subject, or from a different subject or population of healthy subjects. As used herein, a healthy subject is a subject that is apparently free of a disease or disorder at the time the sample is collected.

The control value can also be a predetermined value. The predetermined value or score can be a single cut-off (threshold) value, such as a median or mean, or a level or score that defines the boundaries of an upper or lower quartile, tertile, or other segment of a fluorescent signal that is determined to be statistically different from the other segments. It can be a range of cut-off (or threshold) values, such as a confidence interval. It can be established based upon comparative groups, such as where samples are treated with increasing concentrations of an agent or where presence of aggregation in one defined group is a fold higher, or lower, (e.g., approximately 2-fold, 4-fold, 8-fold, 16-fold or more) than the presence of aggregation in another defined group. It can be a range, for example, where control samples are divided equally (or unequally) into groups, such as a low-DA group, a medium-DA group and a high-DA group, or into quartiles, the lowest quartile being samples with little to no aggregation and the highest quartile being samples with aggregation, or into n-quantiles (i.e., n regularly spaced intervals) the lowest of the n-quantiles being samples with little to no aggregation and the highest of the n-quantiles being samples with aggregation.

In some embodiments, the predetermined level or score is a level or score determined in the same sample, e.g., at a different time point, e.g., an earlier time point, e.g., prior to inducing DNA damage and after inducing DNA damage.

Accordingly, methods described herein include determining if the DA falls above or below a predetermined cut-off value. Appropriate ranges and categories can be selected with no more than routine experimentation by those of ordinary skill in the art.

EXAMPLES

In order that the invention described may be more fully understood, the following examples are provided. The example described in this application is offered to illustrate the systems and methods provided herein and is not to be construed in any way as limiting.

Example 1: Measuring Protein Recruitment in Response to DNA Damage Using Image Correlation Spectroscopy (ICS)

This Example describes quantifying the local clustering at sites of DNA damage directly by performing image correlation spectroscopy (ICS). The results described herein demonstrate that autocorrelation image analysis can quantify protein accumulation and dissolution of accumulated proteins that do not produce visibly resolvable foci.

Quantifying DDR Protein Recruitment

Experimental Details: Cells were treated with drug for 24 hours then fixed with 4% PFA and the protein of interest was labelled using immunofluorescence according to the antibody manufacturers protocol. Cells were then imaged on a fluorescence microscope with a 20× objective and single cell image autocorrelation analysis was performed on segmented nuclei. Average degree of aggregation of single cells was then calculated and plotted as a function of drug dose.

Figure 2A:
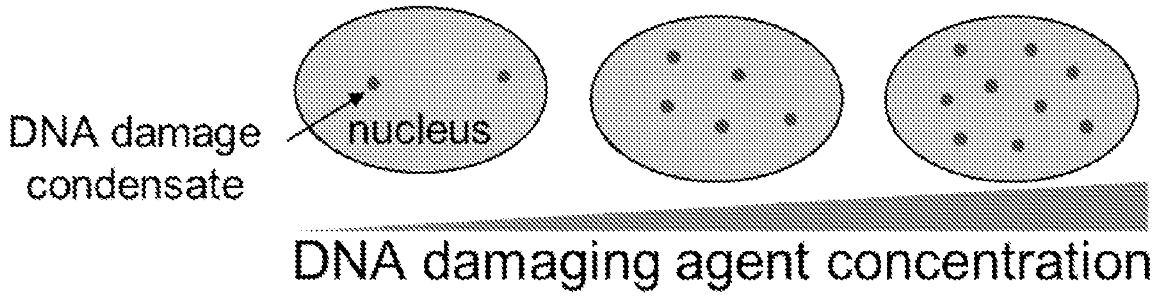
FIGS. 2A-2D: Quantifying DDR protein recruitment.
Figure 2B:
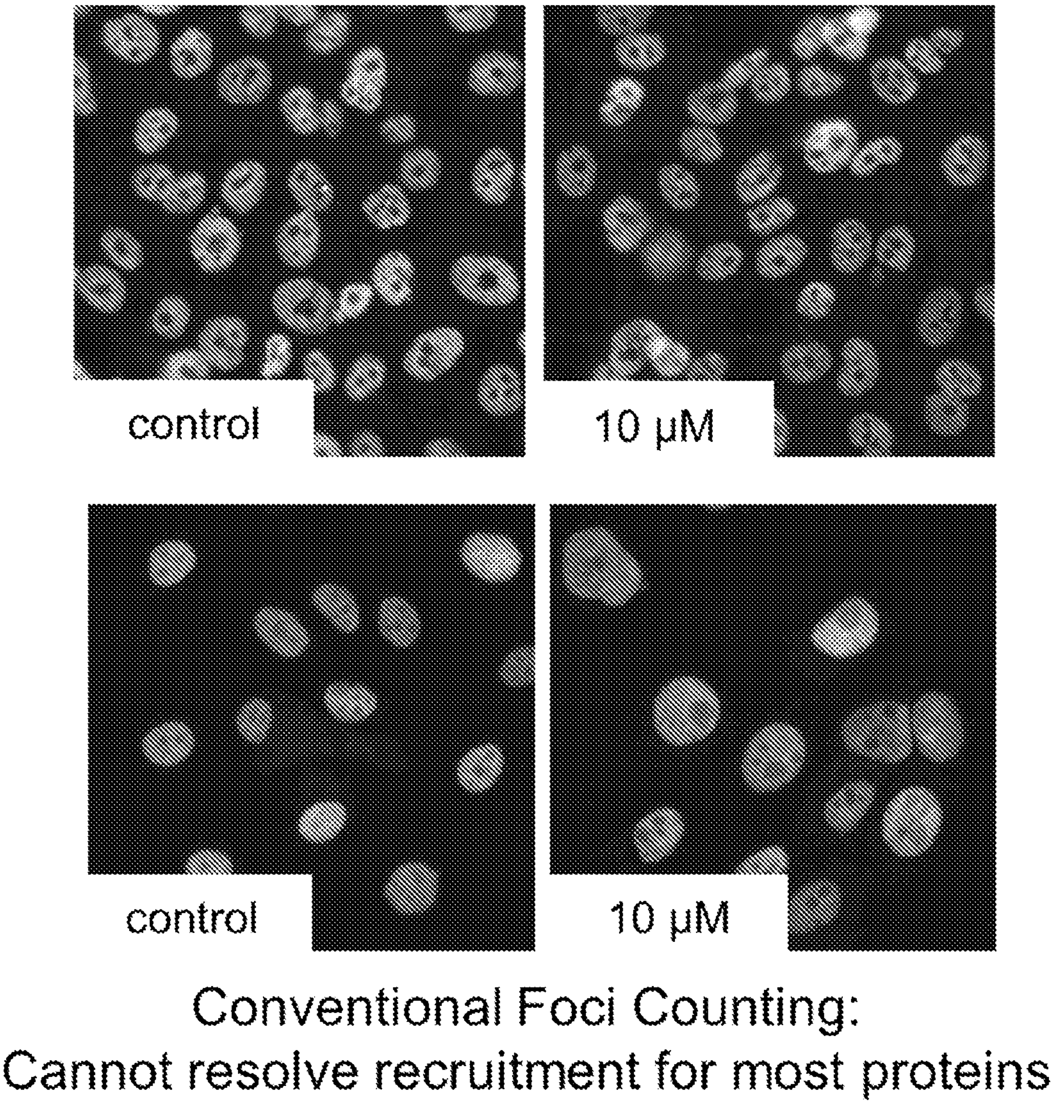

Results: A schematic depiction of experiments performed at multiple DNA damaging agent concentrations is shown in FIG. 2A. Higher concentrations of DNA damaging agent will induced more DNA damage and allowed recruitment patterns to be quantified and statistically tested. Most DDR proteins do not produce resolvable recruitment to sites of DNA damage. For example, as shown in FIG. 2B, resolvable foci are absent in representative IF images of, left, APLF in HCC1395 cells treated with control or 10 μM olaparib, and right, KU80 in UWB cells treated with control or 10 μM olaparib.

Figure 2C:
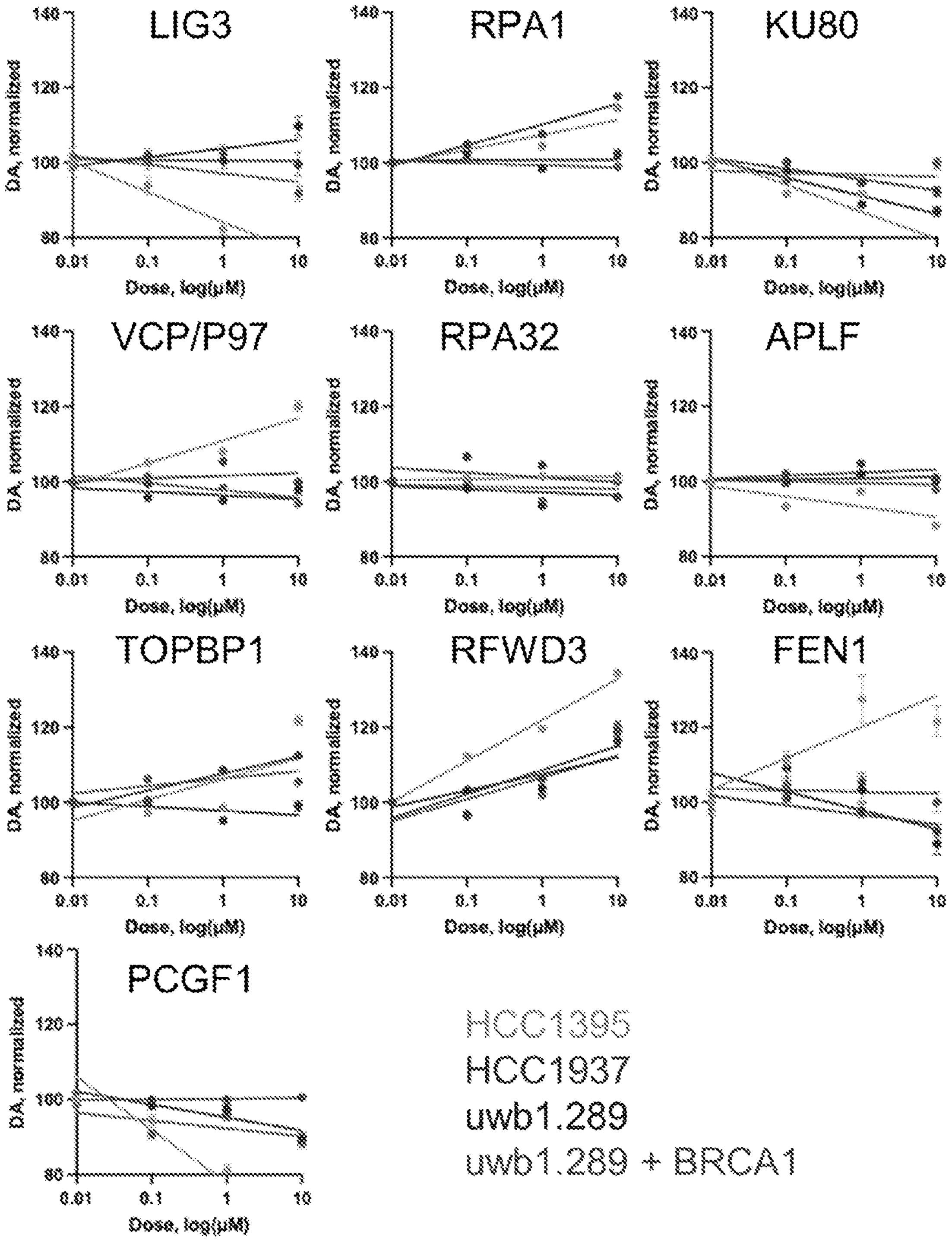

By contrast, as shown in FIG. 2C, ICS methods described herein were able to detect recruitment of 10 different DDR proteins in response to the PARP inhibitor olaparib in 4 cell lines. DA values were normalized to 10 nM dose for comparison. Cell line data color are consistent for each DDR protein. Shown are single cell average with SEM (n>2124 cells per condition over 8 experiments).

Figure 2D:
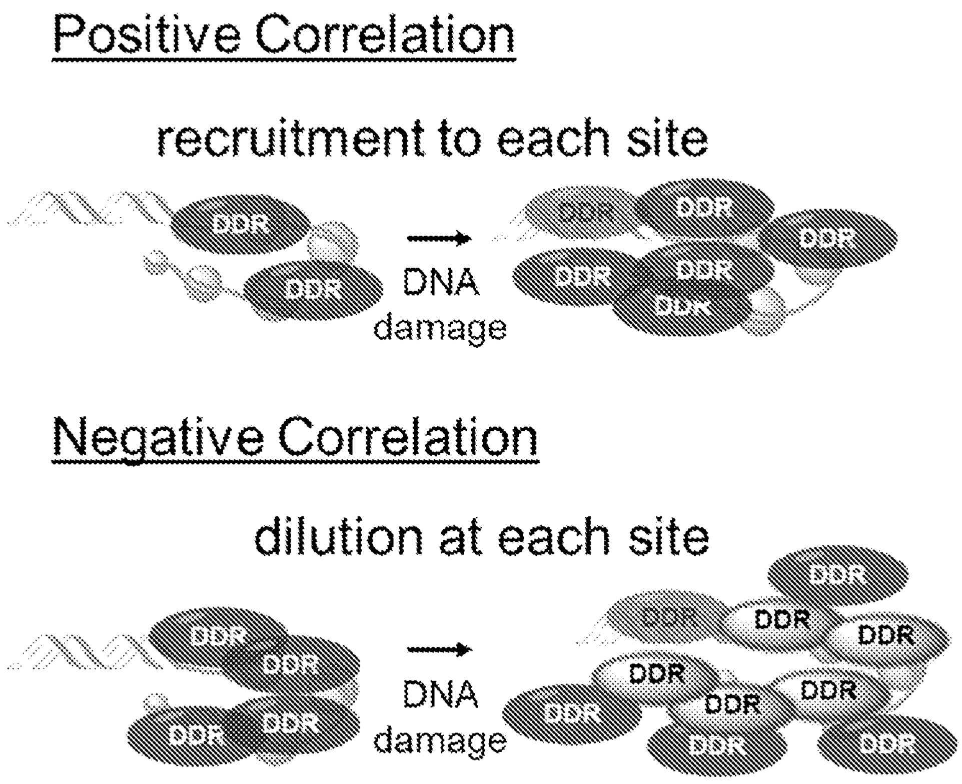

The recruitment patterns of these DDR proteins as a function of olaparib dose demonstrated the underlying recruitment processes driving ICS DA measurement. As schematically illustrated in FIG. 2D, positive correlations indicate that DDR protein being measured (gray) is recruited to sites of DNA damage. Negative correlations indicate that the DDR protein being measured (gray) is dispersed upon DNA damage, which can arise from recruitment of other DDR proteins (light gray) (FIG. 2D).

Taken together, the results described herein demonstrate that autocorrelation image analysis is able to quantify protein recruitment and accumulation or dissolution of accumulated proteins of numerous proteins that do not produce visibly resolvable clustering. These results also suggest that different cell lines have different protein recruitment patterns to drug treatment that may impact the cellular sensitivity to treatment.

Cluster Colocalization of SUMO2/3 With DDR Proteins

Experimental Details: Cells were treated with drug for 24 hours then fixed with 4% PFA and the protein of interest was labelled using immunofluorescence according to the antibody manufacturers protocol. Cells were then imaged on a fluorescence microscope with a 20× objective and single cell image autocorrelation analysis was performed on segmented nuclei. Average degree of aggregation of single cells was then calculated and plotted as a function of drug dose. Cell line coloring remains the same in FIGS. 3C-3E, single cell average with SEM (n>1943 cells over 8 experiments) and linear fit are shown.

Figure 3A:
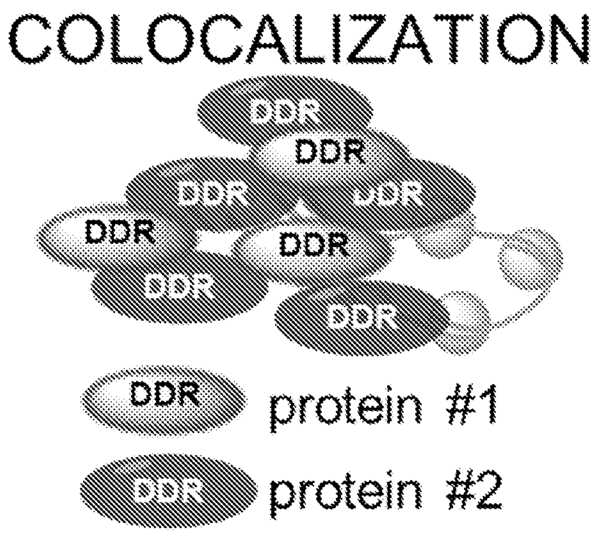
FIGS. 3A-3G: Cluster colocalization of SUMO2/3 with DDR proteins.
Figure 3B:
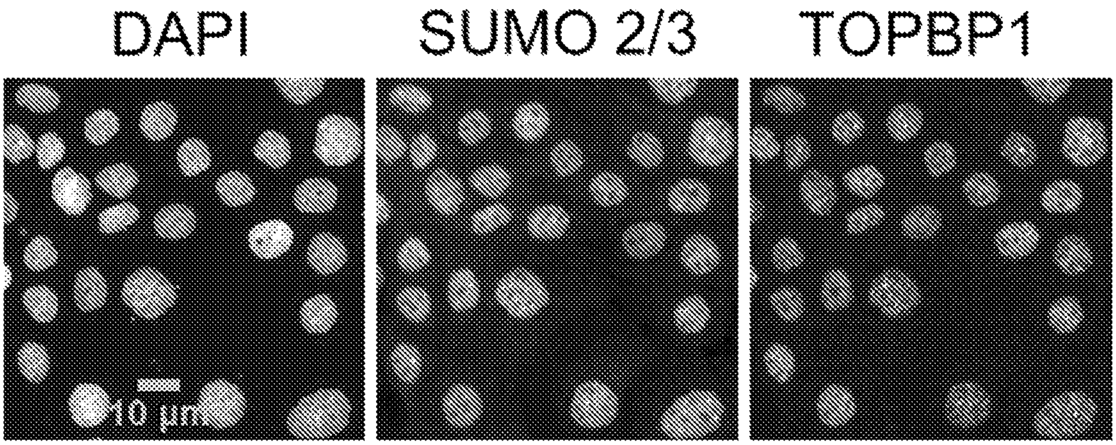
Figure 3C:
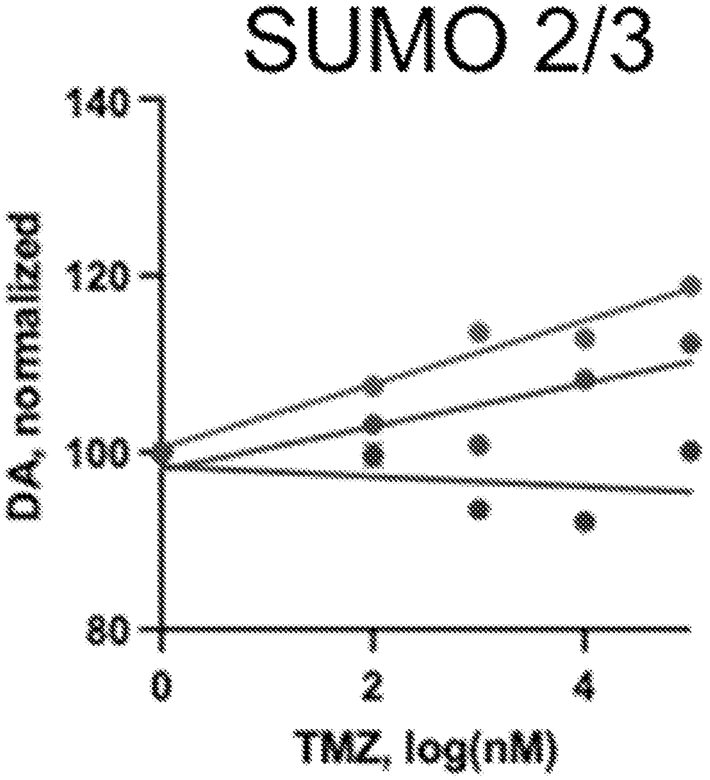

Results: As schematically depicted in FIG. 3A, ICS autocorrelation can directly quantify cluster colocalization of two proteins to determine the degree of co-recruitment to DNA damage. HCC1937 cells were labeled with DAPI to identify the nucleus for segmentation and immuno-labelled for SUMO 2/3 and TOPBP1 using two different fluorophores for simultaneous imaging (FIG. 3B). SUMO-2/3 recruitment to DNA damage was dependent on the temozolomide (TMZ) dose for three different cell lines (FIG. 3C).

Figure 3D:
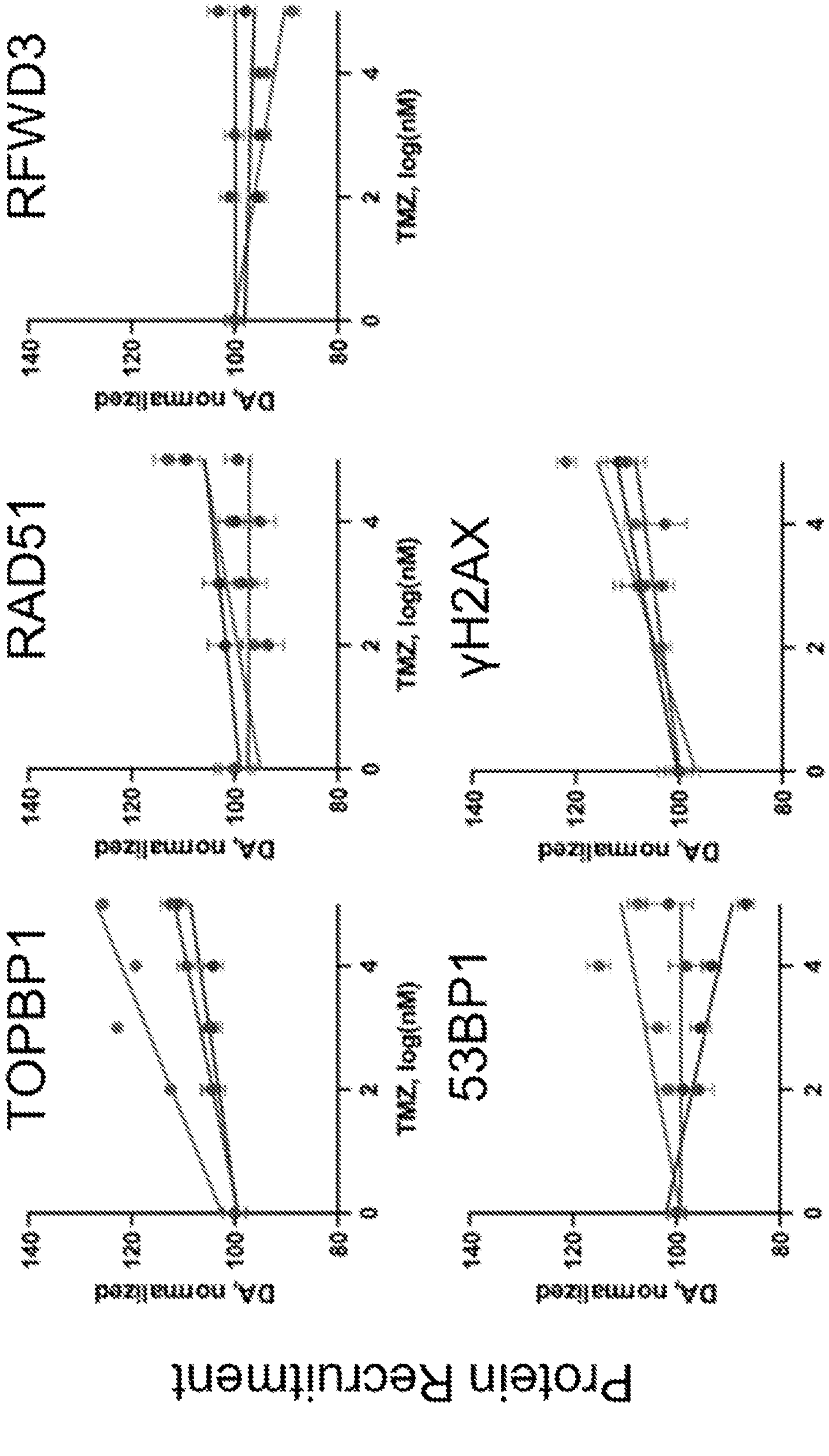
Figure 3E:
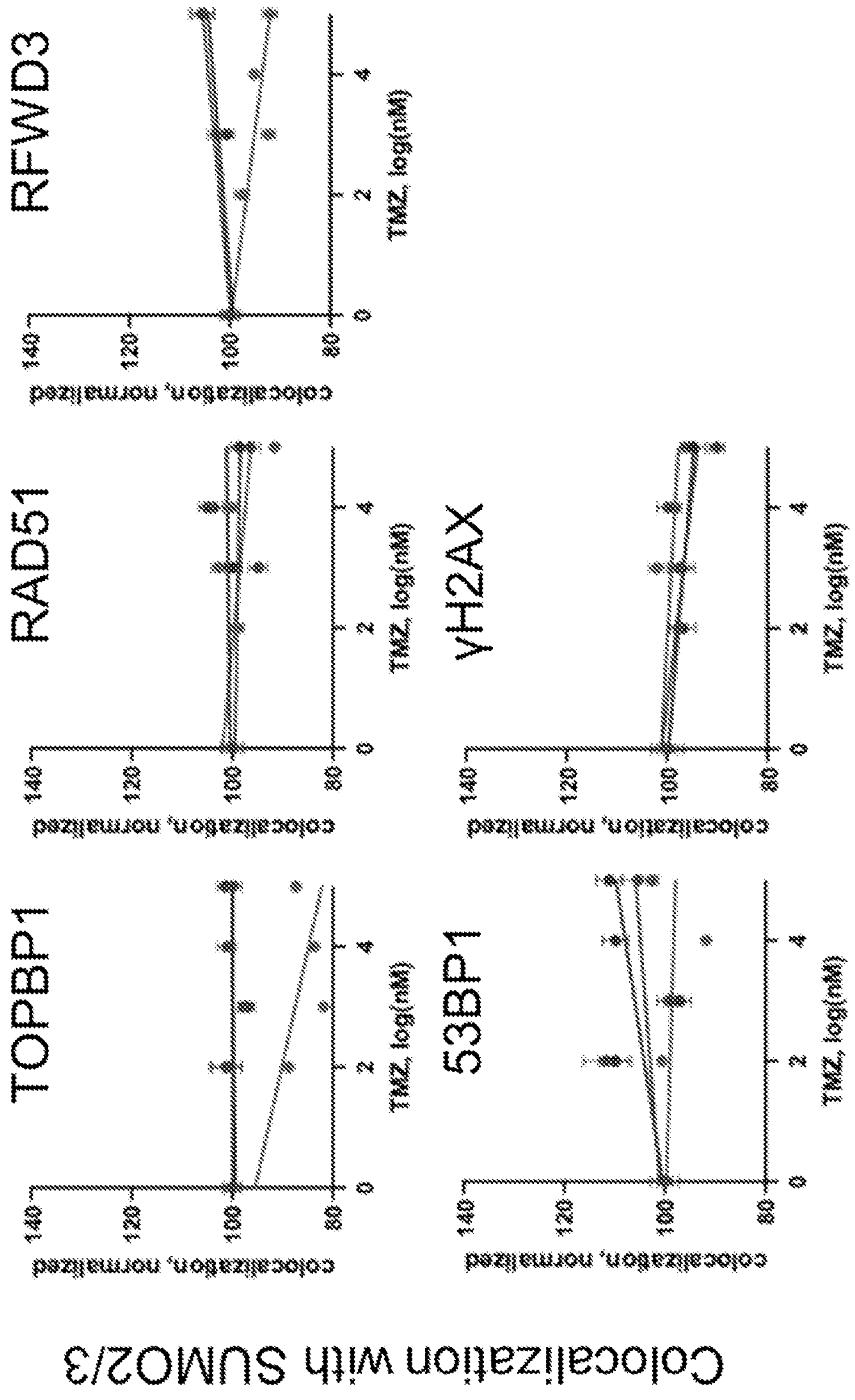
Figure 3F:
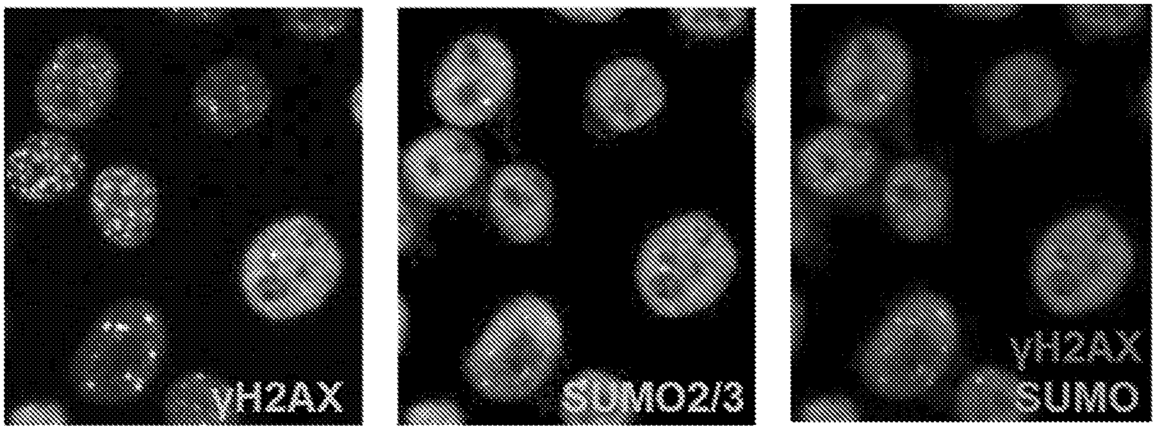

Recruitment of 5 different proteins to TMZ induced DNA damage was measured (FIG. 3D). Cluster colocalization of each protein with SUMO-2/3 was dependent on TMZ induced DNA damage (FIG. 3E). Cluster colocalization of γH2AX and SUMO-2/3 is not observable in representative images of UWB1.289 cells labeled for γH2AX and SUMO-2/3 (FIG. 3F).

Figure 3G:
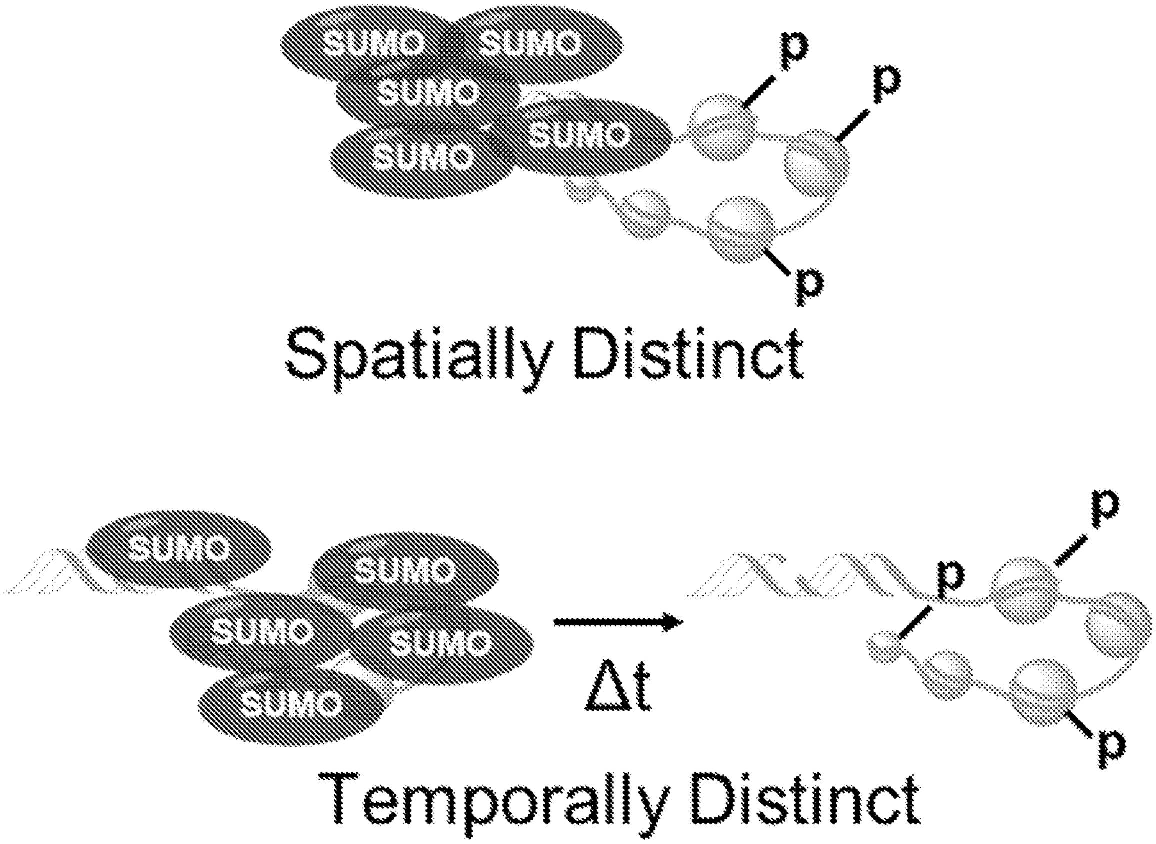

As schematically illustrated in FIG. 3G, differences in cluster colocalization can arise from recruitment into different spaces or recruitment at different times. Anti-correlation of SUMO and phosphorylated γH2AX can be caused by either separation at the site of DNA damage or recruitment at different time points. As shown in FIG. 3G, differences in cluster colocalization can arise if SUMO is recruited and dissipates before H2AX is phosphorylated.

Taken together, the results described herein demonstrate that cross correlation analysis of two fluorescently labeled proteins in a single image determined the degree of colocalization of the two proteins as a function of drug treatment. Different cellular response to drug treatment suggests that recruitment patterns impact the cellular sensitivity to drugs.

Imaging with Low and High Magnification Objectives

Experimental Details: HCC1937 cells were plated into 384 well plates at 3,000 cells/well and allowed to adhere overnight. Drug or DMSO control was added to each well and cells were incubated for 24 hours. Cells were then fixed in 4% PFA, and labeled for immunofluorescence imaging for γH2AX and PCNA according to the antibody manufacturers instructions (cell signaling #9718 and #2586). Wells (6-8/condition) were imaged in a Nikon widefield microscope using either a 20× or 60× oil immersion objective. Autocorrelation analysis was then performed and the average single cell degree of aggregation calculated for each condition. Plotted are average value with SEM.

Figure 4A:
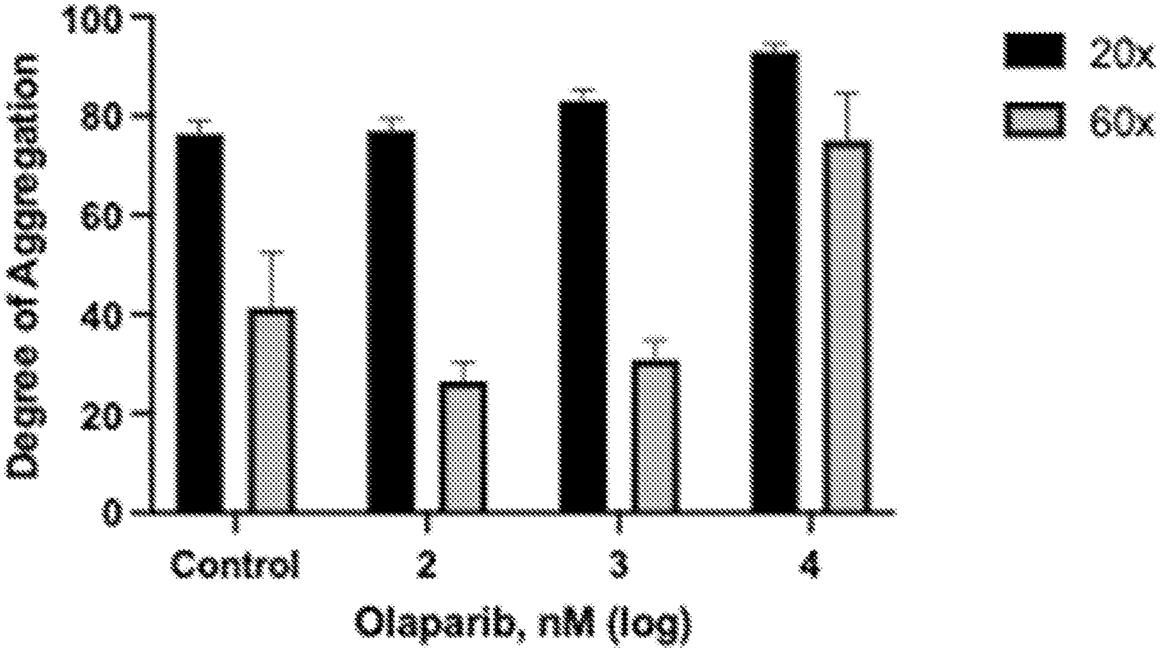
FIGS. 4A-4B: Graphs showing degree of aggregation for γH2AX (FIG. 4A) and PCNA (FIG. 4B) calculated from cells imaged in a Nikon widefield microscope using either a 20× or 60× oil immersion objective.
Figure 4B:
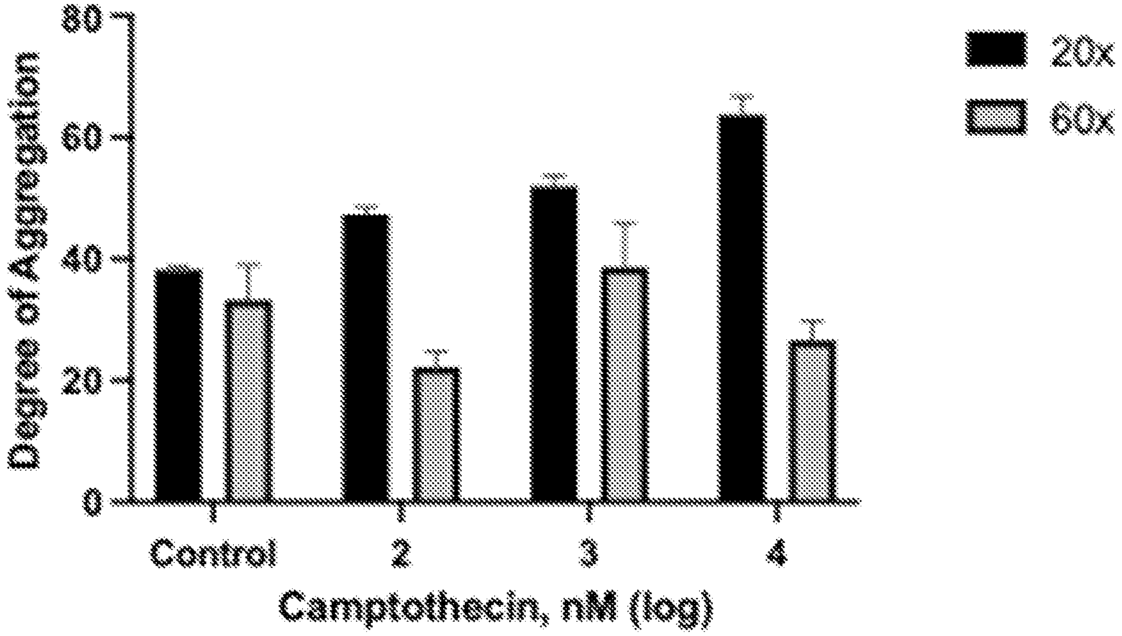

Results: Olaparib induces an accumulation of DNA damage and double strand breaks, driving increased γH2AX clustering in foci. Camptothecin damages DNA and induces cell cycle arrest in S phase, resulting in increased PCNA accumulation on DNA and at damaged sites. For both γH2AX and PCNA, ICS analysis of images acquired using an example of a low magnification objective (20×) provided a more accurate measurement of the expected impact of drug treatment on γH2AX (FIG. 4A) and PCNA (FIG. 4B) accumulation into DNA damage response foci than ICS analysis of images acquired using an example of a high magnification objective (60×). These results demonstrate that imaging at 20× provided the ability to measure γH2AX and PCNA recruitment into DNA damage foci despite a lack of dimer formation or tight associations between γH2AX and PCNA.

Example 2: Deciphering DNA Damage Using Fluorescence Fluctuations: Don't Count, Correlate This Example describes quantifying the local clustering at sites of DNA damage directly by performing image correlation spectroscopy (ICS). The results described herein demonstrate that ICS calculated degree of aggregation (DA) provided a more reliable measure of dose dependent DNA damage analyzed by imaging antibody labeled γH2AX than spot detection. Furthermore, the measured DA was able to capture the dose dependent clustering of two proteins that do not form resolvable foci, RPA1 and RAD51.

Materials and Methods

Models

Figure 6A:
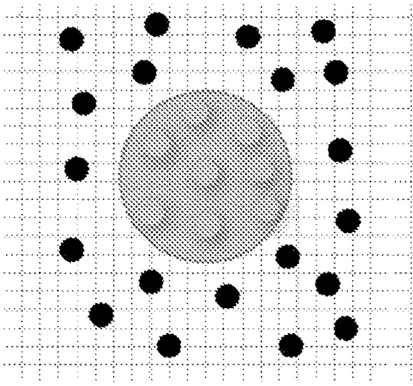
FIGS. 6A-6F: Counting foci using image correlation spectroscopy correlates with optimized measurements using existing approaches.
Figure 6B:
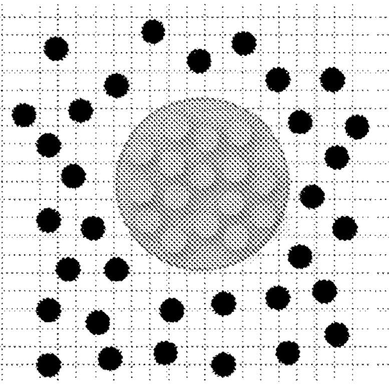

Image correlation spectroscopy is based on the analysis of fluorescence intensity fluctuations arising from variations in the number of fluorescent particles within focal spots imaged in space and/or time using a fluorescence microscope. Under the assumptions of particle ideality and linear fluorescence emission (i.e., no signal saturation or energy transfer), the detected mean fluorescence intensity of tagged molecules varies linearly with the concentration of fluorophores in a focal spot (FIGS. 6A-6B). The square relative intensity fluctuation (intensity variance/mean intensity, Eq. 1) will be the mean number of detected independent fluorescent particles per focal spot, since ideal behavior entails that the molecules obey Poisson statistics within the volume:

$$\frac{\langle(\delta i)^2\rangle}{\langle i\rangle^2} = \frac{1}{\langle n\rangle} \tag{1}$$

given intensity fluctuations defined as $\delta i = i - \langle i \rangle$, where $\langle i \rangle$ is the mean intensity and $\langle n \rangle$ is the mean number of independent fluorescent particles per focal spot area.

To obtain this number density information independent of white noise sources (such as shot noise), ICS calculates the mean intensity normalized spatial autocorrelation function of fluorescence intensity fluctuations (Eq. 2) of a region of interest (ROI). The orthogonal spatial lag variables $\xi$ and $\eta$ represent discrete pixel shifts in x and y directions in an image at which the spatial correlation is calculated. The zero spatial lags value of the spatial autocorrelation function is the square relative intensity and hence the particle number density.

$$r(\xi,\eta) = \frac{\langle \delta i(x,y)\delta i(x+\xi, y+\eta)\rangle}{\langle i\rangle^2} \tag{2}$$

For computational speed, the spatial correlation function is calculated using Fourier methods (Eq. 3)[28], where F is the discrete 2D spatial fast Fourier transform of the ROI, F* is the complex conjugate and $F^{-1}$ is the inverse Fourier transform.

$$r(\xi,\eta) = \frac{F^{-1}[F(i(x,y))F^*(i(x,y))]}{\langle i\rangle^2} - 1 \tag{3}$$

The calculated spatial intensity fluctuation correlation functions are then each fit to a 2D Gaussian (Eq. 4) using a non-linear least-squares algorithm, where the zero lags point is not weighted due to white noise contributions. Output fit parameters are g(0, 0), the zero-lags amplitude, $\omega_0$, the $e^{-2}$ Gaussian correlation radius, and $g_\infty$, the long spatial lag offset.

$$r(\xi,\eta) = g(0,0)\exp\left[-\frac{\xi^2+\eta^2}{\omega_0^2}\right] + g_\infty \tag{4}$$

The best fit zero lags amplitude of the correlation function is an estimate of the square relative fluctuation from Eq. 1, with an inverse that is the mean number of independent fluorescent particles per focal spot area, $\langle n \rangle$ (Eq. 5). The total number of particles (TNoP) in the ROI can be calculated using the image area and wo (Eq. 6).

$$\langle n \rangle = \frac{1}{g(0, 0)} \quad (5)$$

$$TNoP = \frac{\text{Image Area}}{g(0, 0) \cdot \pi\omega_0^2} \quad (6)$$

Figure 6C:
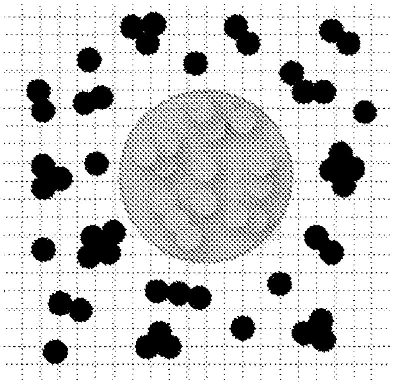

When fluorescent molecules undergo aggregation or clustering, the clusters/aggregates are not resolvable using diffraction limited optical microscopy (i.e., confocal) unless large aggregates are present (such as individually distinguishable foci). However, aggregation manifests in the ROI as larger relative intensity fluctuations from a smaller number of brighter fluorescent particles per focal spot. If the number of overall fluorophores does not change, the mean fluorescent intensity should be constant, but the number of independent fluorescent particles (formed of one or more fluorophores) should decrease after clustering (FIGS. 6B-6C). Since the average intensity of the ROI is proportional to the total number of fluorophores $\langle n_f \rangle$ after background correction and a constant (c) relating intensity to fluorophore count, a degree of aggregation (DA) measurement can be calculated using the average intensity, $\langle i \rangle$, and the mean number of fluorescent particles, $\langle n \rangle$;

$$DA = \frac{\langle i \rangle}{\langle n \rangle} = c\frac{\langle n_f \rangle}{\langle n \rangle} \quad (7)$$

To first order, the degree of aggregation is proportional to the mean number of fluorophores per aggregate if the variance of the aggregate distribution is small[29].

Image Analysis

For the ICS analysis, nuclei were segmented from the DAPI channel using a watershed approach in MATLAB. Briefly, we applied a difference of gaussians for size-based feature extraction of nuclei in the image (upper gaussian $\sigma$=100, lower gaussian $\sigma$=2-5 dependent on cell size). This feature enhanced image was then binarized to create a primary mask (using the function imbinarize) and connected components under 100 pixels were removed (using the function bwareaopen). We then created a distance transform of the resulting binary image (using the function bwdist). Seed points were determined by finding the regional maximum of a gaussian filtered image, with a gaussian $\sigma$ of appropriate size for seed point detection ($\sigma$×7 or 8 dependent on cell size). The seed points were applied to the distance transform, and we applied the watershed function to the resulting image to obtain masks for each nucleus (extracted using the function regionprops).

Using the nucleus masks, we performed ICS analysis on the antibody-stained channel, within size limitations for a nucleus (objects >400 and <2400 pixels). Intensity, DA and TNOP were calculated for each cell. In this analysis, since the ROI is defined by the nucleus mask (segmented from nuclear signal using DAPI staining), TNoP represents the total number of particles per nucleus, with the image area being the number of pixels in each nuclear mask.

Measurements across experiments were normalized by the control in each dataset. The confocal imaging settings were kept the same across each dataset to provide comparable measurements per dataset. Data were plotted in Prism and statistical analysis was performed in Excel.

Local maxima were used to count foci in ImageJ/FIJI, using the tool Find Maxima under the Process menu[30]. This tool requires a threshold input parameter (Prominence/Tolerance), where a threshold is set at the maximum value minus noise tolerance and local maxima must be greater than this threshold to be counted. To compare the effect of the input parameter, we performed measurements at Tolerance=300 and 600. The final measurement was taken at the user-defined threshold where the user visually inspected different Tolerance values and chose a value that visually removed background (thresholds between 300 and 600)—a subjective process.

Imaris spots analysis were performed with Imaris 9.8 with background subtraction, using a spot size of 1 μm that was measured from the smallest distinguishable foci from the control image. For images with multiple nuclei, ImarisCell was used with the detection type "cell and vesicles", where the nucleus in the DAPI channel was modelled as the "cell" and antibody-labeled foci were modelled as the "vesicles". This enabled us to count the number of foci per nucleus for multiple cells. In each dataset, the automatic "quality" threshold was determined from the control image and the same threshold was used for every image in the dataset to be able to compare the outputs across datasets. Similar to the ICS analysis, only cells with an area between 400-2400 voxels were included for analysis.

Materials and Cell Culture

All chemicals were purchased from Sigma unless otherwise noted. All drugs were purchased from Selleck Chemicals. Cells were cultured in media supplemented with 10% fetal bovine serum and 1% penicillin/streptomycin. OVCA429 were originally obtained from Dr. Michael Birrer and cultured in DMEM. SKOV3 was obtained from ATCC and cultured in RPMI. For MMS treatment, cells were incubated for 6 hours before fixation with 4% formaldehyde, whereas for treatment with PARP inhibitors, cells were incubated for 24 hours before fixation.

Cell Dose Dependence Response

Cells were plated in a 96-well plate at $2\times10^3$ cells per well and treated with drug for 5 days in five replicate wells. Cell viability was then determined using Presto Blue (Thermo Fisher). Signal was averaged over replicate wells and normalized to blank (no cells) as well as to the levels of untreated wells. A sigmoidal response curve was fit to the average of two experiments in Prism.

Immunofluorescence and Fluorescence Microscopy

Cells were plated in 8-well slides (Fisher) to achieve 50% confluence overnight. Cells were then treated and fixed with 4% formaldehyde in PBS at room temperature for 10 minutes. Antibody staining was performed according to the manufacturers protocol (Cell Signaling Technologies or Abcam). Primary antibodies used were γH2AX (CST, #2577), RPA1 (CST, #2267) and RAD51 (Abcam, 63801), with Anti-rabbit IgG Fab2 Alexa Fluor 647 (CST, #4414) as the secondary fluorescent antibody. After antibody labeling, prolong gold with DAPI (CST) was added and samples were stored for up to 1 week prior to imaging. Confocal imaging was performed on an Olympus FV1000 multiphoton/confocal microscope using an Olympus XLUMPlanFL N 20× objective, NA 1.00 with chromatic correction, and 3× digital zoom. DAPI was excited with a 405 nm laser, while Alexa Fluor 647 was excited with a 635 nm laser. A multiband (DM 405/488/561/633 nm) dichroic mirror was used to direct the excitation laser and collect emission. Emission was then separated into two channels through a dichroic mirror (490 nm) and DAPI signal was cleaned up by diffraction grating according to the microscope settings.

Results

Counting Foci Via Fluctuation Analysis

Figure 5A:
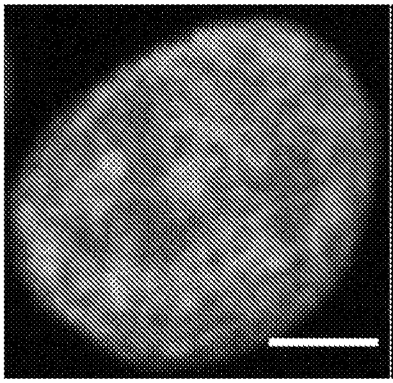
FIGS. 5A-5I: Common approaches to count DNA damage foci.
Figure 5B:
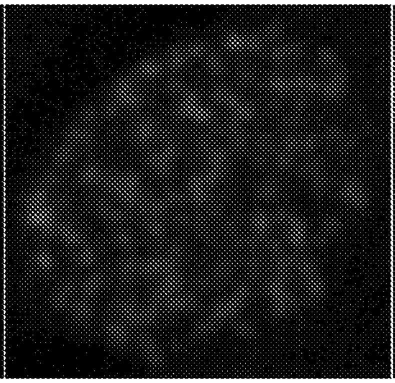
Figure 5C:
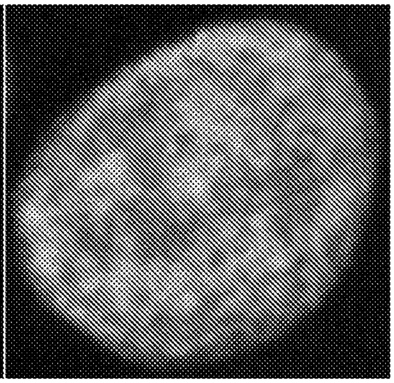
Figure 5D:
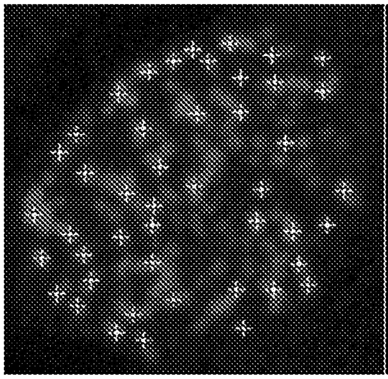
Figure 5E:
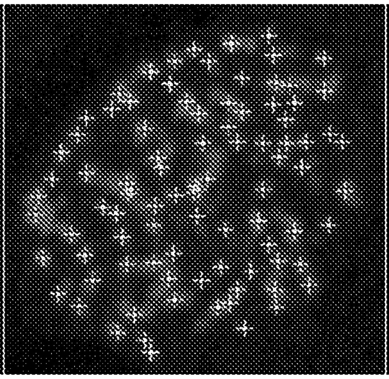

Most foci counting methods are based on finding the local fluorescence intensity maxima either through intensity thresholding to create masks of high intensity single foci or implementing local maxima finding algorithms. Here, we evaluated traditional local maxima finding algorithms on the ovarian cancer cell line SKOV3 by creating resolvable DNA damage with the PARP inhibitor olaparib (10 μM) and antibody-labeling γH2AX to visualize foci (FIG. 5B). To enable clean isolation of nuclei, the cells were also labeled with DAPI (FIG. 5A). First, we used the Find Maxima tool in ImageJ/FIJI which detects local maxima to define individual foci. However, this approach relies heavily on the intensity threshold parameter (Prominence/Tolerance) used to remove the background signal. This parameter is defined by the user and is highly subjective-set too high might cause some foci to be omitted from the count, yet, conversely, set too low might lead to background signal being counted as foci. Therefore, we evaluated images at 2 different intensity thresholds (FIGS. 5D-5E) in 21 single cells to determine the ambiguity of the threshold parameter (FIG. 5G) before manually determining a threshold for each cell for the final measurement (FIG. 5H).

Figure 5F:
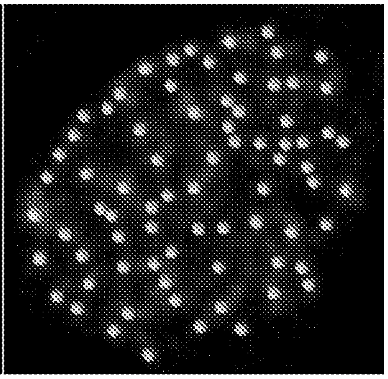
Figure 5G:
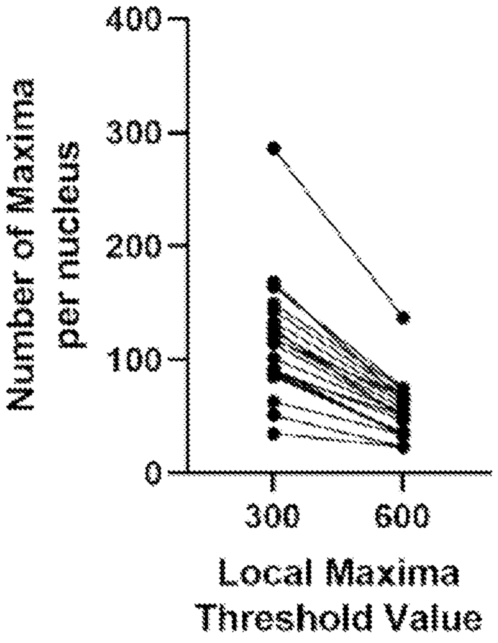
Figure 5H:
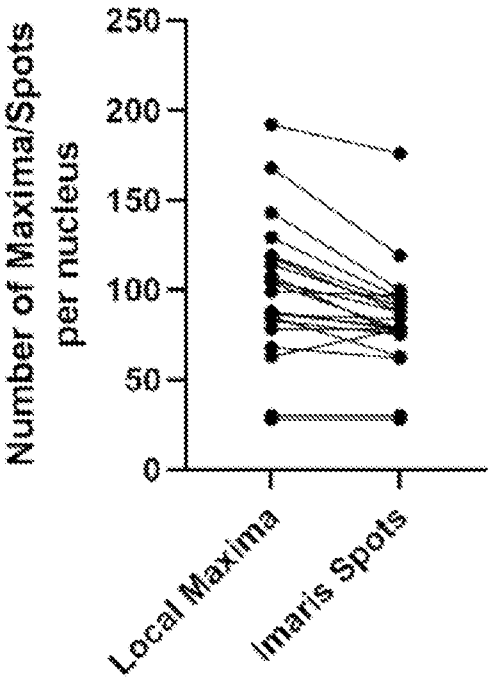
Figure 5I:
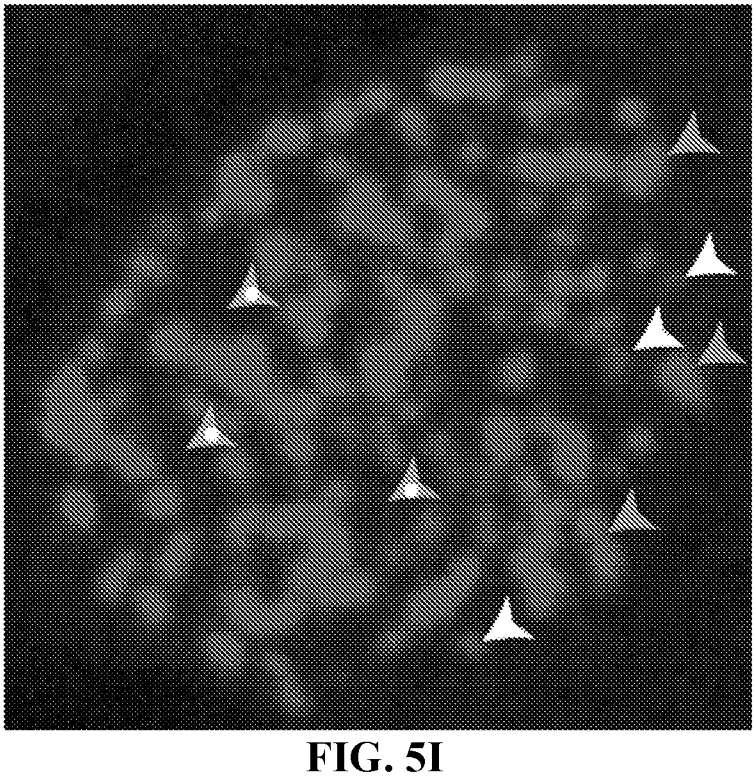

In addition, we implemented a different local maximum finding algorithm with automatic thresholding using Imaris Spots detection (FIG. 5F). Spots detection uses a filter to smooth the image (either a Gaussian or Mexican Hat filter), and foci are then located at the local maxima of the filtered image. The Mexican Hat filter is used when the "Background Subtraction" option is used during spot creation, otherwise the Gaussian filter is the default. The automatic threshold uses a "Quality" filter type, which is the intensity at the center of the filtered spot, where the initial threshold is calculated from all spots based on a k-means statistical method. Spots also allows the user to set the expected detection spot size. This correlative ability to use spot size in foci detection enables detection of multiple spots in a large foci cluster where individual foci are indistinguishable and could be classified as single foci with local maxima detection. Our results produce foci counts that are dependent on the approach used and setting implemented. In our analysis, different thresholds/algorithms give different counts for the same cell due to different intensity foci (white arrows, FIG. 5I), different size foci (gray arrows, FIG. 5I) and non-uniform background intensities (gray arrows with white dots, FIG. 5I).

Figure 6D:
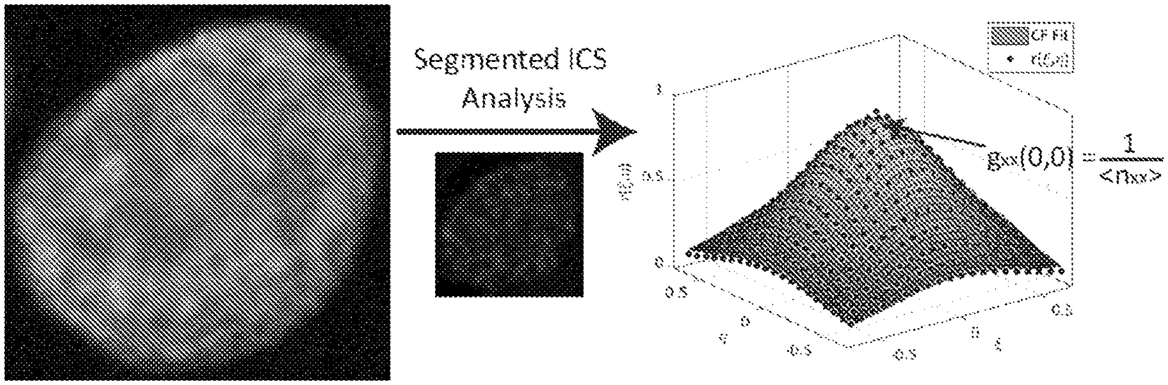
Figure 6E:
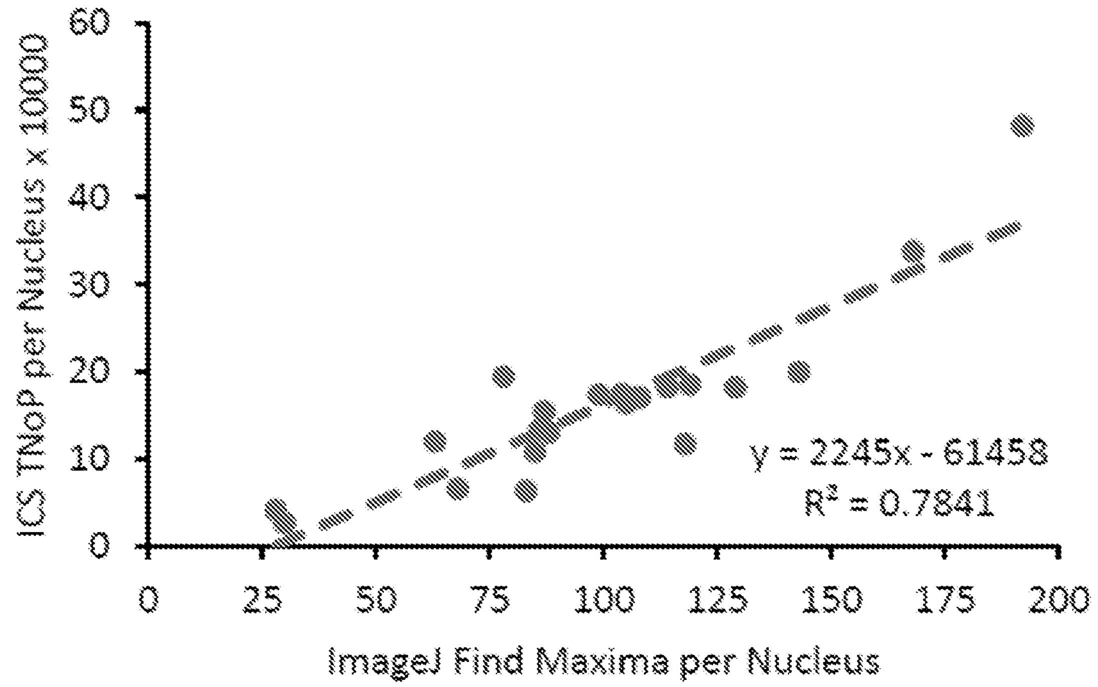
Figure 6F:
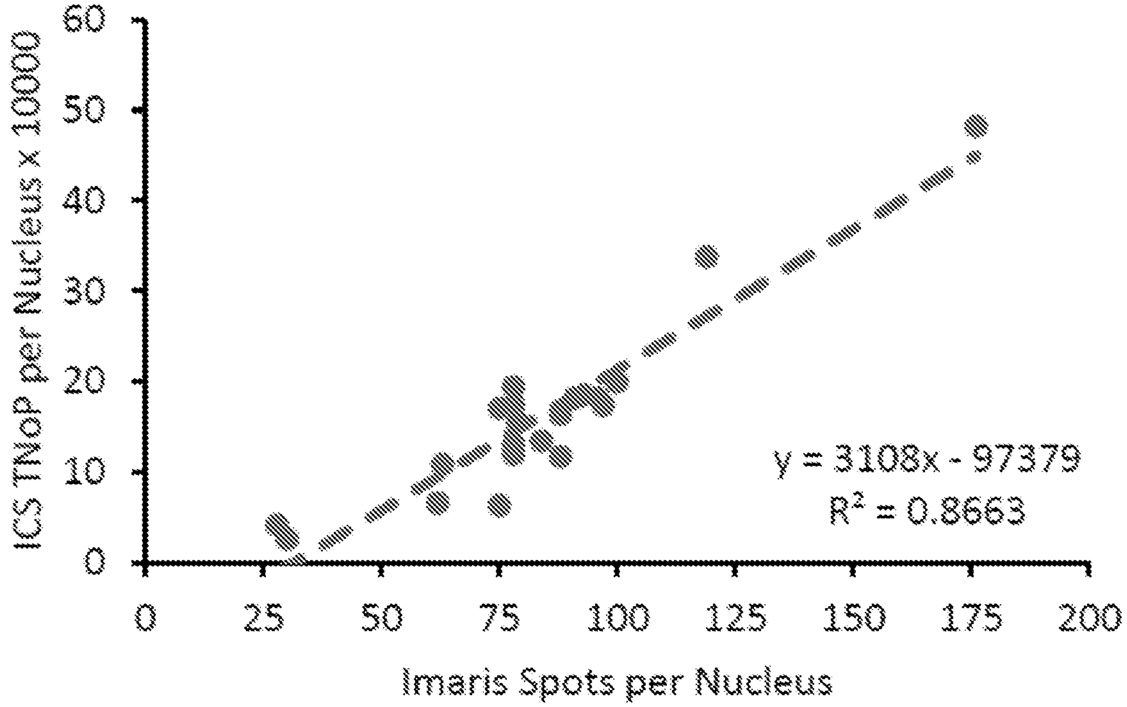

We next employed fluctuation analysis via spatial ICS in the same set of images to analyze the entire dynamic range of detected fluorescence (FIGS. 6A-6C), not just intensity peaks that could be found with local maxima algorithms. Here, the analysis operates on the distribution of the entire fluorescence signal within a region of interest (ROI). We defined each ROI by segmenting nuclei using an automatic threshold in the DAPI channel and performed ICS analysis for each individual nucleus (FIG. 6D). We then calculated the total number of particles (TNOP) parameter per nucleus for comparison to foci counting data from ImageJ/FIJI and Imaris. Direct, cell by cell comparison of ICS TNOP with both the user-optimized threshold ImageJ Find Maxima (FIG. 6E) and Imaris Spots (FIG. 6F) foci counting results produced a strong correlation. Here, ICS is determining the total number of independent particles in the ROI, leading to a TNoP value that is not directly counting resolvable foci.

Particle Counting Versus Aggregation in γH2AX Signal

The main goal of foci counting in cells is to determine the degree of DNA damage. Therefore, after validating our foci counting methods at the individual cell level, we sought to evaluate ICS as a tool to quantify the DDR response in bulk populations of cells. We first treated SKOV3 cells with varying concentrations of methyl methane-sulfonate (MMS) or the PARP inhibitors veliparib or olaparib and evaluated DNA damage through immunofluorescence of γH2AX. MMS is a DNA alkylating agent that directly damages DNA by modifying guanine and adenine to instigate mispairing of bases and replication blocks[31]. PARP inhibitors, however, do not necessarily directly induce DNA damage, but stall the DNA damage response by "trapping" PARP1 and preventing recruitment of critical DNA damage response proteins[23,32-34]. Therefore, these two drug classes should have different impacts on foci formation and foci composition.

Figures 7A, 7B, 7C:
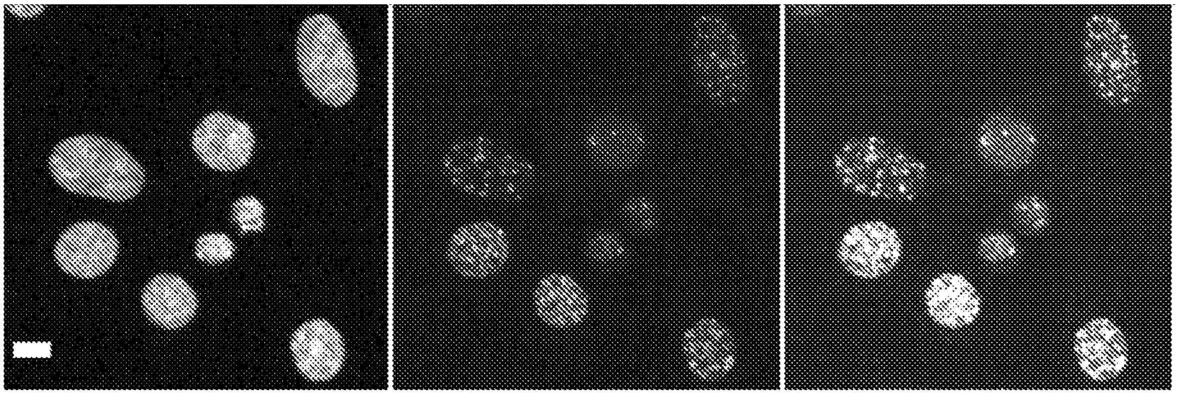

MMS treatment produces a wide range of γH2AX intensity and visible foci across individual cells (FIGS. 7A-7C; 0.1 mM MMS). Thus, analysis capable of detecting both low intensity foci and overlapping, highly abundant foci within a single experiment is needed for accurate measurements over a range of conditions. In the non-contrast adjusted γH2AX image (FIG. 7B), brighter γH2AX foci are clearly distinguishable, however once the image is contrast adjusted (FIG. 7C), lower intensity foci are apparent and the higher intensity foci appear as large foci clusters, especially in nuclei demonstrating more DNA damage. To overcome the inherent distribution of DNA damage across cells, we scaled up the analysis to examine hundreds of cells per image by acquiring large, stitched images. Here, due to the dependency of selecting the proper background intensity per cell, we omitted the ImageJ Find Maxima analysis and analyzed data using ICS and Imaris Spots. To directly compare analyses, each measurement within an experiment was normalized to the untreated control cells.

Figure 7D:
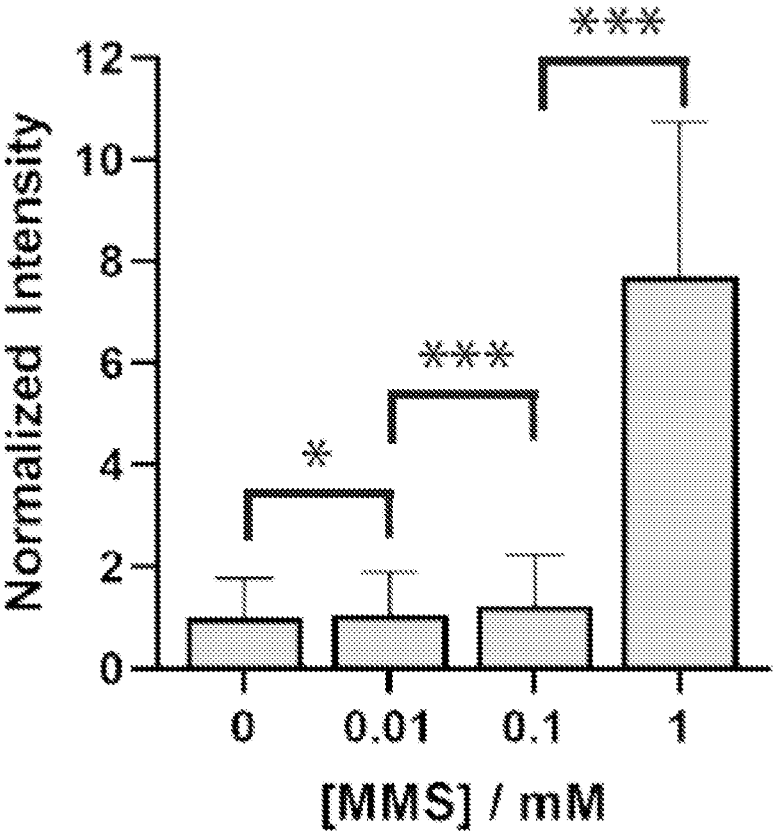
(FIG. 7D, FIG. 7H, and FIG. 7L) Normalized γH2AX Intensity, (FIG. 7E, FIG. 7I, and FIG. 7M) Normalized Imaris Spots analysis on γH2AX, (FIG. 7F, FIG. 7J, and FIG. 7N) Normalized ICS total number of particles per nuclei (TNOP) and (FIG. 7G, FIG. 7K, and FIG. 7O) Normalized ICS degree of aggregation (DA) of γH2AX signal across different MMS (FIGS. 7D-7G), veliparib (FIGS. 7H-7K) and olaparib (FIGS. 7L-7O) in SKOV3 cells. Results are pooled from 3 independent experiments where each set of concentrations were normalized to the relevant control. MMS; N=2423-3160, veliparib; N=1818-2922, olaparib; N=1489-2956. * indicates $p<0.05$,  indicates $p<0.001$, * indicates $p<1\times10^{-10}$ via one-way ANOVA significance testing. Error bars are standard deviations.
Figure 7E:
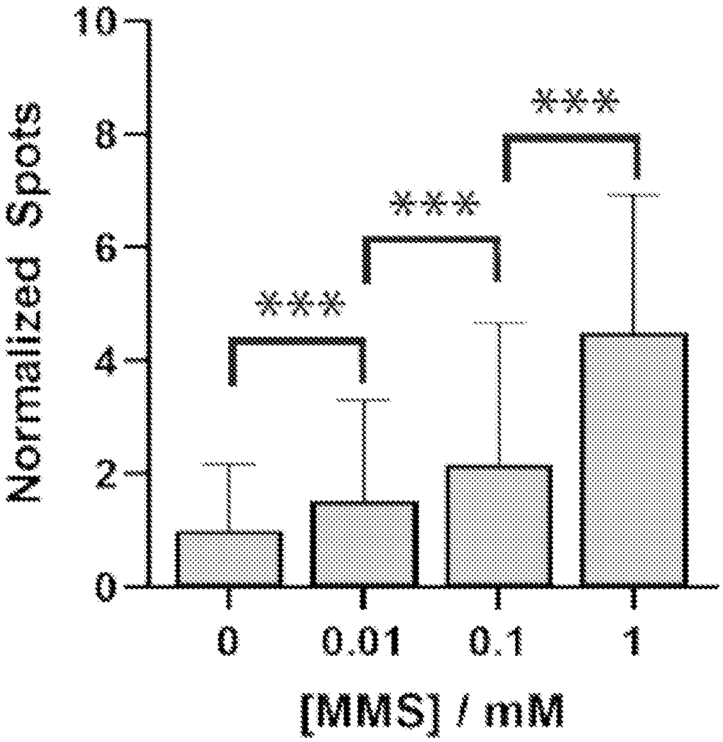
Figure 7F:
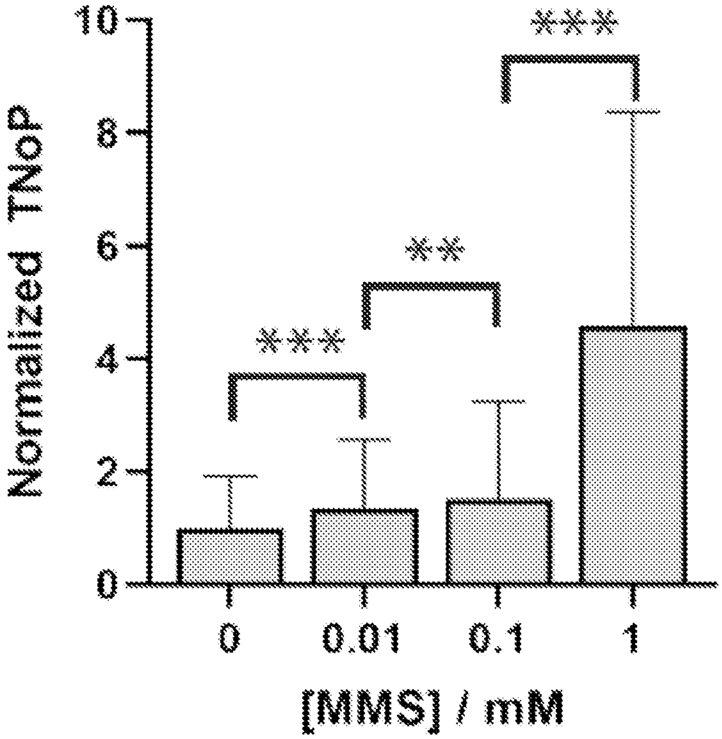
Figure 7G:
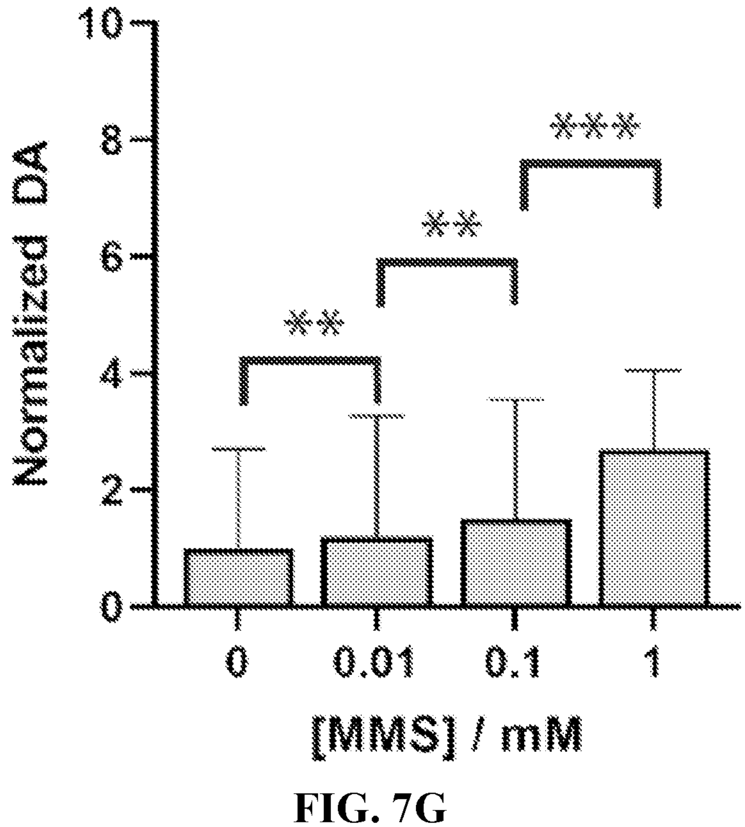
Figure 7H:
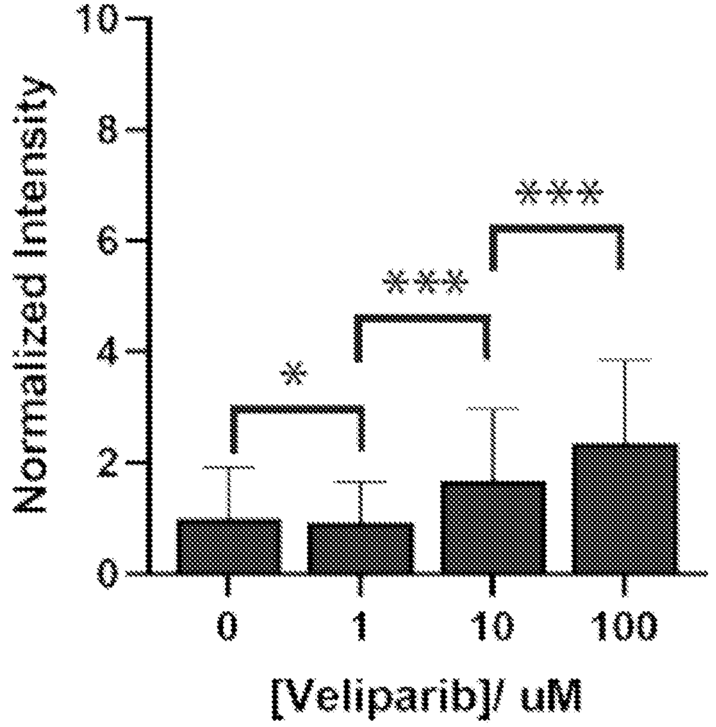
Figure 7I:
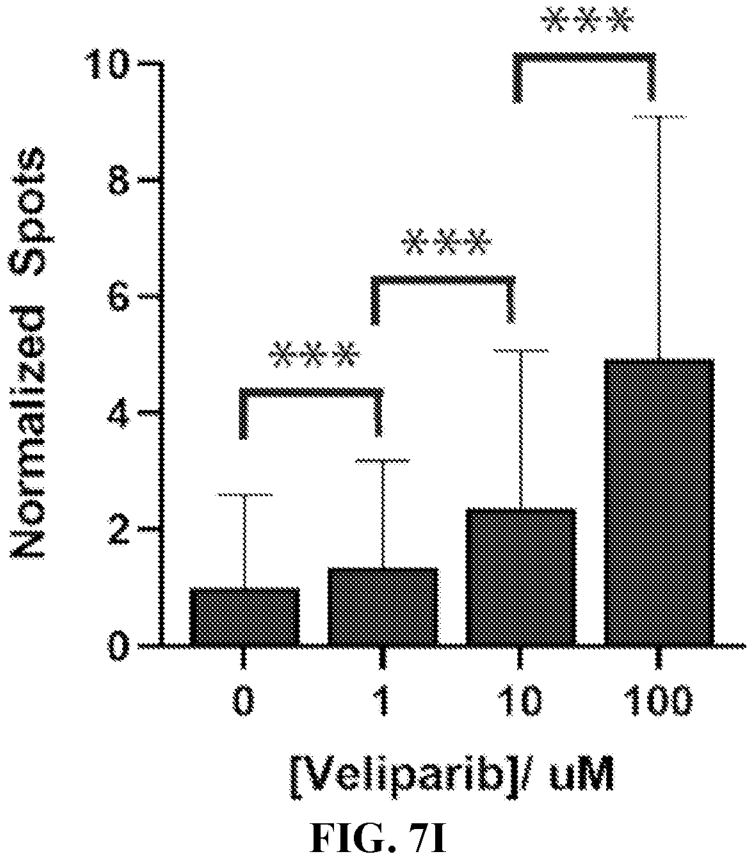
Figure 7J:
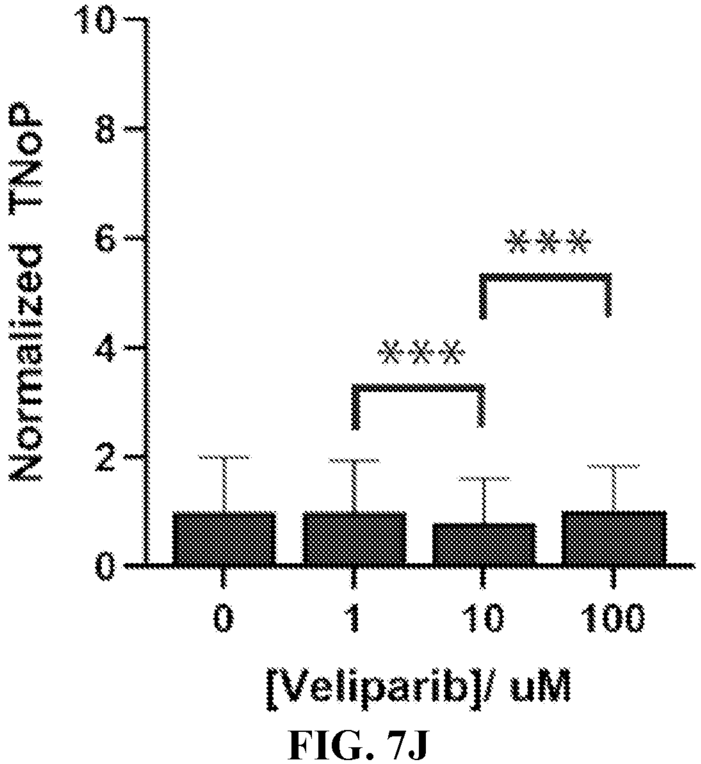
Figure 7K:
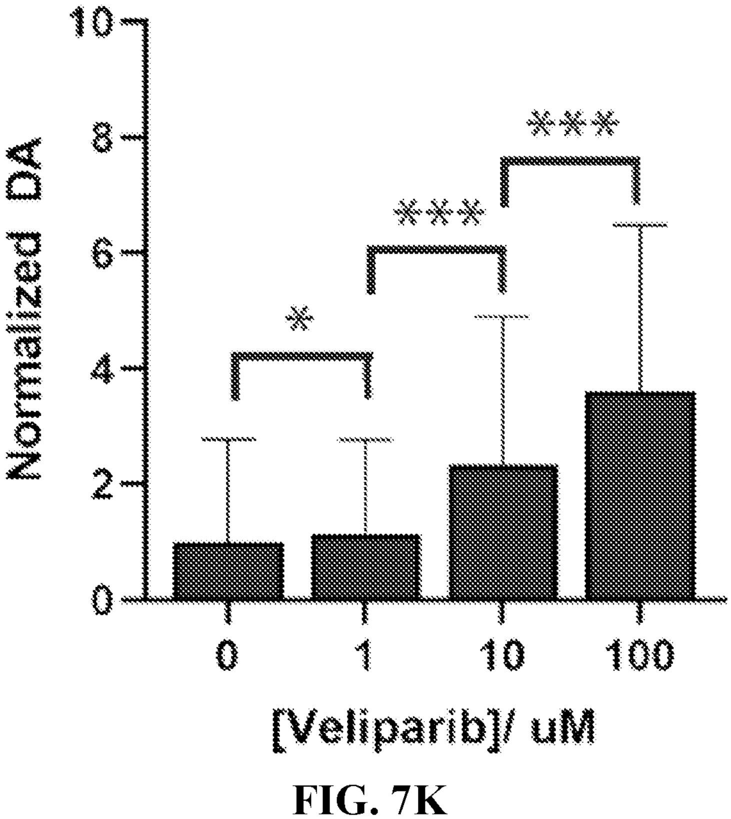
Figure 7L:
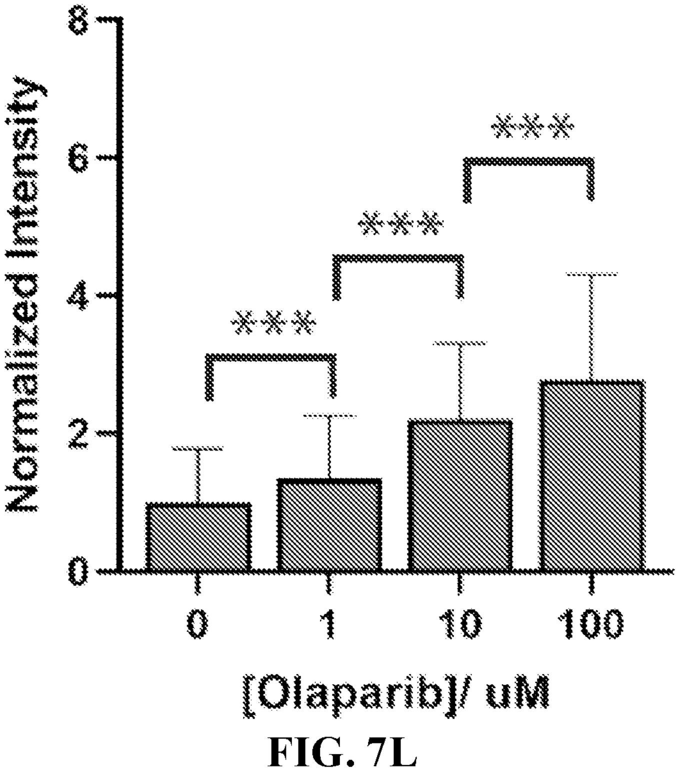
Figure 7M:
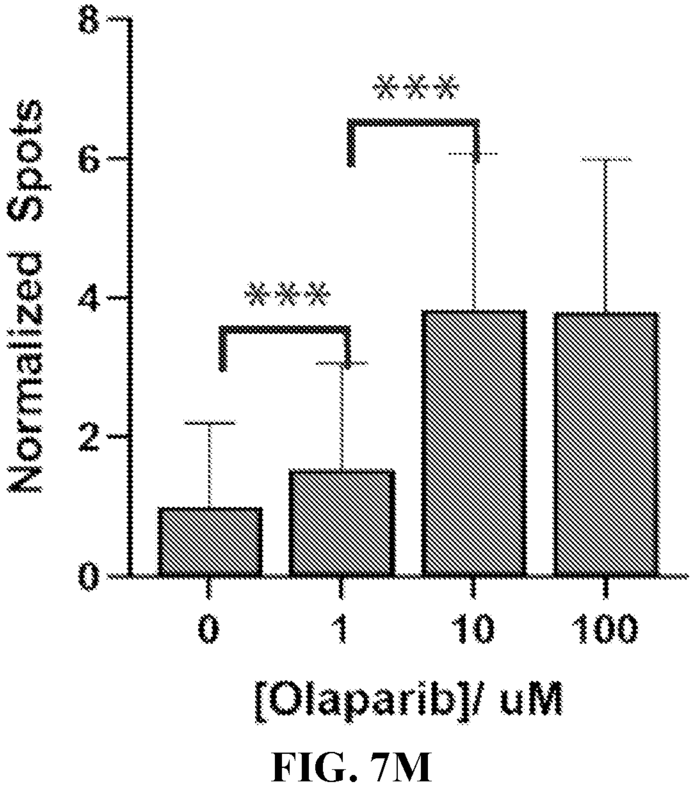

In analyzing DNA damage, the amount of γH2AX per cell is represented by the normalized integrated fluorescence intensity (FIG. 7D, FIG. 7H, and FIG. 7L). We found that γH2AX intensity experienced small, significant increases at lower MMS doses but showed a massive (nearly 8×), significant increase at the highest dose, results that agree with SKOV3 sensitivity to MMS. PARP inhibitor treatment produced similar results except for a slight decrease at 1 μM veliparib. The number of spots determined by Imaris captures the dose dependent DNA damage induced by MMS and PARP inhibitors as expected (FIG. 7E, FIG. 7I, and FIG. 7M), with the highest (100 μM) olaparib dose being the exception where it was not significant compared to the 10 μM dose. Yet, surprisingly, at the highest dose of PARP inhibitor, the number of foci was higher under veliparib treatment, the weaker PARP inhibitor.

Figure 7N:
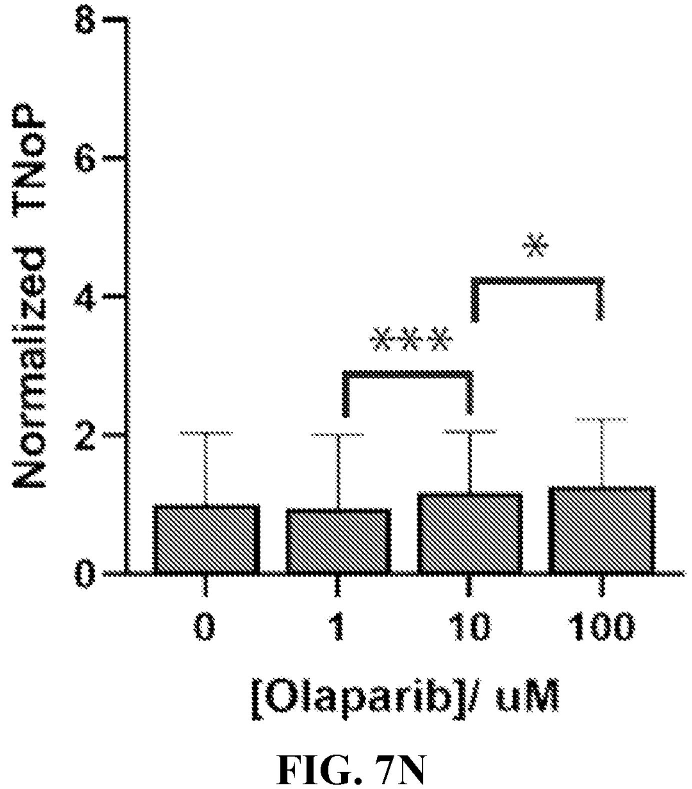
Figure 7O:
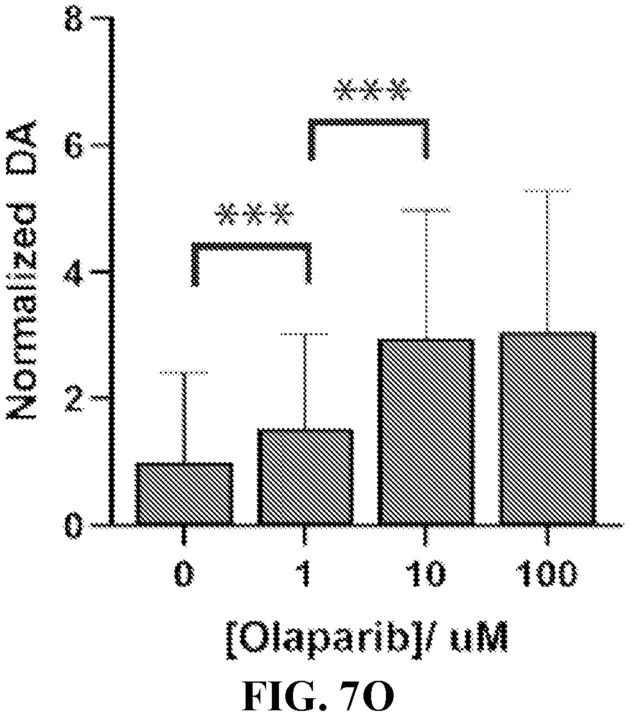

Analyzing the images with ICS TNOP (FIG. 7F, FIG. 7J, and FIG. 7N) produced a similar MMS dose response to Spots analysis. However, TNOP analysis of cells treated with PARP inhibitor failed to capture the dose dependence seen in Spots analysis. While olaparib treatment produced a slight TNOP dose dependence, veliparib treatment failed to induce any correlative TNOP dose dependence, despite displaying significant differences between doses. Yet, large and/or aggregated foci in fluorescence microscopy can represent a cluster of individual foci that are not distinguishable. Indeed, microscopic number density calculated by ICS often decreases in cases of significant aggregation, resulting in a smaller number of more densely packed clusters[35,36], therefore we calculated the ICS degree of aggregation (DA) as well as TNoP, since an aggregation parameter may shed more light on protein clustering in foci. When the DA was calculated from ICS analysis (FIG. 7G, FIG. 7K, and FIG. 7O), the results demonstrated both MMS and PARP inhibitor dose dependence, similar to results obtained with Imaris Spots. Like Spots analysis, the ICS DA analysis of 100 μM veliparib produced a higher value than 100 μM olaparib, compared to their respective controls. The difference between TNoP and DA analysis suggests that PARP inhibitor-induced γH2AX is leading to more clustering as opposed to increasing the TNOP, resulting in more aggregated γH2AX at similar TNoP levels at the molecular level. Here DA proved capable of capturing DNA damage dose dependence through a canonical DDR biomarker with similar efficacy to Imaris Spots counting.

Figures 8A, 8B, 8C:
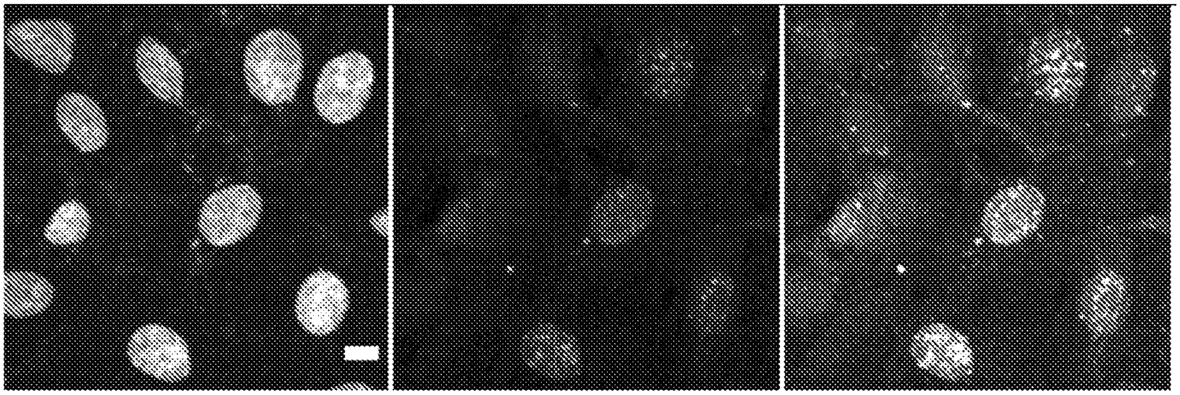
Figure 8D:
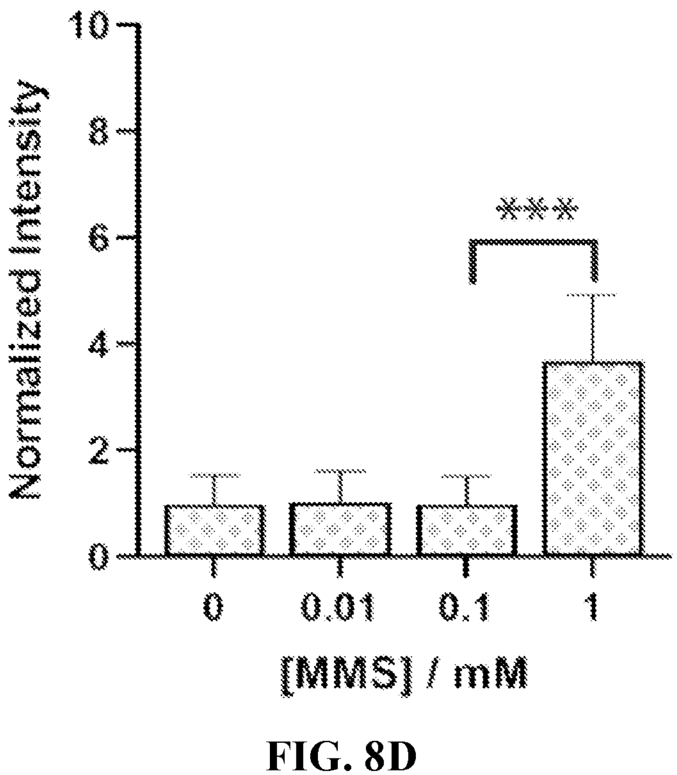
(FIG. 8D, FIG. 8H, and FIG. 8L) Normalized γH2AX Intensity.
Figure 8E:
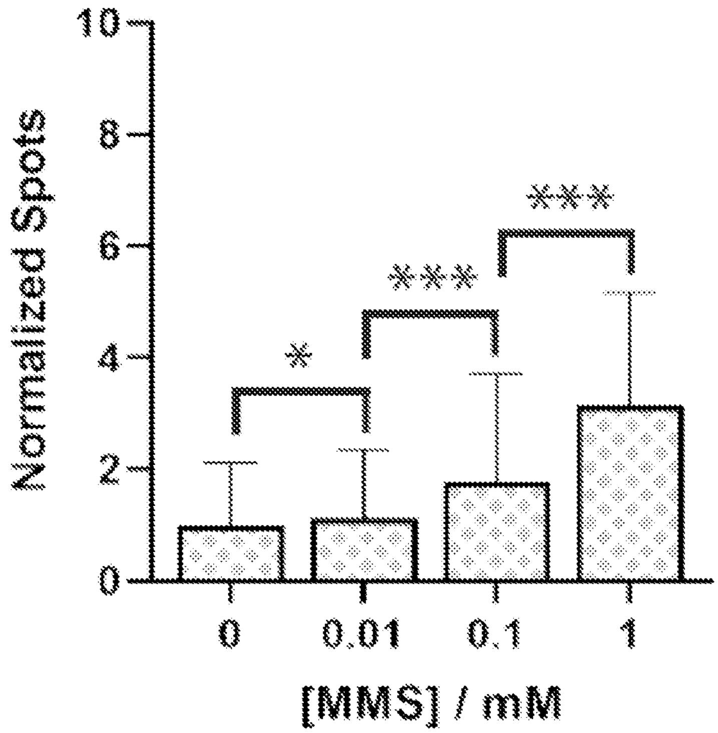
(FIG. 8E, FIG. 8I, and FIG. 8M) Normalized Imaris Spots analysis on γH2AX.
Figure 8F:
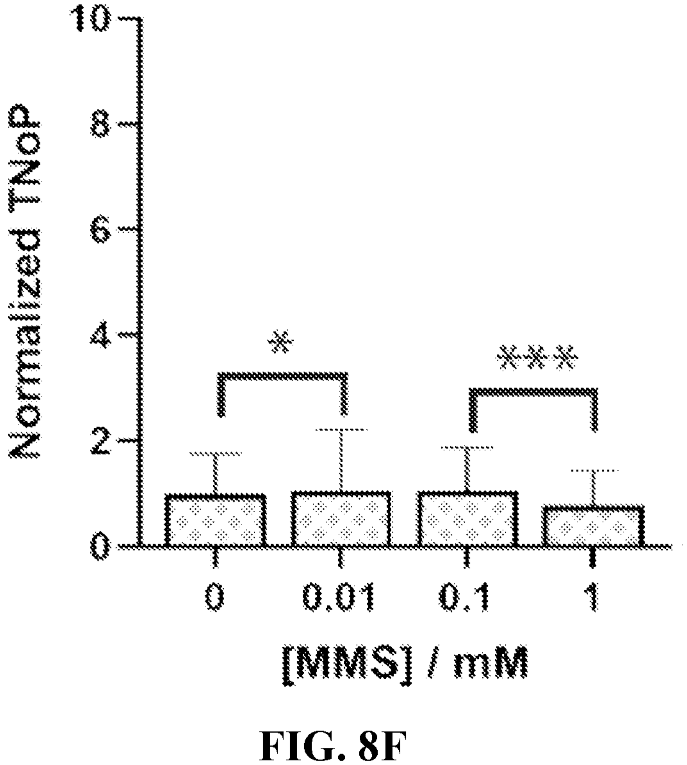
(FIG. 8F, FIG. 8J, and FIG. 8N) Normalized ICS TNOP.
Figure 8G:
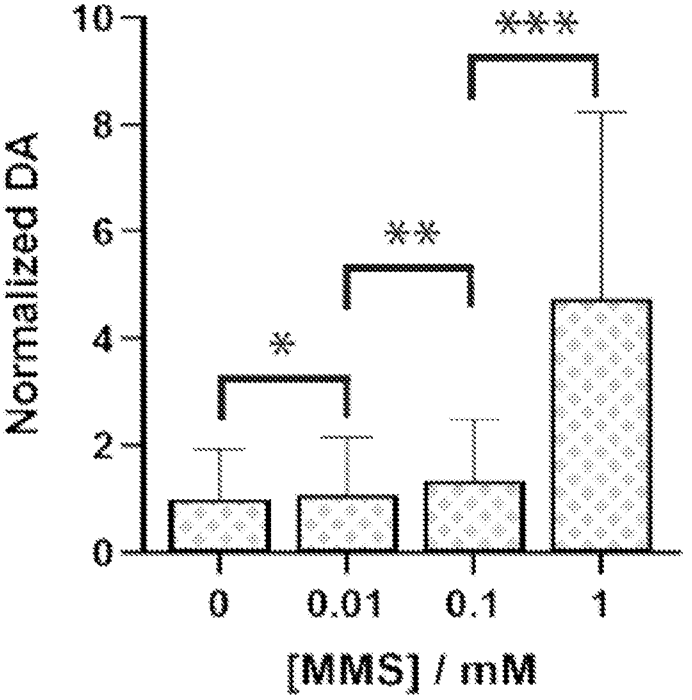

We next analyzed DNA damage dose dependence in another cell line, OVCA429. FIGS. 8A-8C displays OVCA429 cells exposed to 0.1 mM MMS, highlighting a range of γH2AX signal, spanning from only low diffuse signal in the nucleus, to single distinguishable γH2AX foci in the diffuse signal, to large clusters of different sizes in high intensity nuclei (FIG. 8C). γH2AX intensity drastically increases at 1 mM MMS (FIG. 8D) and Spots analysis captured the MMS dose dependent DNA damage (FIG. 8E). However, ICS TNOP analysis did not produce any MMS dose dependence (FIG. 8F), but calculating the DA produced results similar to Spots analysis (FIG. 8G). These results are indicative of a high degree of aggregation demonstrating the high levels of molecular clustering of γH2AX due to dose-dependent DNA damage in OVCA429 cells.

Figure 8H:
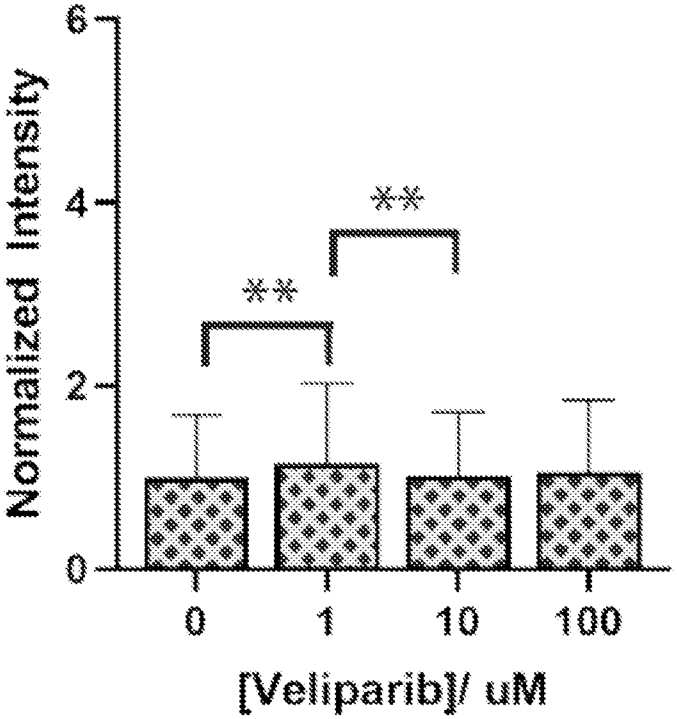
Figure 8I:
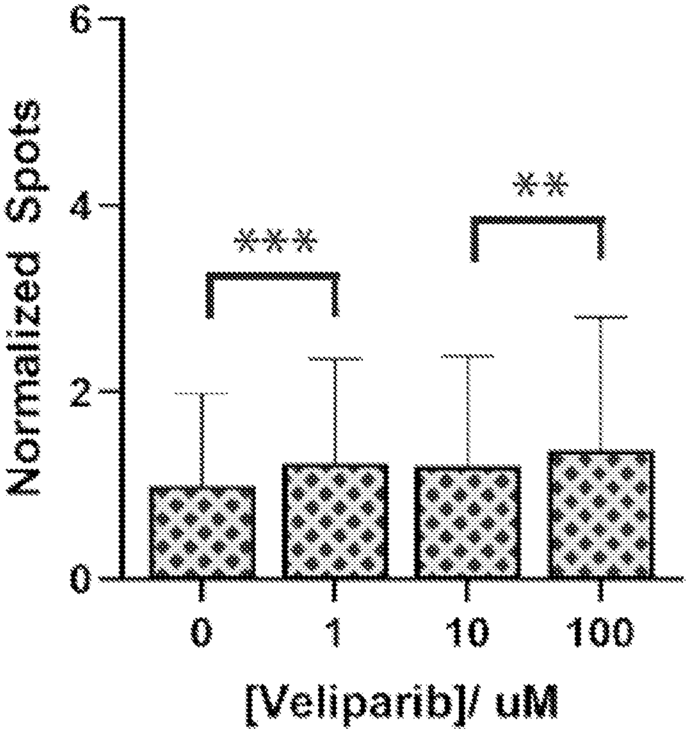
Figure 8J:
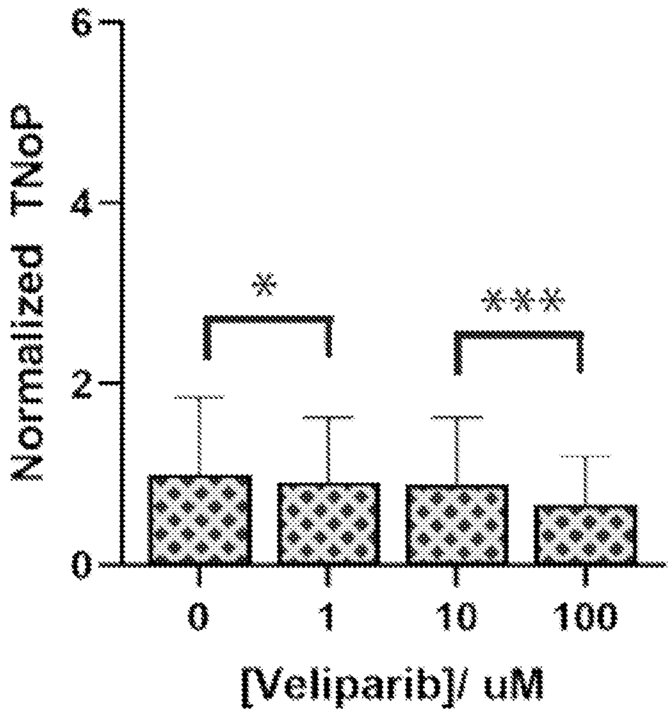
Figure 8K:
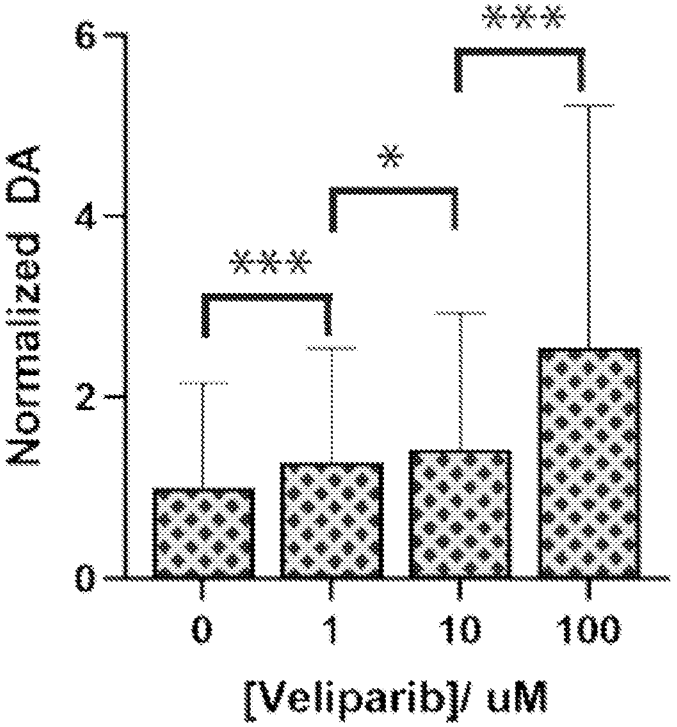
Figure 8L:
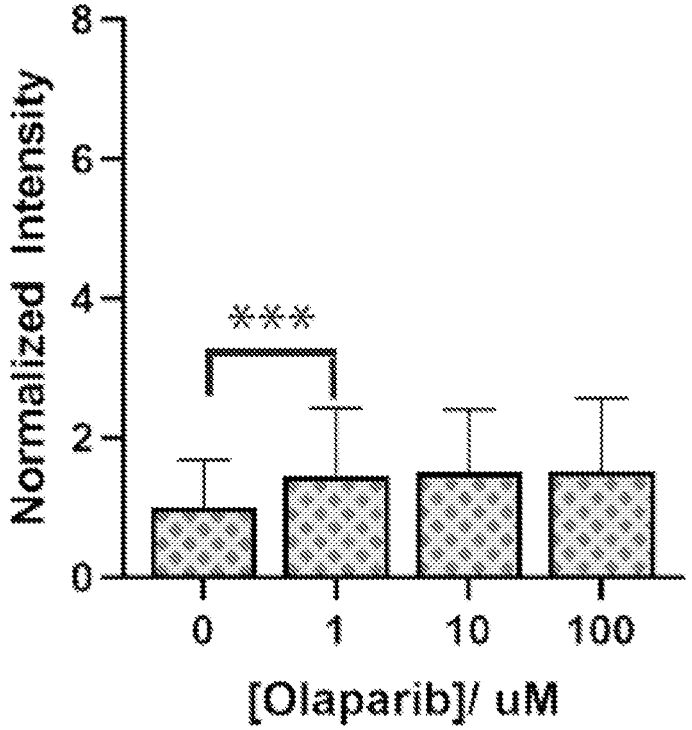
Figure 8M:
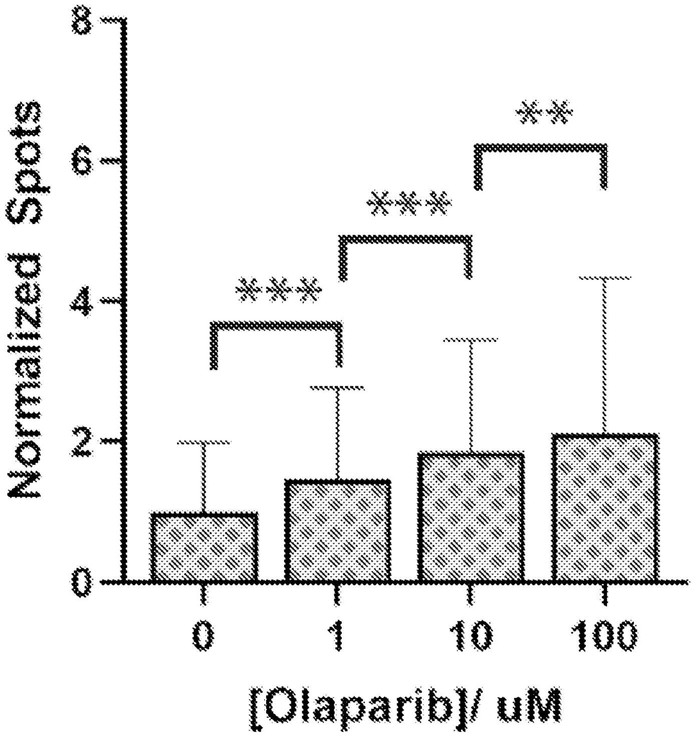
Figure 8N:
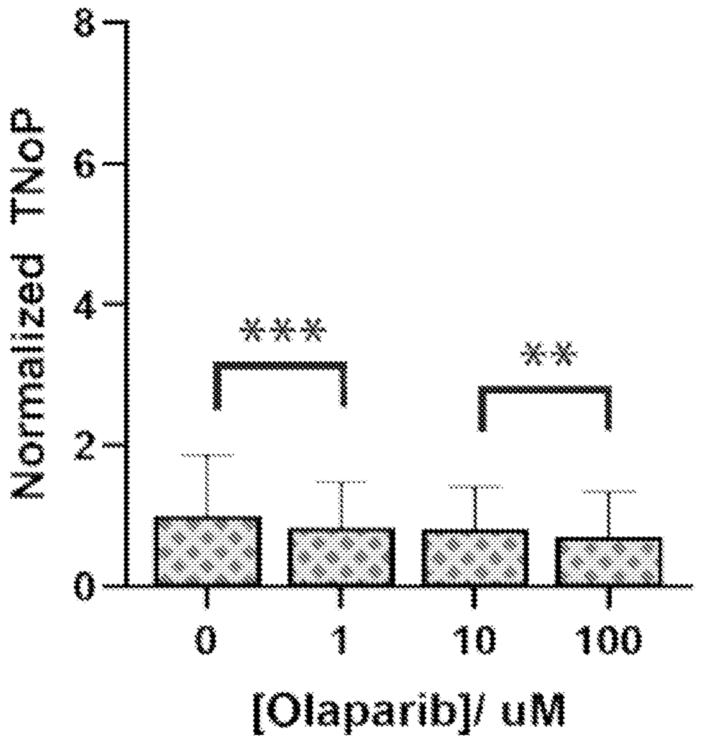
Figure 8O:
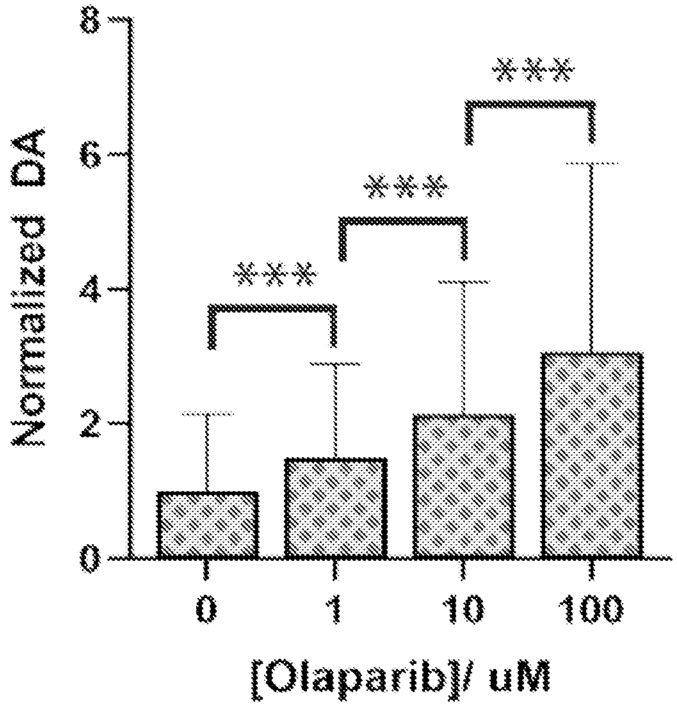

Contrary to SKOV3 analysis, despite similar sensitivity to olaparib and veliparib, γH2AX intensity in OVC429 did not show a dose dependence for both PARP inhibitors (FIG. 8H and FIG. 8L). Similarly, Imaris Spots analysis failed to capture the full dose dependent DNA damage induced by veliparib (FIG. 8I) but was able to capture olaparib dose dependence (FIG. 8M), suggesting that the increased γH2AX signal in olaparib treatment enables Spots to analyze the increased foci formation (FIG. 8L). While ICS analysis produced a partial PARPi dose dependent decrease in TNOP (FIG. 8J and FIG. 8N), DA captured the full dose dependent increases in γH2AX clustering for both veliparib (FIG. 8K) and olaparib treatment (FIG. 8O). Overall, in OVCA429, ICS DA produced similar results to Imaris Spots in olaparib treated cells, but measured dose dependent response in cells treated with veliparib where Imaris Spots was unable to capture the dose dependency.

ICS Captures Clustering of DNA Damage Proteins that do not Form Resolvable Foci

Figures 9A, 9B, 9C:
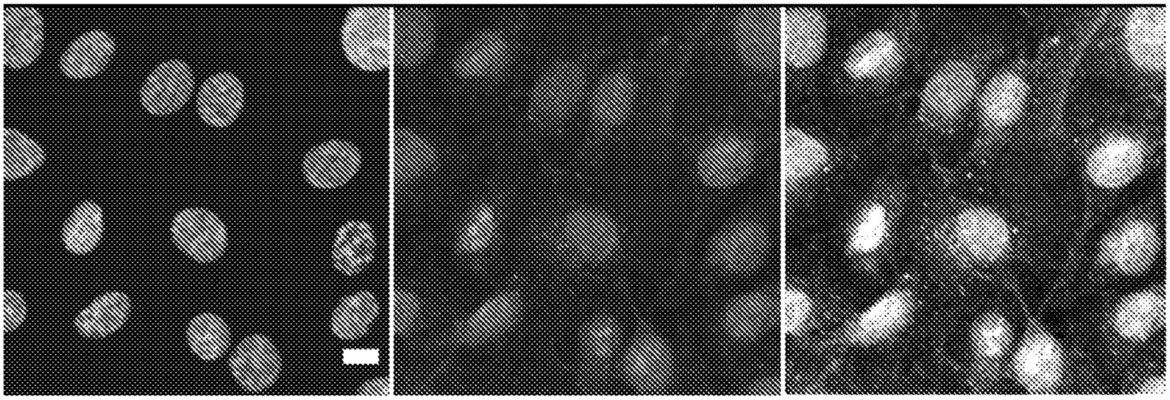

Next, we sought to quantify the behaviour of proteins that do not form resolvable foci during DNA damage without immunofluorescence pre-extraction, specifically Replication Protein A1 (RPA1) and RAD51. The RPA complex is required for major DNA repair pathways and modulates RAD51 recruitment to sites of DNA damage[37,38]. However, increased RPA1 and RAD51 concentrations created at sites of DNA repair are not always resolvable as individual foci[38,39]. In the absence of induced DNA damage, RPA1 immunofluorescence produces a diffuse signal throughout the nuclei in SKOV3 cells (FIGS. 9A-9C). Only with contrast adjusting (FIG. 9C), does heterogeneous distribution of RPA1 become visible.

Figures 9D, 9E, 9F:
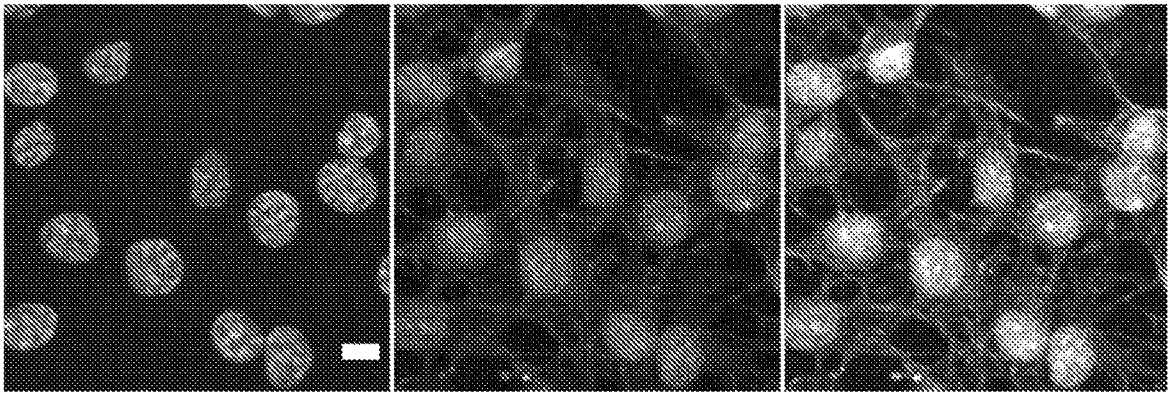

We used MMS to induce DNA damage on SKOV3 and OVCA429 cells. As expected, normalized intensity for RPA1 and RAD51 values did not display a dose dependence on MMS concentration. In SKOV3 cells treated with 1 mM MMS (FIGS. 9D-9F), RPA1 recruitment to sites of DNA damage is observed alongside the diffuse signal of the nuclei. We first quantified the dose-dependent distribution of RPA1 with both Imaris Spots analysis (FIG. 9G and FIG. 9I) and ICS DA measurements (FIG. 9H and FIG. 9J). In SKOV3 cells, both Spots analysis (FIG. 9G) and ICS DA analysis (FIG. 9H) captured a dose dependent increase in RPA1 clustering. In OVCA429 cells, spots analysis demonstrated a more modest increase with increasing MMS dose (FIG. 9I), however, DA analysis produced a larger increase in aggregation exceeding 2.5× of control at 1 mM MMS (FIG. 9J). While, similarly to analysis of γH2AX, ICS TNOP did not show a full dose-dependent reaction in SKOV3 cells. Analysis of γH2AX clustering in OVCA429 cells treated with MMS (FIG. 9G) demonstrates a large increase at 1 mM MMS, suggesting that RPA1 DA analysis (FIG. 9J) is capturing DNA damage with a similar sensitivity to γH2AX analysis. The increased sensitivity in ICS DA versus Spots also indicates that measuring aggregation instead of foci counting could be more sensitive when analyzing proteins that do not form resolvable foci.

Figure 10A:
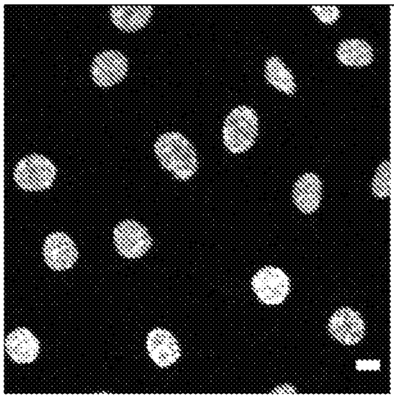
Figure 10B:
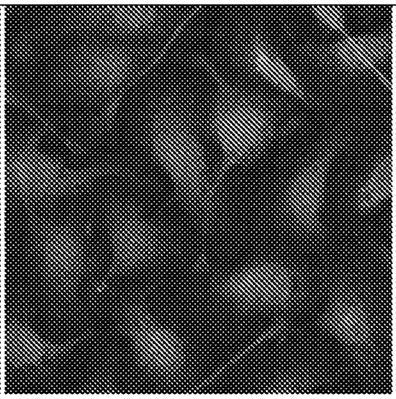
Figure 10C:
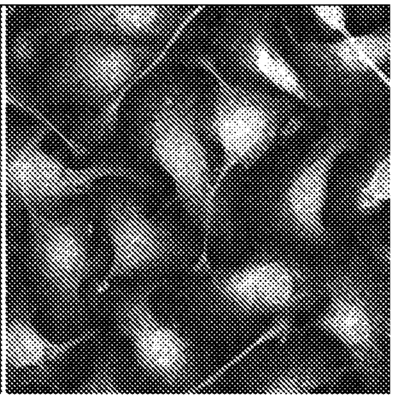
Figure 10D:
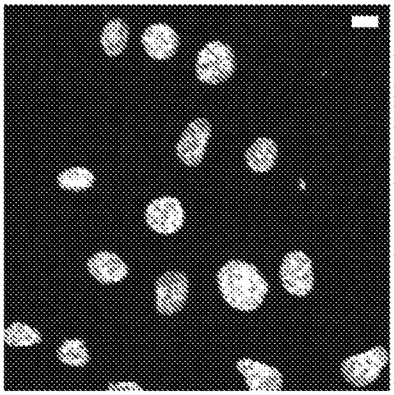
Figure 10E:
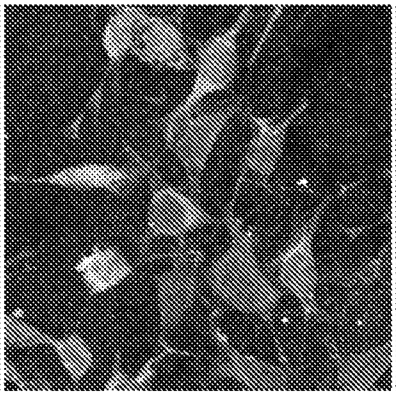
Figure 10F:
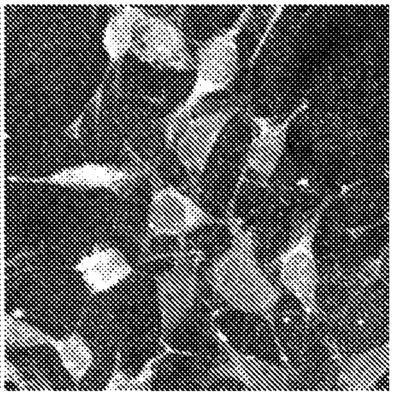

Similar to RPA1, RAD51 does not form distinguishable foci in the nuclei in cells (SKOV3, FIGS. 10A-10C: untreated cells, FIGS. 10D-10F: cells treated with 1 mM MMS). With MMS treatment, Spots analysis of RAD51 foci did not show an overall MMS dose dependency in either cell line (FIG. 10G and FIG. 10I), revealing some concentrations increases where the number of spots slightly decreased. However, ICS DA analysis captured dose dependent increases in aggregation (FIG. 10H and FIG. 10J), with a 3× increase over control in SKOV3 at 1 mM MMS. Similar to RPA1 labeling experiments, the MMS dose dependence observed with RAD51 DA analysis is comparable to trends observed with γH2AX DA analysis for both cell lines.

DISCUSSION

Fundamentally, DDR foci are resolvable when the labeled protein concentration difference between foci and the rest of the nucleus is high enough to distinguish in fluorescence microscopy. The local concentration at sites of DNA damage is driven by either protein recruitment, or, in the case of γH2AX, post translational modifications[40]. Yet, most DDR proteins do not cluster in DNA damage at concentrations high enough to resolve recruitment in the absence of massive, artificial DNA damage. γH2AX is the most prominent marker of DNA damage foci, largely because H2AX phosphorylation occurs primarily at sites of double stranded breaks producing a marker with very low background signal. However, recent super resolution results identify γH2AX foci as groups of smaller foci[22], suggesting that not all foci are equal, and large foci in diffraction-limited microscopy represent a greater degree of DNA damage than smaller foci. Therefore, foci count alone may not accurately represent DNA damage.

Clustering analysis with ICS overcomes both limits of counting traditional markers and measuring non-traditional markers as metrics of DNA damage or to study their role in the DDR. Initially we used the TNOP parameter to match foci counts in individual cells from two methods, however, we discovered that ICS calculated degree of aggregation (DA) was a more accurate measurement, capturing overall clustering of protein. Using ICS DA, we were able to detect the dose dependent response to two PARP inhibitors, matching or exceeding dose-dependent sensitivity of foci counting via Imaris Spots. Furthermore, ICS DA was uniquely able to measure dose-dependent DNA damage using RPA1 and RAD51 as DNA damage markers. The accuracy of these measurements was validated by the similarity of the dose dependency to γH2AX measurements. Therefore, ICS is able to evaluate DNA damage with non-traditional markers or evaluate the recruitment of proteins to DNA damage.

ICS analysis of γH2AX in OVCA429 cells treated with PARP inhibitors, where there was not a dose dependent increase of γH2AX intensity, revealed a decrease in TNOP, indicating larger foci cluster formation was a merging of smaller clusters to produce an overall decrease in the number of foci clusters[35,36]. The formation of large foci can impact foci counting methods, however, Imaris Spots uses a spot size parameter that aids in placing multiple smaller spots per large foci. Yet, this spot size parameter failed to consistently capture the dose dependent increases in DNA damage where γH2AX intensity was not also increased. Spatial ICS is well suited to measure large aggregations and has previously been used to count distinguishable objects larger than the diffraction limit such as fluorescent beads[28] and dendritic spines[41], by using an intensity threshold to remove the background signal. This can be supplemented by various image analysis algorithms such as Gaussian filters to smooth out fluctuations in the objects so they can be detected as one object. However, we did not need an intensity threshold to remove the background signal, and only used a background subtraction that represented the intensity in a part of the image with no cells to account for autofluorescence outside of the cells.

Here, we demonstrated that ICS is an alternative technique to foci counting, where the clustering involved in protein recruitment during DNA damage can be fully captured on the molecular level. ICS measures the degree of clustering and considers the low intensity signal contributions that are lost during foci segmentation. Our findings correlate with prior studies characterizing foci formation/clustering and the DNA damage response using advanced optical techniques such laser micro-irradiation[42] and super resolution microscopy[22]. Advantageously, ICS can be implemented on any fluorescence image as long as the square relative fluorescence intensity fluctuations are detectable above noise fluctuations. ICS does not require laser micro-irradiation to induce detectable clustering[23,42,43]. Also, it overcomes the complications introduced when using pre-extraction in immunofluorescence[44], where soluble protein is removed through permeabilizing the cell for an arbitrary amount of time, likely removing some recruited protein as well. Thus, ICS enables simple, standard immunofluorescence labeling techniques. The overall approach, using a combination of conventional fluorescence microscopy, antibody labeling, and ICS analysis, provides a molecular level understanding for characterizing protein recruitment and signaling in a variety of applications from capturing the DNA damage response to evaluating cancer therapies. We expect adoption of this approach will both lead to a more objective measure of DNA damage and provide a tool to evaluate the role of every DDR protein during the DNA damage response.

REFERENCES

1 Giglia-Mari, G., Zotter, A. & Vermeulen, W. DNA damage response. *Cold Spring Harb Perspect Biol* 3, a000745, (2011).

2 Zhou, B. B. & Elledge, S. J. The DNA damage response: putting checkpoints in perspective. *Nature* 408, 433-439, (2000).

3 Jackson, S. P. & Bartek, J. The DNA-damage response in human biology and disease. *Nature* 461, 1071-1078, (2009).

4 Hoeijmakers, J. H. Genome maintenance mechanisms for preventing cancer. *Nature* 411, 366-374, (2001).

5 Maynard, S., Fang, E. F., Scheibye-Knudsen, M., Croteau, D. L. & Bohr, V. A. DNA Damage, DNA Repair, Aging, and Neurodegeneration. *Cold Spring Harb Perspect Med* 5, (2015).

6 Hoeijmakers, J. H. DNA damage, aging, and cancer. *N Engl J Med* 361, 1475-1485, (2009).

7 Figueroa-Gonzalez, G. & Perez-Plasencia, C. Strategies for the evaluation of DNA damage and repair mechanisms in cancer. *Oncol Lett* 13, 3982-3988, (2017).

8 Grimaldi, K. A., McGurk, C. J., McHugh, P. J. & Hartley, J. A. PCR-Based Methods for Detecting DNA Damage and its Repair at the Sub-gene and Single Nucleotide Levels in Cells. *Molecular Biotechnology* 20, 181-196, (2002).

9 Olive, P. L. & Durand, R. E. Heterogeneity in DNA damage using the comet assay. *Cytometry A* 66, 1-8, (2005).

10 Sutherland, B. M., Georgakilas, A. G., Bennett, P. V., Laval, J. & Sutherland, J. C. Quantifying clustered DNA damage induction and repair by gel electrophoresis, electronic imaging and number average length analysis. *Mutat Res* 531, 93-107, (2003).

11 Cortes-Gutierrez, E. I., Fernandez, J. L., Davila-Rodriguez, M. I., Lopez-Fernandez, C. & Gosalvez, J. Use of DBD-FISH for the study of cervical cancer progression. *Methods Mol Biol* 1249, 291-301, (2015).

12 Mitchell, D. L. Quantification of photoproducts in mammalian cell DNA using radioimmunoassay. *Methods Mol Biol* 113, 165-173, (1999).

13 Loo, D. T. TUNEL assay. An overview of techniques. *Methods Mol Biol* 203, 21-30, (2002).

14 Featherstone, C. & Jackson, S. P. Ku, a DNA repair protein with multiple cellular functions? *Mutation Research/DNA Repair* 434, 3-15, (1999).

15 Paull, T. T. et al. A critical role for histone $H_2AX$ in recruitment of repair factors to nuclear foci after DNA damage. *Current Biology* 10, 886-895, (2000).

16 Brem, R. & Hall, J. XRCC1 is required for DNA single-strand break repair in human cells. *Nucleic Acids Res* 33, 2512-2520, (2005).

17 Bocker, W. & Iliakis, G. Computational Methods for analysis of foci: validation for radiation-induced gamma-H2AX foci in human cells. *Radiat Res* 165, 113-124, (2006).

18 Hernandez, L., Terradas, M., Martin, M., Tusell, L. & Genesca, A. Highly sensitive automated method for DNA damage assessment: gamma-H2AX foci counting and cell cycle sorting. *Int J Mol Sci* 14, 15810-15826, (2013).

19 Jucha, A. et al. FociCounter: a freely available PC programme for quantitative and qualitative analysis of gamma-H2AX foci. *Mutat Res* 696, 16-20, (2010).

20 Lapytsko, A., Kollarovic, G., Ivanova, L., Studencka, M. & Schaber, J. FoCo: a simple and robust quantification algorithm of nuclear foci. *BMC Bioinformatics* 16, 392, (2015).

21 Oeck, S., Malewicz, N. M., Hurst, S., Rudner, J. & Jendrossek, V. The Focinator—a new open-source tool for high-throughput foci evaluation of DNA damage. *Radiat Oncol* 10, 163, (2015).

22 Natale, F. et al. Identification of the elementary structural units of the DNA damage response. *Nat Commun* 8, 15760, (2017).

23 Aleksandrov, R. et al. Protein Dynamics in Complex DNA Lesions. *Mol Cell* 69, 1046-1061 e1045, (2018).

24 Spegg, V. & Altmeyer, M. Biomolecular condensates at sites of DNA damage: More than just a phase. *DNA Repair* (*Amst*) 106, 103179, (2021).

25 Meyer, T. & Schindler, H. Particle counting by fluorescence correlation spectroscopy. Simultaneous measurement of aggregation and diffusion of molecules in solutions and in membranes. *Biophysical Journal* 54, 983-993, (1988).

26 Palmer, A. G. & Thompson, N. L. Fluorescence correlation spectroscopy for detecting submicroscopic clusters of fluorescent molecules in membranes. *Chemistry and Physics of Lipids* 50, 253-270, (1989).

27 Thompson, N. L. in *Topics in Fluorescence Spectroscopy: Techniques* (ed Joseph R. Lakowicz) 337-378 (Springer US, 1999).

28 Petersen, N. O., Hoddelius, P. L., Wiseman, P. W., Seger, O. & Magnusson, K. E. Quantitation of membrane receptor distributions by image correlation spectroscopy: concept and application. *Biophysical Journal* 65, 1135-1146, (1993).

29 Wiseman, P. W. & Petersen, N. O. Image Correlation Spectroscopy. II. Optimization for Ultrasensitive Detection of Preexisting Platelet-Derived Growth Factor-β Receptor Oligomers on Intact Cells. *Biophysical Journal* 76, 963-977, (1999).

30 imagej.nih.gov/ij/docs/guide/146-29.html

31 Lundin, C. et al. Methyl methanesulfonate (MMS) produces heat-labile DNA damage but no detectable in vivo DNA double-strand breaks. *Nucleic Acids Res* 33, 3799-3811, (2005).

32 Murai, J. et al. Trapping of PARP1 and PARP2 by Clinical PARP Inhibitors. *Cancer Res* 72, 5588-5599, (2012).

33 Shen, Y., Aoyagi-Scharber, M. & Wang, B. Trapping Poly(ADP-Ribose) Polymerase. *J Pharmacol Exp Ther* 353, 446-457, (2015).

34 Padella, A. et al. Targeting PARP proteins in acute leukemia: DNA damage response inhibition and therapeutic strategies. *J Hematol Oncol* 15, 10, (2022).

35 Gopal, A. A. et al. Netrin-1-Regulated Distribution of UNC5B and DCC in Live Cells Revealed by TICCS. *Biophys J* 110, 623-634, (2016).

36 Gopal, A. A. et al. Spatially Selective Dissection of Signal Transduction in Neurons Grown on Netrin-1 Printed Nanoarrays via Segmented Fluorescence Fluctuation Analysis. *ACS Nano* 11, 8131-8143, (2017).

37 Hass, C. S., Lam, K. & Wold, M. S. Repair-specific functions of replication protein A. *J Biol Chem* 287, 3908-3918, (2012).

38 Koury, E., Harrell, K. & Smolikove, S. Differential RPA-1 and RAD-51 recruitment in vivo throughout the *C. elegans* germline, as revealed by laser microirradiation. *Nucleic Acids Res* 46, 748-764, (2018).

39 Sukhodolets, K. E. et al. The 32-kilodalton subunit of replication protein A interacts with menin, the product of the MEN1 tumor suppressor gene. *Mol Cell Biol* 23, 493-509, (2003).

40 Pilch, D. R. et al. Characteristics of gamma-H2AX foci at DNA double-strand breaks sites. *Biochem Cell Biol* 81, 123-129, (2003).

41 Wiseman, P. W., Capani, F., Squier, J. A. & Martone, M. E. Counting dendritic spines in brain tissue slices by image correlation spectroscopy analysis. *J Microsc* 205, 177-186, (2002).

42 Izhar, L. et al. A Systematic Analysis of Factors Localized to Damaged Chromatin Reveals PARP-Dependent Recruitment of Transcription Factors. *Cell Rep* 11, 1486-1500, (2015).

43 Mistrik, M. et al. Cells and Stripes: A novel quantitative photo-manipulation technique. *Sci Rep* 6, 19567, (2016).

44 Smith-Clerc, J. & Hinz, B. Immunofluorescence detection of the cytoskeleton and extracellular matrix in tissue and cultured cells. *Methods Mol Biol* 611, 43-57, (2010).

Example 3: Autocorrelation Analysis of a Phenotypic Screen Reveals Hidden Drug Activity This Example describes the capacity of autocorrelation to detect otherwise undetectable compound activity.

Methods

Images from the original study (8) were accessed through the Image Data Resource (32) API on the Open Microscopy environment. Nuclei were segmented using StarDist (33) on the BFP channel image. Segmented nuclei were then analyzed by image correlation spectroscopy autocorrelation (34) in the TP53BP1 channel and the average degree of aggregation (DA) was calculated. For each cell line, compound induced DA was plotted against the compound concentration and linear regression was performed with a linear model in R. Mechanism of action (MoA) activity was determined for MoAs with at least 5 compounds with linear regression results in each of the cell lines. Active compounds were defined as having significant ($p<0.05$) non-zero linear regressions, either negative or positive. The activity score was determine by summing the direction of each active compound and dividing by the total number of compounds in the MoA.

Image access and autocorrelation analysis was performed in Python, while results analysis and plotting were performed in R and Prism.

Introduction

Phenotypic screening is a potent tool to identify compounds that alter cellular function or properties (1). Historically, phenotypic screening has played a significant role in identifying many of the drugs that are currently in the clinic (2). More recent applications of phenotypic screening, or image based profiling (3), use high throughput fluorescence imaging of cells with fluorescent labels that capture the shape and structure of the cell and organelles (4). Morphological profiling of large datasets (5) enables assignment of compound mechanism of action by comparing morphological properties to known compounds or characterization of the impact of genetic perturbations (6). Because these screens don't rely on a priori knowledge of key targets, they can provide profound insight in the drug discovery pathway (7).

Recently a screen of 1,008 compounds generated mechanism of action (MoA) identification of compounds with unclear mechanisms through comparison to known MoAs (8). The screen included three different cells types that expressed combinations of fluorescently labeled proteins: ACTB-RAB5A, CANX-COX411, GM130-SQSTMI, TUBAIB-RELA, and TP53BP1-CLTA, generating 15 different cell lines. Phenotypic analysis extracted features from segmented cells to classify compound MoA based on unique MoA descriptors. The screen accurately ranked roughly half the testable MoAs of the reference compounds. Yet, a substantial number of MoAs did not produce identifiable activity. For all three cell lines, TP53BP1-CLTA labeled cells did not produce increased sensitivity to compounds with DNA damage, DNA damage response, or cell cycle MoAs. A surprising result considering 53BP1 is a canonical DNA damage response marker (9).

53BP1 is a component of the DNA double strand break response pathway and recruited to sites of DNA damage into foci that form around damaged DNA (10). There are a myriad of components that impact 53BP1 activity, including ATM activity (11), cell cycle (12) and epigenetic modifications (13). Therefore, compounds that induce DNA damage, alter the cell cycle, impact DNA signaling or alter the DNA damage response are expected to affect the nuclear location of 53BP1. In theory, any altered localization of 53BP1 would be identified by a phenotypic screen to reveal compound activity in cells with labeled 53BP1. However, this was not the case in the original analysis of the imaging data. Therefore, we tested whether image autocorrelation analysis of 53BP1 images would reveal altered 53BP1 localization that was not detectable using traditional phenotypic screening. Image autocorrelation enables quantification of the spatial heterogeneity of fluorophores that is not possible with traditional analysis due to background noise present in all fluorescent imaging (14). Thus, autocorrelation provides a potentially more sensitive measurement of compound induced changes in 53BP1 localization.

Results

We accessed the original phenotypic screen (8) images through the IDR API on the Open Microscopy server. The screen contained three different cell lines that had endogenous TP53BP1 labeled GFP as a marker protein. We first identified all the images from these three cell lines (>60,000 images in total), then segmented the nuclei of each cell using the BFP channel image. Segmented nuclear regions were then transferred to the TP53BP1 image and image autocorrelation was performed on each nucleus. The degree of aggregation (DA, a measurement of fluorophore clustering) for each nucleus was then averaged to produce an overall image 53BP1 DA that corresponded to the compound and compound concentration. The dataset contained repeats of four different doses for each compound. The activity of each compound in each cell line was then determined by fitting a linear regression to the DA as a function of compound concentration. The slope and significance versus the null hypothesis (slope equal to zero) of DA vs. concentration was then determined. Active compounds were defined as those having a significant ($p<0.05$) slope of DA vs. concentration.

53BP1 DA is a measure of protein labeled fluorophore clustering within the nucleus. A positive regression of DA vs. concentration indicates that the compound induces 53BP1 recruitment to foci at sites of DNA repair and/or processing. Increases in 53BP1 recruitment can occur either through induction of DNA damage or altered repair pathways, such as shifting the response from homologous recombination to non-homologous end joining. Conversely, a negative regression indicates that the compound prevents 53BP1 recruitment to DNA damage or reduces the amount of DNA damage in the cell. However, it should be noted that, as a phenotypic measurement, there are other potential mechanisms of altered 53BP1 clustering that could drive observed compound activity. Yet, given the highly characterized role of 53BP1 in the DNA damage response (9), recruitment to DNA damage response foci is likely the most prominent driver of measured activity.

Figure 11A:
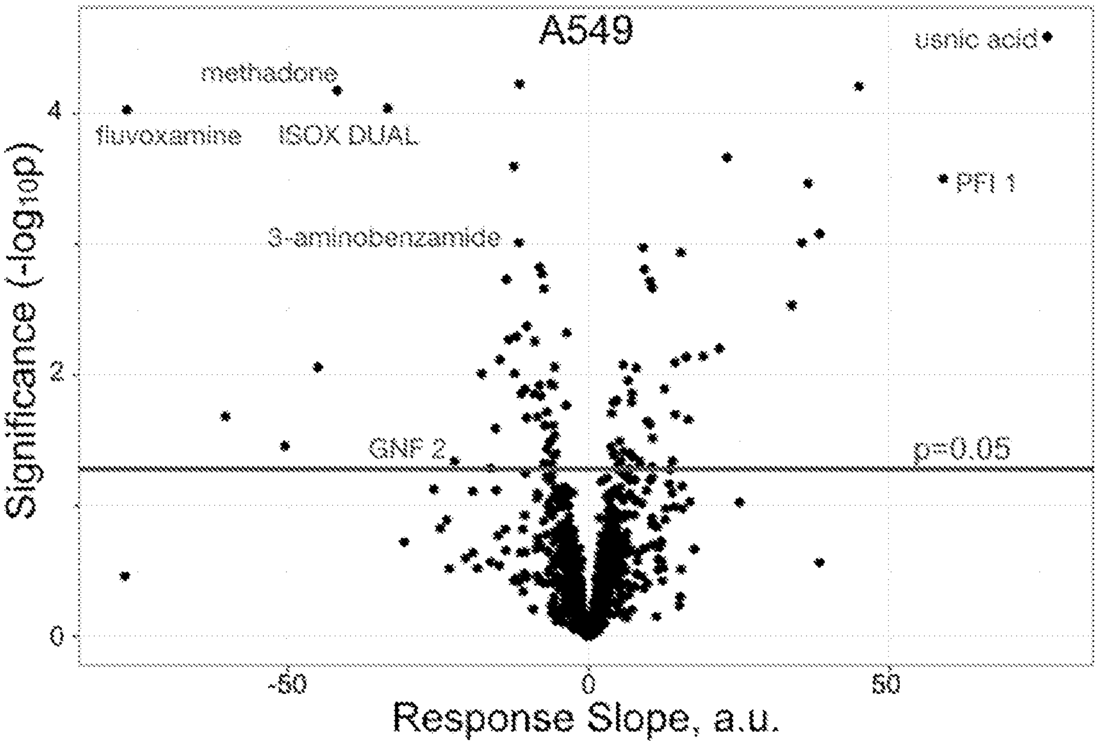
FIGS. 11A-11C: Compound activity on 53BP1 recruitment. Volcano plots for DA vs. concentration response slope linear regressions for each cell line (FIG. 11A, A549.
Figure 11B:
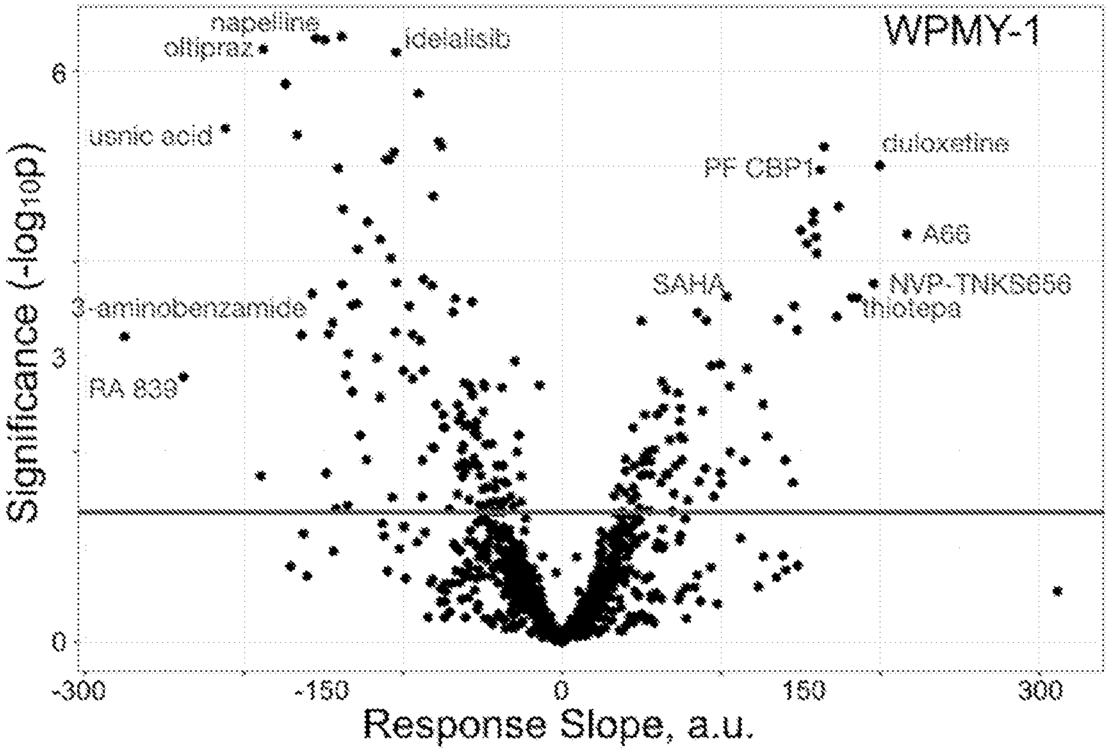
Figure 11C:
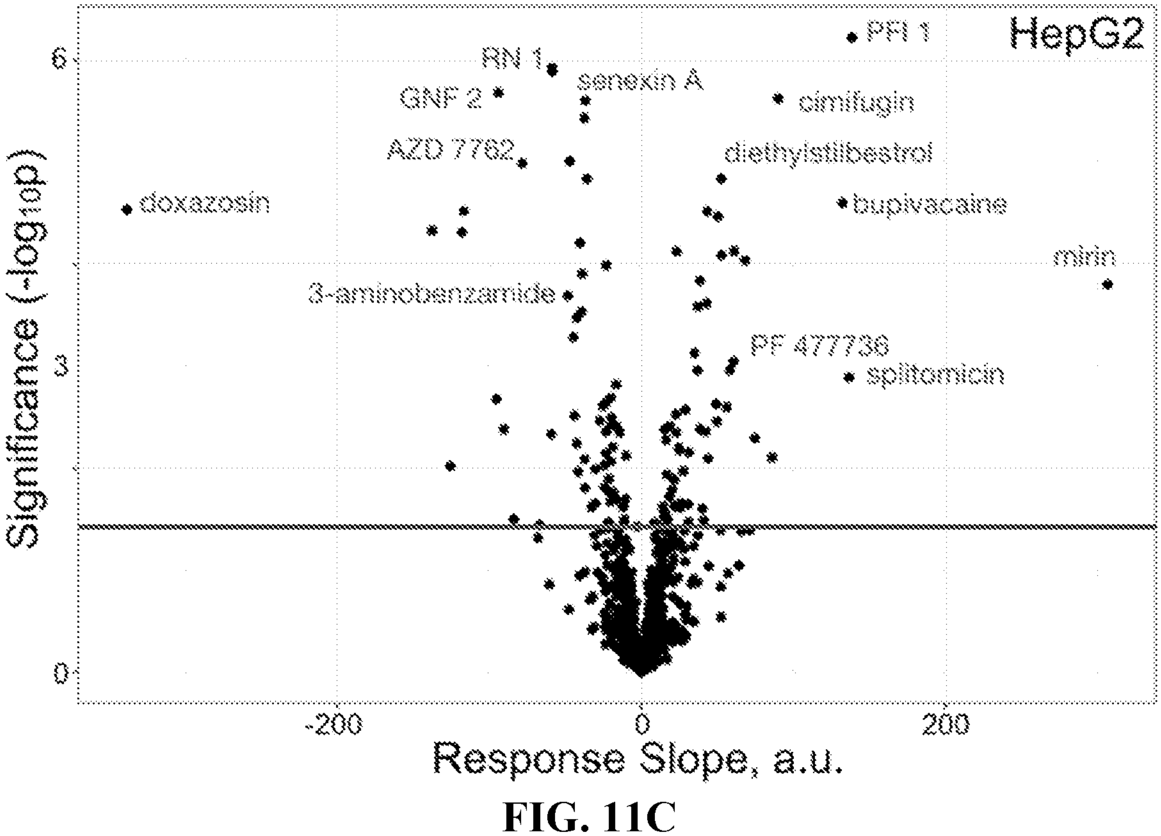

Volcano plots for each cell line were generated to visualize the results (FIGS. 11A-11C). A few compounds with significant activity and targets known to be involved in DNA handling, DNA damage response or cellular cycle are identified in the results. Overall, the majority of compounds with the strongest activity have mechanisms of action that impact the DNA damage response. Mirin, which inhibits Mre11 competition with 53BP1 at stalled replication forks (15) produced a strong response in HepG2. Bromodomain inhibitors impact 53BP1 signaling (16), consistently PFI-1 showed strong positive activity in both HepG2 and A549 cell lines, while PF CBP1, another bromodomain inhibitor, has strong activity in WPMY-1 cells. Other compounds that impact the DNA damage response were also strong inducers of 53BP1 recruitment. These include, in WPMY-1 cells: A66 (a p110α selective PI3K inhibitor), thiotepa (a DNA alkylating agent), and SAHA (a HDAC inhibitor).

However, numerous compounds had significant activity reducing the recruitment of 53BP1. As an example, Nrf2 activators oltipraz and RA839 were two of the strongest 53BP1 recruitment-reducing compounds in WPMY-1 cells. Nrf2, a transcription factor, plays a role in the DNA damage response (17) and promotes homologous recombination repair (18), which reduces 53BP1 recruitment. Other compounds that impact DNA damage also have activity in our analysis. For example, the ABL1 inhibitor GNF 2 reduced 53BP1 recruitment in both HepG2 and A549 cells, likely through decreasing DNA damage (19). Curiously, usnic acid strongly induced 53BP1 recruitment in A549 cells but strongly prevented recruitment in WPMY-1 cells. However, the mechanism of action of usnic acid in the cellular DNA damage response remains unresolved (20), warranting further exploration of the differences between these cell lines.

We also determined a mechanism of action (MoA) activity score for each MoA containing results from at least 5 compounds through calculating the fraction of compounds with significant activity. Compounds that prevent 53BP1 recruitment have a negative score while compounds that increased 53BP1 have a positive score. Thus, for MoAs with compounds that are both negative and positive, such as PARP inhibitors, the activity score is lower than the total number of active compounds. The MoAs that have the most activity in inducing 53BP1 DNA damage recruitment are ATM, GSK3 and MBT domain inhibitors, all compounds that canonically impact the DNA damage response. Conversely, some of the lowest scoring MoAs were ABL1 inhibitors, which reduce DNA damage (19), FAK inhibitors and LXR agonists, which both impact DNA repair without clear roles (21, 22), mechanistically suggesting that 53BP1 recruitment is reduced in cells treated with these compounds.

Some MoAs contained compounds that either reduced 53BP1 recruitment or increased recruitment. For example, the PARP inhibitor 3-aminobenzamide reduced 53BP1 recruitment in each of the 3 cell lines. However, the PARP inhibitors NVP-TNKS656, NU 1025, and 4-HQN increased 53BP1 recruitment in at least one cell line. Given the history of PARP inhibitors being misclassified (23) and the absence of more advanced clinical PARP inhibitors in the screen, these divergent results could stem from promiscuous or mis-identified compound MoAs.

In the original phenotypic analysis, DNA alkylating agents had no measured activity while PARP inhibitors had very low activity—a surprising finding since both MoAs impact 53BP1 signaling (24, 25). However, our analysis found that DNA alkylating agents indeed have activity: 33% in WPMY-1, 25% in HepG2, and 11% in A549 cells—and PARP inhibitors have a higher activity than previously measured-33% in WPMY-1, 15% in HepG2, and 17% in A549 cells. Overall, the increased activity observed in WPMY-1 cells could arise from higher 53BP1 signaling in these cells or aspects of the imaging and analysis. Unfortunately, images in the phenotypic screen have binned pixels. Binning serves to reduce the number of pixels over which the 53BP1 signal can be autocorrelated and increase the pixel size to limit spatial heterogeneity, which both impact the sensitivity of our analysis (26). In the images, HepG2 cells had the smallest nuclei, while A549 cell nuclei had a 15% bigger area and WPMY-1 cell nuclei were 40% larger. Therefore, autocorrelation analysis of the WPMY-1 is expected to be more sensitive to changes in 53BP1 recruitment. Non-binned pixels would generate 4 times more pixels per nucleus with a quarter of the area, suggesting that non-binned images would generate greater analysis sensitivity.

Discussion

In the original analysis of the imaging dataset no DNA alkylating agents compounds were found to be active. Furthermore, in A549 and WPMY-1 cell lines, the use of TP53BP1 as a marker actually reduced the ability to detect PARP inhibitor activity compared to other protein markers. This was similar for other MoAs that act on DNA or the DNA damage response, such as bromodomain inhibitors and HDAC inhibitors. Considering that 53BP1 is heavily involved in the DNA damage response pathway (27, 28) and many MoAs of the compounds screened act to interfere with the DNA damage response, alter the cell cycle or impact the amount of DNA damage in a cell, it was surprising that TP53BP1 was not a more sensitive marker in the phenotypic screen.

Yet, the recruitment of 53BP1 to sites of DNA damage is typically only resolved through pre-extraction and immunofluorescence (29). In this process, labile nuclear 53BP1 protein is extracted from the cell prior to fixation to reduce the background concentration and increase the resolution of chromatin-bound 53BP1 in DNA damage foci. The phenotypic screen analyzed here used live cells with fluorescently labeled, endogenous 53BP1, which prevents removal of protein not interacting with DNA and reduces the ability to resolve 53BP1 foci. This limitation likely prevents traditional phenotypic analysis from detecting non-resolvable spatial signaling of DNA damage response proteins. Furthermore, pre-extraction is a subjective process that potentially removes protein associated with chromatin and DNA and thus not a robust approach for phenotypic screening generally (30, 31).

Applying spatial image autocorrelation overcomes the limitation of high non-foci background fluorescence to quantify the degree of 53BP1 protein clustering within the nucleus. Here, we found autocorrelation analysis is able to detect compound activity of compounds that generated no activity when analyzed by traditional phenotypic analysis. These results confirm that many of the compounds associated with DNA damage, DNA damage response or cell cycle indeed have activity in the cell lines used in the screen. The results also demonstrate the power of spatial image autocorrelation of labeled specific proteins to quantify compound activity where traditional approaches have less sensitivity. Overall, these results suggest that more complex analysis of specific, yet broadly functional fluorescent labels can reveal compound activity that is not otherwise detectable.

REFERENCES

1. F. Vincent et al., Phenotypic drug discovery: recent successes, lessons learned and new directions. *Nature Reviews Drug Discovery* 21, 899-914 (2022).
2. D. C. Swinney, J. Anthony, How were new medicines discovered? *Nat Rev Drug Discov* 10, 507-519 (2011).
3. J. C. Caicedo, S. Singh, A. E. Carpenter, Applications in image-based profiling of perturbations. *Curr Opin Biotechnol* 39, 134-142 (2016).
4. M. A. Bray et al., A dataset of images and morphological profiles of 30 000 small-molecule treatments using the Cell Painting assay. Gigascience 6, 1-5 (2017).
5. M.-A. Bray et al., Cell Painting, a high-content image-based assay for morphological profiling using multiplexed fluorescent dyes. *Nature Protocols* 11, 1757-1774 (2016)
6. M. Haghighi, J. C. Caicedo, B. A. Cimini, A. E. Carpenter, S. Singh, High-dimensional gene expression and morphology profiles of cells across 28,000 genetic and chemical perturbations. *Nature Methods* 19, 1550-1557 (2022).
7. J. G. Moffat, F. Vincent, J. A. Lee, J. Eder, M. Prunotto, Opportunities and challenges in phenotypic drug discovery: an industry perspective. *Nat Rev Drug Discov* 16, 531-543 (2017).
8 M. J. Cox et al., Tales of 1,008 small molecules: phenomic profiling through live-cell imaging in a panel of reporter cell lines. *Scientific Reports* 10, 13262 (2020).
9 S. Panier, S. J. Boulton, Double-strand break repair: 53BP1 comes into focus. *Nature Reviews Molecular Cell Biology* 15, 7-18 (2014).
10. A. Celeste et al., Histone H2AX phosphorylation is dispensable for the initial recognition of DNA breaks. *Nat Cell Biol* 5, 675-679 (2003).
11. R. A. DiTullio, Jr. et al., 53BP1 functions in an ATM-dependent checkpoint pathway that is constitutively activated in human cancer. *Nat Cell Biol* 4, 998-1002 (2002).
12. J. R. Chapman, M. R. Taylor, S. J. Boulton, Playing the end game: DNA double-strand break repair pathway choice. *Mol Cell* 47, 497-510 (2012).
13. M. V. Botuyan et al., Structural basis for the methylation state-specific recognition of histone H4-K20 by 53BP1 and Crb2 in DNA repair. *Cell* 127, 1361-1373 (2006).
14. P. W. Wiseman, N. O. Petersen, Image correlation spectroscopy. II. Optimization for ultrasensitive detection of preexisting platelet-derived growth factor-beta receptor oligomers on intact cells. *Biophys J* 76, 963-977 (1999).
15. J. Her, C. Ray, J. Altshuler, H. Zheng, S. F. Bunting, 53BP1 Mediates ATR-Chk1 Signaling and Protects Replication Forks under Conditions of Replication Stress. *Mol Cell Biol* 38, (2018).
16. X. Li et al., BRD4 Promotes DNA Repair and Mediates the Formation of TMPRSS2-ERG Gene Rearrangements in Prostate Cancer. *Cell Rep* 22, 796-808 (2018).
17. X. Sun et al., NRF2 preserves genomic integrity by facilitating ATR activation and G2 cell cycle arrest. *Nucleic Acids Research* 48, 9109-9123 (2020).
18. S. Jayakumar, D. Pal, S. K. Sandur, Nrf2 facilitates repair of radiation induced DNA damage through homologous recombination repair pathway in a ROS independent manner in cancer cells. *Mutat Res* 779, 33-45 (2015).
19. N. Brady, T. J. Gaymes, M. Cheung, G. J. Mufti, F. V. Rassool, Increased error-prone NHEJ activity in myeloid leukemias is associated with DNA damage at sites that recruit key nonhomologous end-joining proteins. *Cancer Res* 63, 1798-1805 (2003).
20. W. Wu et al., Usnic Acid Inhibits Proliferation and Migration through ATM Mediated DNA Damage Response in RKO Colorectal Cancer Cell. *Curr Pharm Biotechnol* 22, 1129-1138 (2021).
21. J. Zhou, Q. Yi, L. Tang, The roles of nuclear focal adhesion kinase (FAK) on Cancer: a focused review. *Journal of Experimental & Clinical Cancer Research* 38, 250 (2019).

22. B. Yang et al., The lipogenic LXR-SREBF1 signaling pathway controls cancer cell DNA repair and apoptosis and is a vulnerable point of malignant tumors for cancer therapy. *Cell Death Differ* 27, 2433-2450 (2020).
23. J. Mateo, M. Ong, D. S. P. Tan, M. A. Gonzalez, J. S. de Bono, Appraising iniparib, the PARP inhibitor that never was—what must we learn? *Nature Reviews Clinical Oncology* 10, 688-696 (2013).
24. J. E. Jaspers et al., Loss of 53BP1 causes PARP inhibitor resistance in Brcal-mutated mouse mammary tumors. *Cancer Discov* 3, 68-81 (2013).
25. L. Zhang et al., 53BP1 regulates heterochromatin through liquid phase separation. *Nature Communications* 13, 360 (2022).
26. P. W. Wiseman, Image correlation spectroscopy: principles and applications. *Cold Spring Harb Protoc* 2015, 336-348 (2015).
27. C. Escribano-Díaz et al., A Cell Cycle-Dependent Regulatory Circuit Composed of 53BP1-RIF1 and BRCA1-CtIP Controls DNA Repair Pathway Choice. Molecular Cell 49, 872-883 (2013).
28. A. Fradet-Turcotte et al., 53BP1 is a reader of the DNA-damage-induced $H_2A$ Lys 15 ubiquitin mark. *Nature* 499, 50-54 (2013).
29. L. B. Schultz, N. H. Chehab, A. Malikzay, T. D. Halazonetis, p53 binding protein 1 (53BP1) is an early participant in the cellular response to DNA double-strand breaks. *J Cell Biol* 151, 1381-1390 (2000).
30. M. A. Melan, G. Sluder, Redistribution and differential extraction of soluble proteins in permeabilized cultured cells. Implications for immunofluorescence microscopy. *J Cell Sci* 101 (Pt 4), 731-743 (1992).
31. U. Schnell, F. Dijk, K. A. Sjollema, B. N. G. Giepmans, Immunolabeling artifacts and the need for live-cell imaging. Nature Methods 9, 152-158 (2012).
32. E. Williams et al., Image Data Resource: a bioimage data integration and publication platform. *Nature Methods* 14, 775-781 (2017).
33. U. Schmidt, M. Weigert, C. Broaddus, G. Myers, in *Medical Image Computing and Computer Assisted Intervention—MICCAI* 2018, A. F. Frangi, J. A. Schnabel, C. Davatzikos, C. Alberola-López, G. Fichtinger, Eds. (Springer International Publishing, Cham, 2018), pp. 265-273.
34. N. O. Petersen, P. L. Höddelius, P. W. Wiseman, O. Seger, K. E. Magnusson, Quantitation of membrane receptor distributions by image correlation spectroscopy: concept and application. *Biophysical Journal* 65, 1135-1146 (1993).

Example 4: PARP Trapping is Governed by the PARP Inhibitor Dissociation Rate Constant This Example describes how poly(ADP-ribose) polymerase (PARP) inhibitors (PARPi) trap PARP1 onto DNA. The results described herein show that trapping is not the physical stalling of PARP1 on DNA, rather the high probability of PARP re-binding damaged DNA in the absence of other DNA binding protein recruitment.

Materials and Methods

Cell Culture

Cells were cultured in media supplemented with 10% fetal bovine serum and 1% penicillin/streptomycin. OVCA429 were originally obtained from Dr. Michael Birrer and cultured in DMEM. All other cell lines were obtained from ATCC and cultured in either RPMI or DMEM. PARP1 knockout cells were created using the LentiCrisprV2 system (a gift from Feng Zhang (Addgene plasmid #52961)) (58) and the gRNA targeting PARP1. HCC1937 expressing 53BP1-mApple were described previously (45). UWB1.289 were grown to be olaparib resistant by culturing cells in increasing concentrations of olaparib up to 10 μM.

Anisotropy and Confocal Microscopy

All fluorescence imaging was performed on an Olympus FV1000 multiphoton/confocal microscope. Anisotropy measurements were performed through custom modifications to the imaging system as previously described (30). Briefly, linear polarization of two photon excitation light at 910 nm (MaiTai femtosecond laser, Spectra Physics) was controlled by a glan-thompson prism and half wave plate. Excitation was collected in orthogonal orientations through two detectors, parallel and perpendicular to excitation polarization, through a polarizing beam splitter that replaced a dichroic mirror in the emission filter cube. The alignment and detector gain and noise were validated each imaging session through measurements of a standard slide. Images were taken with an Olympus 25× XLPlan N objective, NA 1.05, and 3× digital zoom. Confocal imaging was performed with an Olympus XLUMPlanFL N 20× objective, NA 1.00 with chromatic correction, and 3× digital zoom.

Drug Dissociation Assay

Cells were grown on 25 mm round, uncoated, sterilized glass coverslips in 6-well plates for 24 hours. Cells were then incubated with PARPi (1 μM) and/or labeled drug (500 nM) in imaging media (phenol-red free DMEM supplemented with 10% FBS and 1% pen-strep) for at least 15 minutes. Coverslips were removed from the 6-well plates, mounted onto a perfusion chamber (Warner Instruments), sealed with vacuum grease and perfused with a custom tubing setup. The chamber was then mounted onto the microscope and temperature was maintained at 37° C. using a heating pad and feedback loop. Cells were initially located using fluorescent drug or autofluorescence and allowed to temperature equilibrate on the microscope stage for at least 5 minutes. Images were acquired using the anisotropy configuration as described above. After initial images were acquired, the chamber was perfused with 10× volume of the wash media containing fluorescent drug while chamber media and excess wash media were aspirated out of the chamber with vacuum. Images were then acquired at the desired time points while correcting for any drift. Association of fluorescent drug measurements were performed through rapid addition of media containing fluorescent drug (500 nM) and immediate image acquisition.

Nuclei were segmented in MATLAB and the average nuclear intensity and anisotropy were calculated using the regionprops function. The ΔrINT value was calculated as previously described (29) (Supplemental Data). Values were then plotted as a function of time, with t=0 when PARPi was removed, in Prism (Graphpad) and a one phase association curve was fit to obtain the binding rate. The fitted association rate was used to determine the dissociation or association constant.

Immunofluorescence

Cells were plated in 8-well 12-well slides (Thermo or Ibidi) to achieve 50% confluence overnight. Cells were then treated and fixed with 4% paraformaldehyde in PBS at room temperature for 10 minutes. Antibody staining was performed according to the manufacturers protocol. Following fluorescent secondary antibody labeling, prolong gold with DAPI (Cell Signaling Technologies) was added and samples were stored for up to 1 week prior to imaging.

Image Correlation Spectroscopy

ICS analysis was performed in MATLAB as previously described (41). Briefly, nuclei were segmented from the DAPI channel with the MATLAB function, imbinarize, converting the greyscale image to a binary dependent on an automatically defined threshold. The MATLAB function, regionprops, was used to identify single nuclei as objects. Each nucleus was used as a mask to perform ICS analysis on the antibody-stained channel, within size limitations for a nucleus (objects >400 and <3000 pixels). To ensure the analysis of antibody stained nuclei, nuclei under an average intensity of 200 au after background subtraction were excluded. The spatial autocorrelation functions were calculated using Fourier methods, then fit to a 2D Gaussian using a nonlinear least-squares algorithm (41). Using the outputs of the fitting, the mean number of independent emitting fluorescent entities per focal spot area and subsequently the DA were determined (59). DA measurements across experiments were normalized by the control in each dataset. The confocal imaging settings were kept the same across each dataset to provide comparable measurements per dataset. Any DA values exceeding 3 standard deviations from the mean were defined as incorrectly segmented and removed. Data were plotted in Prism and analysis performed in Prism or Excel.

Condensate Anisotropy Measurements

Cells were grown on 12 mm round, uncoated, sterilized glass coverslips in 24-well plates for 24 hours. Cells were treated with PARPi and 100 μM TMZ for 1 hour or 10 nM GMX1778 overnight followed by 100 μM TMZ for 1 hour. TMZ was added to stimulate new DNA damage induced condensates in the presence of PARPi or NAD" depletion. Cells were then transferred to the microscope for anisotropy imaging. Images were analyzed in MATLAB. Nuclei were segmented through intensity thresholding and condensates were segmented through further intensity thresholding with a higher threshold. Values of segmented nuclei and condensates were determined through the regionprops function. Segmentation was corrected through area restrictions to ensure that regions of interest were isolated condensates. The thresholding parameters were consistent throughout experiments. The average intensity and anisotropy of each segmented nuclei or condensate was then calculated. Data were plotted in Prism and analysis performed in Prism or Excel.

Dose Response

Cells were plated in a 96-well plate at $2\times10^3$ cells per well and treated with drug for 5 days in three replicate wells. Cell viability was then determined using Presto Blue (Thermo Fisher). Signal was averaged over 3 replicate wells and normalized to blank (no cells) as well as to the levels of untreated wells. A sigmoidal response curve was fit to the average of two experiments in Prism. PARPi z score was calculated for each PARPi using 9 cell lines. The average z score over three PARPi (veliparib, olaparib, talazoparib) was then determined as a representation of cell line PARPi sensitivity.

Western Blotting

Cells were lysed with RIPA buffer (Thermo Fisher) containing protease inhibitors (Thermo Fisher), vigorously vortexed and incubated on ice for 15 minutes. Lysate was then pelleted by centrifugation at 14,000 g for 15 min at 4° C. Supernatant was transferred to a clean tube and total protein was determined using a BCA assay (Pierce). Protein was loaded into a NuPAGE gel (Thermo Fisher) and transferred to nitrocellulose paper (Thermo Fisher). Blocking and antibody labeling was then carried out according to the antibody manufacturer's protocol. For PAR measurements, cells were treated with TMZ for 1 hour, or 1 μM $H_2O_2$ for 10 minutes in 6-well plates. Cells were trypsinized and washed once with PBS prior to cell lysis. Western blot expression levels were quantified by inverting the red channel of an image of the blot in FIJI, subtracting the background intensity and measuring the total intensity of the lane. These values where then normalized to the control signal.

Chromatin Fraction Analysis

Cells in 6-well plates were treated with PARPi or GMX1778 for 24 hours. The media was removed, and cells were scraped off the culture dish in 1 ml PBS. The cells were pelleted by centrifugation at 500 g for 4 minutes at 4° C. and the solution was removed. Pellets were resuspended in 250 μl lysis buffer (10 mM HEPES, 10 mM KCl, 1.5 mM $MgCl_2$, 340 mM sucrose, 10% glycerol, 0.1% Triton X-100, pH 7.9, protease inhibitors (Thermo Fisher)) and incubated on ice for 10 minutes. Nuclei were separated by centrifugation at 1300 g for 5 minutes at 4° C. and the solution was collected (cytoplasm fraction). Nuclei pellets were then washed with 100 μl lysis buffer lacking triton X-100 and centrifuged at 1300 g for 2.5 minutes at 4° C. Pellets were then resuspended in 100 μl nuclear lysis buffer (50 mM HEPES, 250 mM KCl, 2.5 mM $MgCl_2$, 0.1% Triton X-100, pH 7.5, protease inhibitors (Thermo Fisher)), vortexed at the highest setting for 5 seconds and incubated on ice for 10 minutes. The chromatin fraction was then pelleted by centrifugation at 15,000 g for 10 minutes at 4° C. and the solution was collected (nuclear fraction), the pellet was resuspended in 100 μl nuclear lysis buffer and re-pelleted by centrifugation at 15,000 g for 10 minutes at 4° C. The pellet was then resuspended in 50 μl DNA release buffer (50 mM HEPES, 150 mM KCl, 2.5 mM $MgCl_2$, 5 mM $CaCl_2$), 0.05% Triton X-100, pH 7.5, protease inhibitors (Thermo Fisher)) and incubated at 37° C. for 10 minutes. The solution was then centrifuged at 15,000 g for 10 minutes at 4° C. and the solution collected (trapped fraction). All solutes were collected for western blot analysis.

PAR Binding Peptide Synthesis

The PAR binding peptide was synthesized by Genscript and dissolved in PBS containing 100 mM molar tris-carboxyethylphosphine (TCEP), pH 7.4 to a final concentration of 1 mM in 3 ml and degassed with vacuum. BODIPY FL maleimide (Thermo) was dissolved in DMSO to a concentration of 60 mM in 200 μl. The dye was added to the peptide, flushed with argon and allowed to react overnight at 4° C. BODIPY FL peptide was purified by prep-HPLC and validated by LC-MS (Agilent). The fluorescent peptide was lyophilized over two days and dissolved in PBS at 1 mM.

ODE Model of PARP-DNA Binding

Our ODE model is solved in MATLAB using ODE45, a non-stiff solver. The script is available at github.com/dubachLab/parpTrapping/.

This model determines the duration of PARP1 engagement with DNA using previously established binding constants. Starting from the PARP1-DNA complex PARP1 can either release from DNA, self-PARylate to $PAR_n=1$, or bind to PARPi to form the trapped complex. From trapped PARP (PARP1-DNA-PARPi complex) the PARPi-PARP1 pair can dissociate from DNA with the drug occupancy remaining intact or PARPi can dissociate from the PARP1-DNA complex. In our model, each PARylation of PARP1 creates a new species that can undergo any of the steps as the previous PARP1 species. Once PARP1 dissociates from DNA it cannot rebind, thus we are modeling the duration of a singular PARP1-DNA binding event. Here, our initial values consist of complete PARPi-PARP1-DNA complexation with no prior PARylation. For simplicity we consider self PARylation as the only PARylation reaction. Although PARP1 does PARylate numerous other proteins, they theoretically do not impact PARP1-DNA affinity. Thus, omission of these alternative PARylation reactions only impacts the number of PARylation events prior to PARP1 forced removal from DNA, or the effect of PAR accumulation on PARP1 affinity for DNA. However, as is demonstrated by the results, PARP1 dissociation from DNA primarily occurs prior to PARylation forced removal, therefore we do not consider the absence of other PARylation targets to impact the results. Adjusting the rate constants, and other reaction parameters, provides a route to investigate how rates impact PARP1-DNA binding duration. These constants and parameters are defined and described below.

Species

PARP1: Poly(ADP-ribose) polymerase. Here, the PAR status of PARP1 defines the species. For example, unPARylated PARP1 is a different species than PARP1 with one ADP-ribose modification, which is a different species than PARP1 with two ADP-ribose groups.

PARPi: PARP inhibitors.

PAR: Poly(ADP-ribose). PAR can only exist PARP1.

Reactions and Binding Events

For each round of PARP1 PARylation the following reactions and binding events can occur.

PARP1 dissociation from DNA.

PARP1-DNA association with PARPi.

PARPi dissociation from PARP1-DNA.

PARPi-PARP1 dissociation from DNA.

PARP1 self-PARylation.

Constants and Variables

Figure 19A:
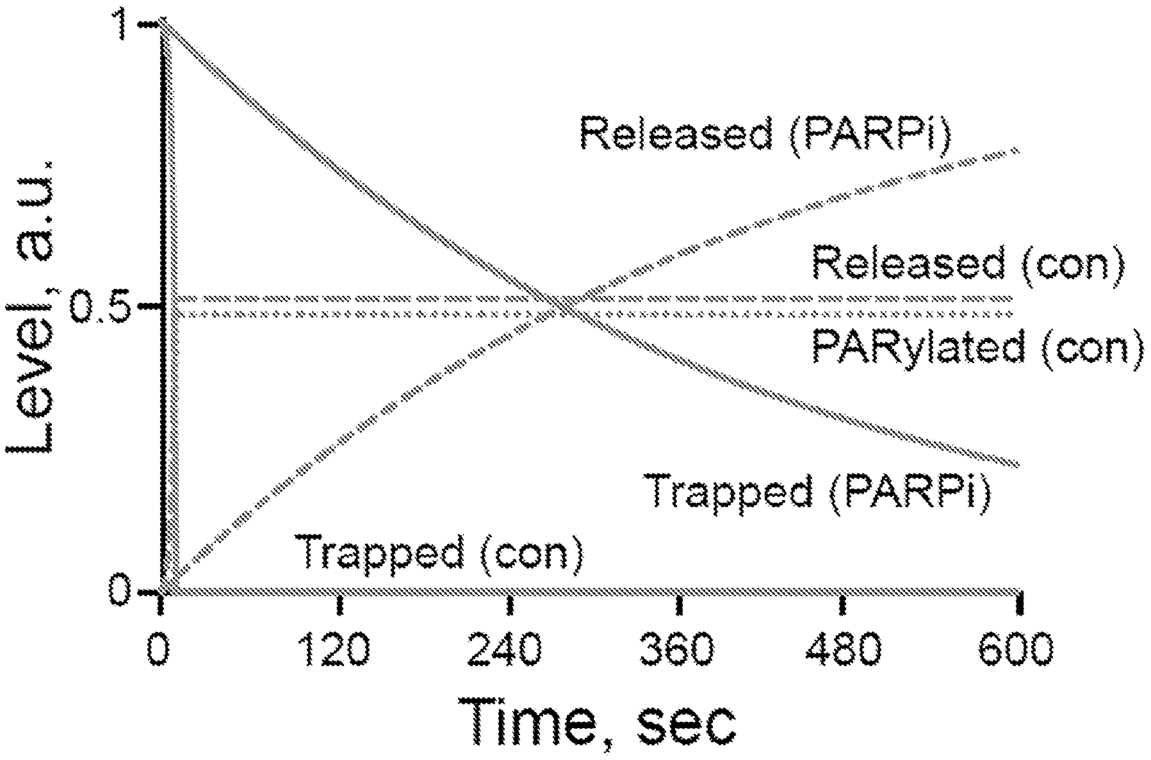
FIGS. 19A-19F: The impact of variables on the ODE model of PARP1-DNA interaction.
Figure 19B:
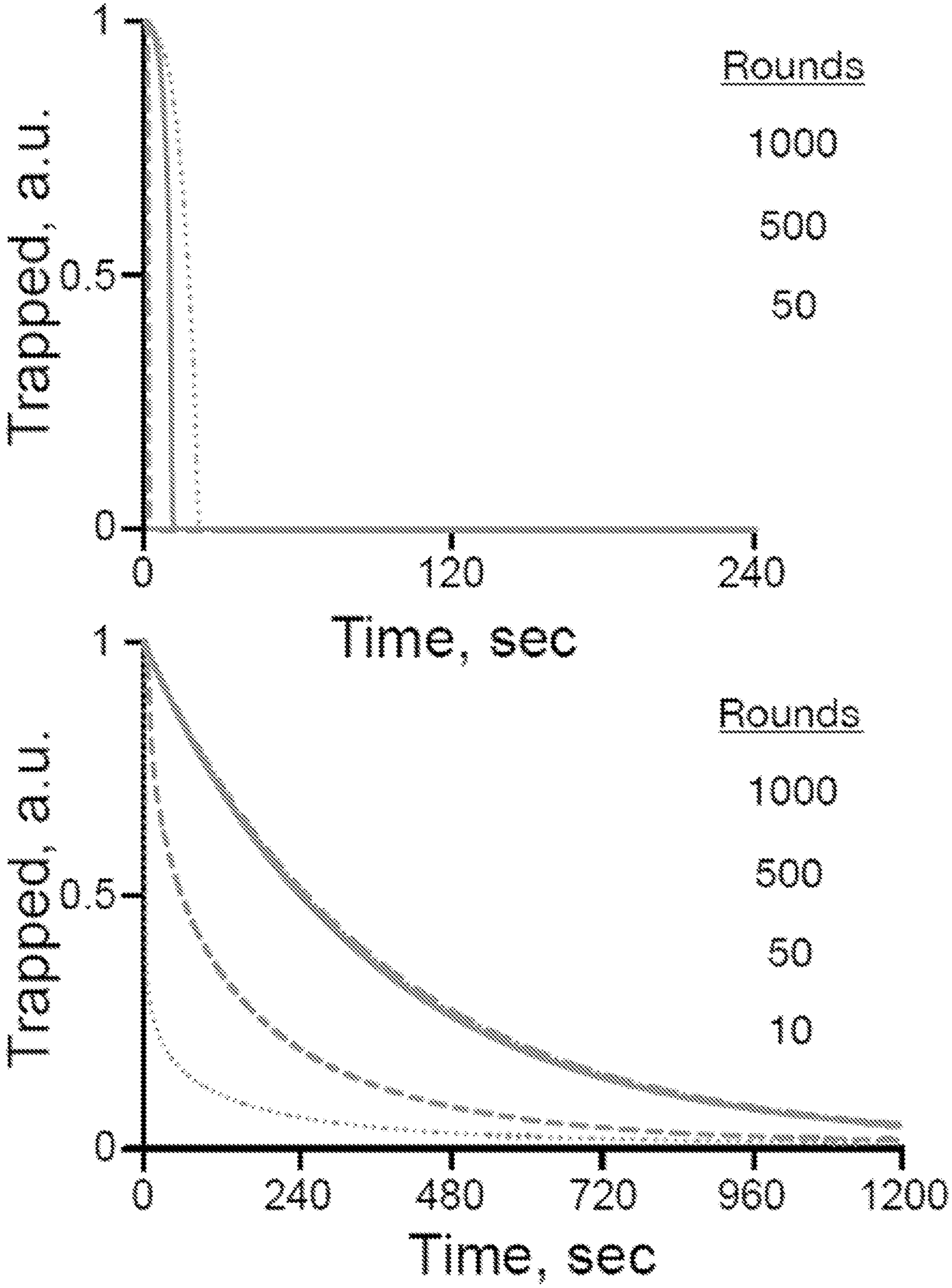

Rounds: The number of PARP1 self-PARylation events that occur prior to electrostatic removal of PARP1 from DNA. Here the default is 500. A higher number of rounds (greater PARylation prior to forced release) only slightly increased PARP1-DNA residence in the absence of drug without impacting trapping in the presence of 1 μM olaparib (FIG. 19B). However, a lower number of rounds decreased the PARP1-DNA residence and olaparib induced PARP1 trapping. The lower number of rounds allows PARP1 to dissociate much faster due to: 1) the γ affinity correction factor being spread out over fewer rounds, and 2) complete PARylation ($PAR_n$=rounds) forcing removal of PARP1 from DNA.

$k_a$ (trap): The association constant of PARPi for PARP1. This rate constant has previously been shown to be independent of PARP1 engagement to DNA18. Values were taken as an average of previous measurements. The default values used were: veliparib $1.8\times10^{6}$ $M^{-1}s^{-1}$; olaparib $2\times10^{5}$ $M^{-1}s^{-1}$; talazoparib $3.6\times10^{5}$ $M^{-1}s^{-1}$.

$k_d$ (trap): The dissociation of PARPi from PARP1-DNA. This rate constant has previously been shown to be independent of PARP1 engagement to DNA18. Values were taken as an average of previous measurements. The default values used were: veliparib $5\times10^{-3}s^{-1}$; olaparib $3\times10^{-4}$ $s^{-1}$; talazoparib $8\times10^{-5}$ $s^{-1}$.

Drug Concentration: The PARPi Concentration in the Cell.

Figure 19C:
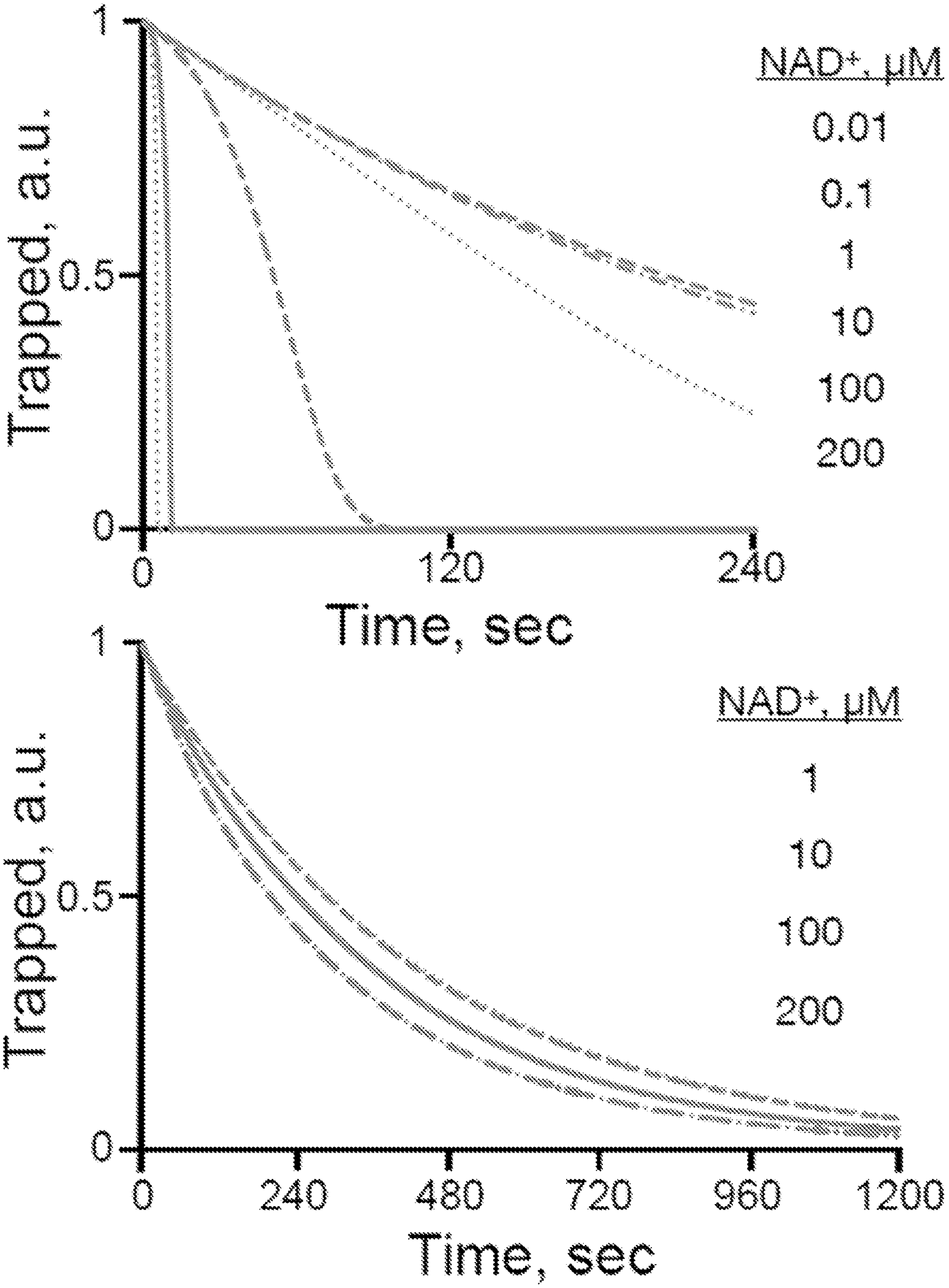

NAD' concentration: The default concentration of NAD" in the nucleus was 100 μM (60, 61). The concentration of NAD" in the ODE solution greatly impacted the PARP1-DNA residency time in the absence of drug, while having slight impact of PARP1 trapping in the presence of 1 μM olaparib (FIG. 19C). A higher concentration increased release of PARP1, while a lower concentration extended PARP1-DNA binding. With olaparib present the increased trapping reaches a plateau at 10 μM, 10% of the actual nuclear concentration. However, in the absence of drug the impact doesn't plateau until a concentration of 100 nM, where the PARP1-DNA residency is similar to that of the presence of 1 μM PARPi under normal $NAD^+$ concentrations. Thus, below 100 nM, PARP1 release from DNA is driven solely by PARP1 affinity for DNA and independent of the impact of PARylation.

Figure 19D:
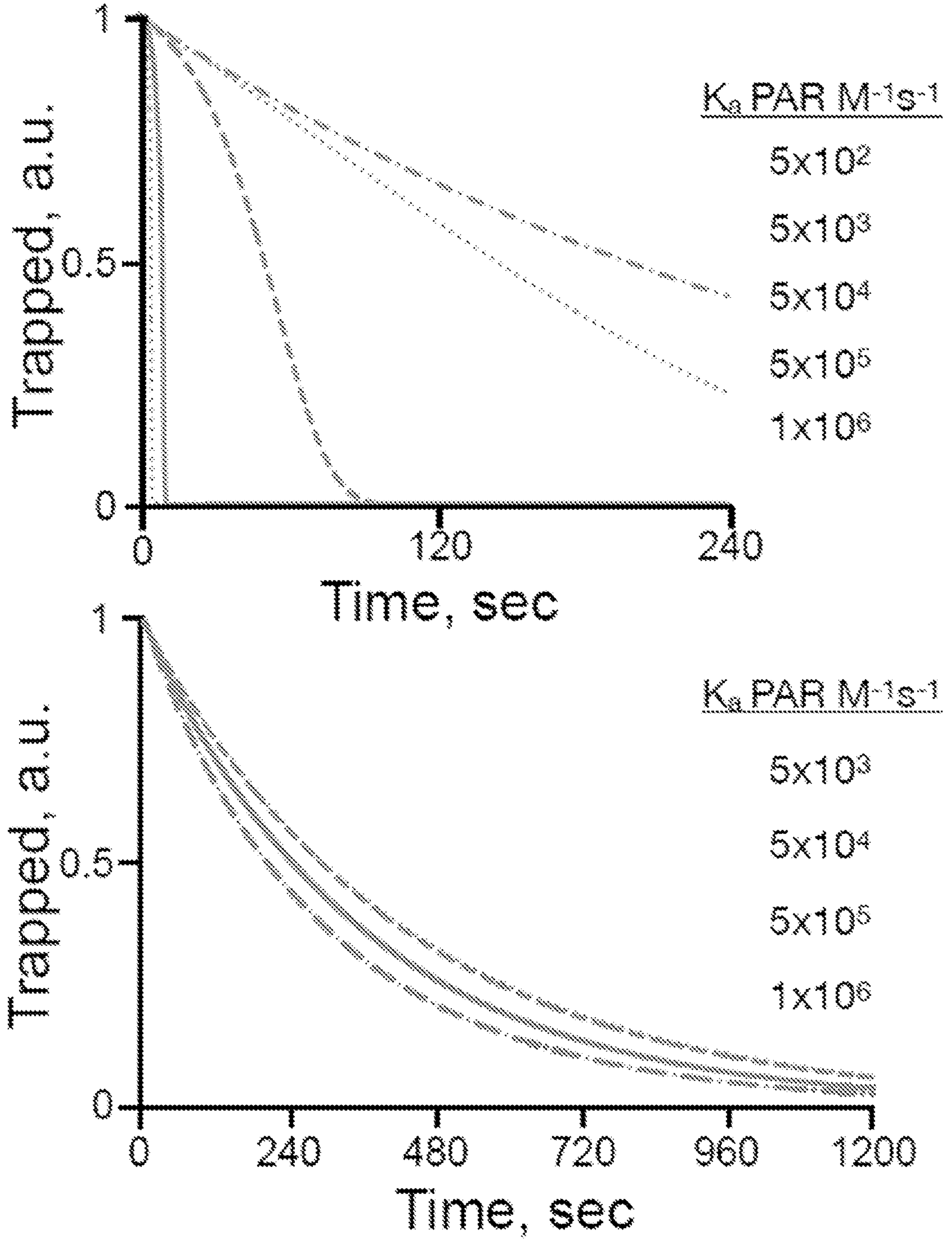
Figure 19E:
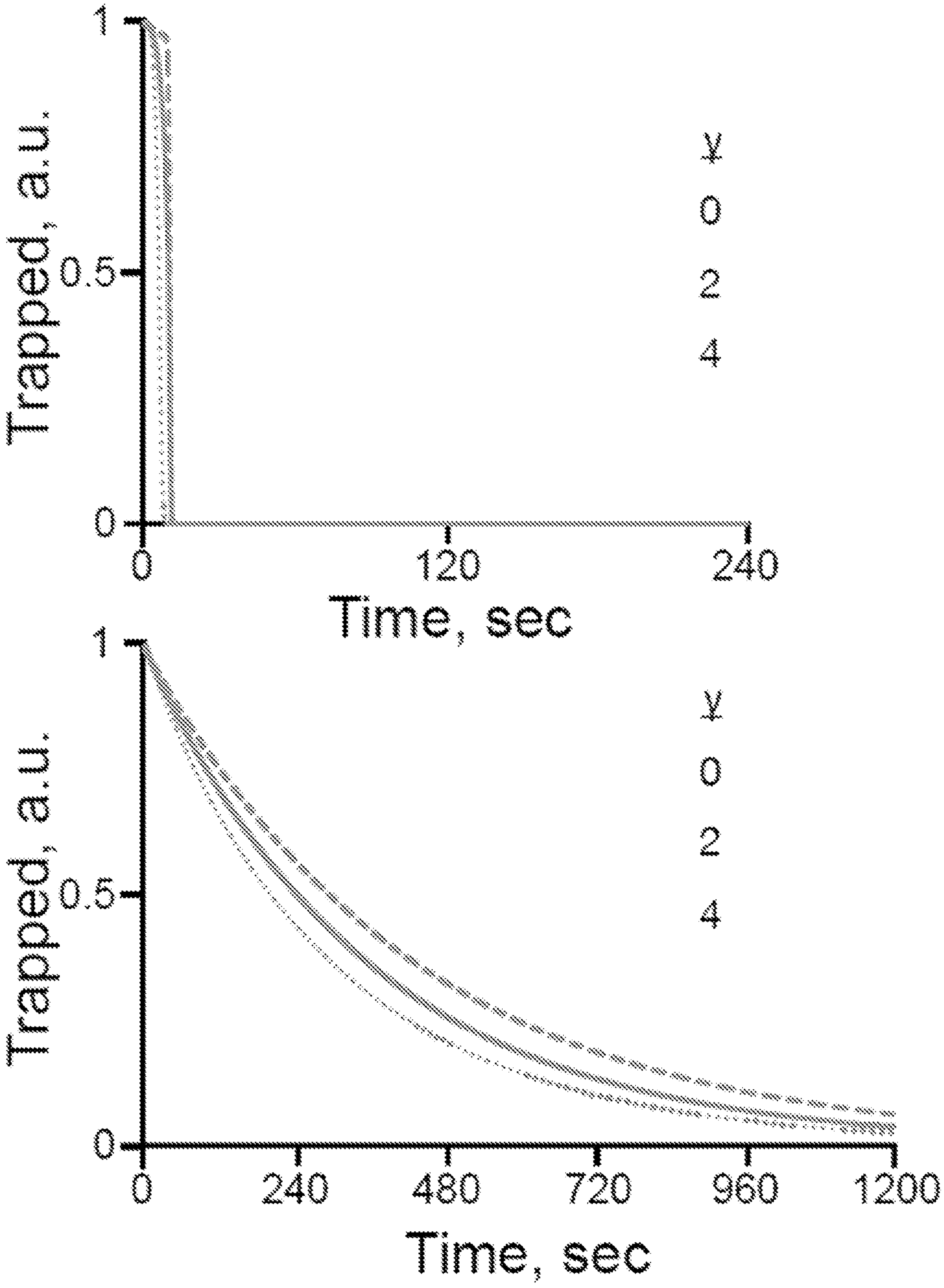

$k_a$ (par): The association constant of NAD" for PARP1. Here, for simplicity, self-PARylation occurs immediately upon $NAD^+$ binding PARP1-DNA. The default value was 5e5 $M^{-1}s^{-1}$, derived from previously measured $K_m$ values[37]. The impact of $k_a$ (par) is nearly identical to the concentration of NAD" since the rate of PARylation is dependent on the product of the two (FIG. 19D).

γ: PARP1 loses affinity for DNA as it becomes PARylated, which arises from electrostatic repulsion. Thus, γ is a correction factor that confers PAR dependency on the affinity of PARP1 for DNA. This correction factor serves to increase the dissociation rate constant of both PARP1 and PARPi bound PARP1 for DNA. The value of γ is the number of order of magnitudes that the rate constants will change over the number of rounds. The correction is applied in a log scale to the binding rate constants. The default of γ is 2, meaning that the binding constants will change two orders of magnitude over the number of rounds. The value of γ slightly altered the PARP1-DNA residence time in the absence of drug and PARP1 trapping in the presence of 1 μM olaparib (FIG. 19E). Lower values of γ increase the PARP1-DNA interaction through maintaining the default PARP1 DNA and PARPi-PARP1 DNA affinity during increasing PARylation. Thus, when γ=0, there is a two-phase response in the absence of drug-initially where PARP1 dissociates from DNA and a more rapid decrease where complete PARylation causes removal from DNA. Higher values of γ decrease the PARP1-DNA interaction through a greater loss of DNA affinity as a function of PARylation.

Figure 19F:
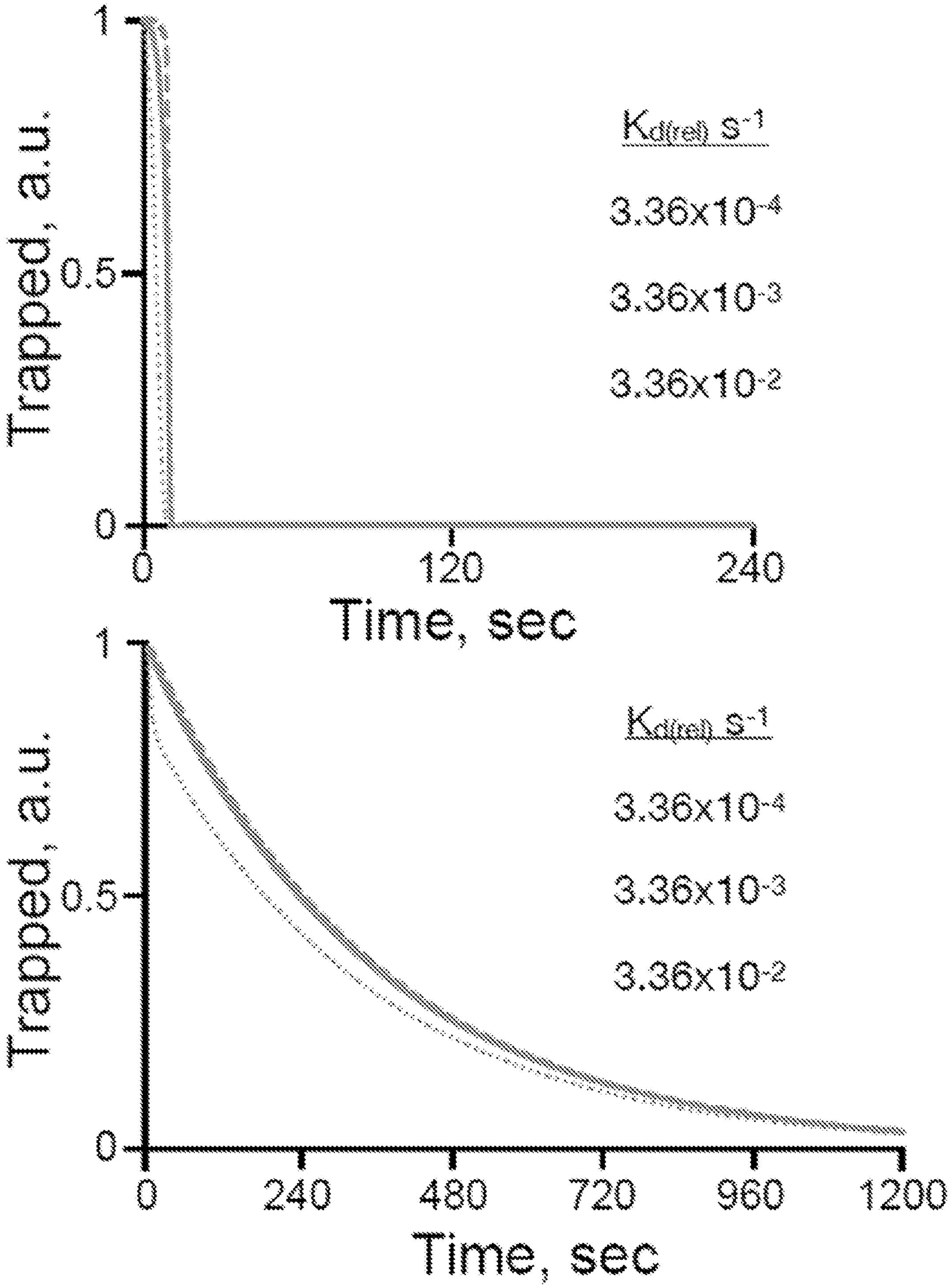

$k_d$ (rel): The dissociation constant of PARP1 from DNA. This rate is dependent on the correction factor γ and the degree of PARP1 PARylation. The default value was $3.36\times10^{-3}$ $s^{-1}$. This constant had minimal impact on PARP1-DNA interactions (FIG. 19F). Lower values (greater affinity) did not impact PARP1 trapping in the presence of 1 μM olaparib, demonstrating that PARP1 is largely occupied by olaparib. Higher values in the presence of 1 μM olaparib lowered the initial starting position as PARP1 dissociated from DNA prior to binding olaparib. In the absence of drug, higher values caused more rapid dissociation from DNA, as expected, while lower values shifted dissociation of PARP1 from DNA toward completely PARylated forced release, creating a delayed, steeper response.

$k_d$ (rel PARPi): The dissociation constant of PARPi-PARP1 from DNA. This rate is dependent on the correction factor γ and the degree of PARP1 PARylation. The default values used were: veliparib $4.08\times10^{-3}$ $s^{-1}$; olaparib $2.31\times10^{-3}$ $s^{-1}$; talazoparib $2.52\times10^{-3}$ $s^{-1}$.

Apparent $K_{OFF}$ Measurement Model

Figure 13A:
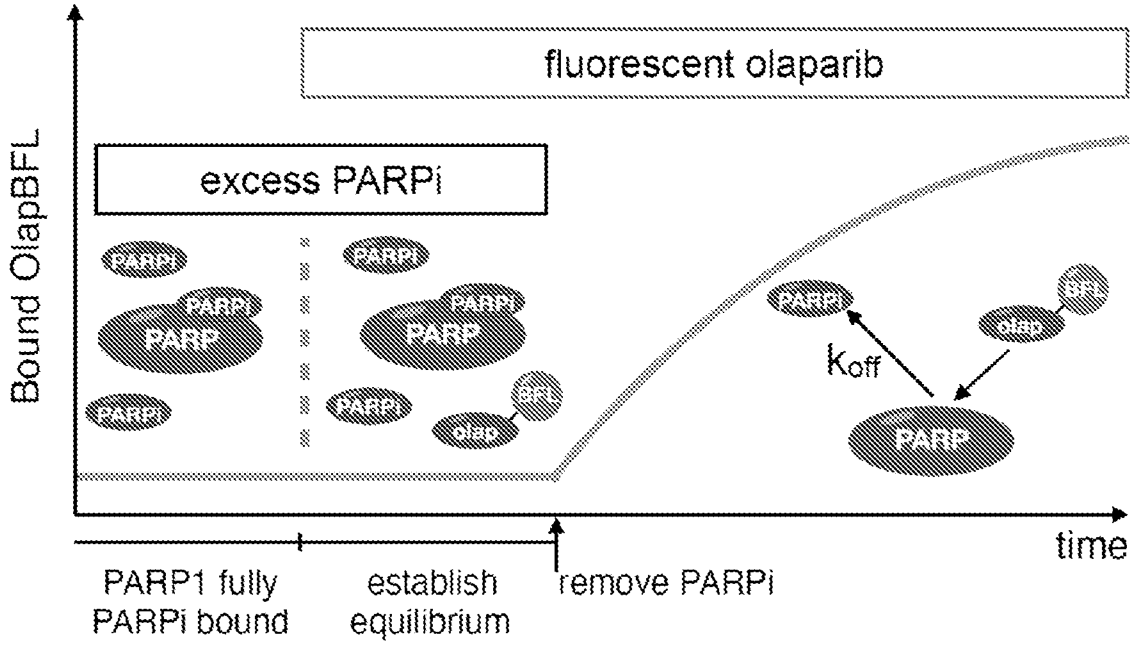
FIGS. 13A-13E: The PARPi-PARP1-DNA complex is not stabilized in cells but is PARP1 activity dependent.

Here we developed an assay to measure the intracellular dissociation constant of PARPi through binding of fluorescently labeled olaparib (FIG. 13A). PARPi at 1 μM is first applied to cells to saturate the target. Fluorescent olaparib at 500 nM is the added and allowed to diffuse into the cell to establish a concentration equilibrium. The higher concentration and affinity of the clinical PARPi ensures the target remains occupied. The unbound clinical PARPi is then removed through excess washing while the fluorescent olaparib remains. The competition experiment to measure intracellular apparent dissociation constants is set up so that t=0 occurs once free, unlabeled drug is removed from the system. The dynamic changes in drug target occupancy can then be defined by a set of ordinary differential equations:

$$\frac{d[RD]}{dt} = -k_{off}[RD] + k_{on}[D][R] \quad (1)$$

$$\frac{d[R]}{dt} = k_{off}[RD] + k_{off}[RD_f] - k_{on}[D_f][R] - k_{on}[D][R] \quad (2)$$

$$\frac{d[RD_f]}{dt} = -k_{off}[RD_f] + k_{on}[D_f][R] \quad (3)$$

where, [R]=the concentration of free target, [D]=the concentration of free drug, [$D_f$]=the concentration of fluorescently labeled drug, [RD]=the concentration of target bound drug, and [$RD_f$]=concentration of target bound fluorescently labeled drug. At t=0 all target is bound by drug ($[R]_{tot}$=[RD]). We also assume that all free drug is removed from the system ($k_{on}$ [D][R]=0). Furthermore, due to the high concentration of fluorescently labeled drug, we assume that all target will be immediately bound by fluorescent drug once unlabeled drug dissociates and that, once engaged to fluorescent drug, target will remain occupied, or $k_{on}$ [$D_f$][R] >>$k_{off}$ [$RD_f$]. Thus, the amount of fluorescent drug bound to target is equal to the total amount of target minus the unlabeled drug bound target:

$$[RD_f] = [R]_{tot} - [RD] \quad (4)$$

Solving the differential equations with the above criteria we obtain:

$$[RD] = [R]_{tot}\exp(-k_{off}t) \quad (5)$$

$$[RD_f] = [R]_{tot}(1 - \exp(-k_{off}t)) \quad (6)$$

with the boundary conditions:

$$\text{at } t = 0,\ [RD] = [R]_{tot}$$

$$\text{at } t = \infty,\ [RD] = 0$$

$$\text{at } t = 0,\ [RD_f] = 0$$

$$\text{at } t = \infty,\ [RD_f] = [R]_{tot}$$

Figure 20A:
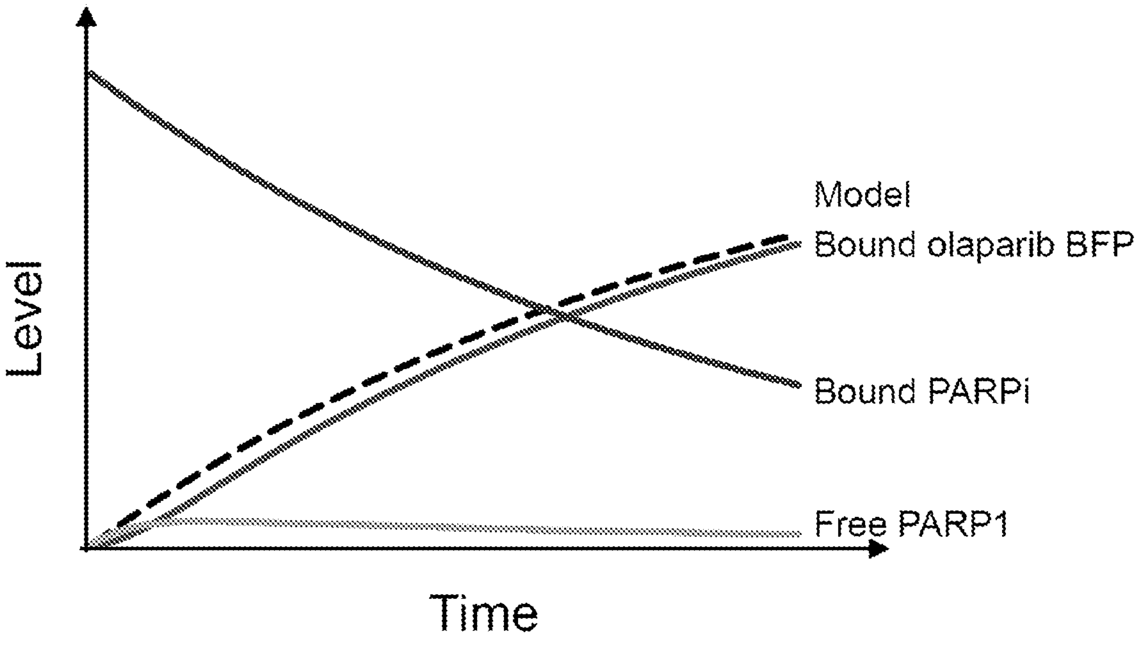
FIGS. 20A-20D: Validation of PARPi dissociation measurements.
Figure 20B:
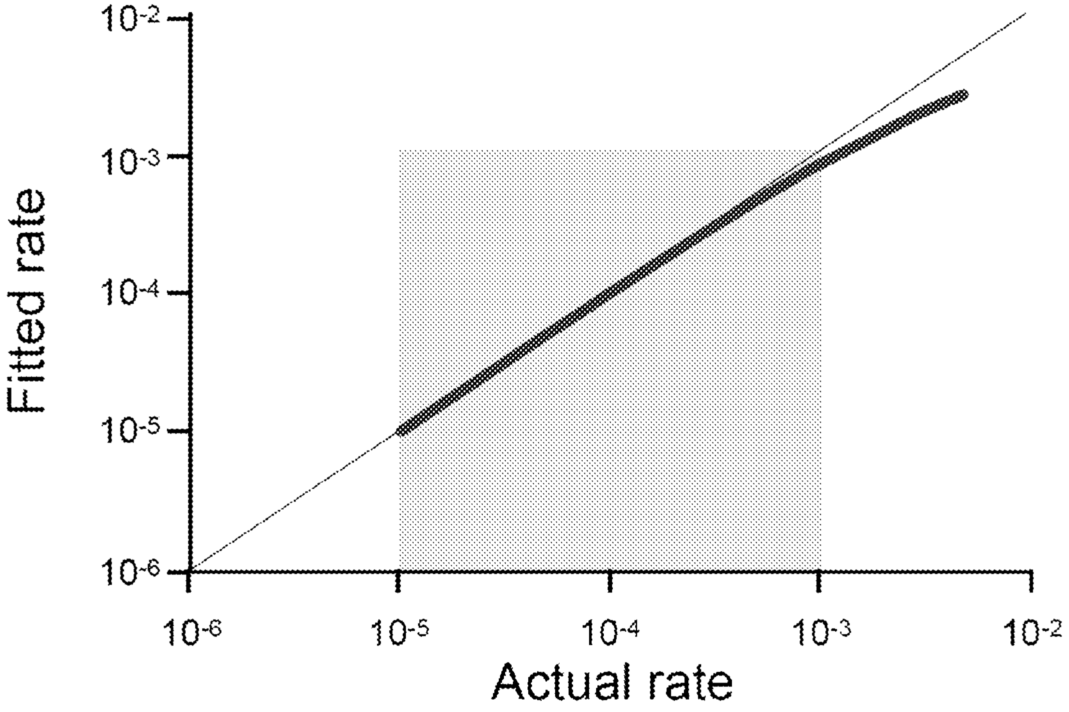
Figure 20C:
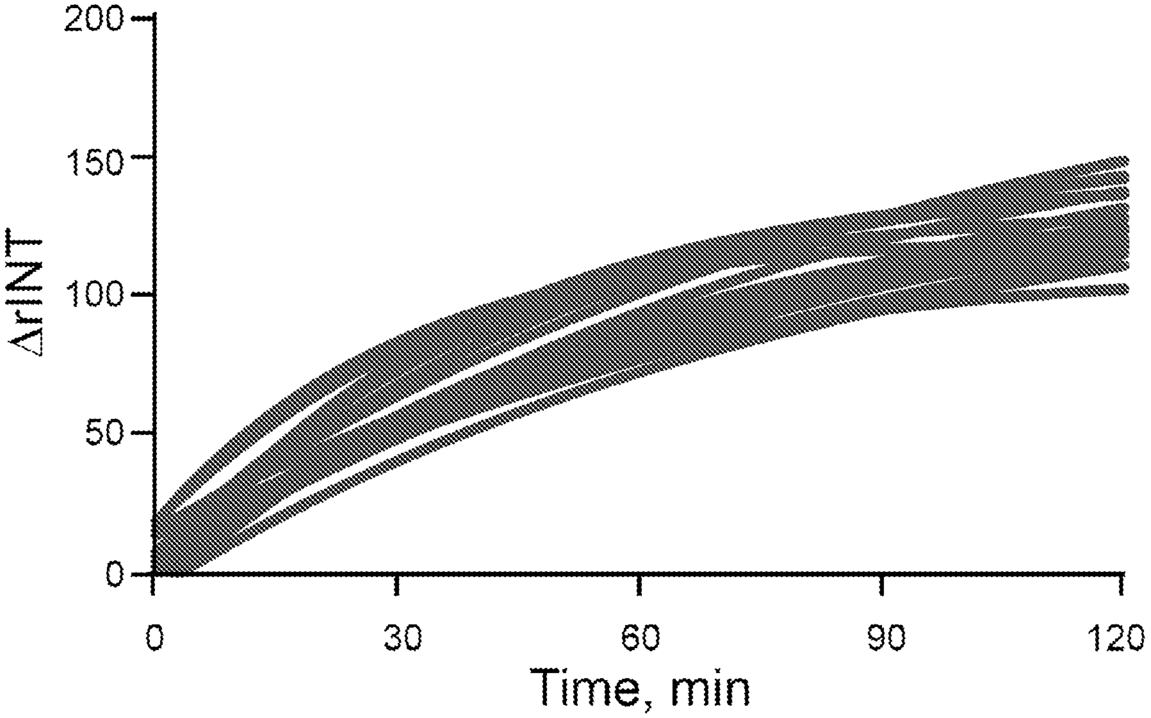
Figure 20D:
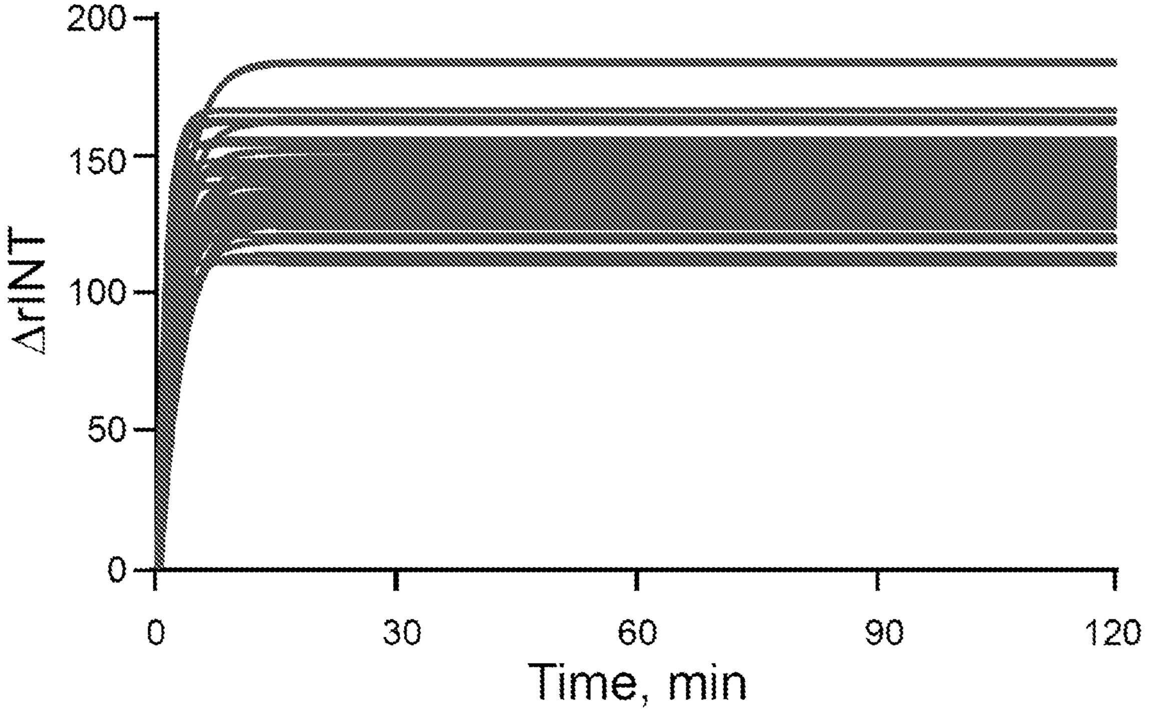

This ODE solution closely approximates discreet ODE solvers (FIG. 20A). This solution only slightly overestimates the amount of bound fluorescent drug as the clinical drug dissociates over time when compared to a stiff ODE solver (ODE15s, MATLAB). Here, we use a drug-target dissociation constant of $3\times10^{-4}$ $s^{-1}$, a fluorescent drug-target dissociation constant of $3\times10^{-6}$ $s^{-1}$, a fluorescent drug-target association constant of $2\times10^{4}$ $M^{-1}s^{-1}$, and a fluorescent drug concentration of 500 nM. The difference between the ODE solution and solver largely arises from the presence of a small amount of free target calculated by the ODE solver (FIG. 20A). In our model we assume any free target is immediately occupied by fluorescent drug. However, both capture the association of fluorescent drug as clinical drug dissociates from the target. And, our approximation is valid through the expected range of dissociation rates (FIG. 20B)

Here we determine the amount of target bound fluorescent drug through measuring the fluorescence anisotropy in each imaging voxel (29, 30). Anisotropy is an ensemble average of discreet anisotropy states of all fluorophores in each voxel, therefore anisotropy can be defined as the following:

$$r = \sum_{n=1}^{i} \frac{r_n N_n}{N_{tot}} \quad (7)$$

where r=anisotropy, In is the anisotropy of the fluorophore state n, $N_n$ is the number of fluorophores in the state n, and $N_{tot}$ is the total number of fluorophores in the voxel. Here, we assume a two-state system where the fluorescent drug can be labile in the cell or bound to the target. Therefore:

$$r = \frac{r_{bound}[RD_f] + r_{labile}[D_f]_{labile}}{[D_f]_{tot}} \quad (8)$$

where $r_{bound}$=anisotropy of a target bound fluorescent drug, [$RD_f$]=the concentration of target bound fluorescent drug, $r_{labile}$=anisotropy of unbound fluorescent drug, $[D_f]_{labile}$=the concentration of unbound fluorescent drug, and $[D_f]_{tot}$=the total concentration of fluorescent drug. Additionally, the total concentration of drug in each voxel is equal to the sum of unbound and bound:

$$[D_f]_{tot} = [D_f]_{labile} + [RD_f] \quad (9)$$

Solving for bound fluorescent drug we derive the expression:

$$[RD_f] = \frac{r - r_{labile}}{r_{bound} - r_{labile}}[D_f]_{tot} \quad (10)$$

If we assume no fluorophore quenching or photobleaching and a linear relationship between fluorescence intensity and fluorescent drug concentration, we can express voxel intensity as:

$$Int = \gamma[D_f]_{tot} \quad (11)$$

where Int=measured intensity and $\gamma$ is a constant. Combining equations 6, 10 and 11 we derive:

$$(r - r_{labile})Int = (r_{bound} - r_{labile})\gamma[R]_{tot}(1 - \exp(-k_{off}t)) \quad (12)$$

where ($r_{bound}$-$r_{labile}$) $\gamma$ $[R]_{tot}$ is a constant expression. Thus, for each voxel, the measured anisotropy corrected by the unbound anisotropy value and multiplied by the intensity is a function of time. This value, (r-$r_{labile}$)Int, which we refer to as ΔrINT, is a measurement of the amount of fluorescent drug bound to target (29). As such, it can be directly used to determine the dissociation constant ($k_{off}$) of unlabeled clinical drug in cells. Here, we determine $k_{off}$ by fitting an exponential using Prism to the ΔrINT signal over time following removal of free clinical drug from the system.

Stochastic Simulation Model

The Gillespie simulation is a stochastic algorithm to advance the binding reactions within a biomolecular condensate through Monte-Carlo inversion steps. Each reaction in the system is associated with a variable propensity function an, where n is the number of possible events. The propensity function is dependent on both the reaction/binding rate and the concentration of the species involved. Each propensity function is updated after every time step. The simulation begins at $t=t_0=0$, and two random numbers are initialized, $r_1$ and $r_2$. The first random number generates the time step, t, otherwise referred to as the sojourn time, at which the next reaction occurs, through the following equation:

$$\tau = \frac{1}{\sum_n a_n}\ln\left(\frac{1}{r_1}\right) \tag{13}$$

The second random number selects the reaction that occurs at $t_1=t_0+\tau$, by minimizing the index n such that:

$$\sum_{i=1}^{i} a_i > r_2 \sum_n a_n \tag{14}$$

Here, the reaction that satisfies the above criteria is selected and the distribution of molecules in the system is updated. The simulation then continues at $t=t_1=t_0+\tau$, where $\tau$ and the selected reaction are determined through newly generated random numbers, and repeats until $t>=t_{end}$, or a maximum number of reactions has occurred.

In our model, if a PARylation reaction is selected, which can only occur if uninhibited PARP1 is bound to DNA, a random PARP1 protein or histone is selected based on the total number of each species in the system. Each PARP1 is separately identified based on the number of ADP-ribose molecules that have previously been attached, however histones serve as a pool of PAR targets and are not tracked individually. After PARylation, either the PAR status of the selected PARP1 is updated, or the histone PAR level is updated, depending on which was selected for PARylation, and the total system PAR level is updated.

If a PARP1 exchange reaction is selected, then the PARP1 that was randomly chosen will be replaced with a PARP1 that lacks ADP-ribosylation—an exchange with PARP1 from outside the condensate. Here, we omit exchange of unPARylated PARP1, since that would not impact the status of the system. Thus, PARP1 in the system that has no PARylation cannot be selected for PARP1 exchange. After an exchange the total PAR in the condensate is updated At each step a random number is generated to stochastically decide if a DNA binding protein will enter the condensate. The likelihood of this protein entering the condensate is a function of both the protein threshold parameter (p.prot_thresh) described below and the total PAR in the condensate. If a DNA binding protein enters the condensate the number of proteins is updated, here these proteins cannot leave the condensate.

We implemented the Gillespie algorithm in MATLAB using the species, reactions, and constants described below.

The script is available at github.com/dubachLab/parpTrapping/.

Species

Damaged DNA: Each condensate contains a single site of DNA damage that is capable of binding PARP1, the PARPi-PARP1 complex or DDR.

DDR: DNA binding proteins that can be recruited to condensates in a PAR dependent manner. DDR can bind to damaged DNA.

PROT: Proteins that are the target of PARP1 PARylation-PARP1 or histones.

Histones: Histone proteins are PAR targets and have a fixed condensate concentration. Here, histones are representative of any PAR targets that accumulate in the condensate and do not leave, however they are unable to bind damaged DNA.

PARP1: Poly(ADP-ribose) polymerase. Here the PAR status of PARP1 defines the species. For example, unPARylated PARP1 is different than PARP1 with one ADP-ribose modification, which is different that PARP1 with two ADP-ribose groups, and so on.

PARPi: PARP inhibitors.

PAR: Poly(ADP-ribose). PAR can only exist on histones or PARP1.

Reactions

DDR binding to damaged DNA.

DDR dissociating from damaged DNA.

PARP 1 reactions. The PARylation state of PARP1 defines each PARP1 molecule and represents a different species. Therefore, the number of PARP1 reactions below is defined by the number of rounds, where each round of PARylated PARP1 (PAR=0,1,2 . . . rounds) can undergo the following reactions.

PARP1 binding to DNA
PARP1 dissociating from DNA
PARP1 binding PARPi
PARP1 dissociating from PARPi
PARP1-PARPi binding to DNA
PARP1-PARPi dissociating from DNA
PARPi binding to PARP1-DNA
PARPi dissociating from PARP1-DNA
PARylated PARP1 exchanging with un-PARylated PARP1
PARP1 binding to NAD+ and PARylating a protein through stochastic selection.

Figure 25A:
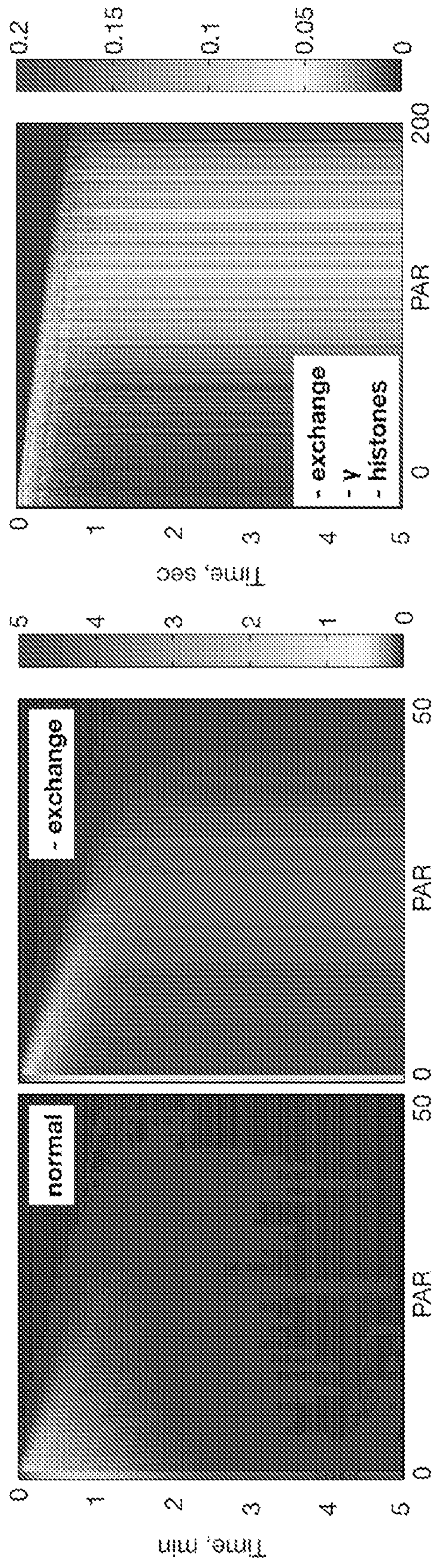
FIGS. 25A-25D: Stochastic model results.
Figure 25B:
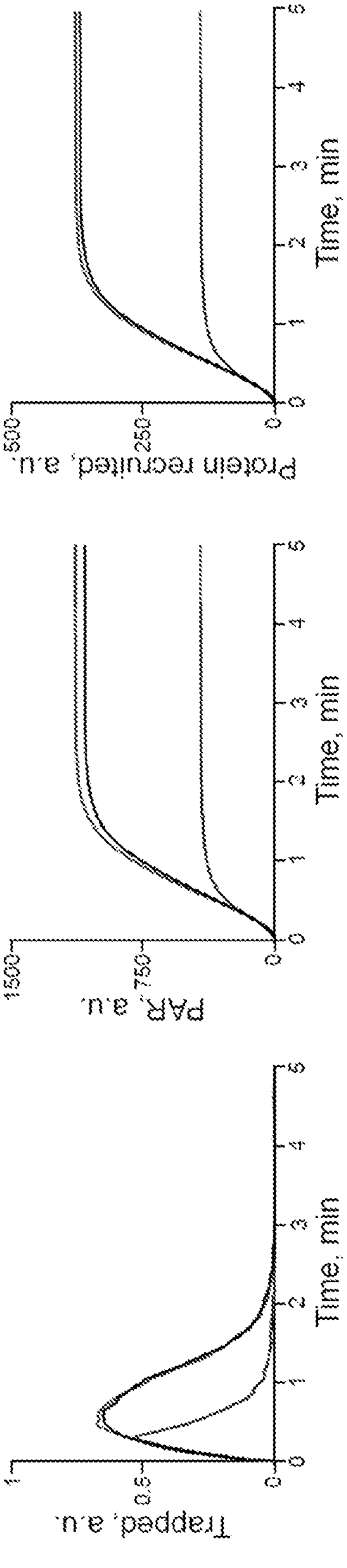
Figure 25C:
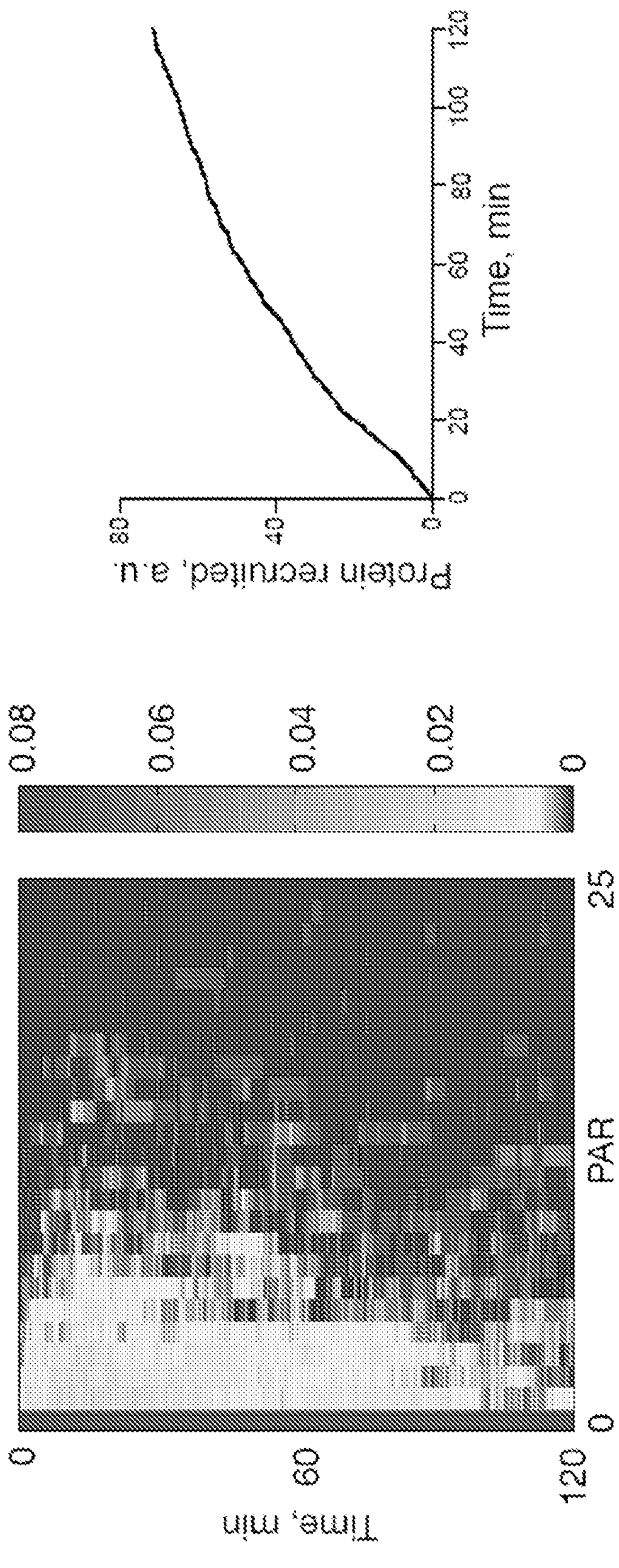
Figure 25D:
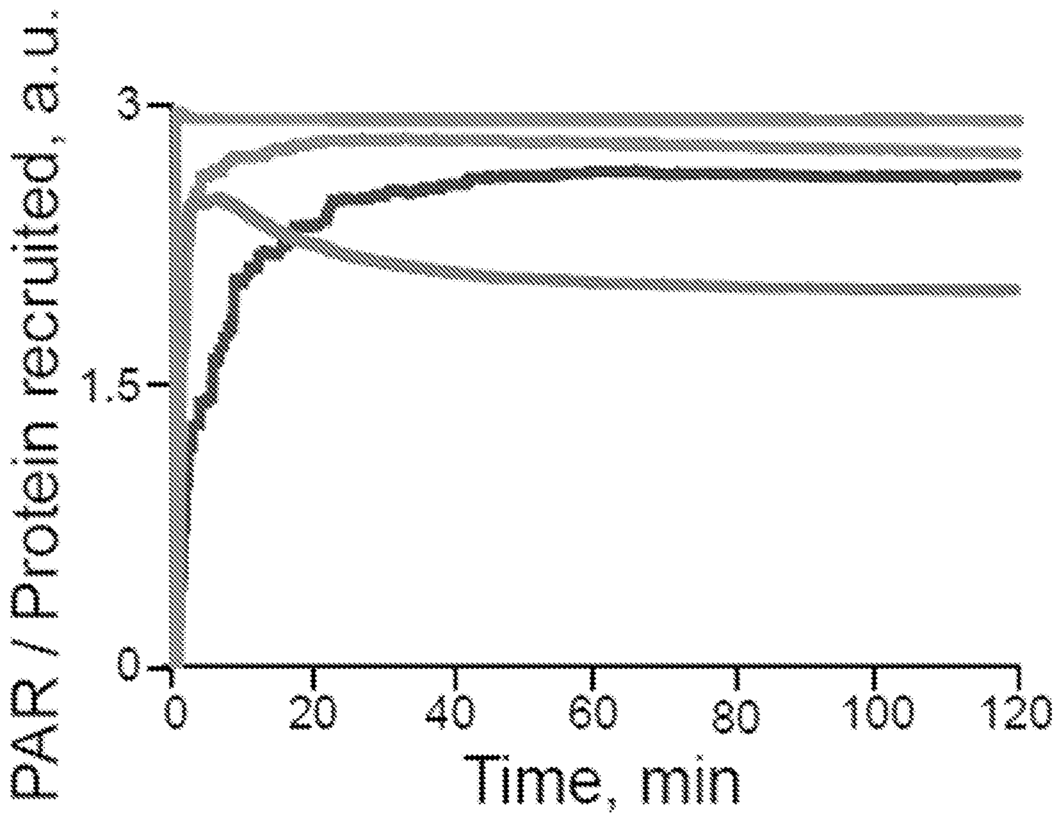

Constants and Variables iterations: The number simulations to run and average.

end_time: the duration of the simulation in seconds.

drug_concentration: The concentration of PARPi in the cell, this is a constant.

rounds: The length of PAR polymer on PARP1 when PARP1 loses affinity for damaged DNA. This value also defines the number of PARP1 states that can exist where each PARP1 state (round) is the length of PAR polymer attached to PARP1. The default value is 50. Under normal conditions in the presence or absence of PARPi, PARP1 does not progress beyond round 50 (FIG. 25A). However, in the absence of PARP exchange, $\gamma$ and histones, PARP1 can progress beyond 100 rounds (FIG. 25A).

Figure 26A:
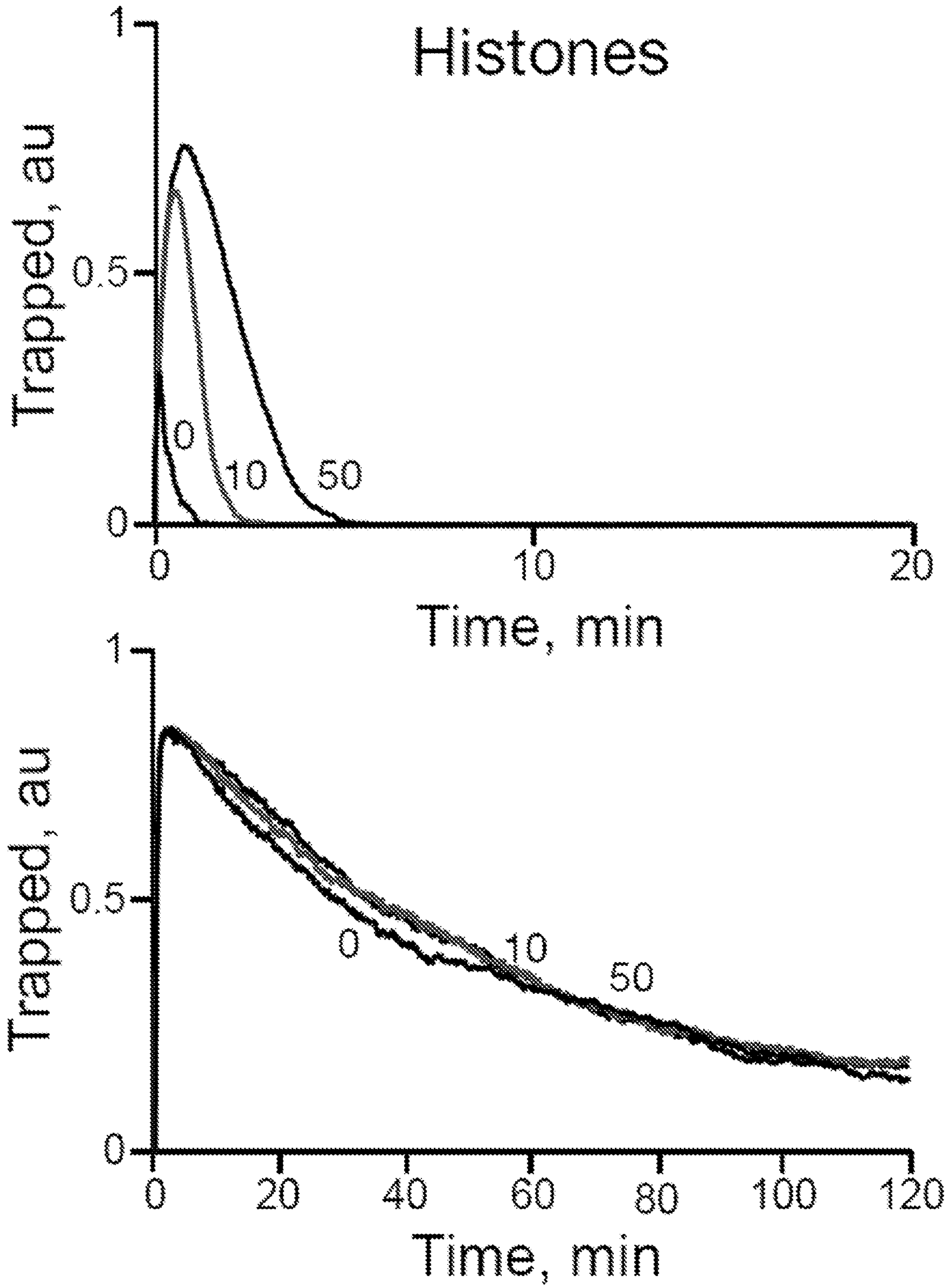
FIGS. 26A-26I: Stochastic model tuning and testing.

PARylation protein target (p.histones): PARP1 PARylates numerous proteins and prominently PARylates histones. The value p.histones defines a fixed concentration PAR receiving proteins in the condensate. This concentration does not change, and the length of PAR polymer is not limited. PARylation of histones when DNA bound PARP1 binds $NAD^+$ is a stochastic selection that competes with PARylation of PARP1 proteins, therefore the relative concentrations of histones and PARP1 govern the probability of PARylation for each species. Here we do not track the PARylation status of individual histones, rather upon histone PARylation the entire non-reversible PAR status of the condensate increases by one unit of PAR. Simulations demonstrate that the concentration of histones does not alter PARP trapping in the presence of 1 μM olaparib, however there is profound dependency on the PARP-DNA residency in the absence of PARPi (FIG. 26A). Therefore, the default value of p.histones was tuned to achieve a PARP1-DNA curve with a duration similar to experimental observations (25, 27). The default value is 10× the concentration of PARP1.

Figure 26B:
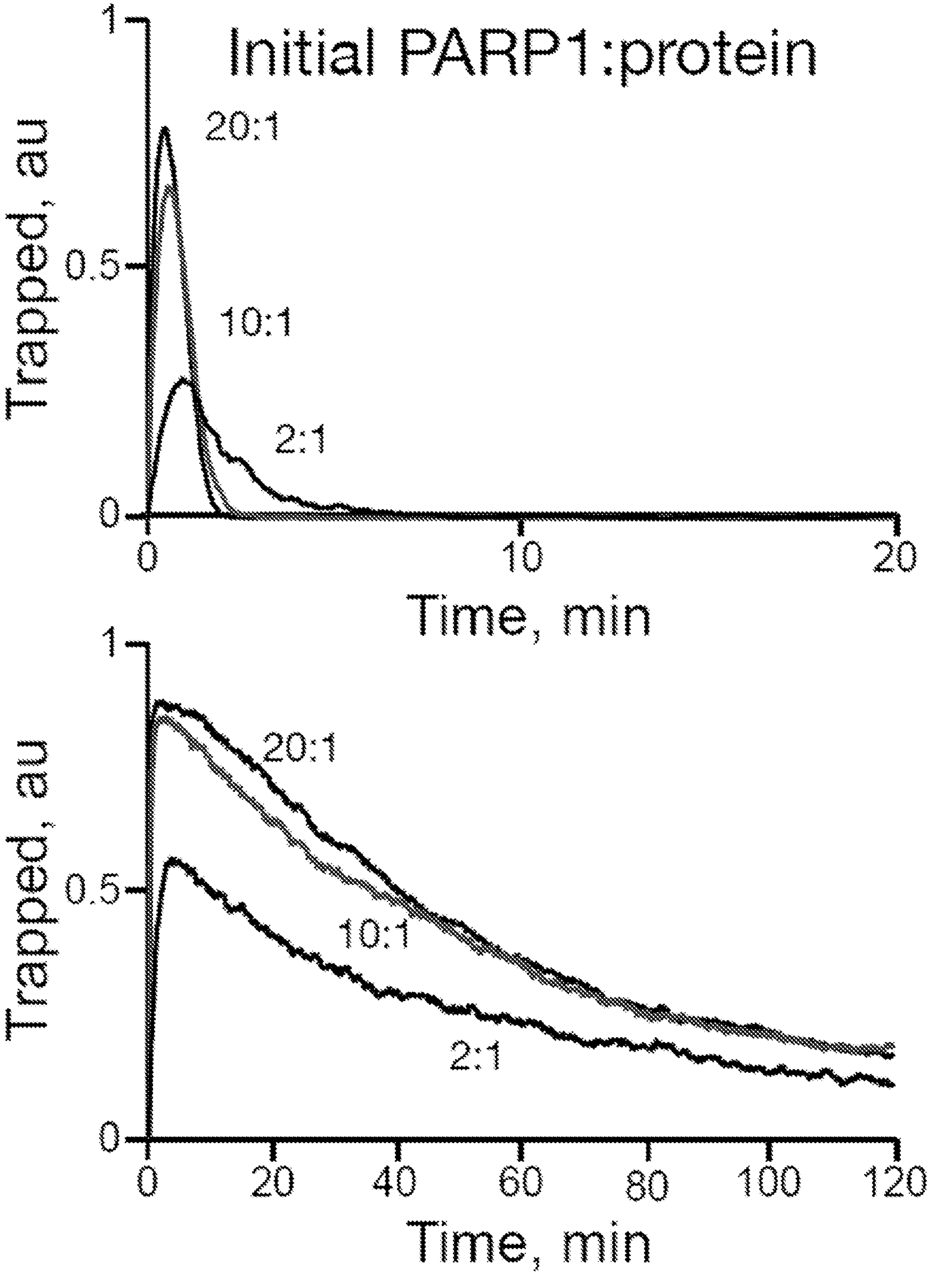

Initial PARP 1 concentration (p.PARP0): The concentration of PARP1 in the condensate. PARP1 concentration was approximated at 1 μM (54). The concentration of total PARP1 in the condensate is constant. The default value is 5 molecules per damaged DNA site. The concentration of PARP1 only impacts trapping when the relative concentration compared to initial DNA binding protein is altered (FIG. 26B).

Initial DNA binding protein concentration in the condensate (p.prot0): The initial concentration of DNA binding proteins in the condensate (DDR). DNA binding proteins are recruited to the condensate in a PAR dependent manner and modeled to not leave the condensate. The default value is 1, however half the simulations are run at the default value and the other half run at p.Proto=0 to capture the stochasticity of protein distribution throughout the nucleus. Therefore, the average default concentration is 10% of the default PARP1 concentration. The initial PARP1: DNA binding protein ratio impacts the maximum amount of PARP1 that is initially trapped in the presence of 1 μM olaparib, but does not alter the rate of loss of trapped PARP1 (FIG. 26B).

Figure 26C:
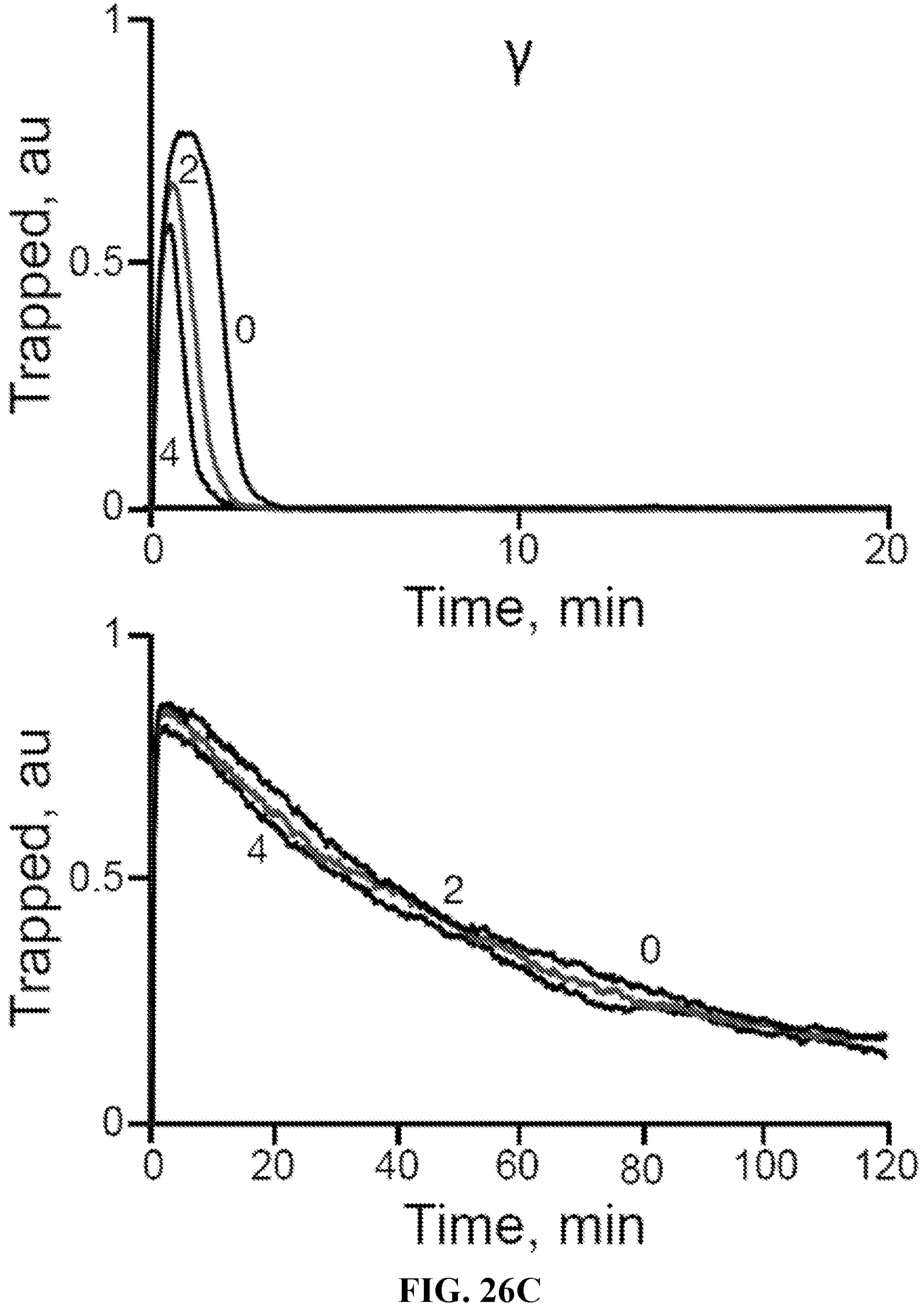

PAR dependent PARP1 DNA affinity (p.gamma): PARP1 loses affinity for DNA as it becomes PARylated, arising from electrostatic repulsion of negatively charged PAR and DNA. Thus, γ is a correction factor that confers PAR dependency on the affinity of PARP1 for DNA. This correction factor serves to both lower the association rate constant and increase the dissociation rate constant of both PARP1 and PARPi-bound PARP1 for DNA. The value of γ is the number of orders of magnitude that the rate constants will change over the number of rounds. The correction is applied in a log scale to the binding rate constants. The default of γ is 2, meaning that the binding constants will change two orders of magnitude over the number of rounds. This constant had no impact on PARP1 trapping in the presence of olaparib, however it did impact DNA residence time in the absence of drug (FIG. 26C) Therefore, the value was tuned to achieve the previously observed PARP1 DNA residence time in cells (25, 27).

Figure 26D:
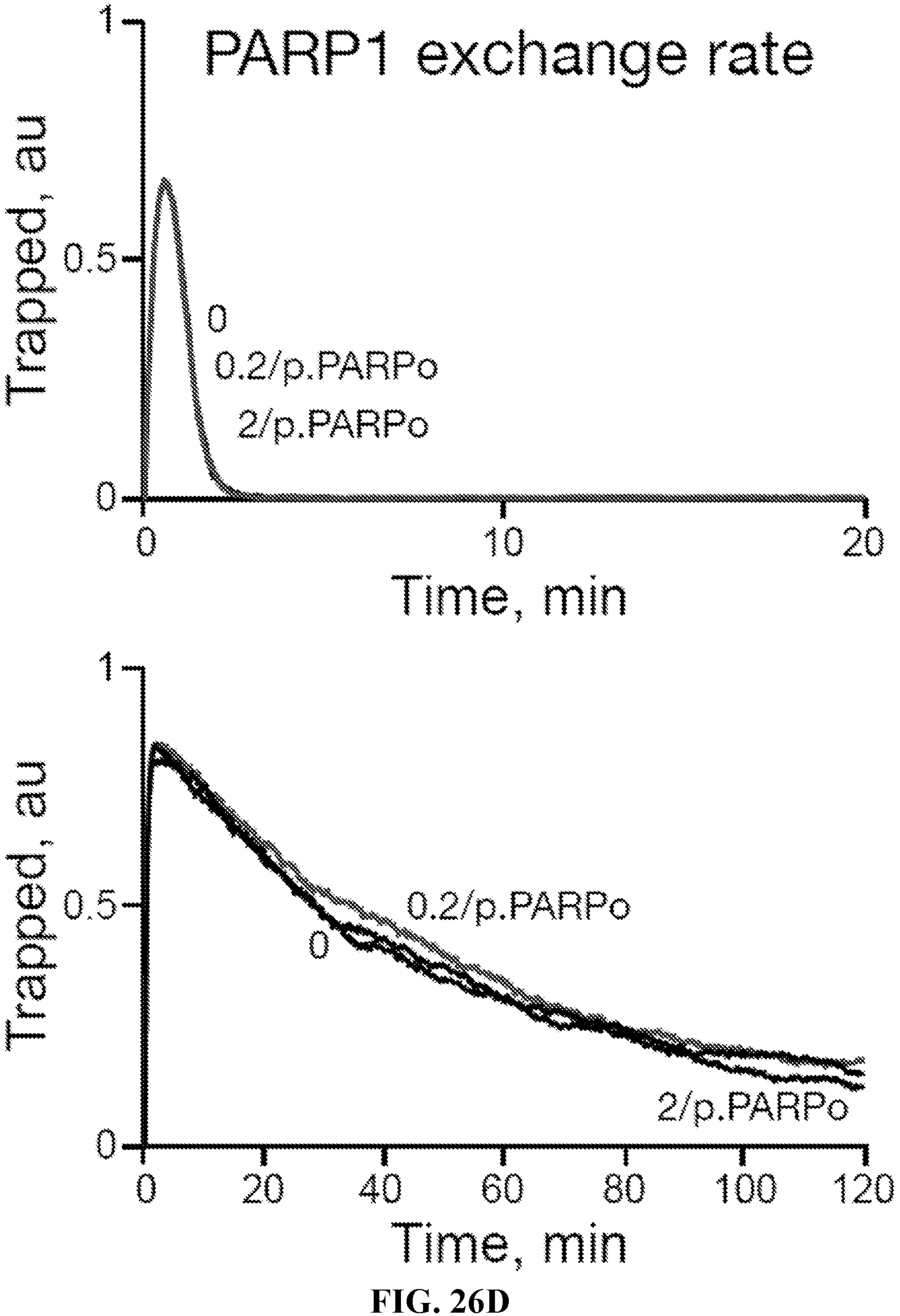

PARP exchange (p.exchange): Shao, et al., demonstrated fluorescent PARP1 recovery after photobleach at sites of UV-induced DNA damage with an initial rate of approximately 20% recovery over 2 seconds (27). We interpreted this initial rate to represent exchange of PARylated PARP1 for unmodified PARP1 at the site of DNA damage. Therefore, 10% of PARP1 molecules in our system exchange with the surrounding PARP1 every second. We fit our exchange rate constant to achieve this approximate rate and derived the expression p.exchange=0.2/p.PARP0, where p.PARP0 is the amount of PARP in the system. However, the PARP1 exchange rate had no impact on olaparib induced PARP1 trapping nor PARP1 DNA residency in the absence of drug (FIG. 26D).

Figure 26E:
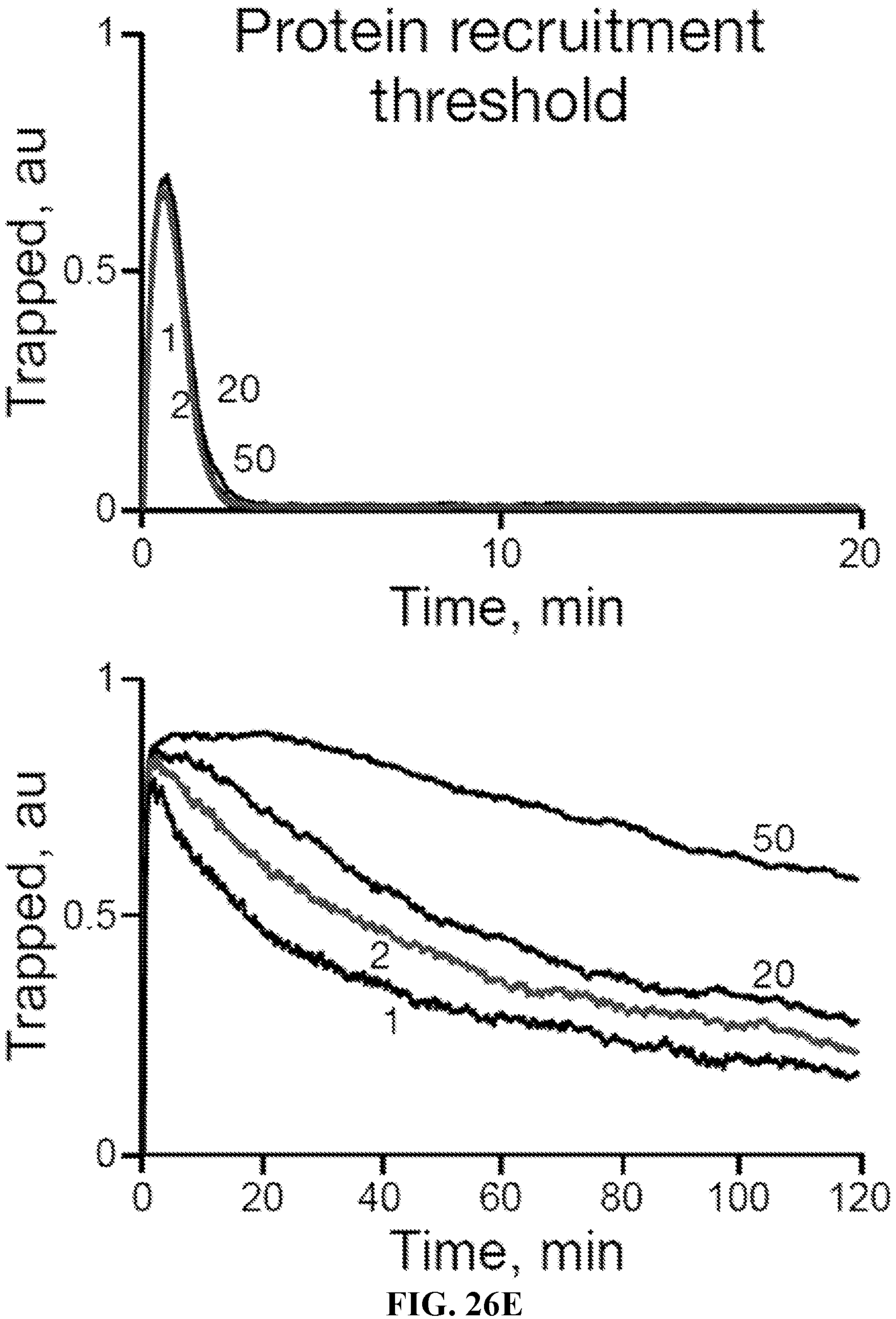
Figure 26F:
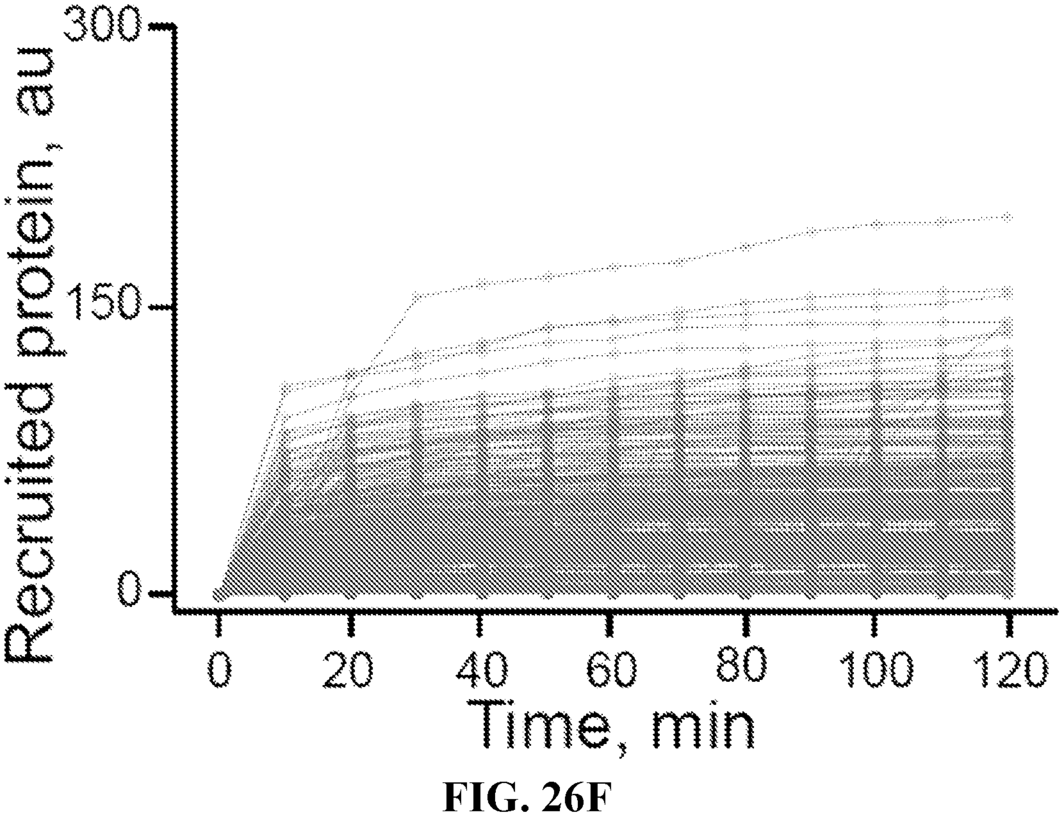
Figure 26G:
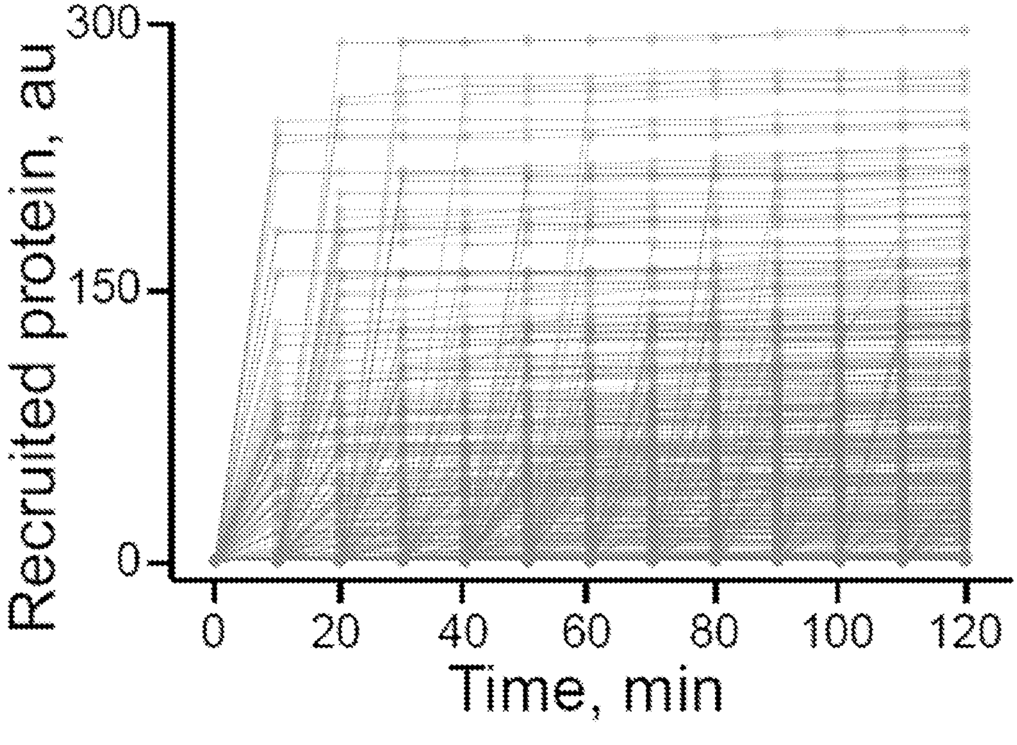
Figure 26H:
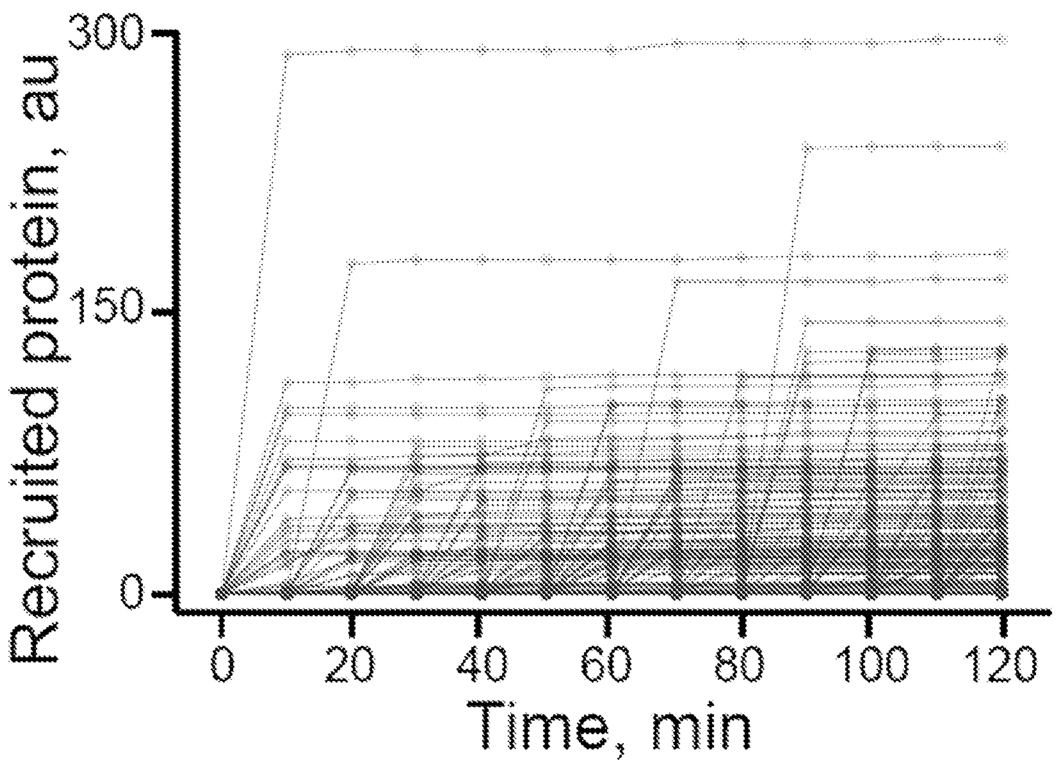
Figure 26I:
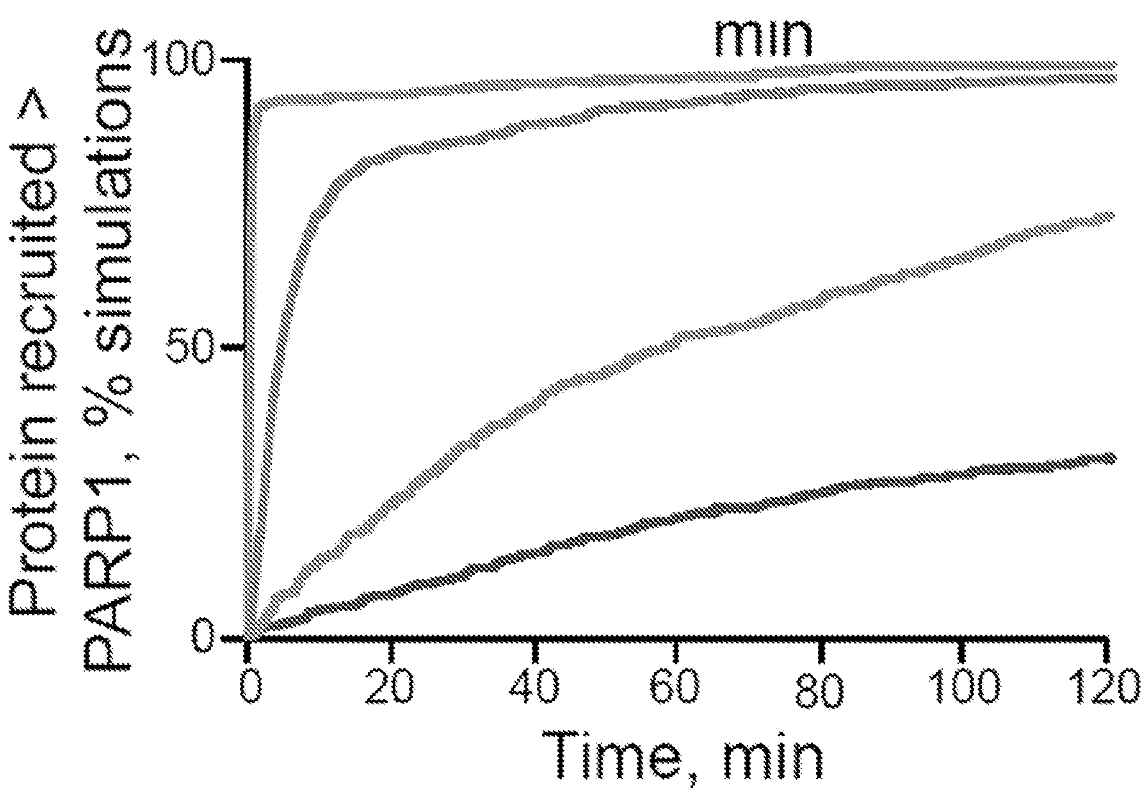

PAR dependent DNA binding protein recruitment (p.prot_thresh): DNA binding proteins are recruited into the condensate as a function of PAR accumulation. The variable p.prot_thresh defines the relationship between PAR and DNA binding protein recruitment. Stochastic selection of protein recruitment is dependent on the value of p.prot_thresh, with a higher value requiring greater PAR accumulation for each protein recruited. The default value of 2 was tuned to achieve the previously observed PARP1 DNA residence time in the absence of PARPi in cells (25, 27). This constant impacts PARP1 trapping in the presence of olaparib (FIG. 26E), but not PARP1 DNA association in the absence of PARPi. The impact of this constant demonstrates the trapping dependency of DNA binding protein (DDR) recruitment.

DNA in the condensate (p.DNA0): Our simulation models a single section of damaged DNA, therefore this value is set to 1 and is constant.

$NAD^+$ concentration (p.NAD)): The default concentration is 100 μM based on previous measurements (60, 61).

Dissociation of PARPi from PARP1 (p.kd_trap): The dissociation constant of each PARPi from PARP1. Values were taken as an average of previous measurements. The default values used were: veliparib $5\times10^{-3}$ $s^{-1}$; olaparib $3\times10^{-4}$ $s^{-1}$; talazoparib $8\times10^{-5}$ $s^{-1}$. This constant impacted PARP1 trapping when the values for olaparib were artificially adjusted (FIG. 28E). Lower values (higher affinity) increased trapping through decreasing the dissociation of PARPi from PARP1, which lowers the amount of PAR generated.

Association of PARPi to PARP1 (p.ka_trap): The association constant of each PARPi on PARP1. Values were taken as an average of previous measurements (Table S1). Rates were corrected to account for the interpretation of PARP1 concentration relative to DNA through multiplying the actual rate by $10^{-7}$. This rate correction was performed for all association constants. The default values used were: veliparib $1.8\times10^{-1}$ $M^{-1}s^{-1}$; olaparib $2\times10^{-2}$ $M^{-1}s^{-1}$; talazoparib $3.6\times10^{-2}$ $M^{-1}s^{-1}$.

Association of $NAD^+$ on PARP1 (p.ka_PAR): The binding association constant of $NAD^+$ to PARP1. For simplicity, the PARylation reaction was modeled as instantaneous upon PARP1 binding to $NAD^+$. This binding constant was defined by previous measurements of PARP1 $K_M$ when bound to damaged DNA (46, 47) and the affinity of an $NAD^+$ analog (62). The default value, corrected for PARP/DNA concentration interpretation, was $5\times10^{-2}$ $M^{-1}s^{-1}$.

Association of DNA binding protein to DNA (p.ka_prot): The binding association constant of DNA binding proteins to DNA was defined by the PARP1-DNA association constant. This value was set to $1\times10^{5}$ $M^{-1}s^{-1}$. Corrected for PARP1/DNA concentration interpretation, the default was $1\times10^{-2}$ $M^{-1}s^{-1}$. This value was set to be the same as the association constant of PARP1 binding to DNA.

Dissociation of DNA binding protein from DNA (p.kd_prot): The dissociation constant of DNA binding proteins from DNA was defined as an order of magnitude lower than the PARP1-DNA dissociation constant. This value was chosen to capture progression along the DNA repair pathway once DDR DNA binding proteins bind to damaged DNA. The default value was $4\times10^{-4}$ $s^{-1}$.

Dissociation of PARP1 from DNA (p.kd_rel0): The dissociation constant of PARP1 from DNA. The value is an average of previous measurements (Table S1). This rate is dependent on the correction factor γ and, thus, the degree of PARP1 PARylation. The default value was $3.36\times10^{-3}$ $s^{-1}$.

Association of PARP1 to DNA (p.ka_rel0): The association constant of PARP1 on DNA. Because of the large variation in values between previous measurements the value is an average of previous measurements and set to $1\times10^{5}$ $M^{-1}s^{-1}$. This rate is dependent on the correction factor γ and, thus, the degree of PARP1 PARylation. Rates were corrected to account for the interpretation of PARP1 concentration relative to DNA through multiplying the actual rate by $10^{-7}$. The default was $1\times10^{-2}$ $M^{-1}s^{-1}$.

Figure 27A:
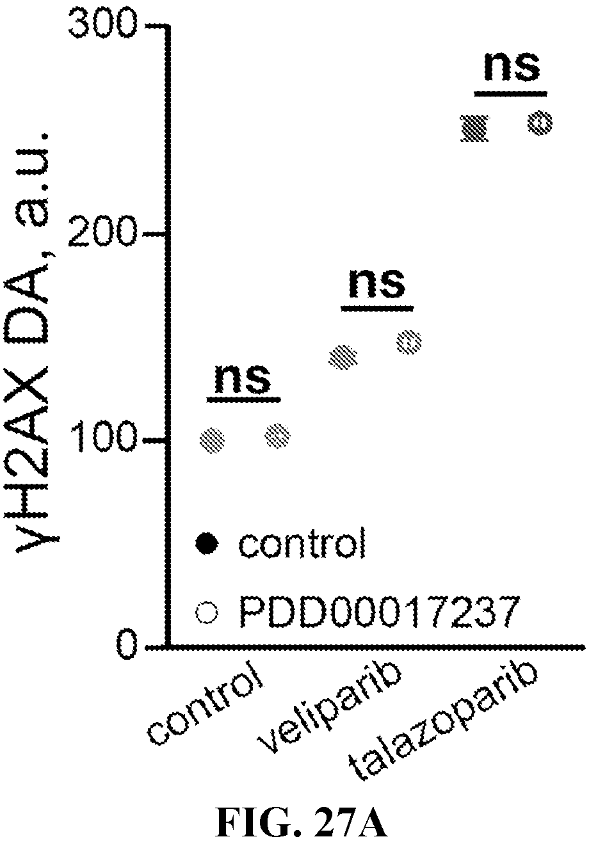
FIGS. 27A-27E: Impact of altered PAR availability on trapping.
Figure 27B:
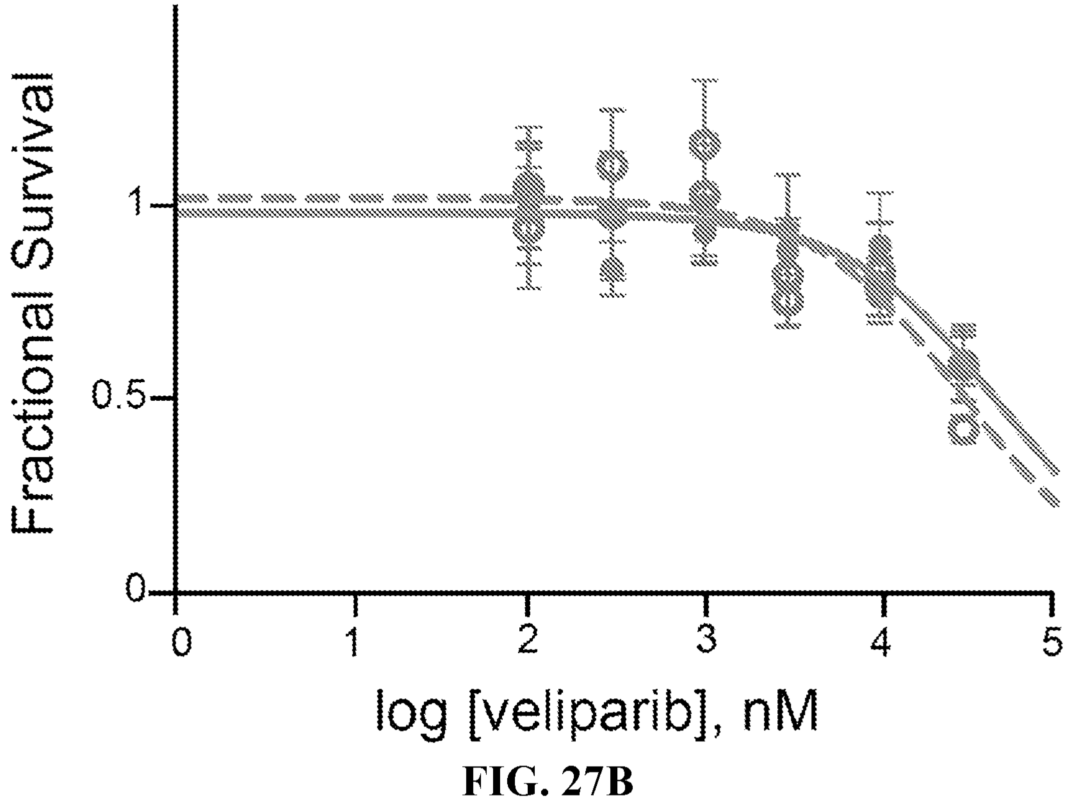
Figure 27C:
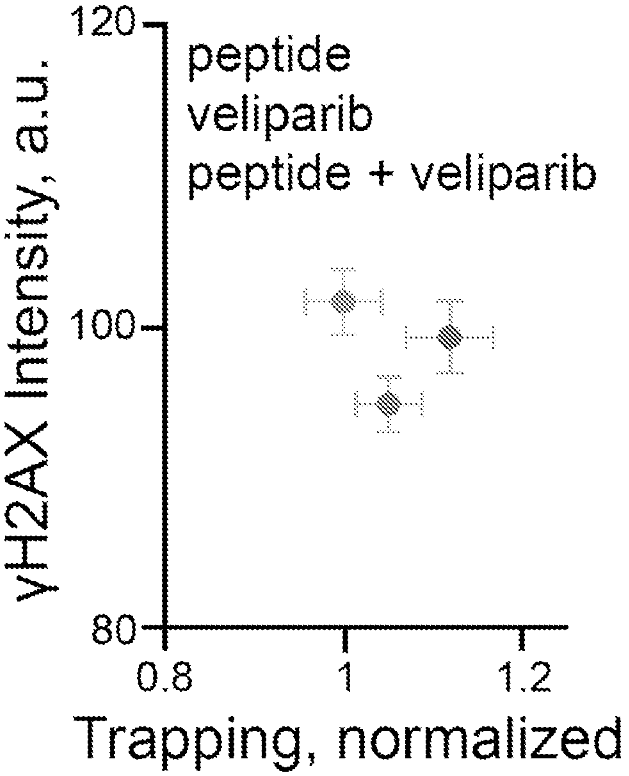
Figure 27D:
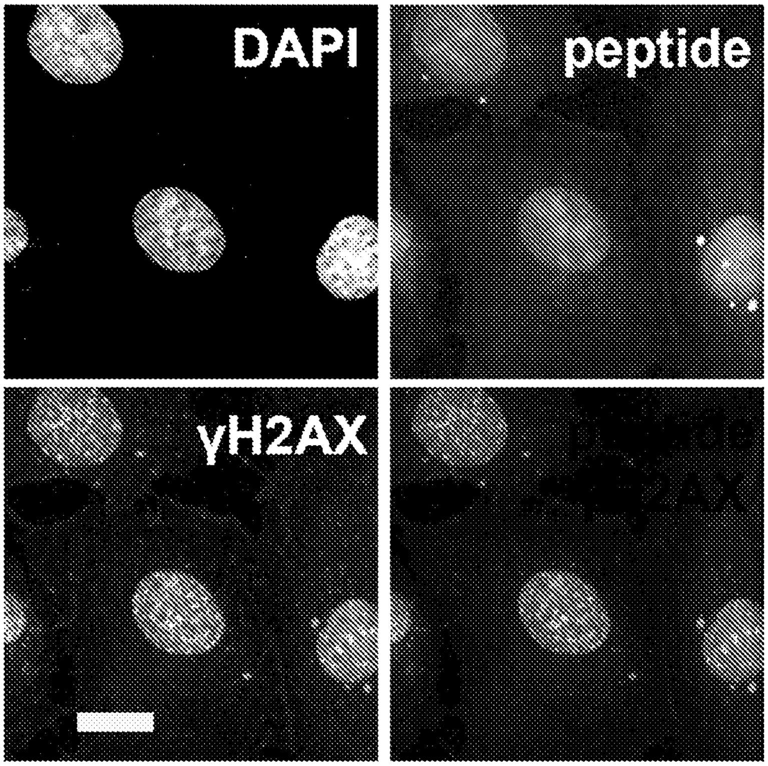
Figure 27E:
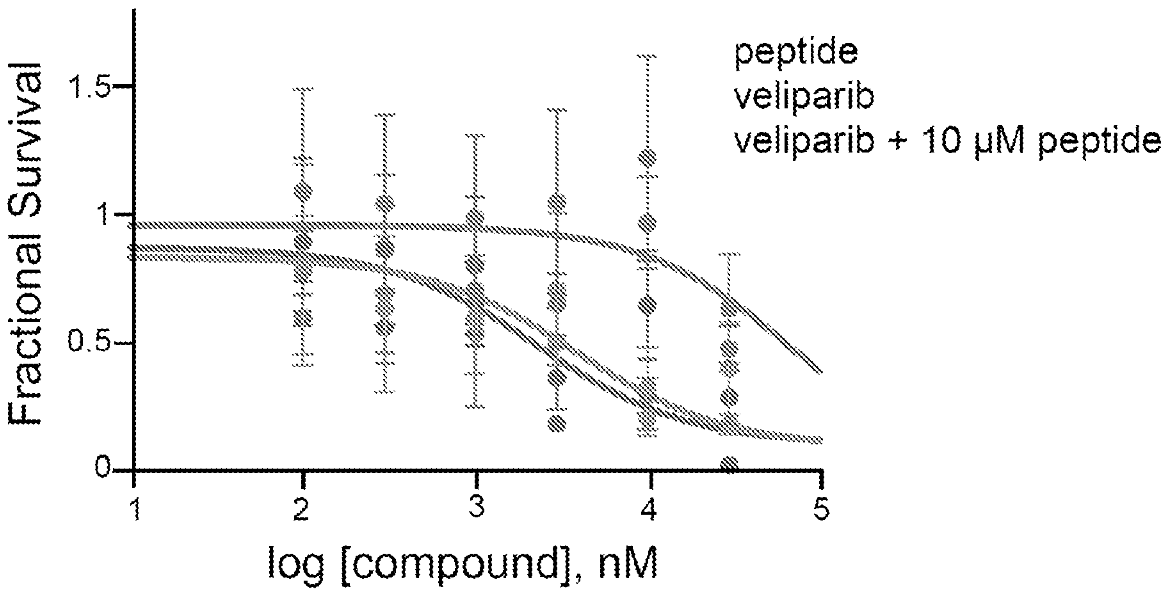

Dissociation of PARPi-PARP1 from DNA (p.kd_relD0): The dissociation constant of PARPi bound PARP1 from DNA. Values were taken from previous findings (25). This rate is dependent on the correction factor γ and, thus, the degree of PARP1 PARylation. The default values used were: veliparib $4.08\times10^{-3}$ $s^{-1}$; olaparib $2.31\times10^{-3}$ $s^{-1}$; talazoparib $2.52\times10^{-3}$ $s^{-1}$. This constant impacted PARP1 trapping when the values for olaparib were artificially adjusted (FIG. 27F). Lower values (higher affinity) increased trapping through changing the competitive binding probabilities of PARP1 relative to DDR proteins.

Association of PARPi-PARP1 to DNA (p.ka_relD0): The association constant of PARPi-bound PARP1 on DNA. Because of the large variation in values between previous measurements the value is the same as PARP1 association to DNA and set to $1\times10^{5}$ $M^{-1}s^{-1}$. This rate is dependent on the correction factor γ and, thus, the degree of PARP1 PARylation. Corrected for PARP1/DNA concentration interpretation, the default was $1\times10^{-2}$ $M^{-1}s^{-1}$.

Introduction

Poly(ADP-ribose) polymerase (PARP) inhibitors (PARPi) are a class of cancer drugs that enzymatically inhibit PARP activity at sites of DNA damage. Yet, PARPi function mainly by trapping PARP1 onto DNA with a wide range of potency among the clinically-relevant inhibitors. How PARPi trap and why some are better trappers remain unknown. Here, we show trapping occurs primarily through a kinetic phenomenon at sites of DNA damage that correlates with PARPi $k_{off}$. Our results suggest PARP trapping is not the physical stalling of PARP1 on DNA, rather the high probability of PARP re-binding damaged DNA in the absence of other DNA binding protein recruitment. These results clarify how PARPi trap, shed new light on how PARPi function and describe how PARPi properties correlate to trapping potency.

PARP1 is an abundant nuclear protein (1) that rapidly binds damaged DNA (2) becoming active through allosteric conformational changes (3). PARP1 is the founding member of the PARP family and, along with the less expressed and functionally similar PARP2, a key component of the DNA damage response (DDR) (4-6). Double knockout of PARP1 and PARP2 is embryonically lethal in mouse models (7). Active PARP1 produces prolific poly(ADP-ribose) (PAR) modification of thousands of proteins (8-10) to recruit other DDR proteins (11), beginning the DNA damage response. As a prominent enzyme in the DDR pathway PARP inhibitors (PARPi) have been developed as a cancer therapeutic and show clinical promise through synthetic lethality in patients with BRCA mutations (12-14). More recently, other defects in the homologous recombination pathway have shown enhanced susceptibility to PARPi (15). However, PARPi resistance remains a critical limitation to clinical efficacy (16, 17).

All PARPi target the NAD" binding pocket to enzymatically inhibit PAR production (18). Curiously, loss of PARP1 does not impact cellular survival as much as PARPi treatment (19-21), revealing that PARPi work largely by "trapping" PARP1 onto DNA. However, some PARPi are profoundly stronger trappers than others and subsequently more potent drugs (19, 20), despite having binding affinities within an order of magnitude, suggesting that non-enzymatic factors are involved. Yet, what drives difference in trapping among PARPi remains unknown.

PARP trapping is thought to occur through an increased duration of the PARP1-DNA interaction in the presence of PARP inhibitors (22, 23). In vitro experiments show the accumulation of self-PARylation on PARP1 decreases the affinity of PARP1 for DNA through charge-based affects (19, 20)—PAR being highly negative, similar to DNA. This mechanism is further supported by an increase in PARP trapping solely from the reduction of cellular of NAD" levels (24), indicating that trapping can be a purely enzymatic phenomenon. Thus, enzymatic inhibition could prevent PARP1 PARylation-induced release from DNA. However, the trapping potencies of PARPi do not correlate well with enzymatic inhibition. Another consideration is PARPi inducing increased affinity of PARP1 for DNA in a PARPi-specific manner. Recent results found that different PARPi impart unique allosteric shifts in PARP1 upon binding DNA, translating to altered binding affinity to damaged DNA (25). Thus, an allosteric component could increase the duration of the PARP1-DNA interaction. However, the observed allosteric shifts do not correlate to cellular PARP trapping. Therefore, it has been hypothesized that a combination of enzymatic inhibition and allosteric shifts in affinity drive an increase in PARP1-DNA binding duration (25, 26). Yet, recent findings that PARP1 diffusion at sites of DNA damage is not impacted by the presence of PARP inhibitors (27) suggests that PARP trapping is not the physical stalling of PARP1 on DNA after all. Here, we sought to determine what causes PARP trapping.

Results

Figure 12A:
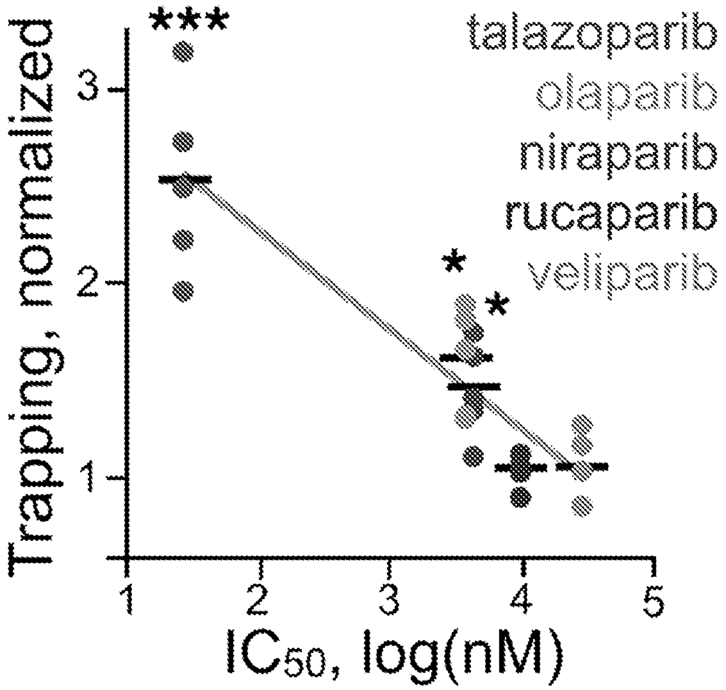
Figure 12B:
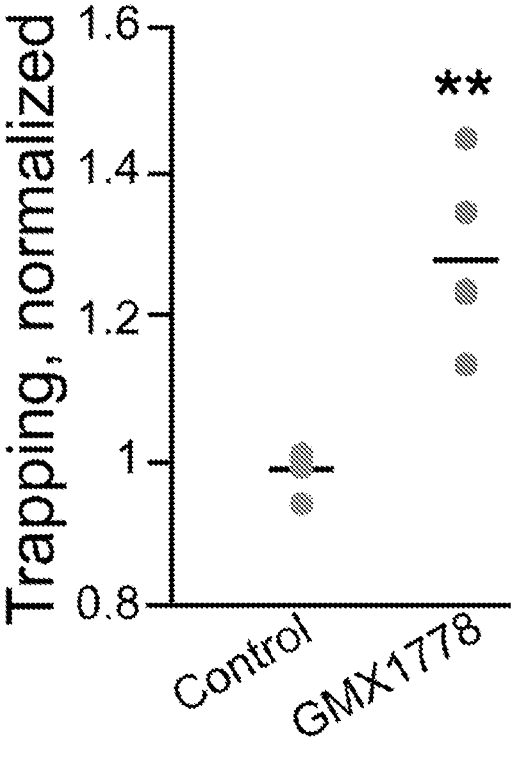
(FIG. 12B) Normalized trapping in HT1080 cells or cells treated with 10 μM GMX1778 overnight, n=5 with average (black line).
Figure 12C:
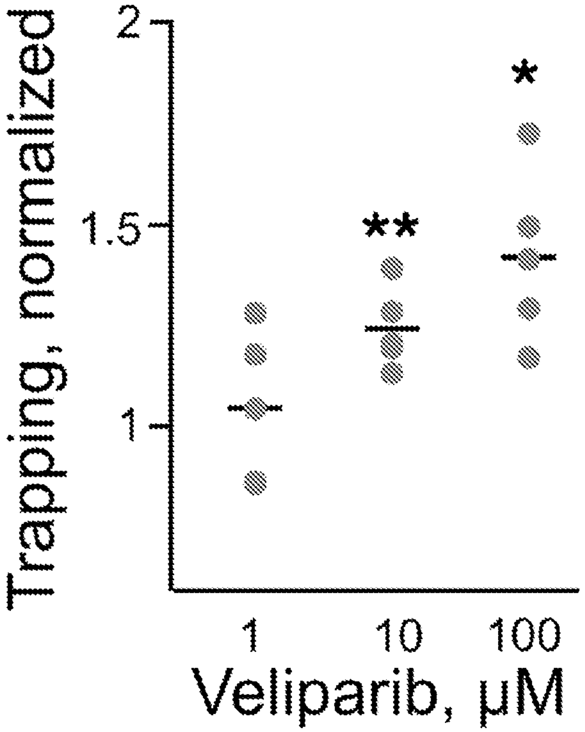
(FIG. 12C) Normalized trapping in HT1080 cells treated with veliparib overnight, n=5 with average (black line).
Figure 17A:
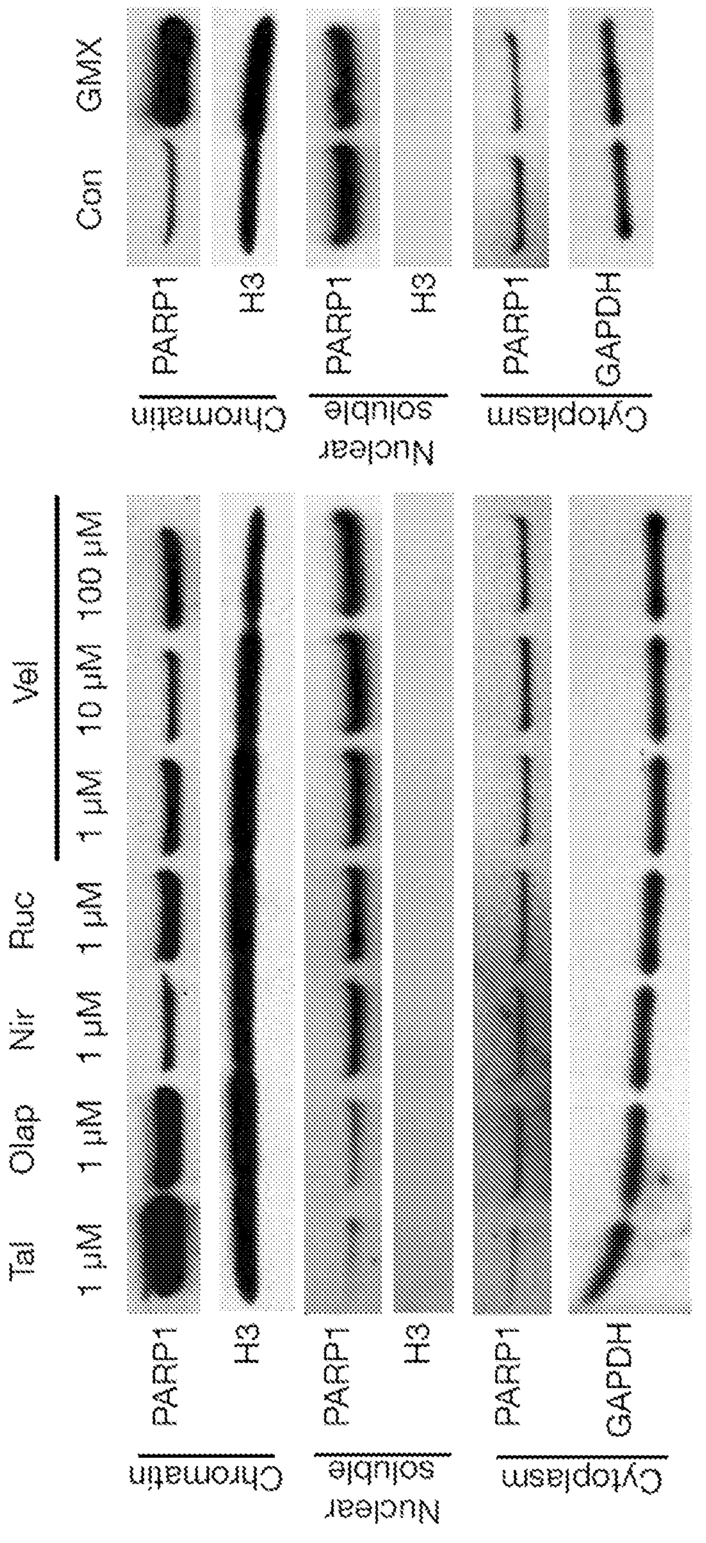
FIGS. 17A-17G: PARPi and GMX1778 impact on cells.
Figure 17B:
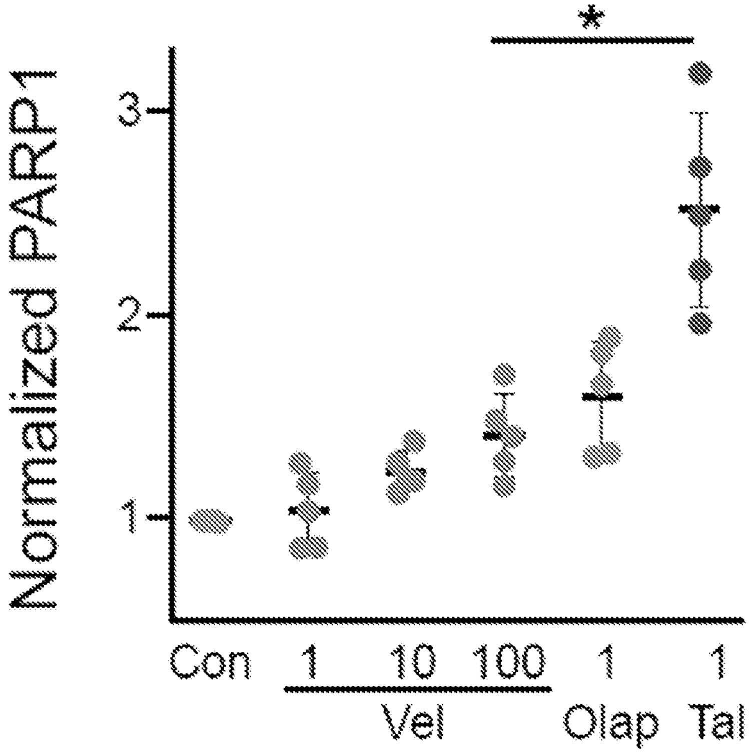
Figure 17C:
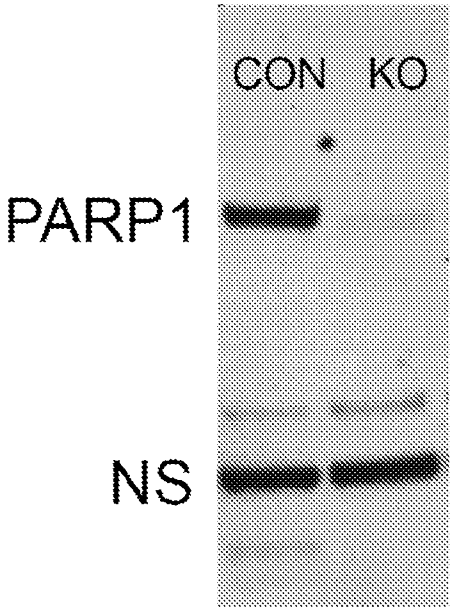
Figure 17D:
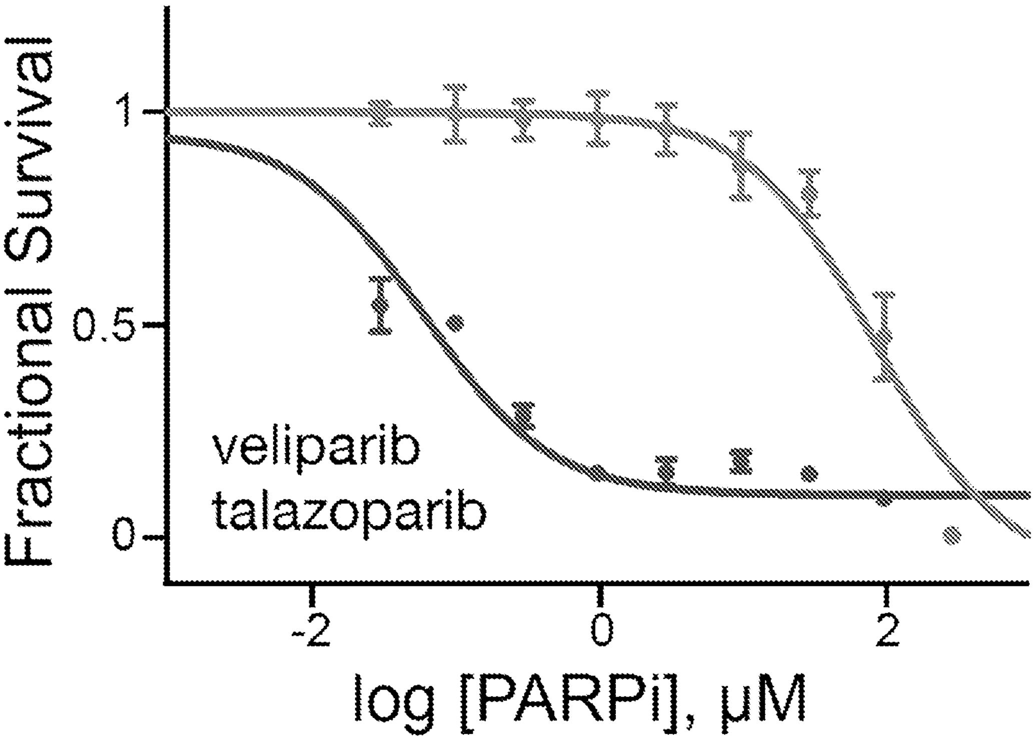
Figure 17E:
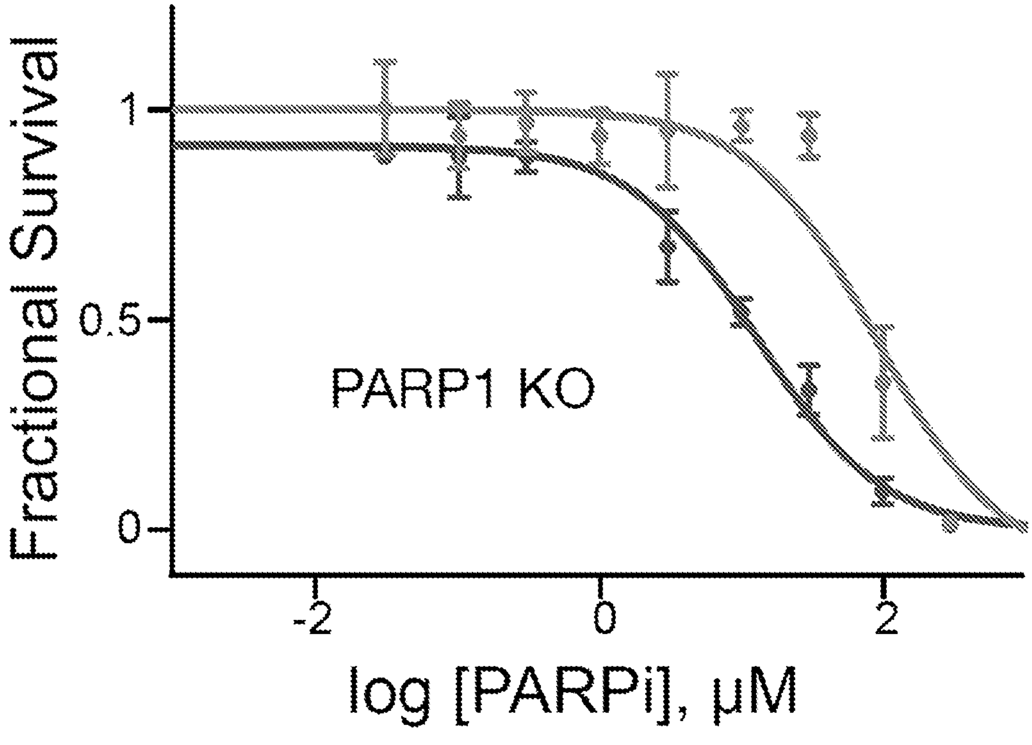
Figure 17F:
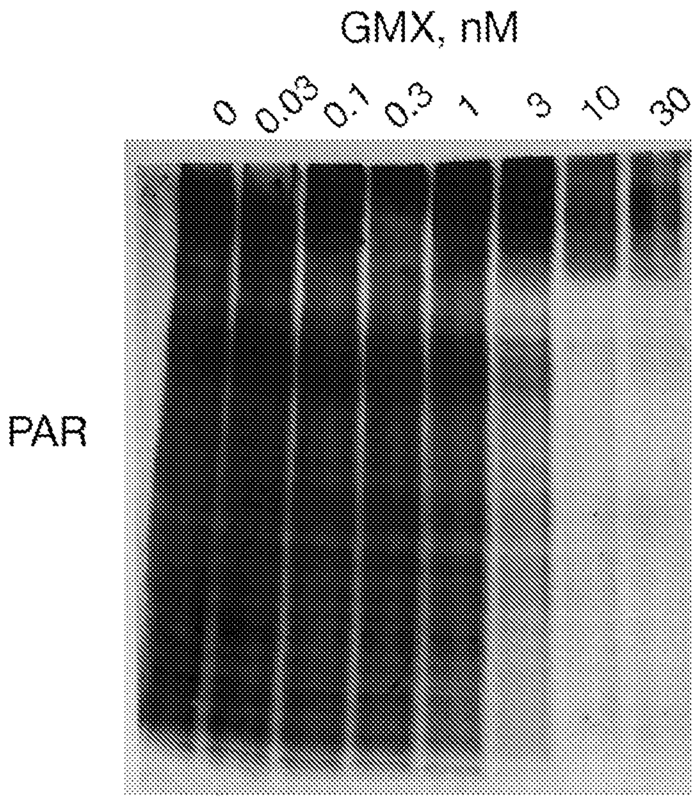
Figure 17G:
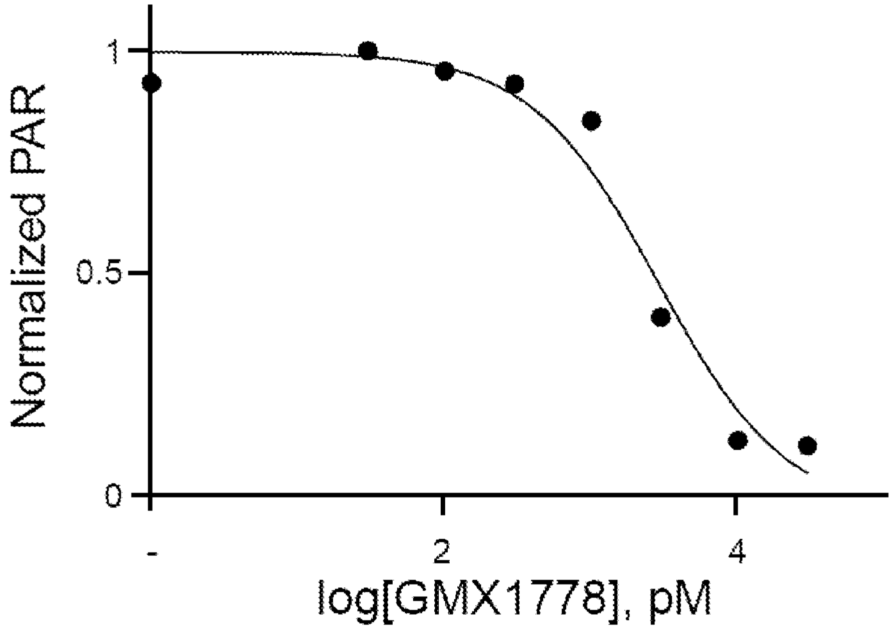
Figure 18A:
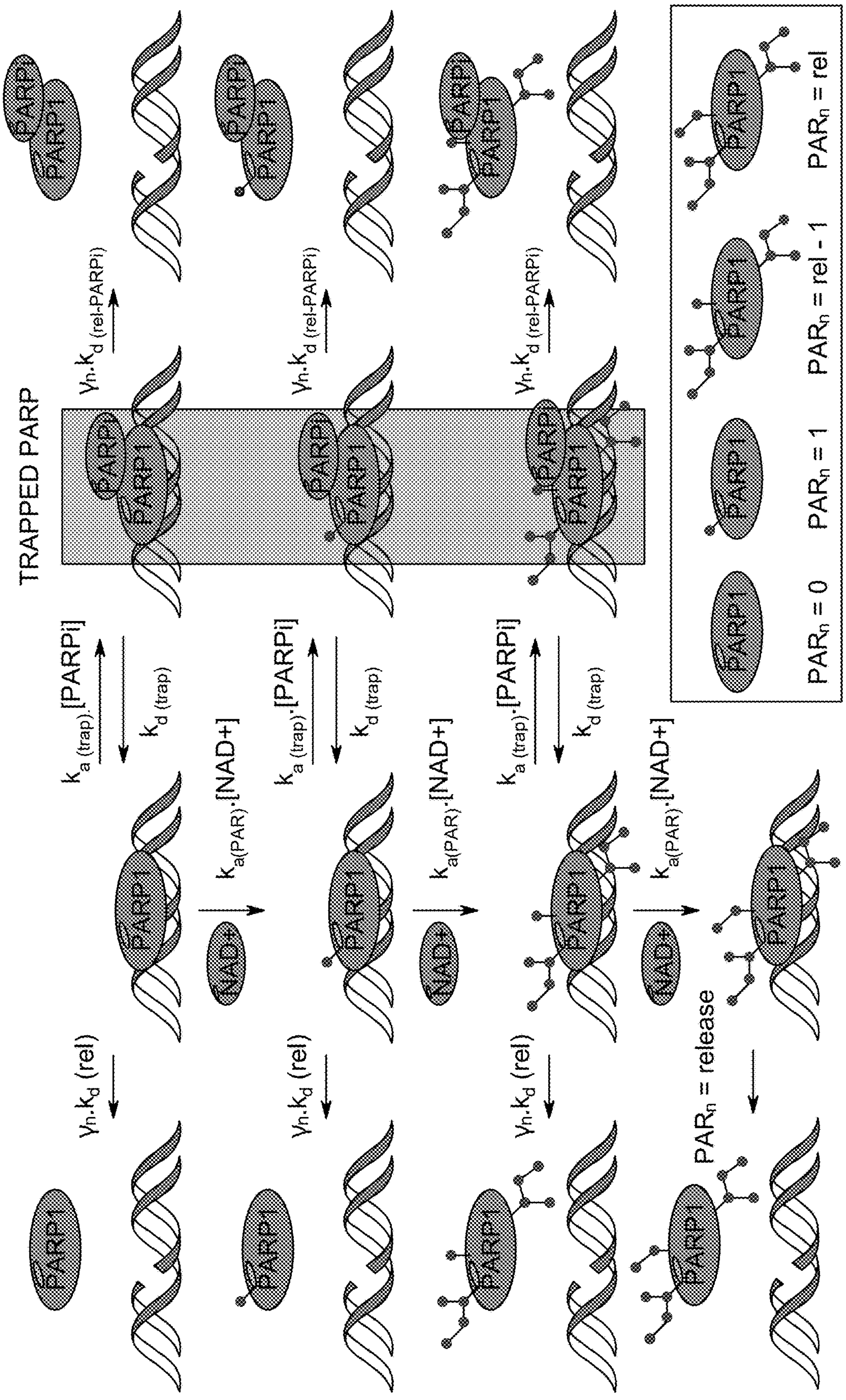

Hallmarks of PARP trapping are: 1) differential trapping across PARP inhibitors that correlates with cellular sensitivity, 2) trapping in the absence of enzymatic activity, and 3) trapping with PARP inhibitor dose dependence. We first validated that all three hallmarks are present in HT1080 fibrosarcoma cells, which have differential sensitivity to PARPi (FIG. 17D). PARPi trapping, measured by chromatin fractionation, was dependent on the PARP inhibitor, with talazoparib producing the most distinct difference in trapping among the five clinical PARPi tested (FIG. 12A)—here trapping was normalized to DMSO control. Trapping also correlates to HT1080 sensitivity through on-target effects (FIG. 12A and FIGS. 17A-17E), with PARPi dependent $EC_{50}$ cell viability values spanning over 3 orders of magnitude. We found that reduction in cellular NAD" concentration through nicotinamide phosphoribosyltransferase (NAMPT) inhibition induces trapping (FIG. 12B and FIGS. 17F-17G) (24). And, trapping in HT1080 cells is PARPi dose dependent (FIG. 12C). But, PARP trapping is not canonically enzymatic. Veliparib at 100 μM is unable to reproduce the trapping observed with just 1 μM talazoparib, despite having a PARP1 affinity only one order of magnitude lower (FIG. 17B).

Figure 12D:
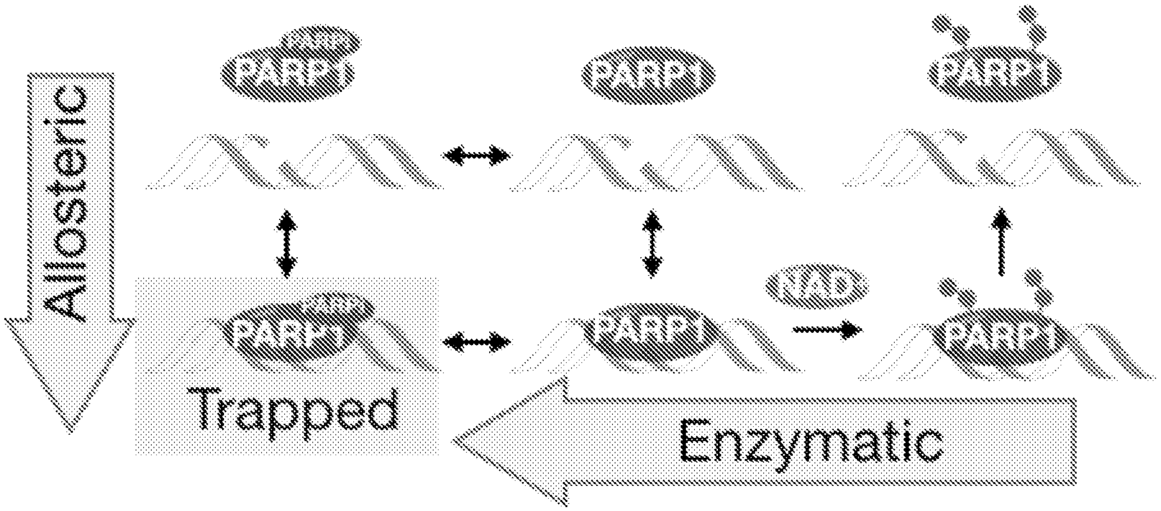
(FIG. 12D) Allosteric shifts in PARP1 affinity for DNA or PARPi enzymatic inhibition are thought to increase trapping.
Figure 12E:
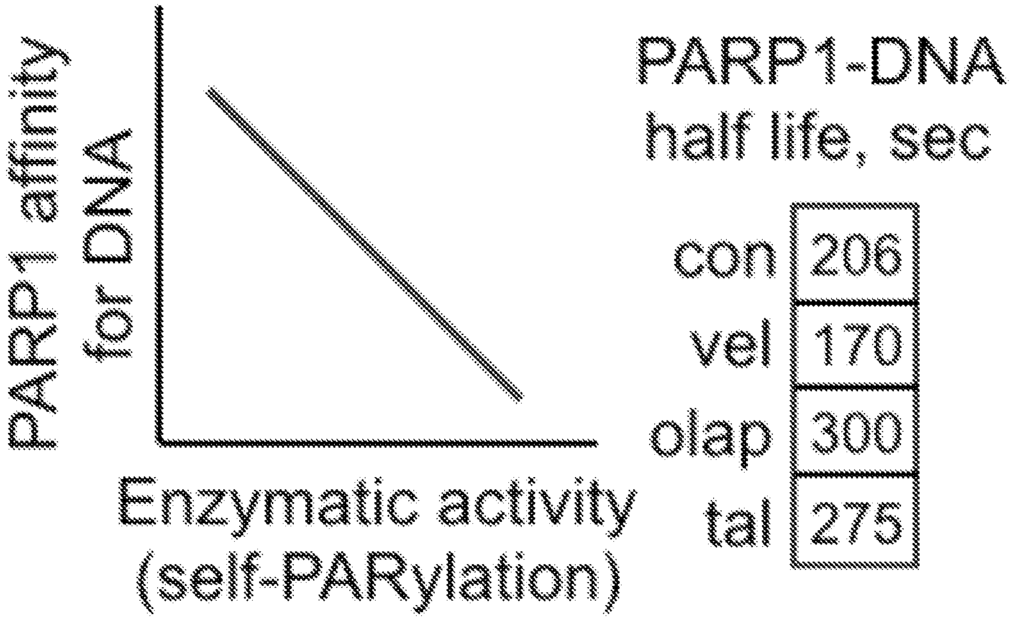
(FIG. 12E) Expected dependency of PARP1 affinity for DNA on self-PARylation and PARP1-DNA half lives in the absence of enzymatic activity.
Figure 12F:
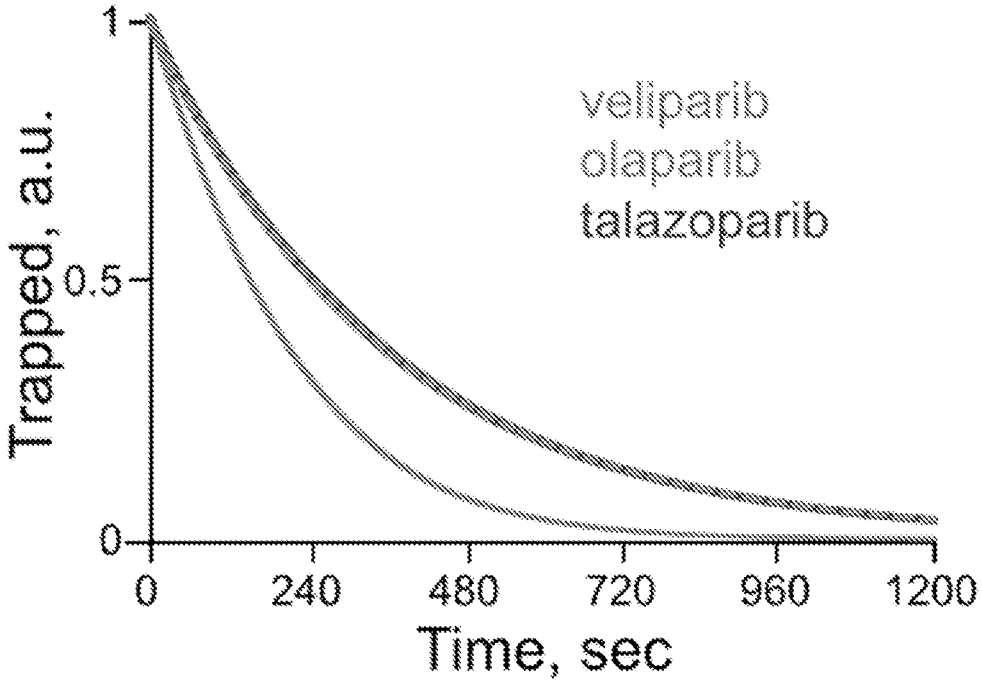

Largely because PARP inhibitor trapping does not strongly correlate with steady state affinity ($k_D$), the current model suggests that trapping arises from both enzymatic inhibition and allosteric effects that enhance the PARP1-DNA interaction in a PARPi-specific manner (FIG. 12D). We tested the current trapping hypothesis through a set of ordinary differential equations (ODE) (FIGS. 18A-18B and FIGS. 19A-19F) using established binding constants. Considering allosteric impact alone, the duration of PARP1 bound to DNA is entirely dependent on the dissociation constant of PARPi-PARP1 from DNA (FIG. 12E). Therefore, based on previous measurements (25), olaparib-bound PARP1 has the longest DNA interaction, which is both shorter than observed cellular trapping (25, 27) and does not agree with established differential PARPi trapping potency (FIG. 12A). We then calculated the enzymatic impact on PARP1-DNA residency through the presence of veliparib at increasing concentrations, which will alter the accumulation rate of self-PARylation. However, our model was unable to reproduce (FIG. 12F) the concentration dependent trapping observed in cells (FIG. 12C).

Figure 12G:
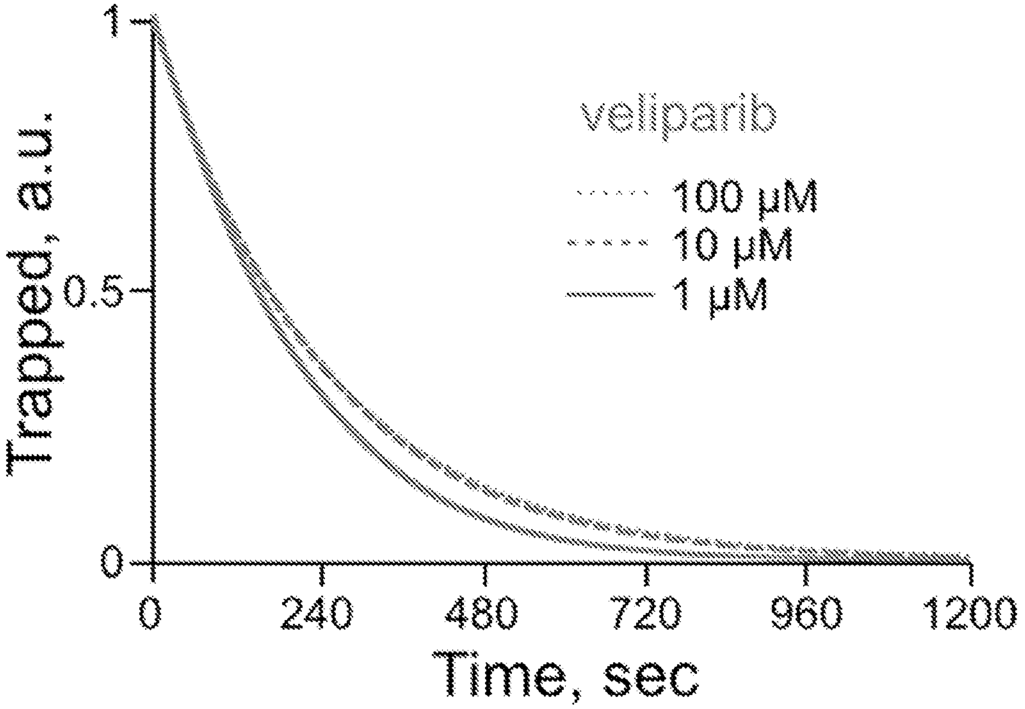
Figure 12H:
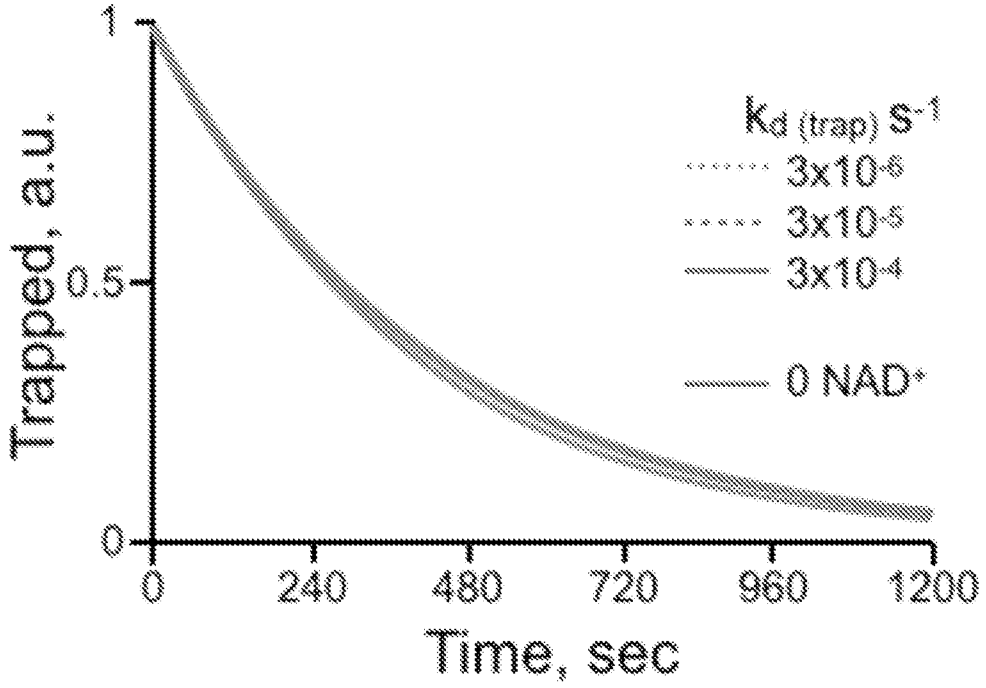
Figure 12I:
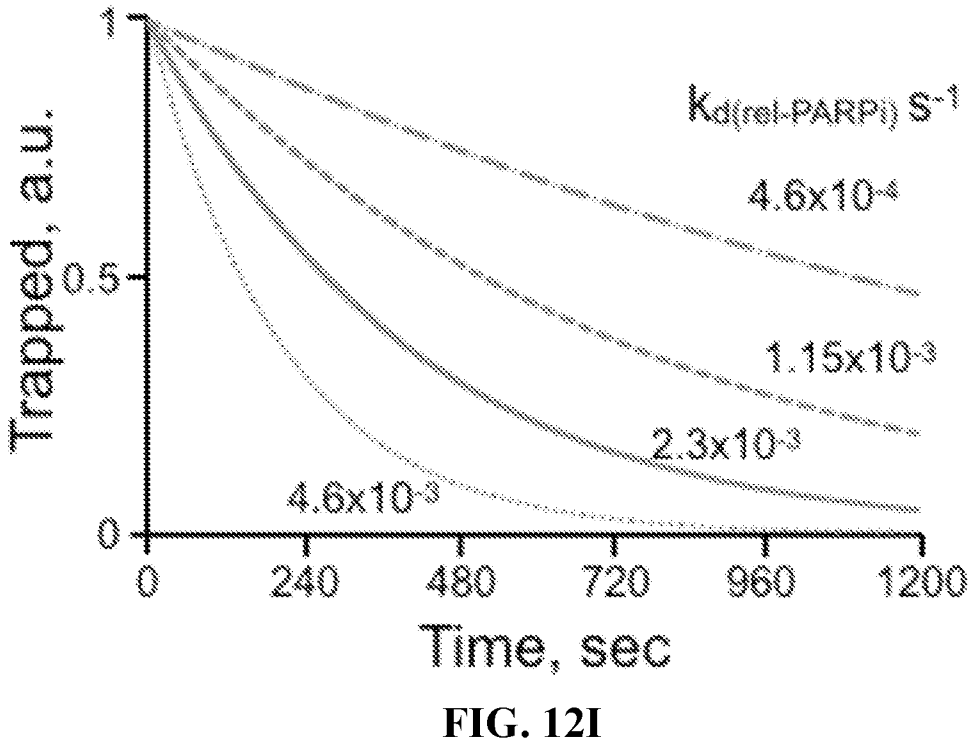

Overall, ODE calculations reveal that the duration of the PARP1-DNA interaction limited by the PARP1 affinity for DNA and therefore, based on measured affinities (25), a single PARP1-DNA interaction is not able to recapitulate cellular trapping. Thus, we reasoned that something within the cellular environment must be impacting trapping. We arrived at three different possible mechanisms (FIG. 12G). First, trapping must involve release and rebinding of PARP1, with self-PARylation accumulation through enzymatic activity reducing PARP1 affinity for DNA in a PARPi-specific manner. Previous in vitro measurements show PARP1-DNA interactions lasting several hours in the presence of PARPi (19, 20), with correlation to differential PARPi trapping observed in cells. However, in cells this mechanism relies on the same PARP1 molecule (or molecules) rebinding DNA and accumulating sufficient self-PARylation. Yet, the recent observation that PARP1 exchanges at sites of DNA damage independent of the presence of PARPi (27) suggests that this is not possible, and it is unclear how unbound PARylated PARP1 would not diffuse away or be replaced by an unPARylated PARP1. Therefore, we removed this mechanism from consideration. A second mechanism could be the presence of cellular proteins that drive increased PARPi-PARP1-DNA interaction in a PARPi-specific manner. This mechanism would be analogous to the presence of HPF1 interacting with PARP1 to induce preferential serine PARylation (28), such as another PARP1/DNA interacting protein serving to trap PARP1 with altered affinity in the presence of PARPi. Lastly, there could be an unknown mechanism driving PARP trapping.

Figure 13B:
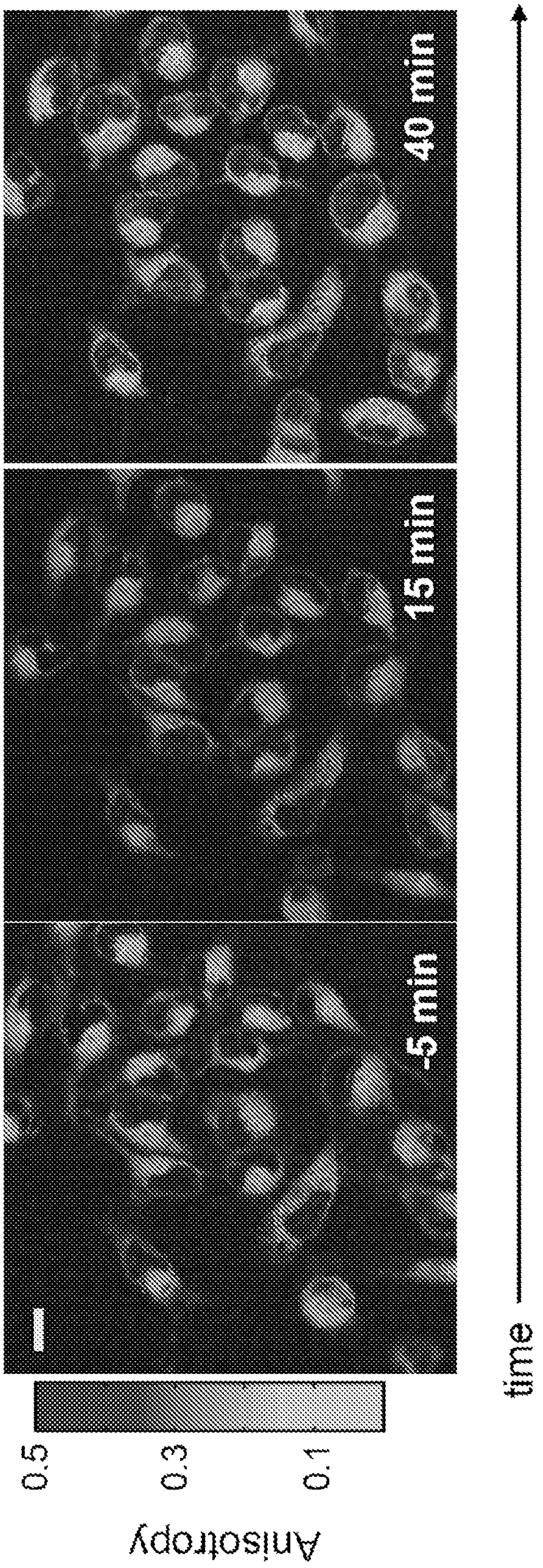
Figure 13C:
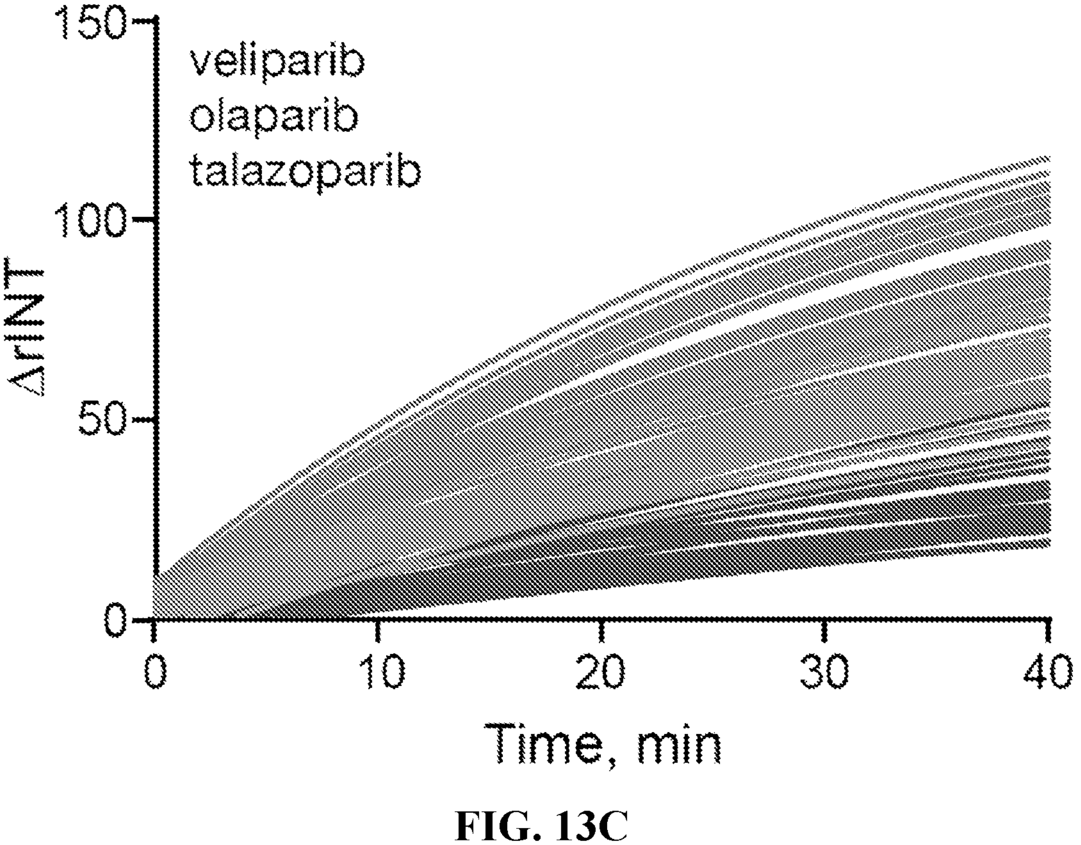
Figure 13D:
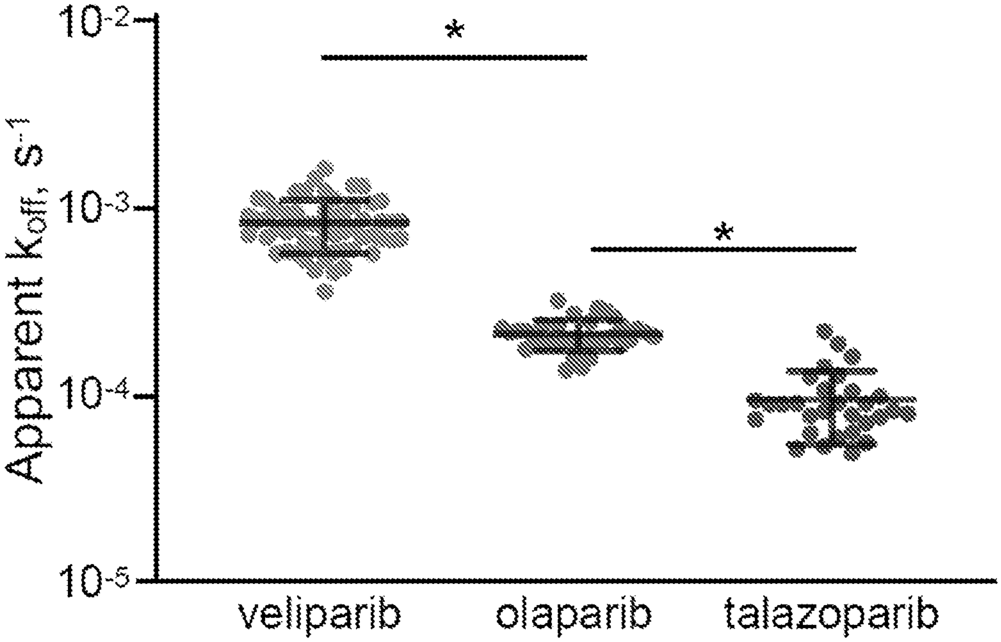
Figure 13E:
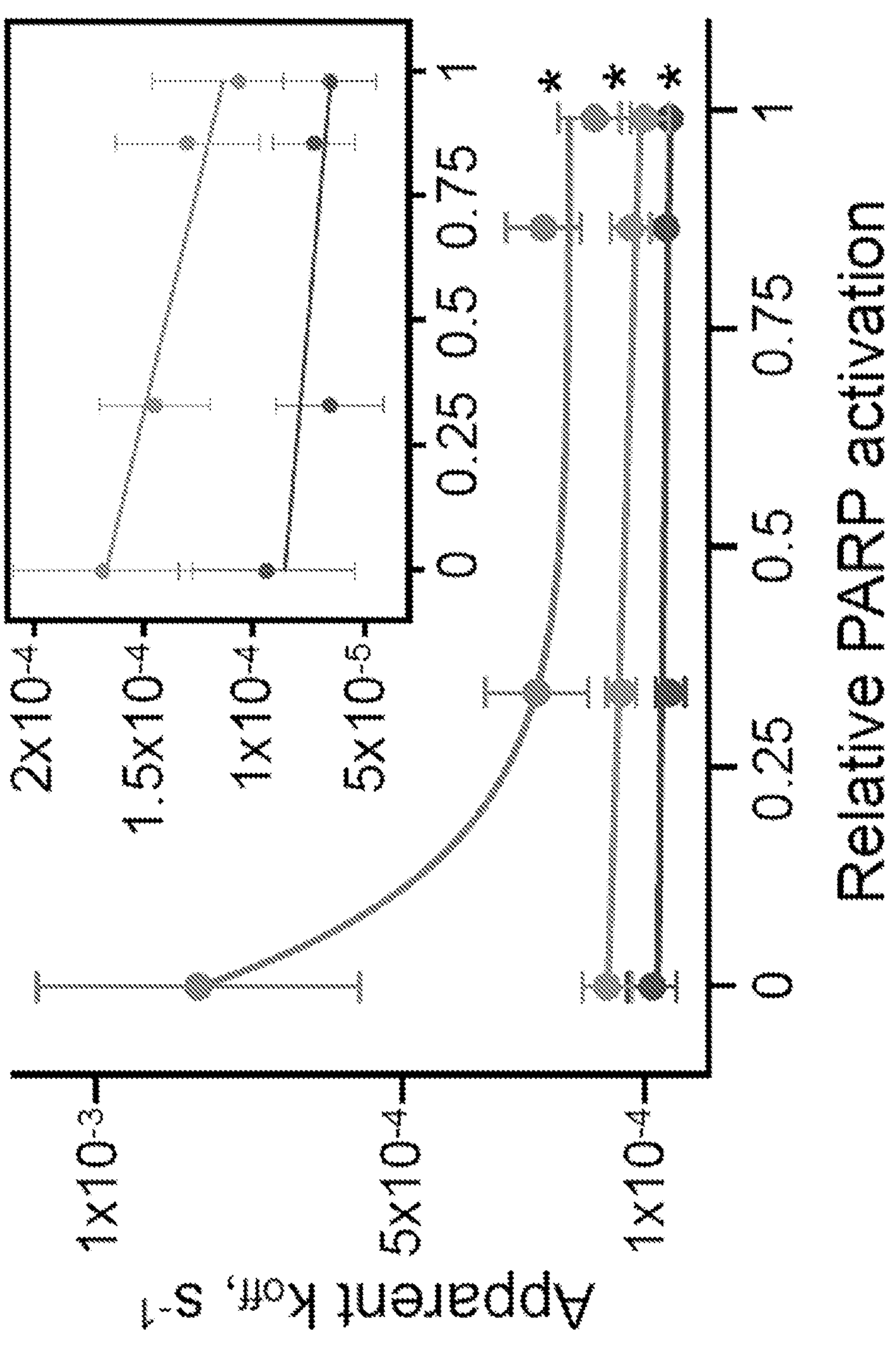
Figure 21A:
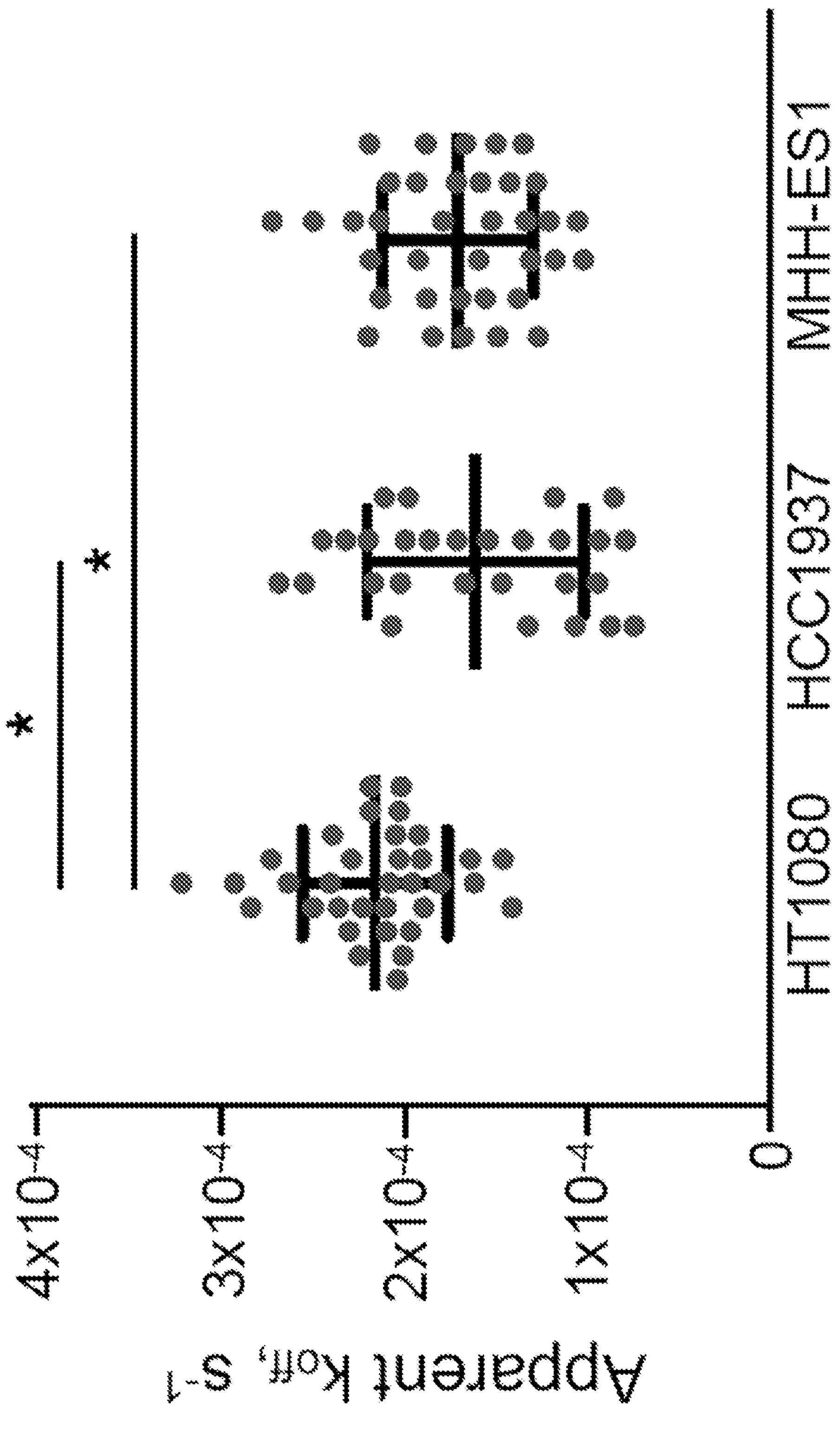
FIGS. 21A-21F: Dissociation constant as a function of PAR production.
Figure 21B:
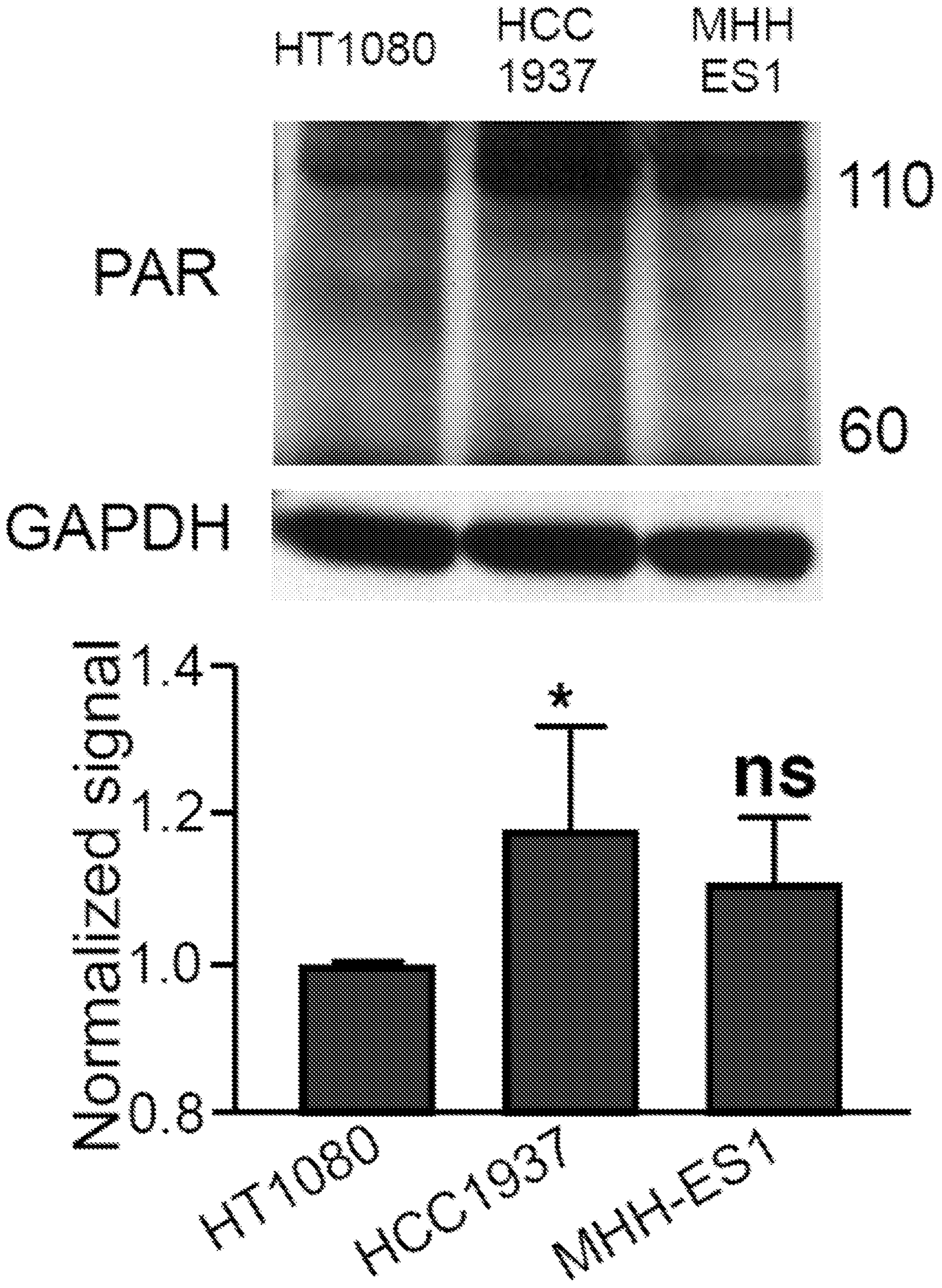
Figure 21C:
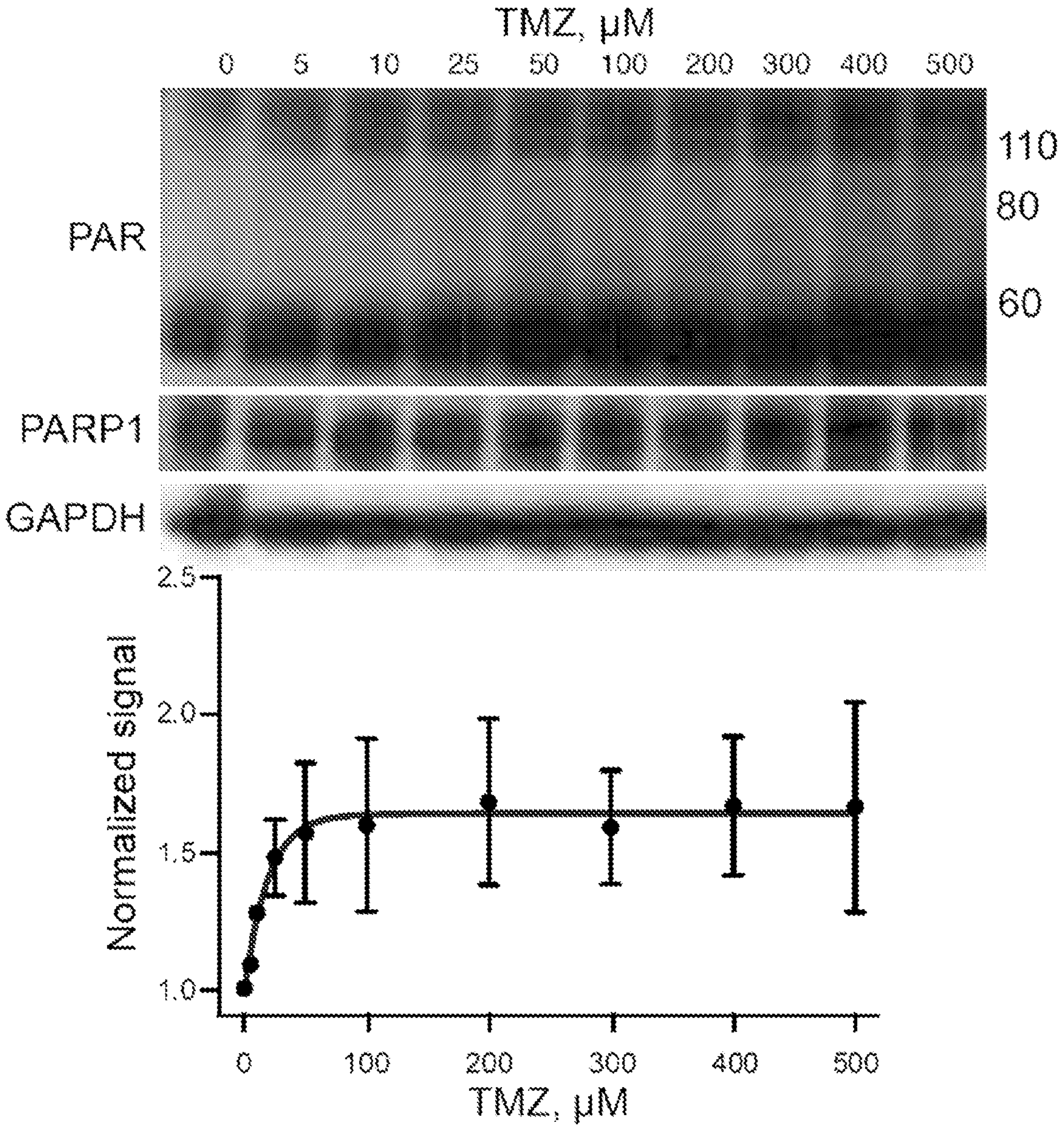
Figure 21D:
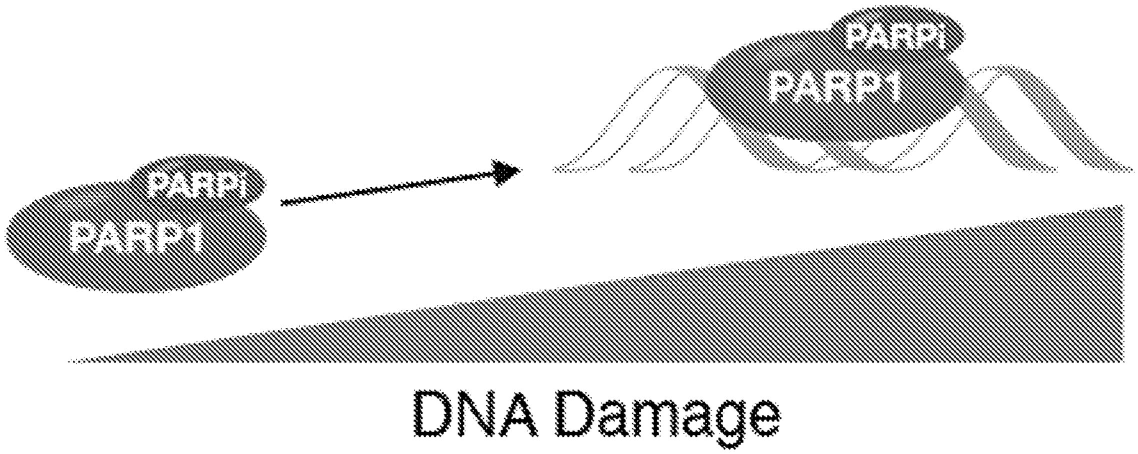
Figure 21F:
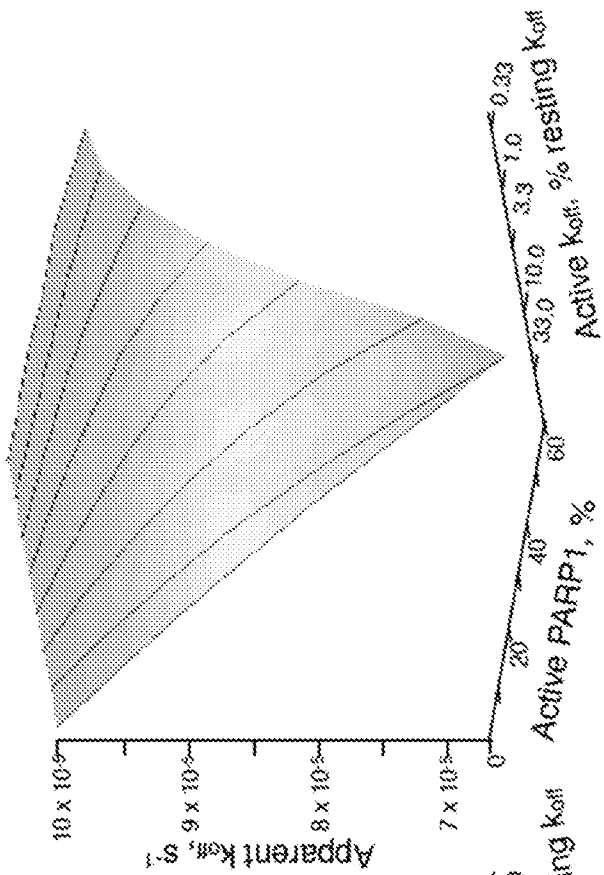
Figure 21E:
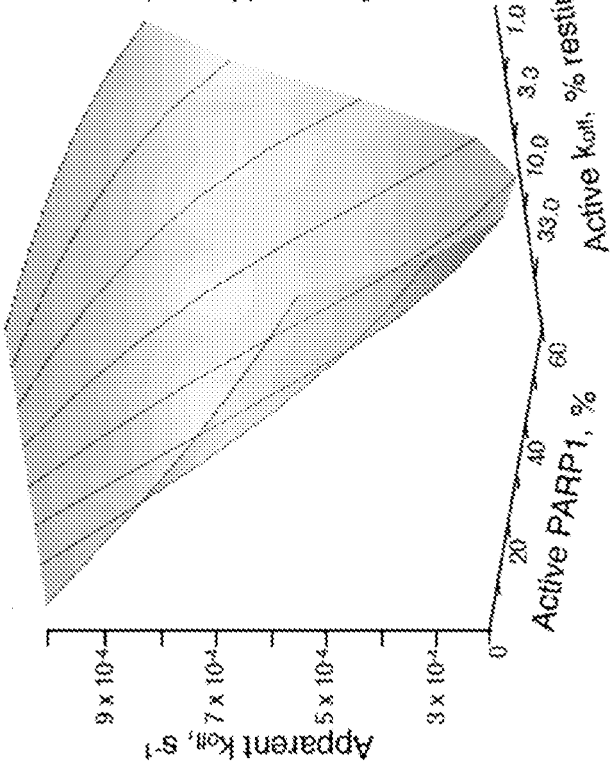
Figure 22A:
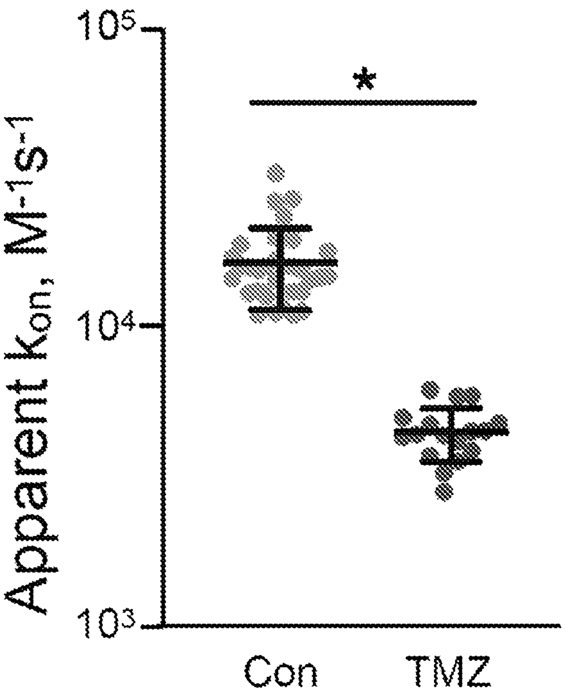
FIGS. 22A-22D: Fluorescent olaparib binding in dissociation measurement assay.
Figure 22B:
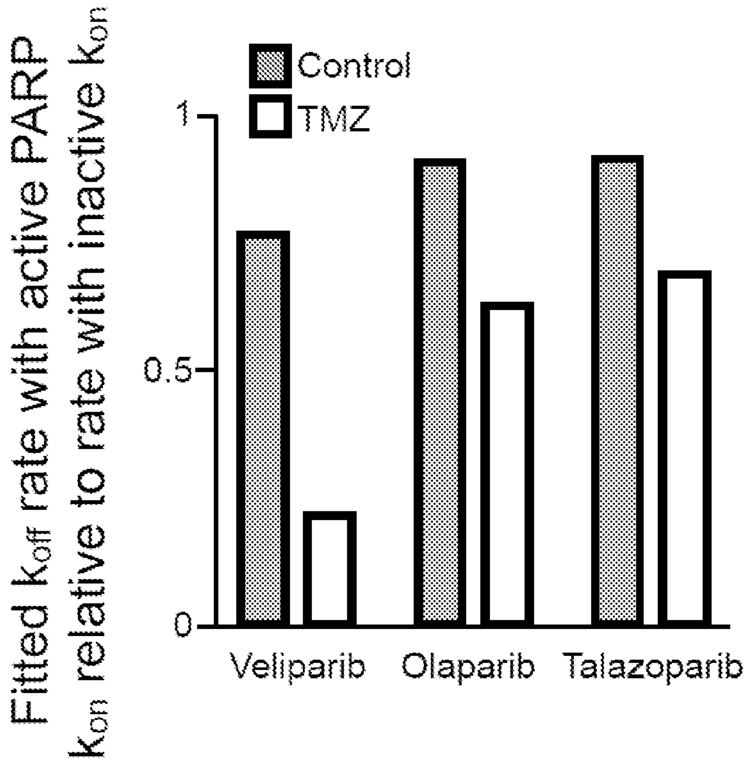
Figure 22C:
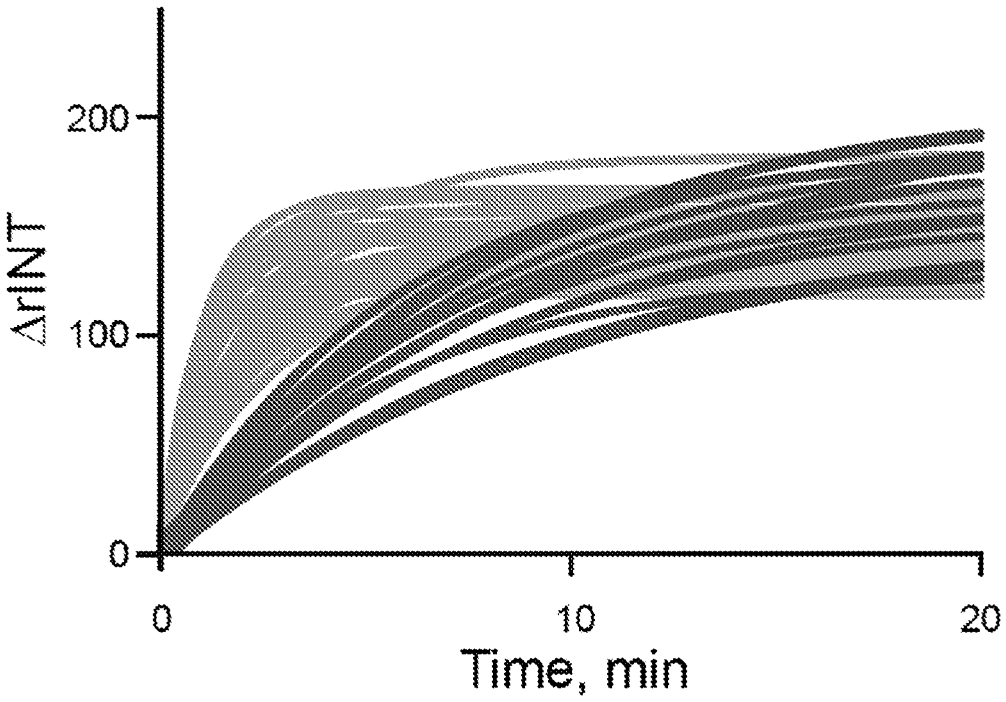
Figure 22D:
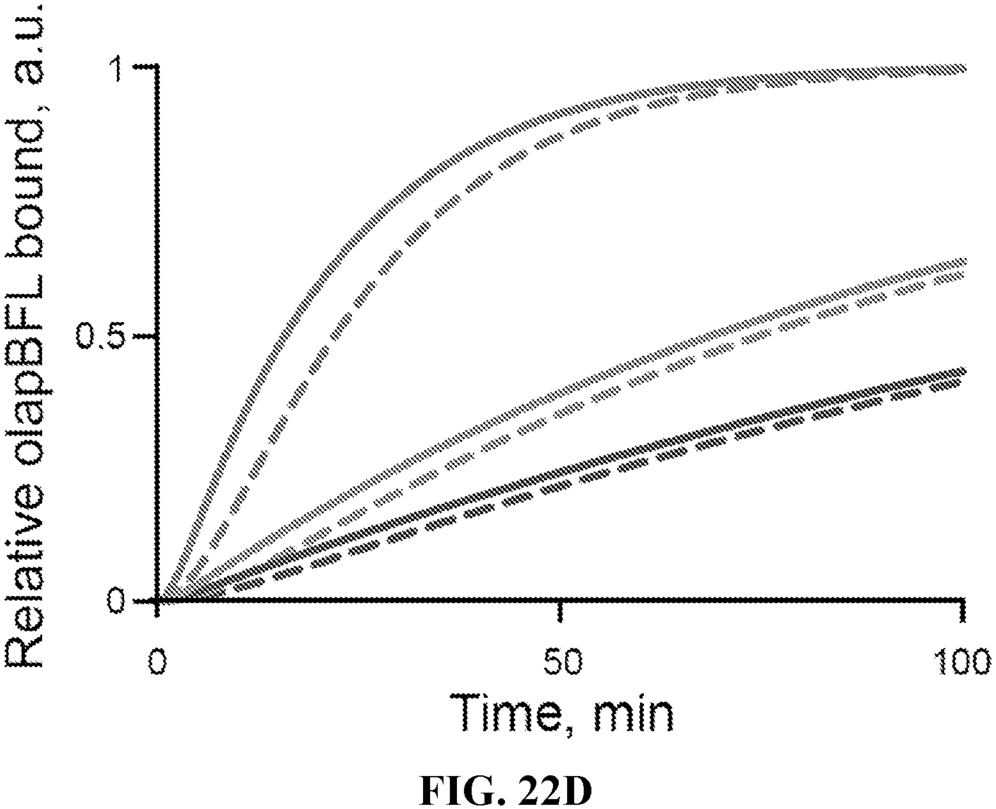

We first sought to determine if the PARPi-PARP1-DNA complex is altered in cells. We previously found that the equilibrium binding affinity inside cells for three PARPi was consistent with in vitro measurements (29). Yet, we reasoned that if another protein were interacting with and extending the duration of the PARPi-PARP1-DNA complex in the cellular environment, the dissociation constant ($k_{off}$) of PARPi from PARP1 would also be extended in a PARPi-specific manner. Thus, we developed an assay to quantify inhibitor $k_{off}$ in live cells (FIG. 13A and FIGS. 20A-20D). Here, we measured fluorescence anisotropy (29) (FIG. 13B) of a fluorescently labeled PARPi, olaparib covalently attached to BODIPY FL (30), in competitive binding experiments. We observed significantly different $k_{off}$ rates for veliparib, olaparib and talazoparib in HT1080 cells (FIGS. 13C-13D), with values similar to those previously determined in purified protein, indicating that the duration of the PARPi-PARP1-DNA complex is not extended in cells. However, we found correlation between apparent $k_{off}$ rates and cell-type basal PARP activity in different cell lines (FIGS. 21A-21B), contrary to the measurements of the equilibrium binding affinity (29). This PARP activity impact was observed in HT1080 cells alone by activating PARP through addition of the DNA alkylating agent temozolomide (TMZ), which causes broad DNA damage repair pathway activation (31) (FIG. 21C). However, the $k_{off}$ values for all three PARPi demonstrated a significant PARP activation dependency (FIG. 13E and FIG. 21C), with a response that reflected the integration of two distinct $k_{off}$ values (FIGS. 21D-21F). Thus, we concluded that the apparent dissociation of PARPi from PARP was slower when PARP was activated, which is in contrast to previous measurements outside cells (24), but this dependency was not unique to higher trapping PARPi. We also found the association binding constant ($k_{on}$) of fluorescent olaparib was significantly slower when PARP was activated (FIG. 22A and FIG. 22C). We modeled the impact of $k_{on}$ on $k_{off}$ measurements and found a lower $k_{on}$ does not fully explain the apparent $k_{off}$ dependency on PARP activation (FIG. 22B and FIG. 22D), yet the shifts in $k_{on}$ and $k_{off}$ are similar. These results indicate there is no PARPi-specific stabilization of the PARPi-PARP1-DNA complex in cells, but all binding rates are lower when PARP is activated.

Figure 14A:
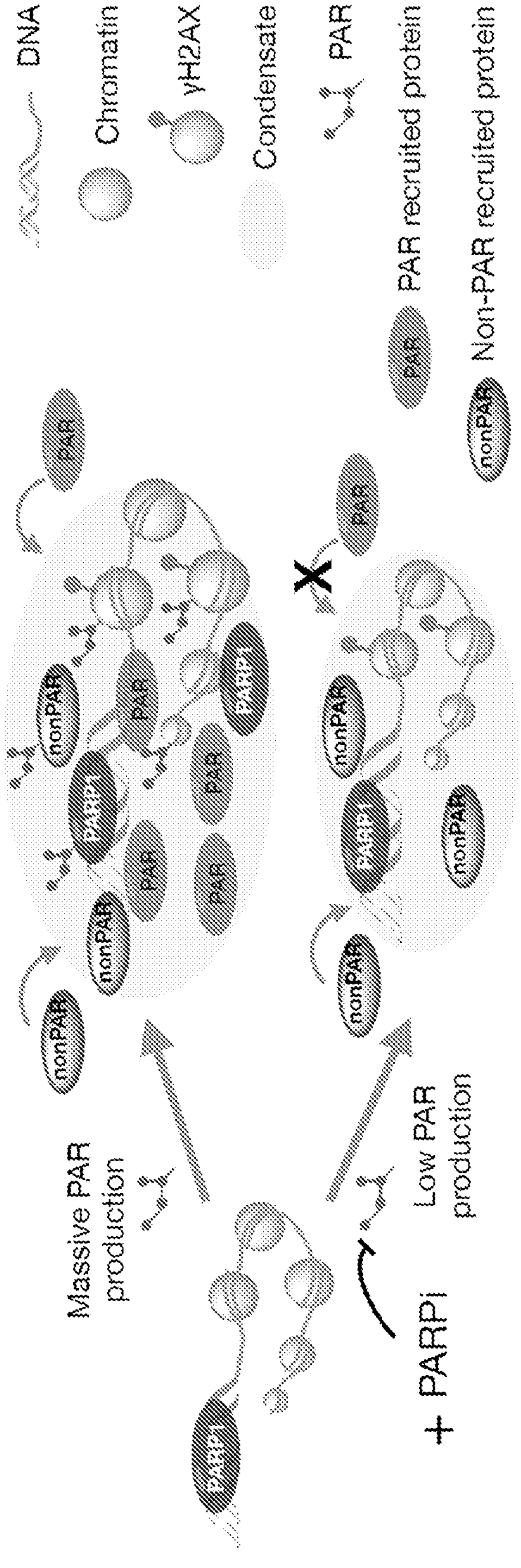
FIGS. 14A-14H: DNA damage biomolecular condensate density correlates to PARP trapping and cell line response to PARPi.
Figure 14B:
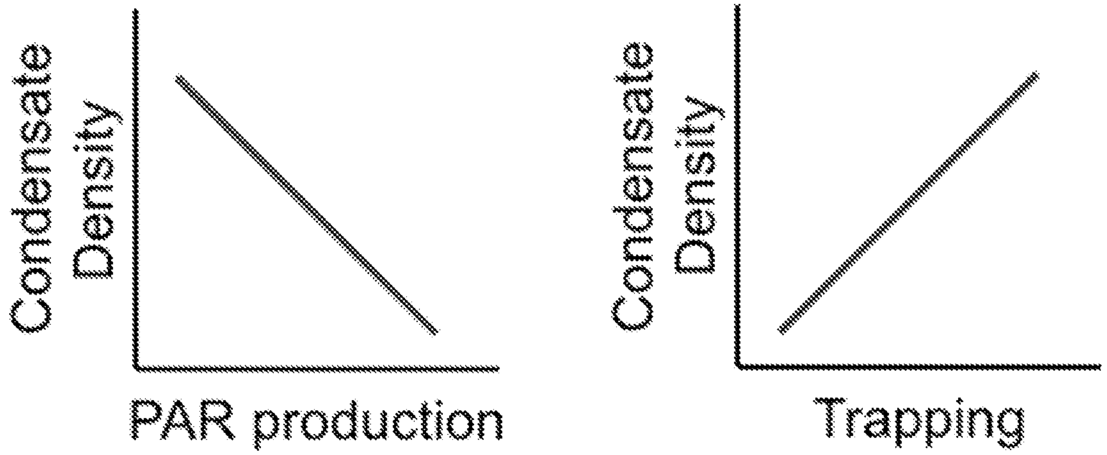
Figure 14C:
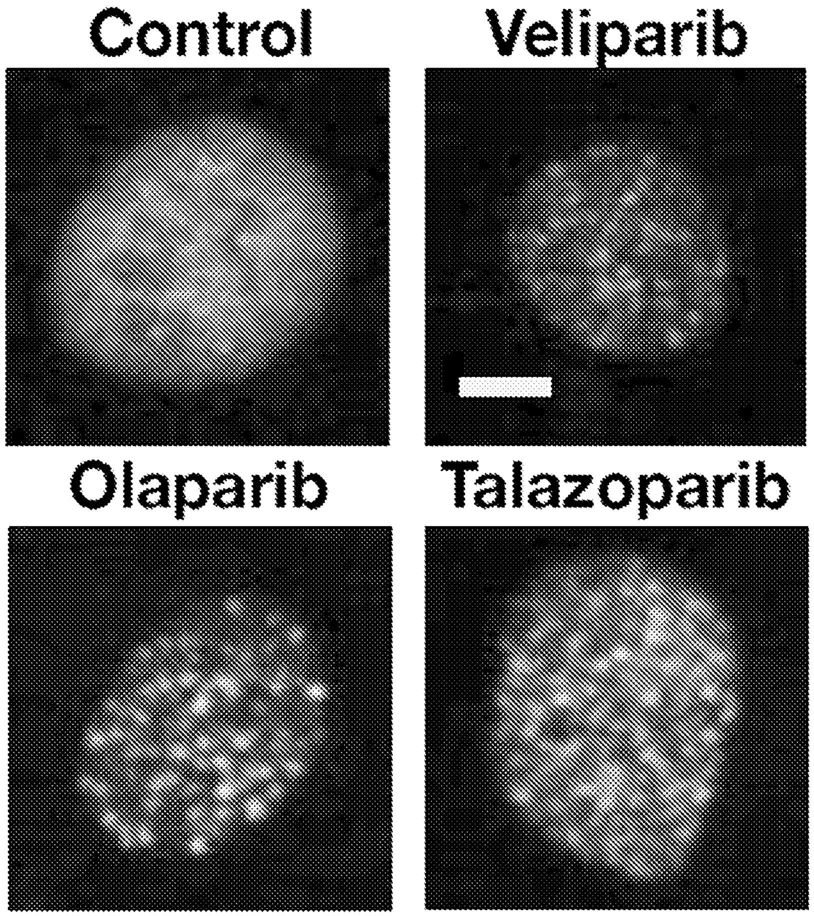
Figure 14D:
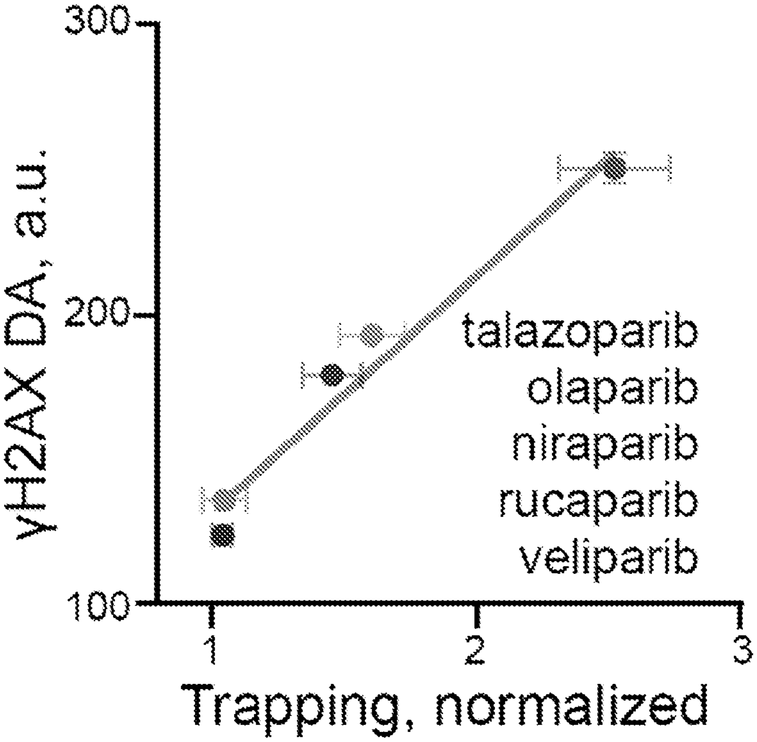
Figure 14E:
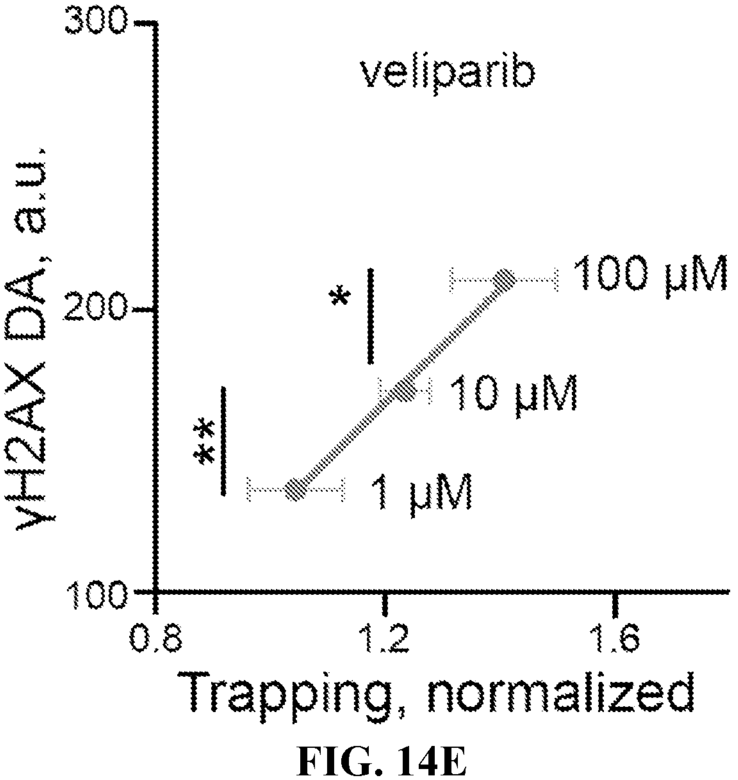
Figure 14F:
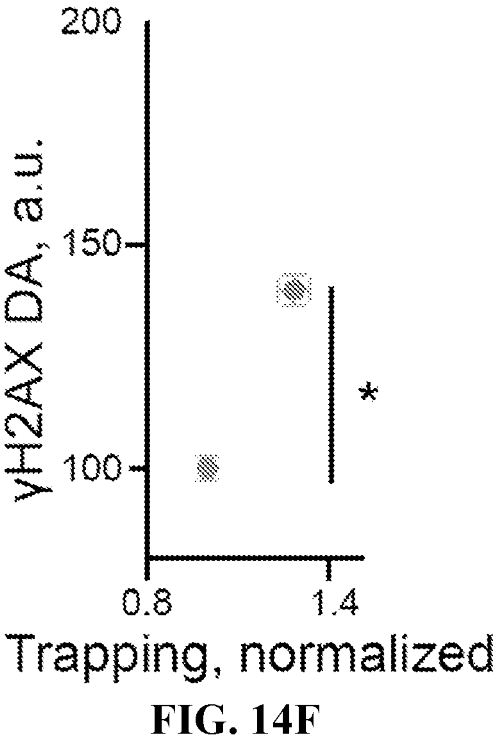
Figure 23A:
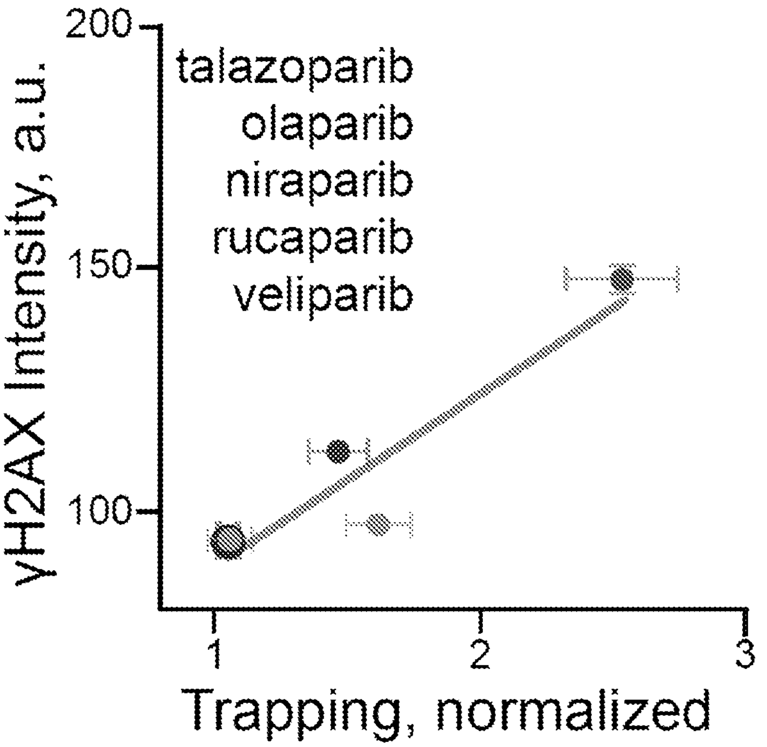
FIGS. 23A-23K: PARPi impact on DNA damage induced condensates.
Figure 23B:
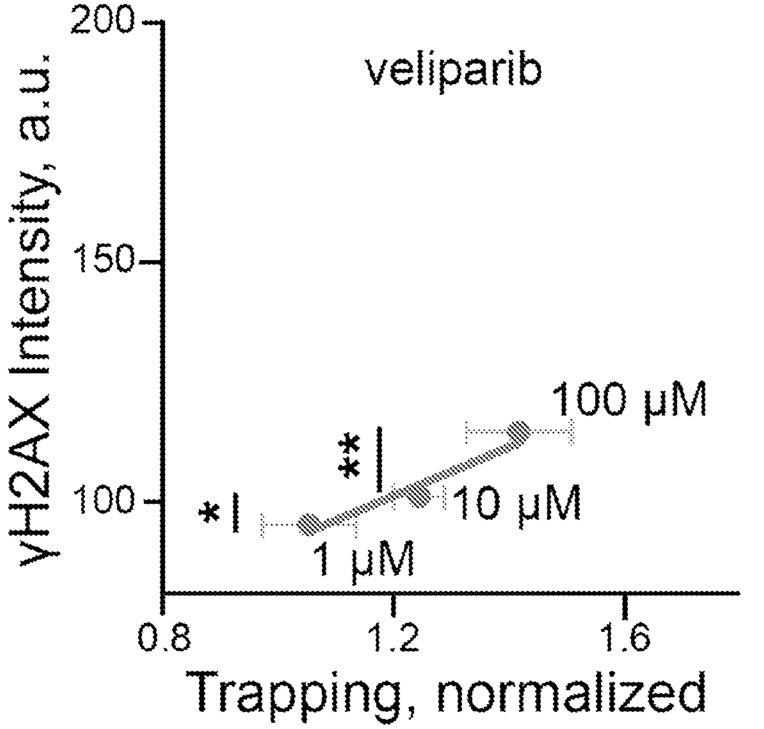
Figure 23C:
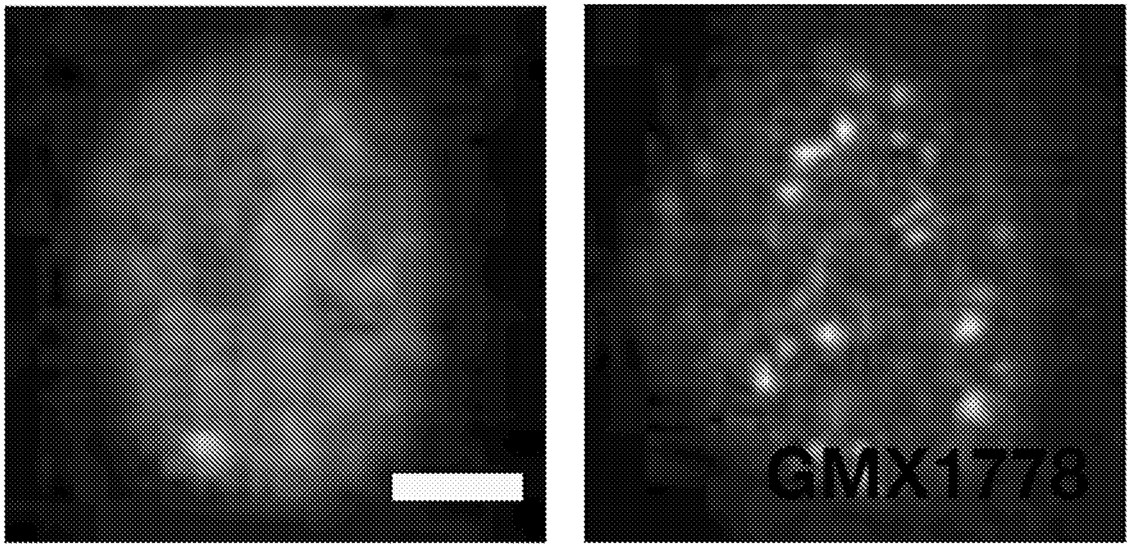
Figure 23D:
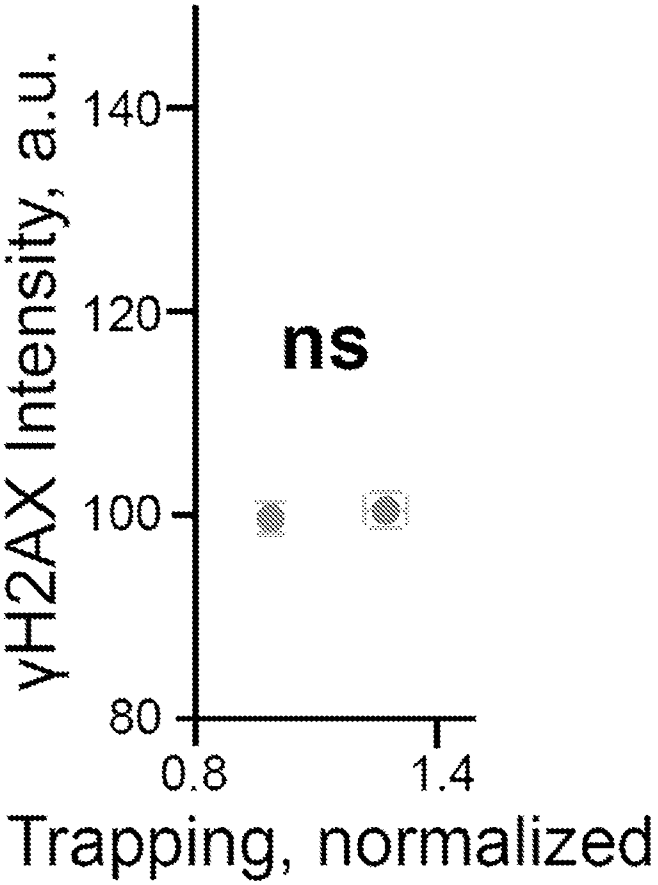

One possible explanation for our observed PARP activation impact on all binding rates is an altered environment. Therefore, we turned our attention to a hallmark of PARP activity—the formation of DNA damage biomolecular condensates through PAR production and protein recruitment (32-37). It is well established that PARPi alter protein recruitment (38-40) and we hypothesized that altered recruitment would enable PARP dissociation from and rebinding to damaged DNA by preventing recruited proteins from displacing PARP. We reasoned that reduced PAR-based recruitment would be reflected in a higher condensate density of PAR-independent markers, and, if this mechanism impacts response to PARPi, condensate density would correlate to trapping (FIGS. 14A-14B). To quantify density within condensates we used segmented image correlation spectroscopy (ICS) (41) of whole nuclei on immunofluorescence (IF) images of $\gamma H_2AX$, a marker of double-strand DNA breaks (42). Here, ICS measures the average aggregation state of $\gamma H_2AX$ within the nucleus. Unlike foci counting, ICS provides a measure of how clustered a $\gamma H_2AX$ is within the nucleus. PARPi treatment overnight at 1 μM induced condensate formation of $\gamma H_2AX$ in HT1080 cells (FIG. 14C), with ICS degree of aggregation (DA—a measure of $\gamma H_2AX$ cluster density) values correlating to trapping across 5 different PARPi (FIG. 14D). However, $\gamma H_2AX$ levels, measured by intensity, did not have as strong of a correlation PARPi trapping (FIG. 23A), and the intensity correlation was driven largely by the high levels of $\gamma H_2AX$ following talazoparib treatment ($R^2$ of the correlation to trapping in the absence of talazoparib is 0.98 for DA and 0.3 for intensity). We also found $\gamma H_2AX$ DA correlated to veliparib concentration dependent trapping (FIG. 14E). And, NAMPT inhibition with GMX1778 alone significantly increased $\gamma H_2AX$ DA, correlating to measured trapping (FIG. 14F), despite no significant difference in $\gamma H_2AX$ levels (FIGS. 23C-23D).

Figure 23E:
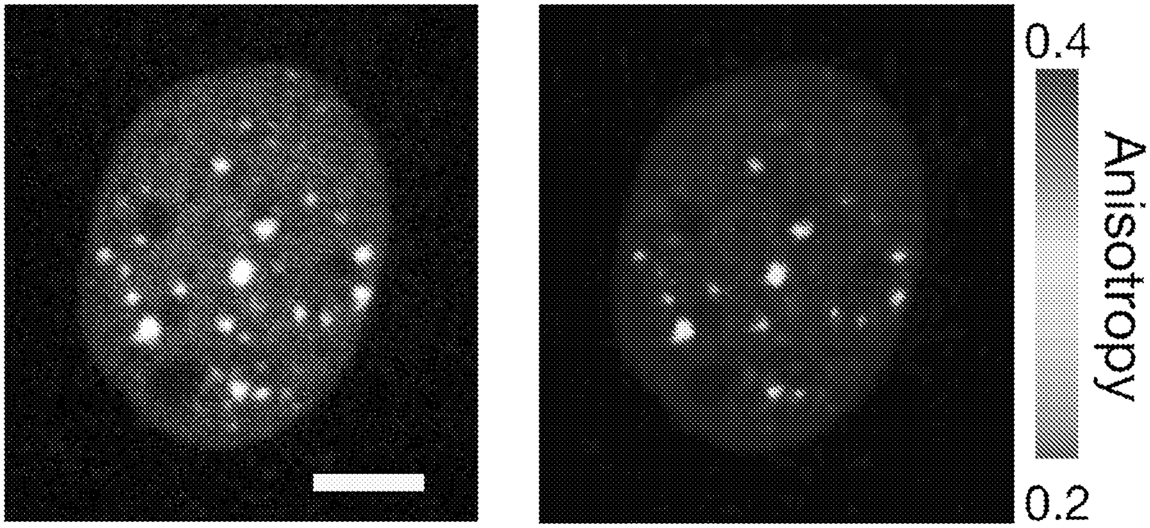
Figure 23F:
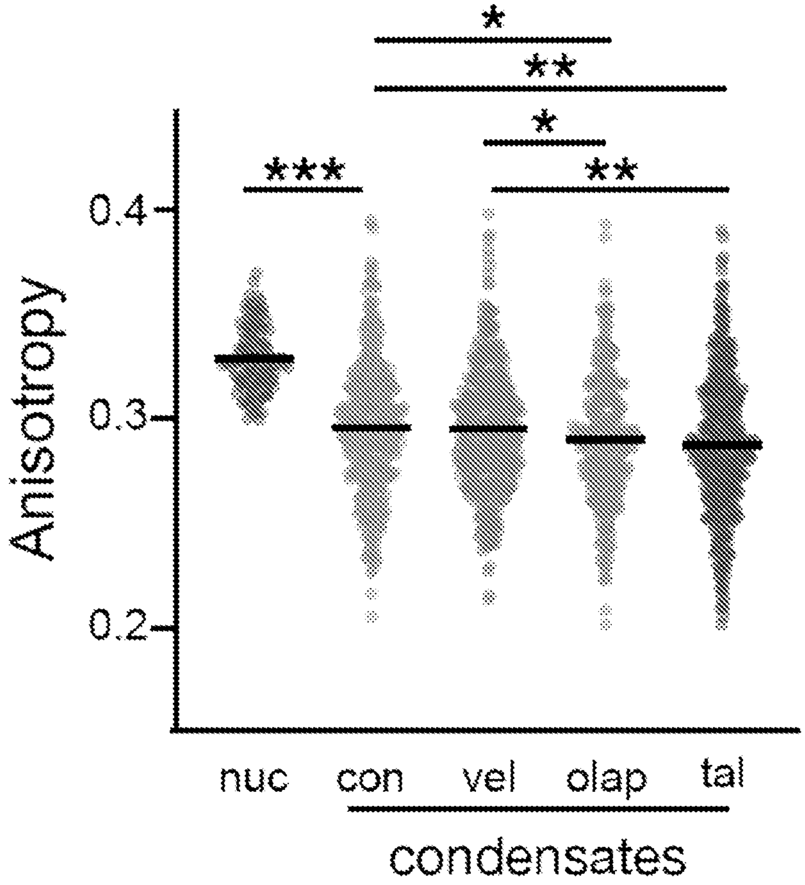
Figure 23G:
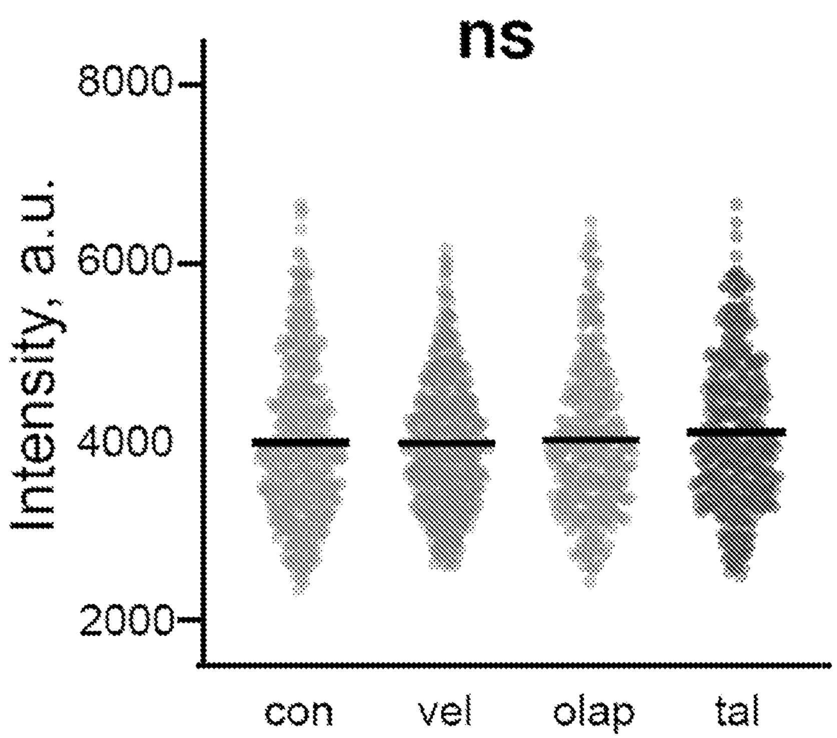
Figure 23H:
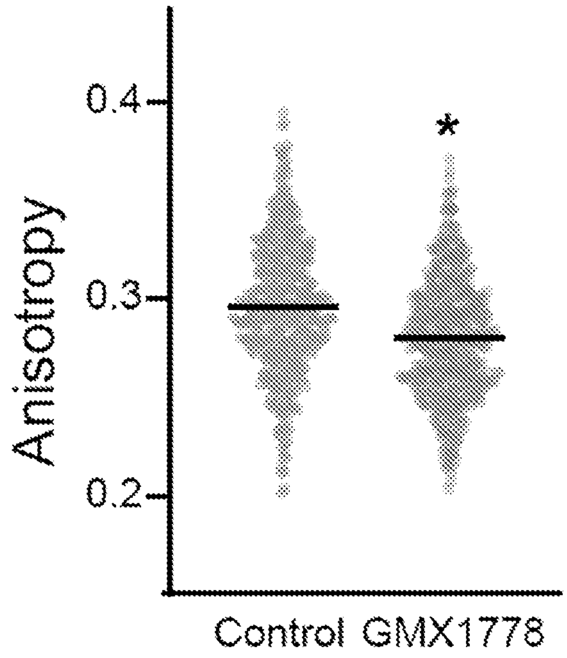
Figure 23I:
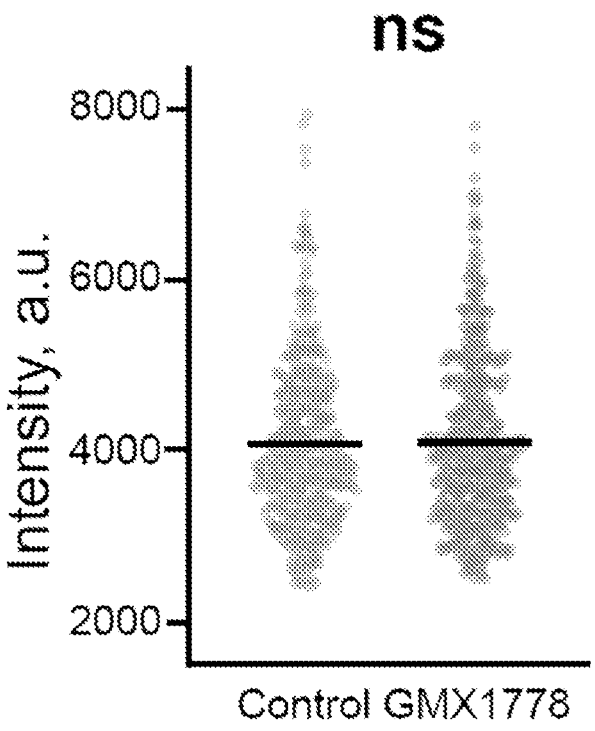
Figure 23J:
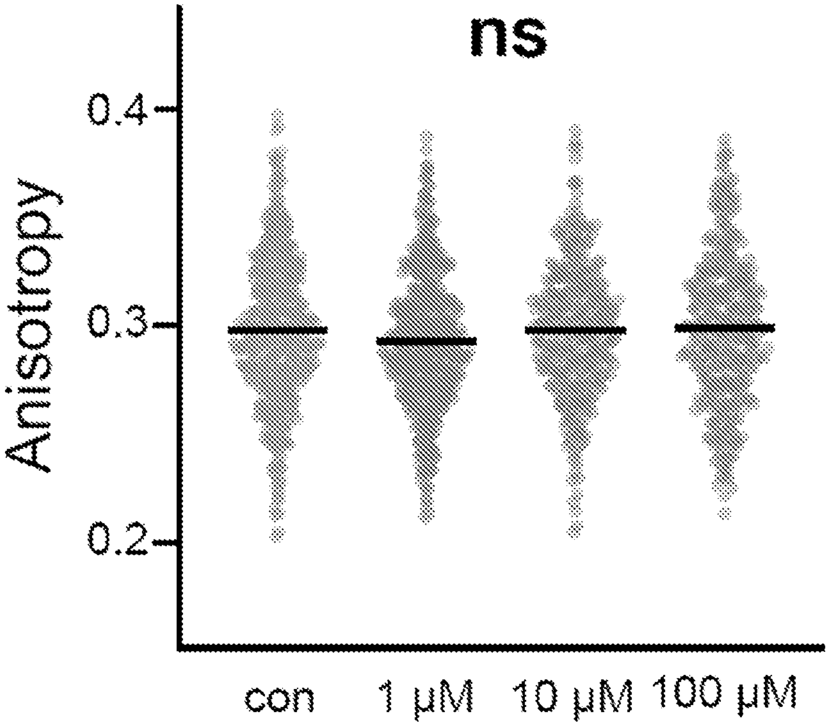
Figure 23K:
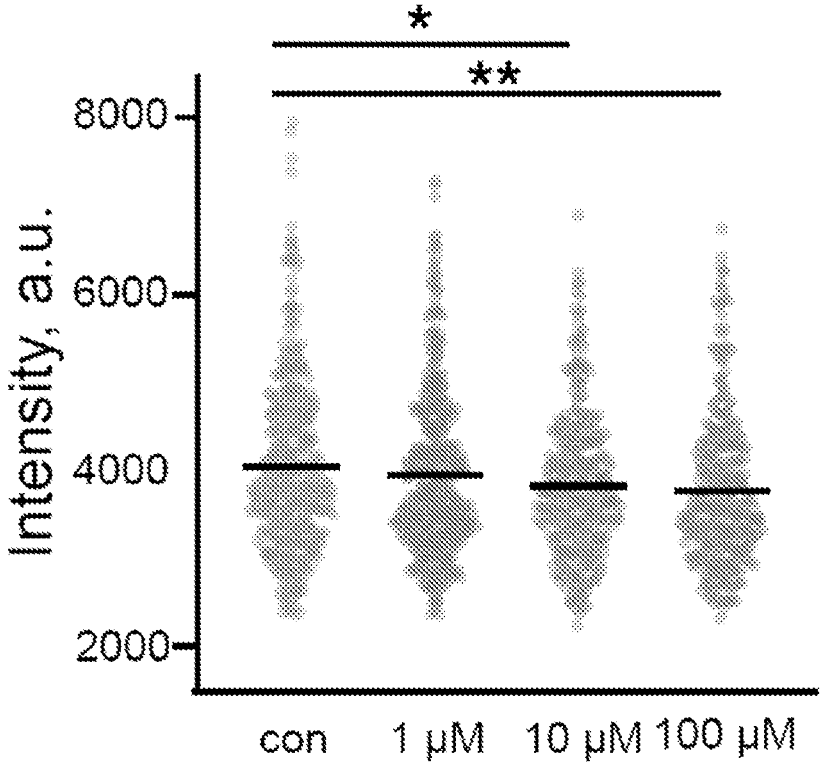

To validate our ICS results, we measured individual condensate density of fluorescently labeled 53BP1 using anisotropy to quantify homo-FRET. In this approach, lower anisotropy is produced by increased homo-FRET, which is driven by increased fluorophore density (+3). We used a truncated 53BP1, which binds to H4K20me2 (44), labeled with mApple (45) (FIG. 23E). The anisotropy of 53BP1-mApple in biomolecular condensates in HCC1937 cells was significantly lower than outside of condensates (FIG. 23F), demonstrating the increased density of condensates. However, similar to ICS measurements, condensate anisotropy was dependent on the presence and type of PARPi. We found significantly lower condensate anisotropy compared to control when cells were treated with 1 μM olaparib or talazoparib, but not with 1 μM veliparib, with no significant intensity differences (FIG. 23G). Furthermore, treatment with GMX1778 overnight significantly lowered condensate anisotropy without impacting condensate intensity (FIGS. 23H-231), while increased veliparib lowered condensate 53BP1-mApple intensity suggesting recruitment is diminished at high veliparib concentrations (FIGS. 23J-23K).

Figure 14G:
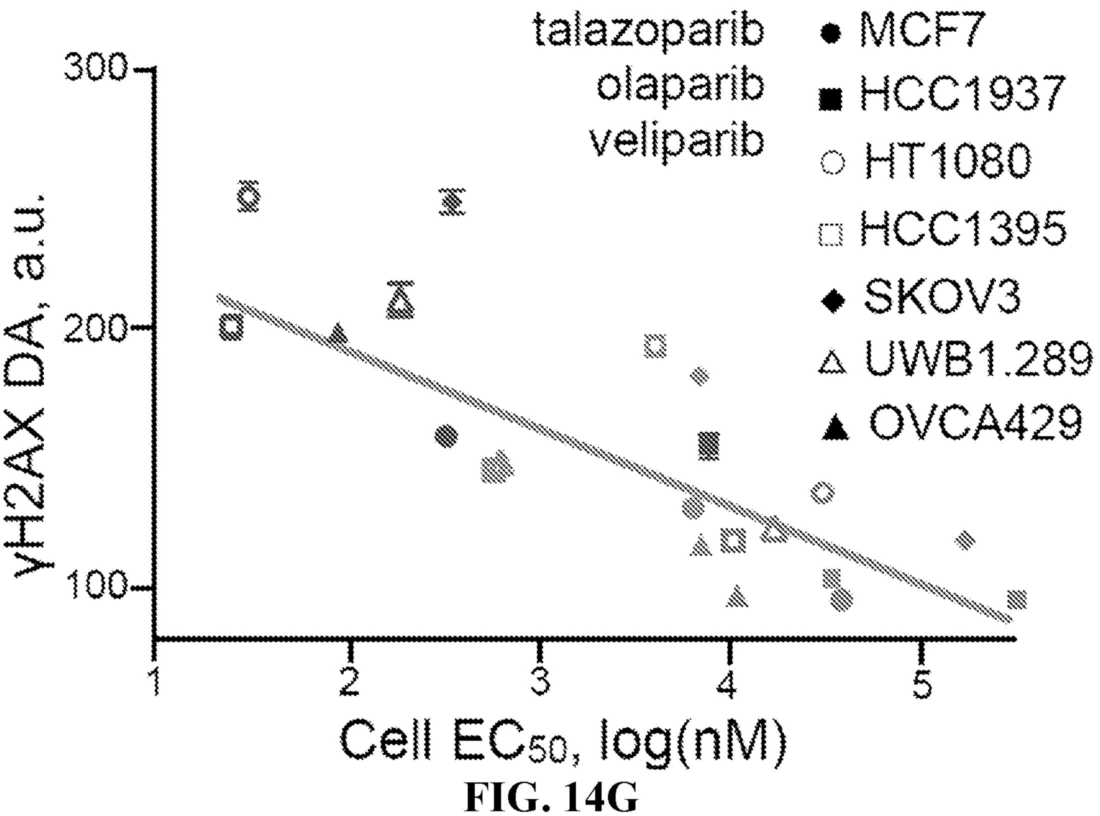
Figure 14H:
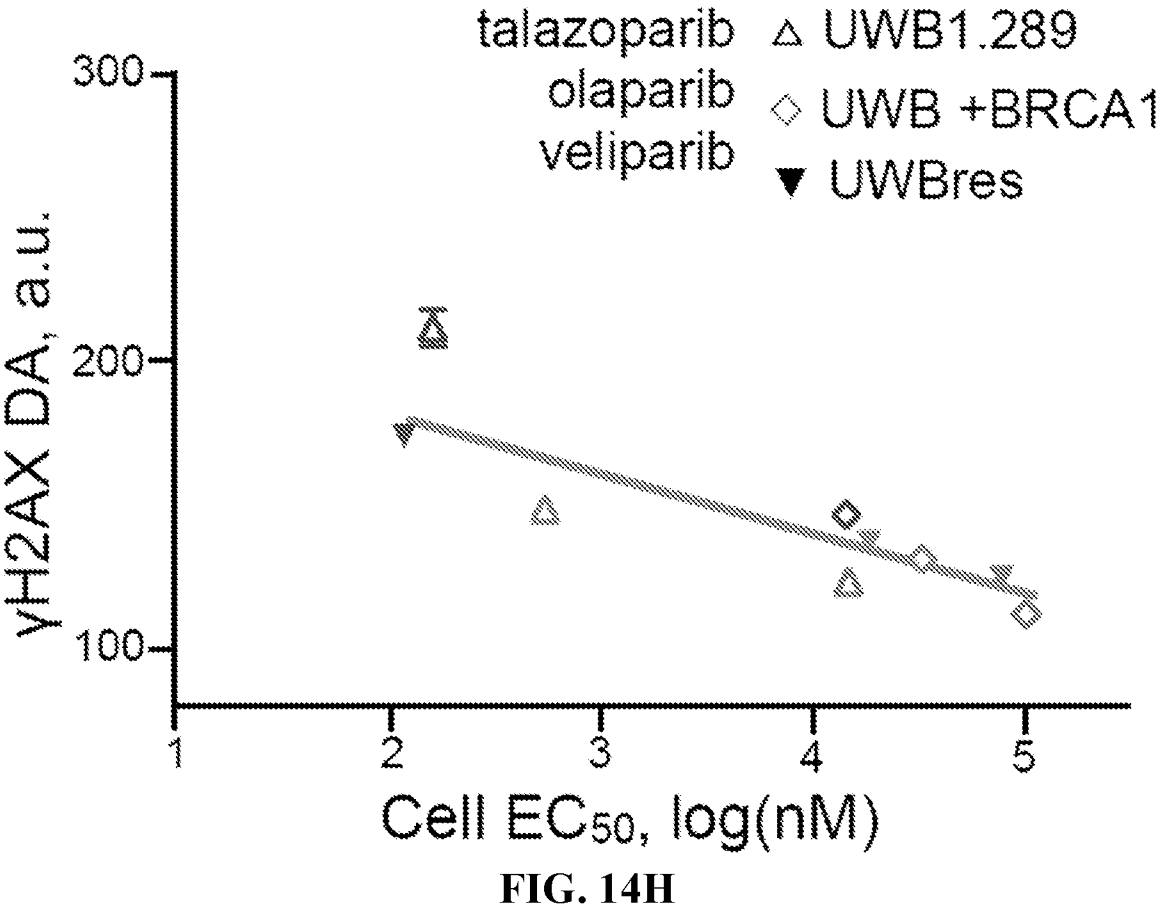
Figure 24A:
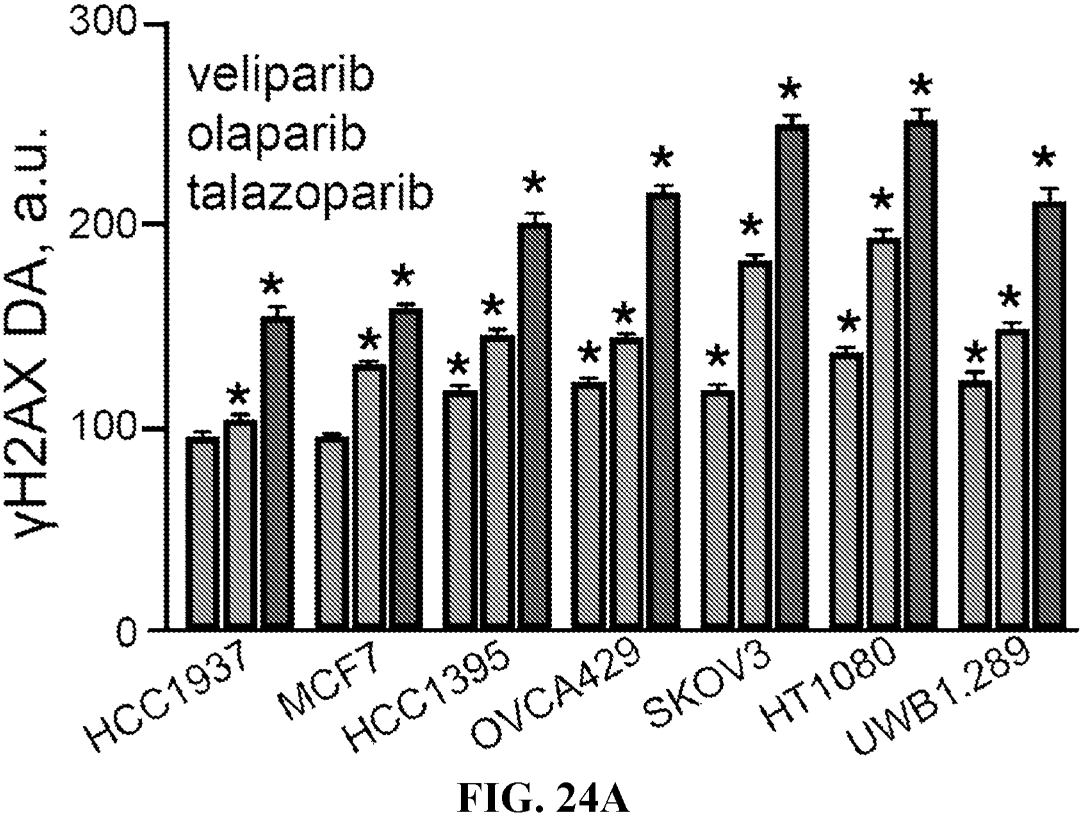
FIGS. 24A-24F: PARPi impact on $\gamma H_2AX$ DA in multiple cell lines.
Figure 24B:
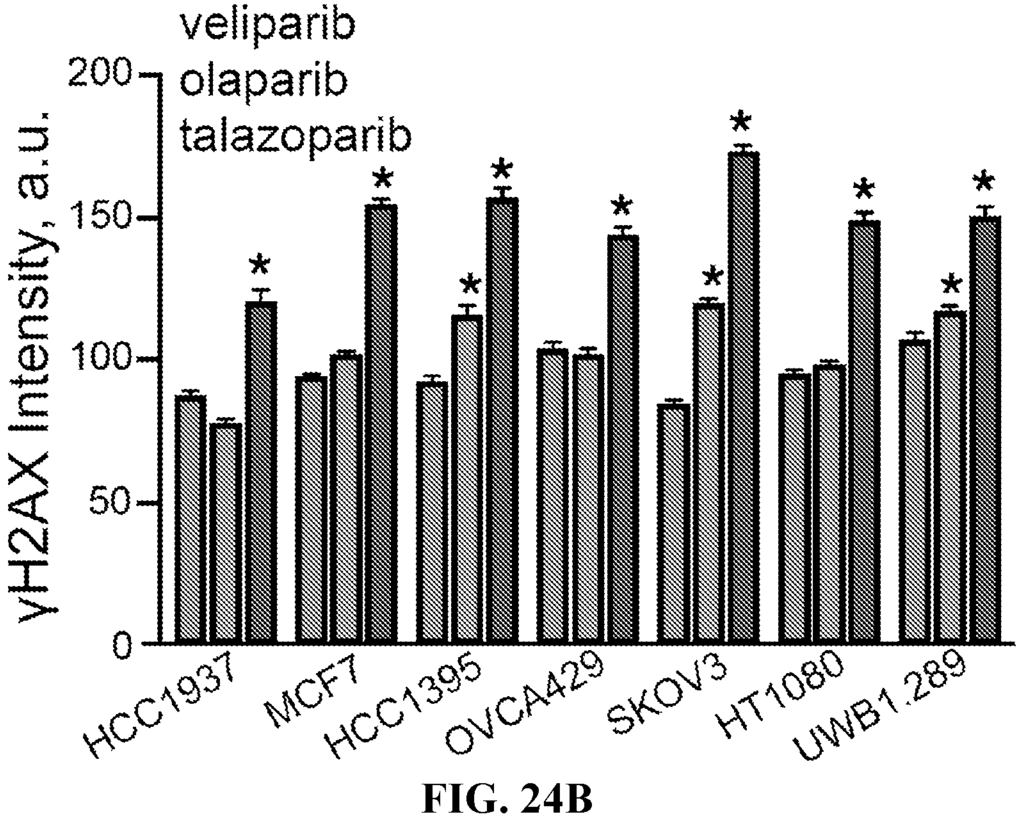
Figure 24C:
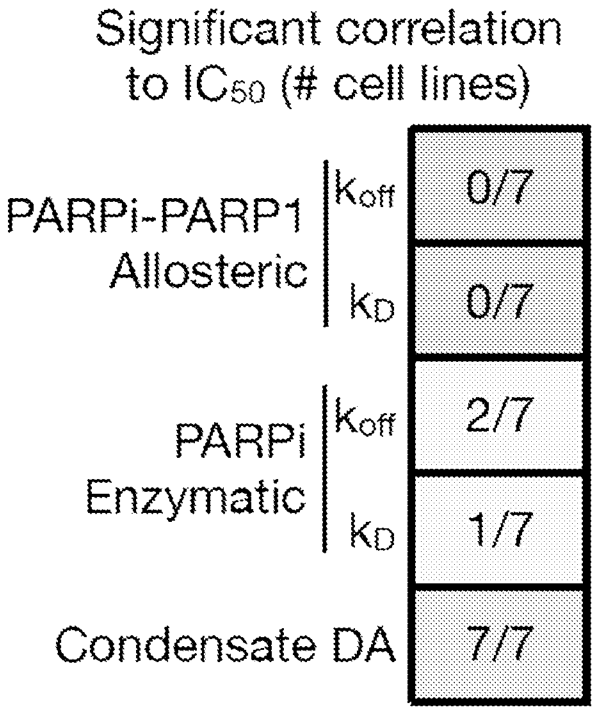
Figure 24D:
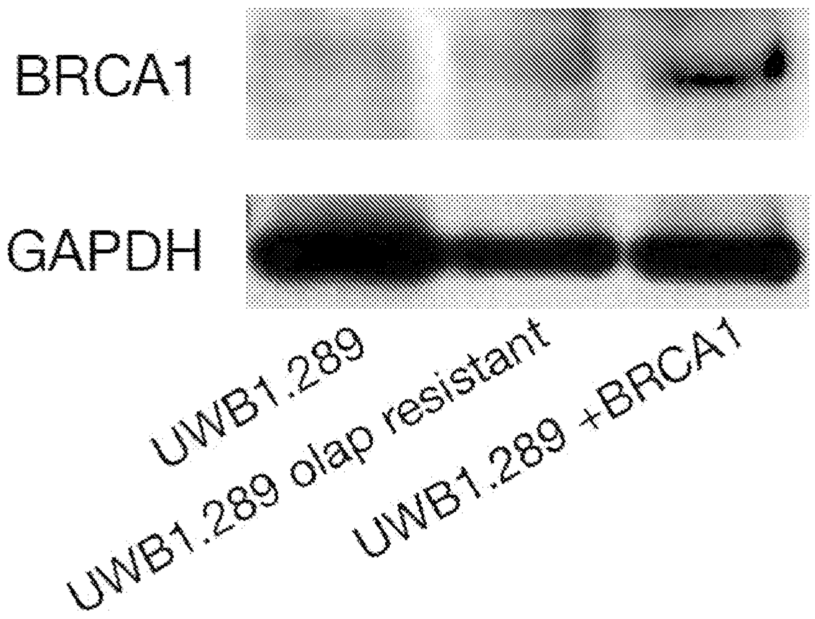
Figure 24E:
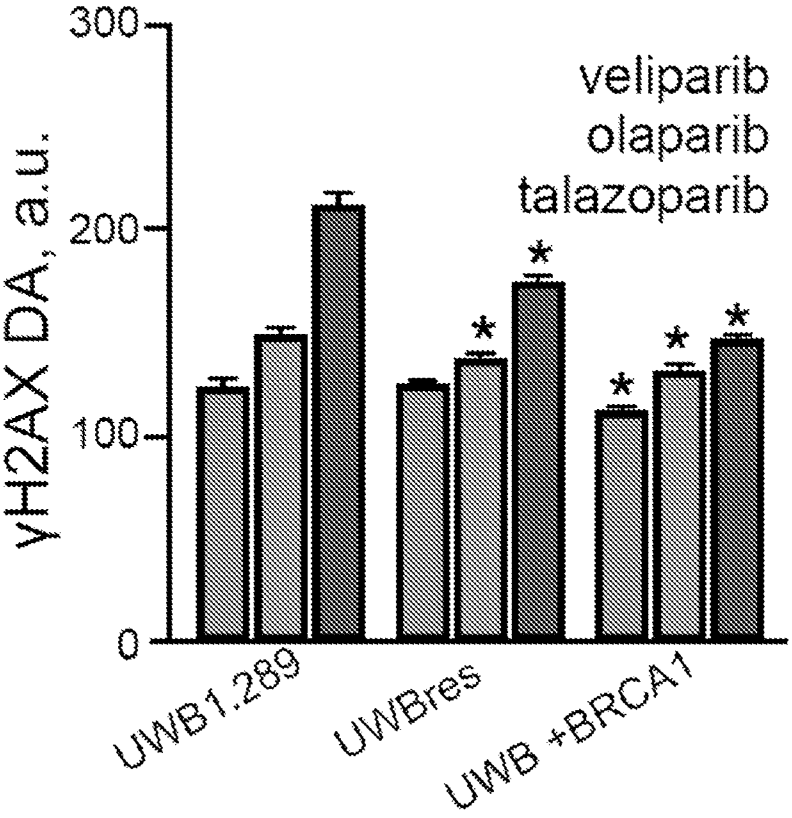
Figure 24F:
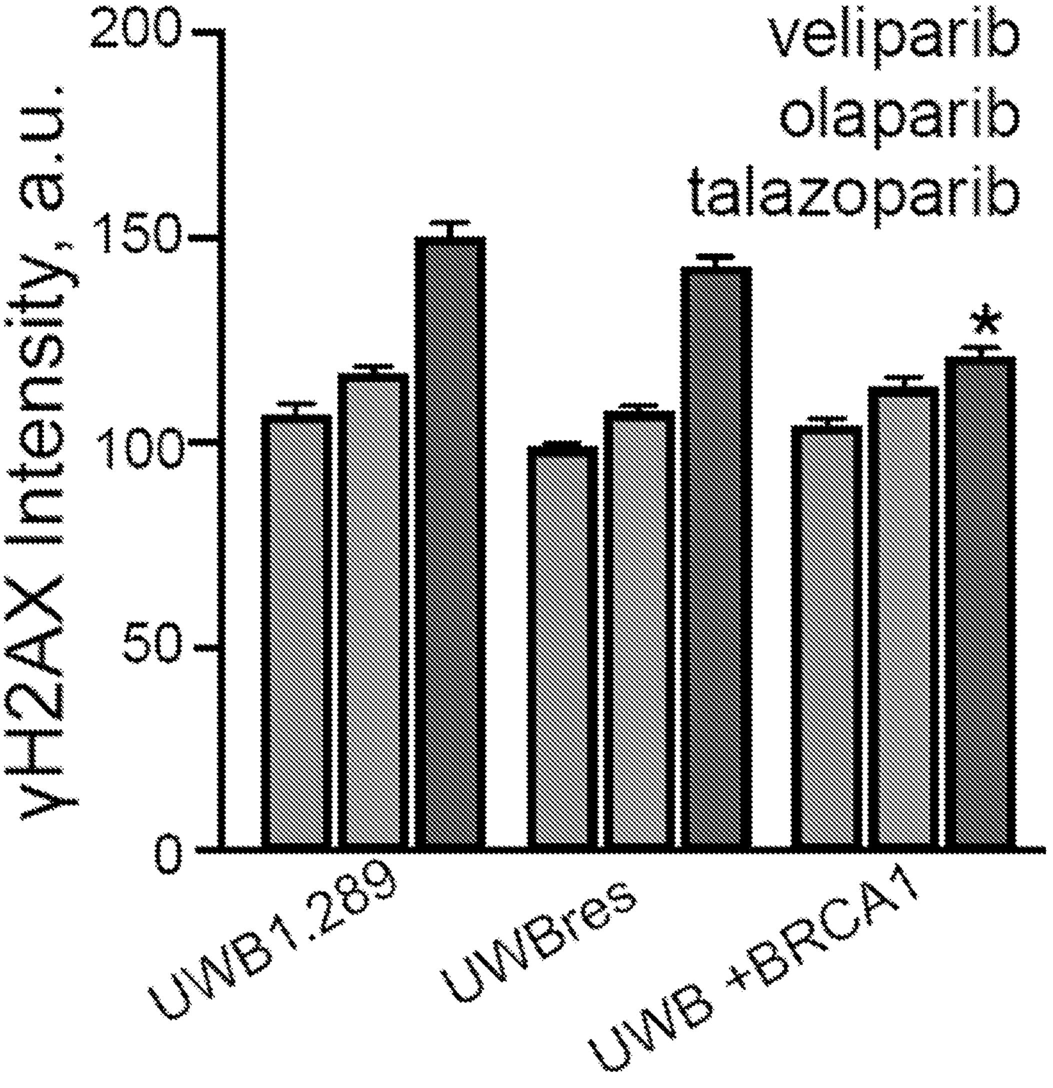

We then correlated $\gamma H_2AX$ ICS DA to cell line PARPi response for 3 PARPi in 7 cell lines (FIG. 14G). All cell lines showed a PARPi dependent $\gamma H_2AX$ DA that correlates with PARPi efficacy (FIG. 24A), contrary to the allosteric impact of PARP1 DNA affinity or enzymatic properties of PARPi (FIG. 24C). In HCC1937 cells, a poor responder to PARPi treatment, talazoparib results clustered with olaparib treatment for other cell lines, and olaparib results similarly clustered with veliparib treatment, suggesting that $\gamma H_2AX$ DA correlates to PARPi efficacy independent of both cell line and PARPi species. Unlike DA, some treatment conditions showed no significant increase in $\gamma H_2AX$ levels over control, yet for all cell lines talazoparib treatment increased $\gamma H_2AX$ levels (FIG. 24B). $\gamma H_2AX$ DA also correlated to cell response in isogenic cell lines UWB1.289, UWB1.289+BRCA1 and UWB1.289 resistant to olaparib (FIG. 14H and FIGS. 24D-24F). Overall, these results show that PARPi altered DNA damage condensate density correlates to both PARP trapping and PARPi efficacy, suggesting that protein recruitment plays a role in PARP trapping.

Figure 15A:
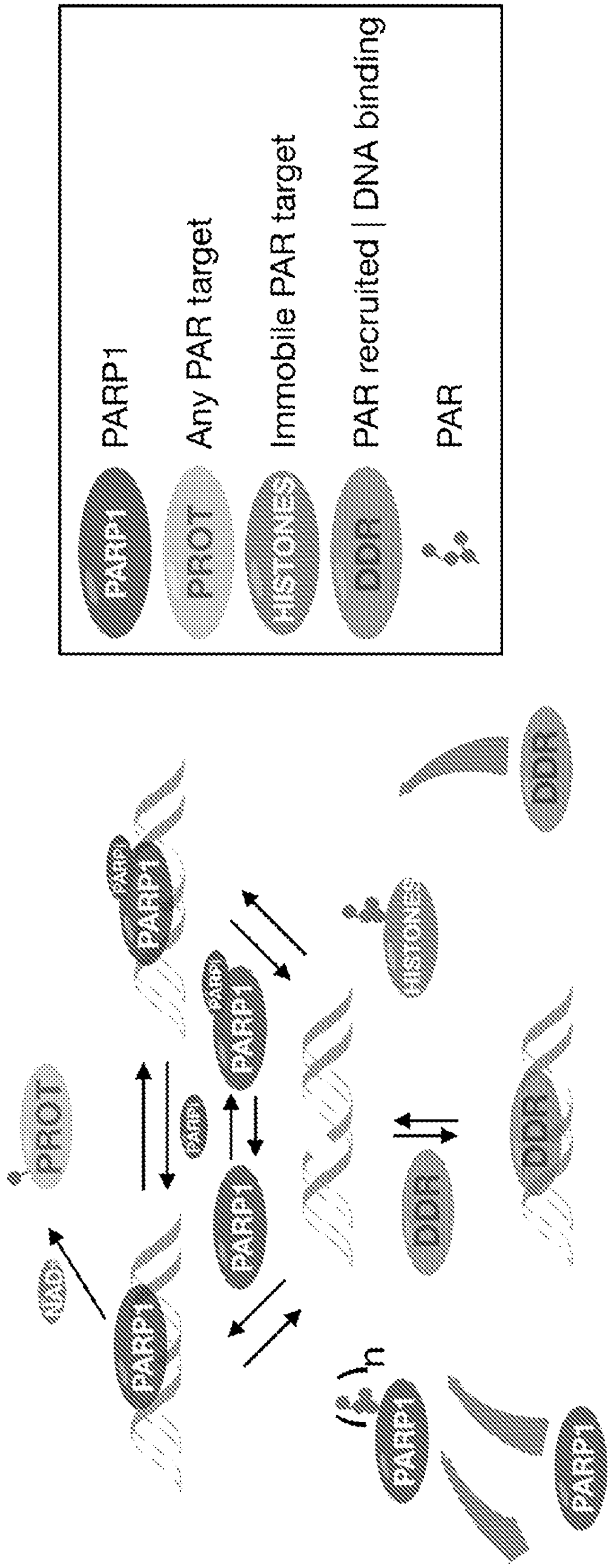
FIGS. 15A-15H: PARP trapping arises from altered PAR-dependent protein recruitment to biomolecular condensates.

To further test our hypothesis that altered protein recruitment would increase PARP trapping by enabling PARP1 to dissociate from and rebind DNA we modeled all the PARP1 binding events that occur within a condensate. In our model (FIG. 15A), PARP1, PARPi and damaged DNA undergo binding and release following first order binding kinetics. When DNA-bound PARP1 binds NAD", it rapidly PARylates nearby proteins—a model simplification based on the fast PARP1 enzymatic activity (46, 47) and rapid release of PARP1 in the absence of PARPi (25, 27). Our model also incorporates PARP1 diffusion away from and into condensates, includes non-diffusible PARylation targets (histones), stochastically selects which protein is PARylated and stochastically recruits other DNA binding proteins (DDR) into the condensate in a PAR-dependent manner.

Figure 15B:
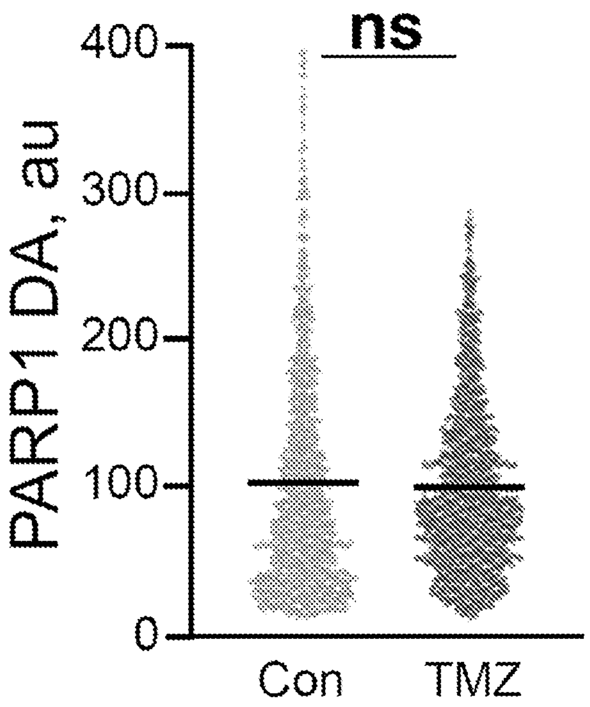
Figure 15C:
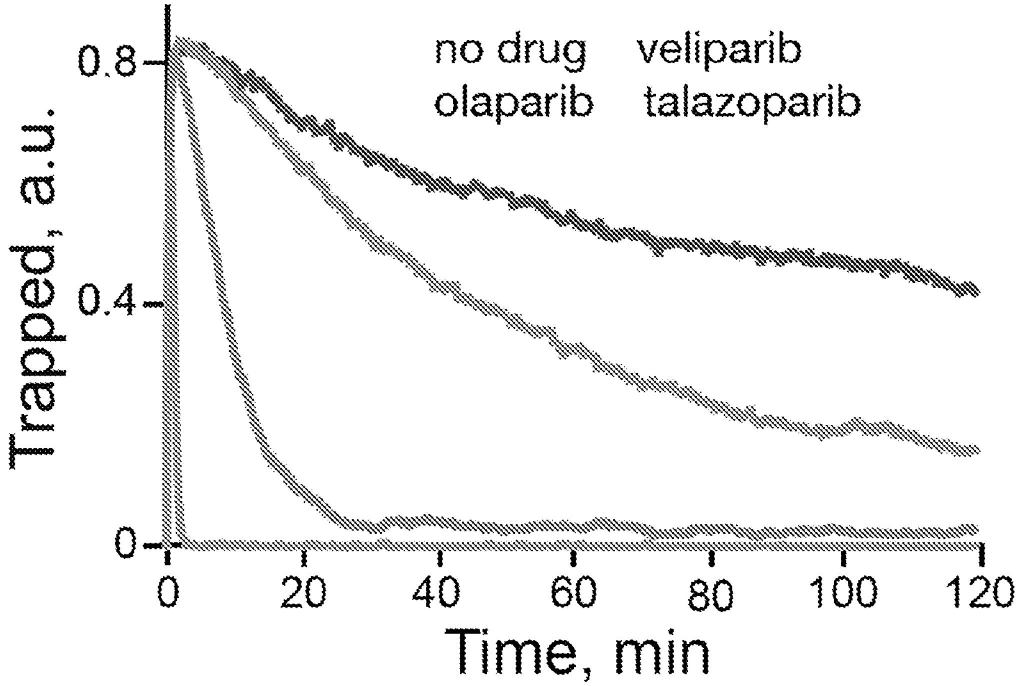
Figure 15D:
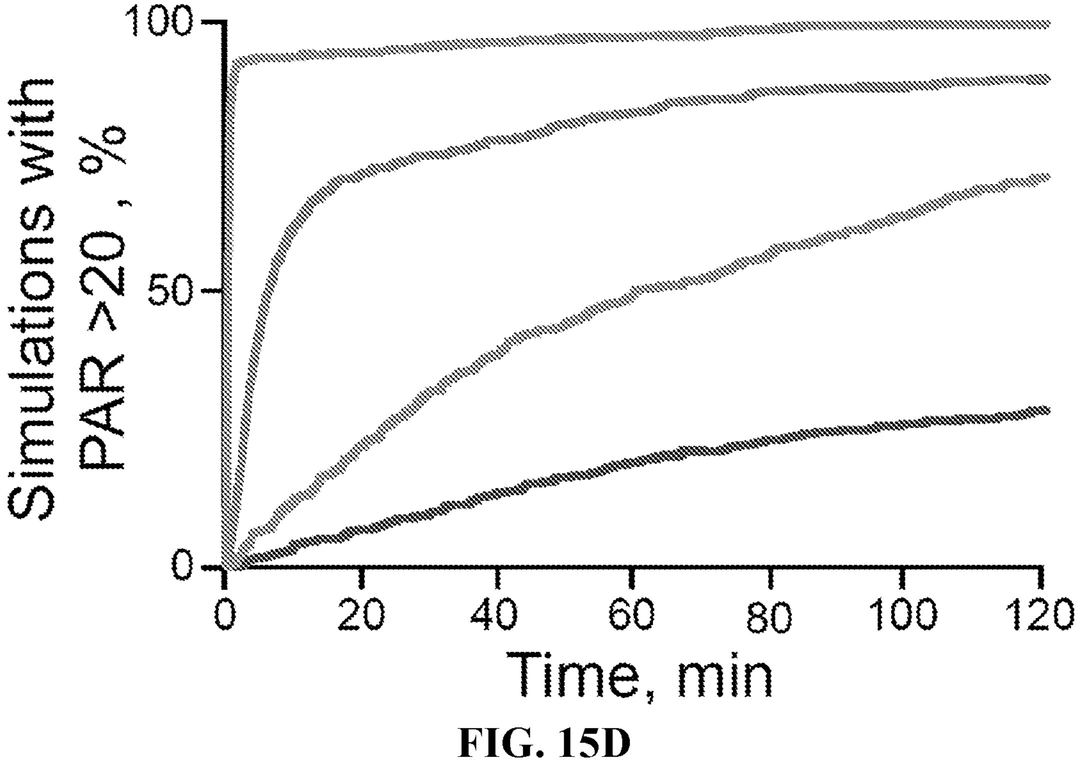

We first sought to determine if PARP1 itself accumulates at sites of DNA damage. Experiments where DNA damage is induced through local, high intensity irradiation (UV laser exposure) show rapid accumulation of PARP1 (48). Yet, it remains uncertain if increased local PARP1 concentration occurs through multiple PARP1 proteins being recruited to single sites of DNA damage, or rather a high density of damaged DNA sites. When we induced DNA damage uniformly through incubation of cells with TMZ we found PARP1 does not aggregate (FIG. 15B), therefore the total PARP1 concentration in our model was kept constant. To implement our model we used the Gillespie algorithm (49) (FIGS. 25A-25D). We tuned our simulation to achieve a trapped PARP duration in the absence of PARPi similar to observations in previous studies (25, 27) (FIGS. 26A-26G). Here, PARP1 DNA occupancy was reduced to 20% within 2 minutes (FIG. 15C). Once tuned, we tested the impact of the presence of PARPi. Talazoparib proved to be the most potent trapper, with a trapping half-life at 1 μM of 122 minutes compared to 44 and 6 minutes for olaparib and veliparib, respectively. These simulations produce results similar to observed cellular PARPi trapping (25, 27) (FIG. 12A). And, we found trapping was associated with large decreases in PAR production and, as a result, PAR-binding protein recruitment (FIG. 15D and FIGS. 26F-26I).

Figure 15E:
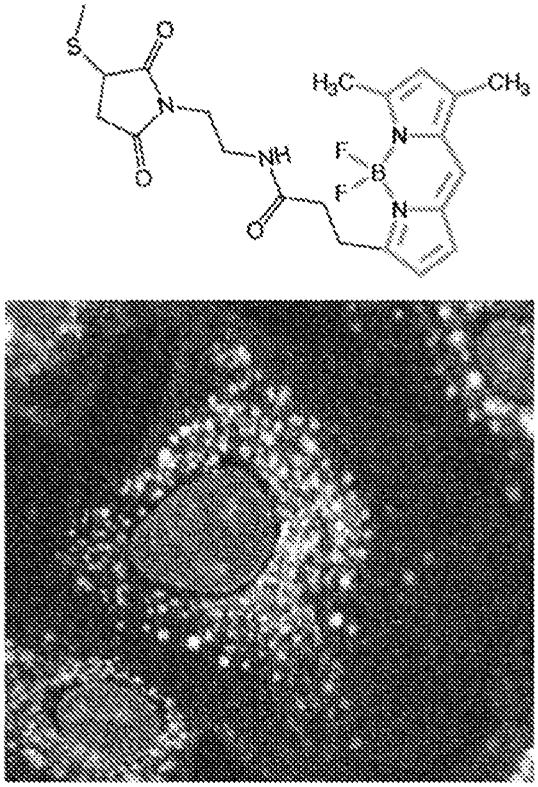
Figure 15F:
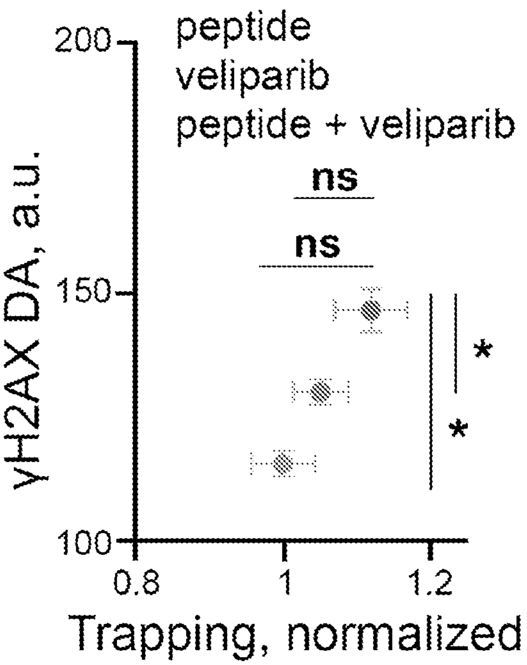
Figure 15G:
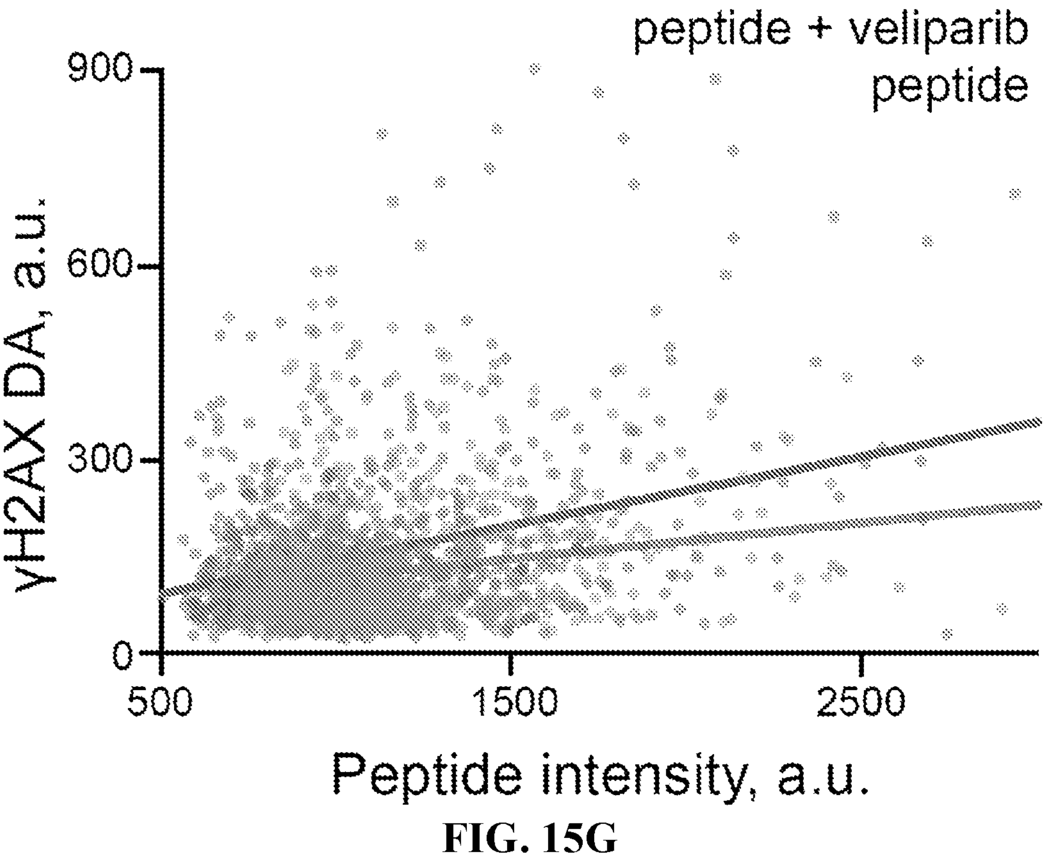
Figure 15H:
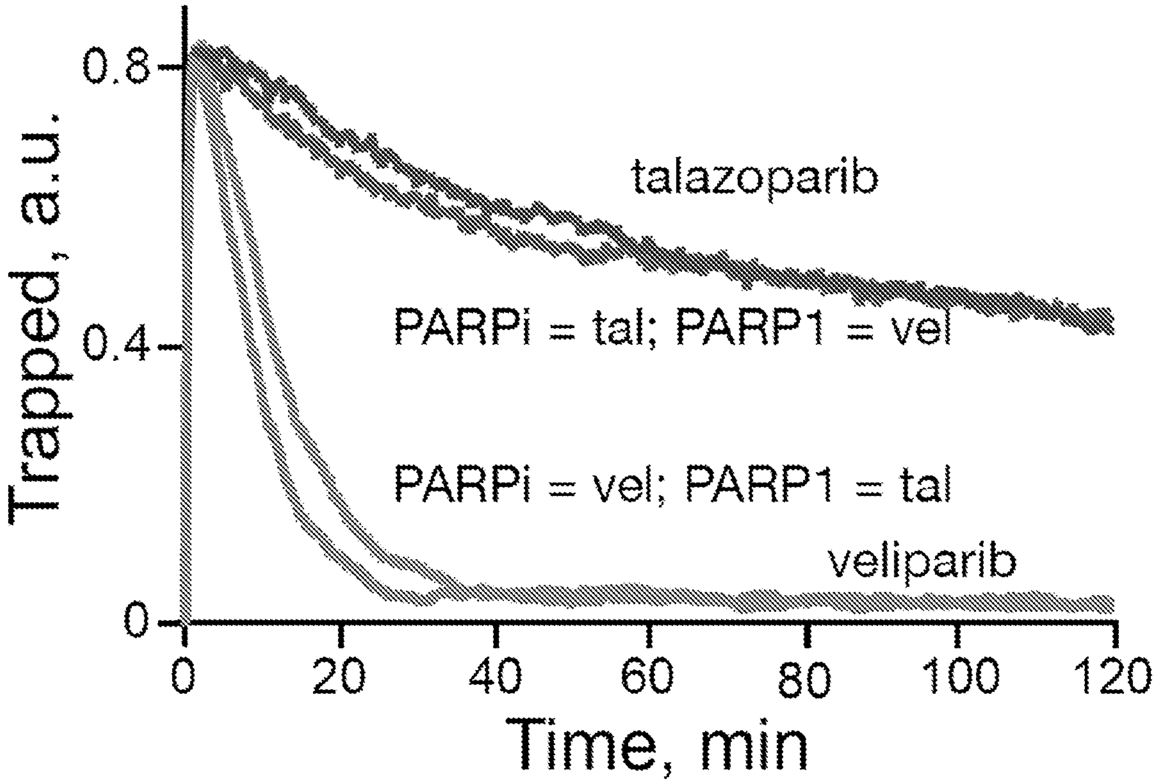
Figure 16A:
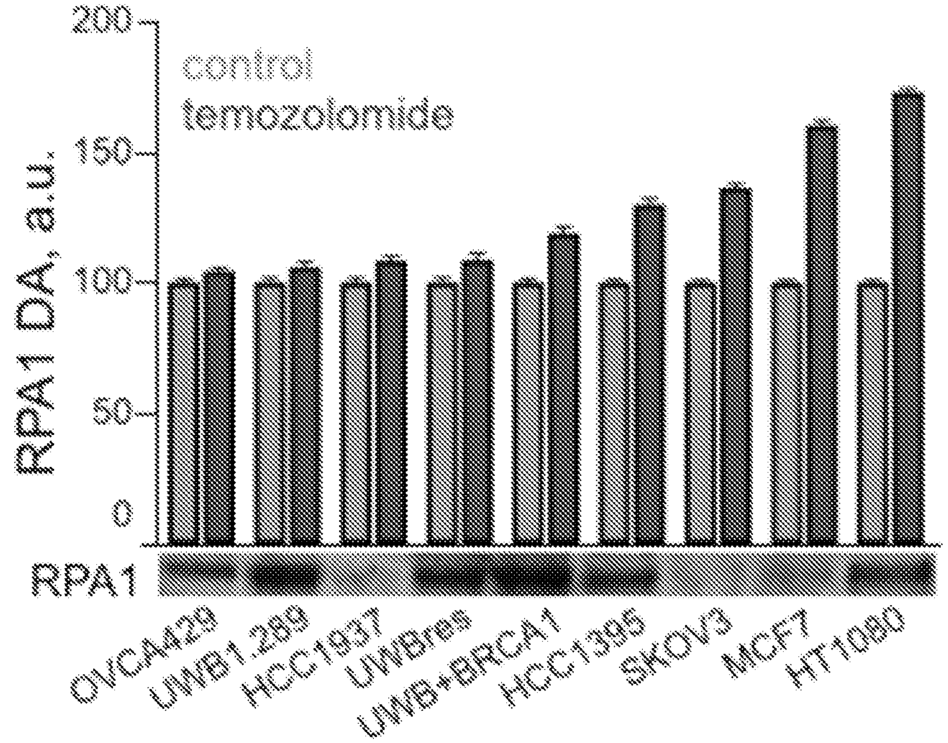
FIGS. 16A-16F: RPA1 recruitment correlates with cell sensitivity to PARPi.
Figure 16B:
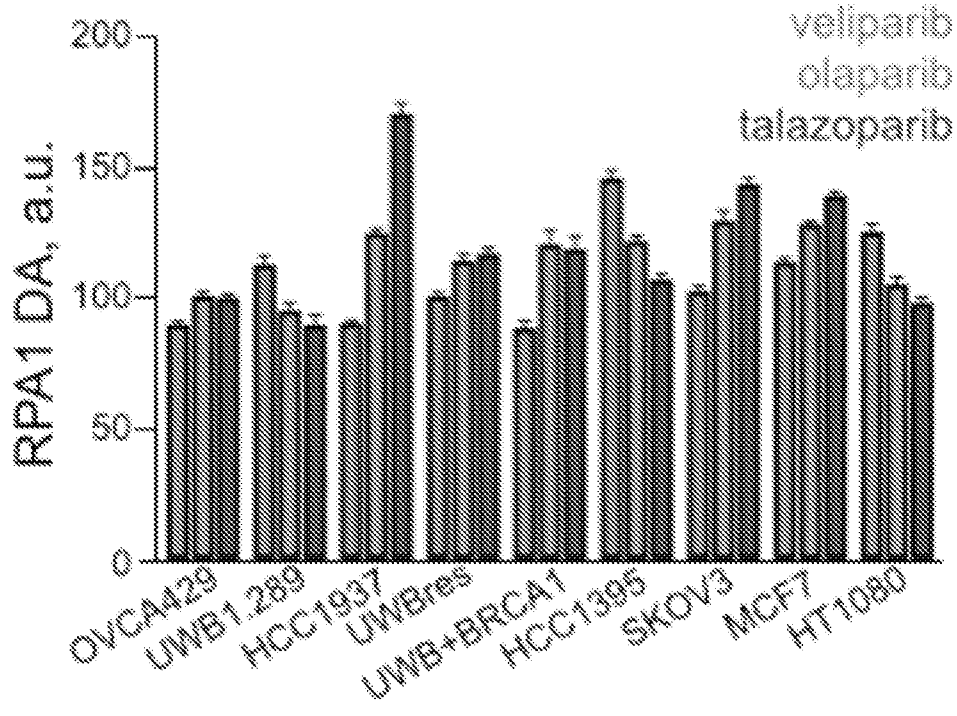
Figure 16C:
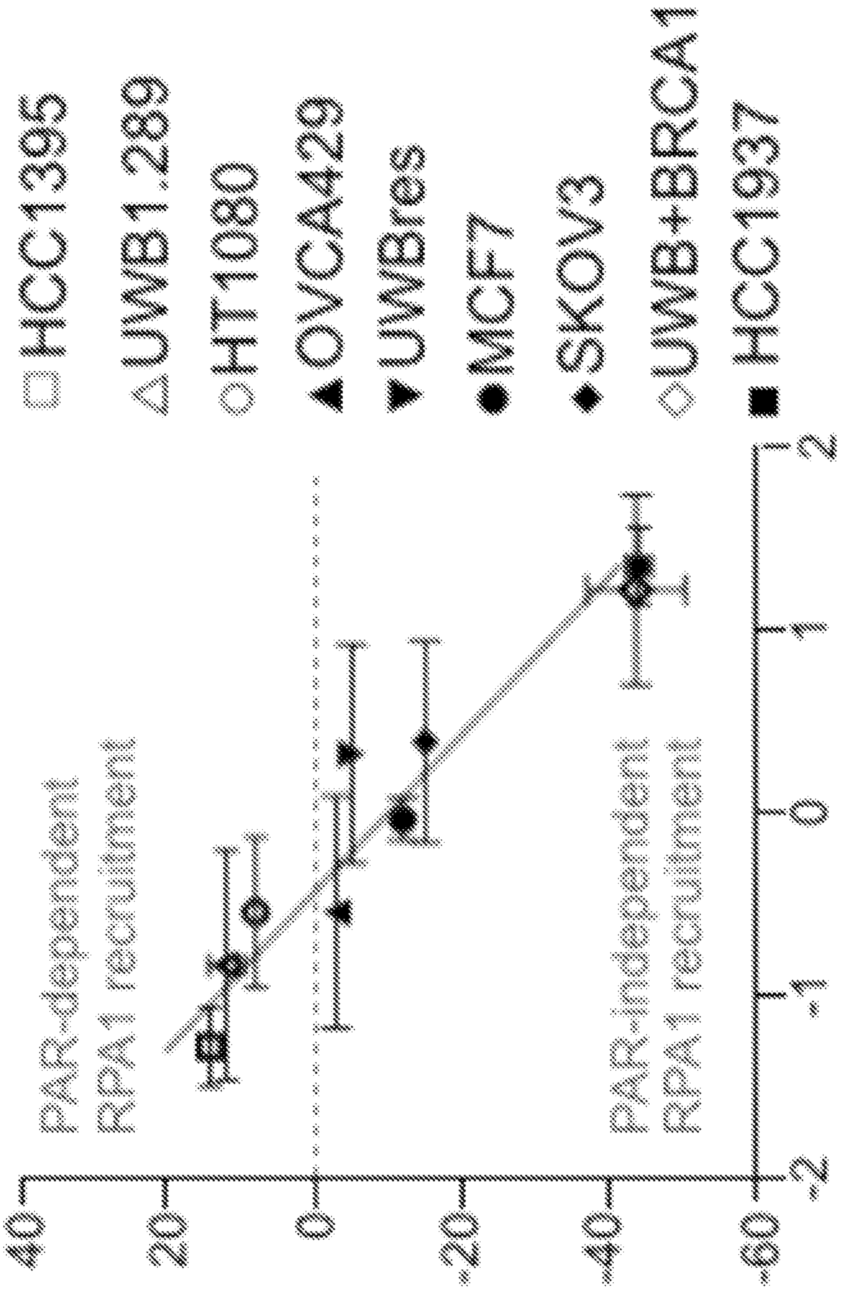
Figure 16D:
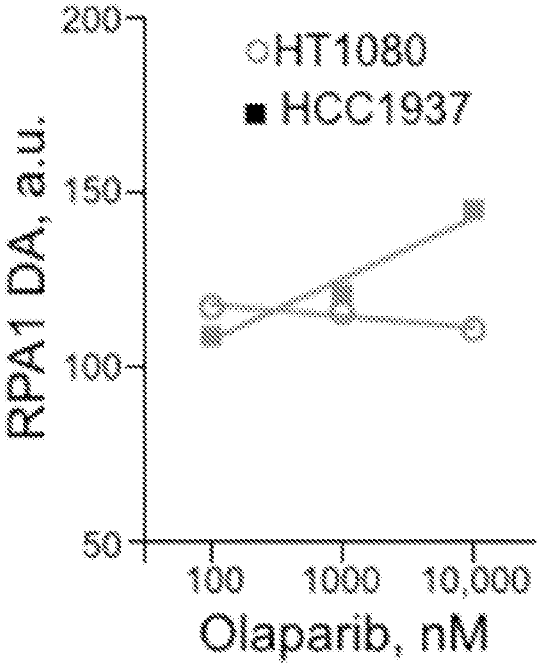
Figure 16E:
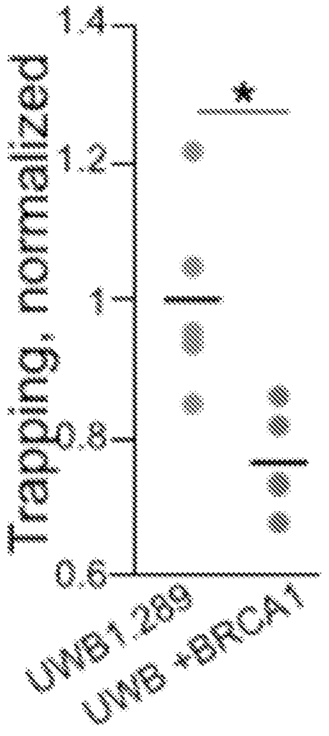
Figure 16F:
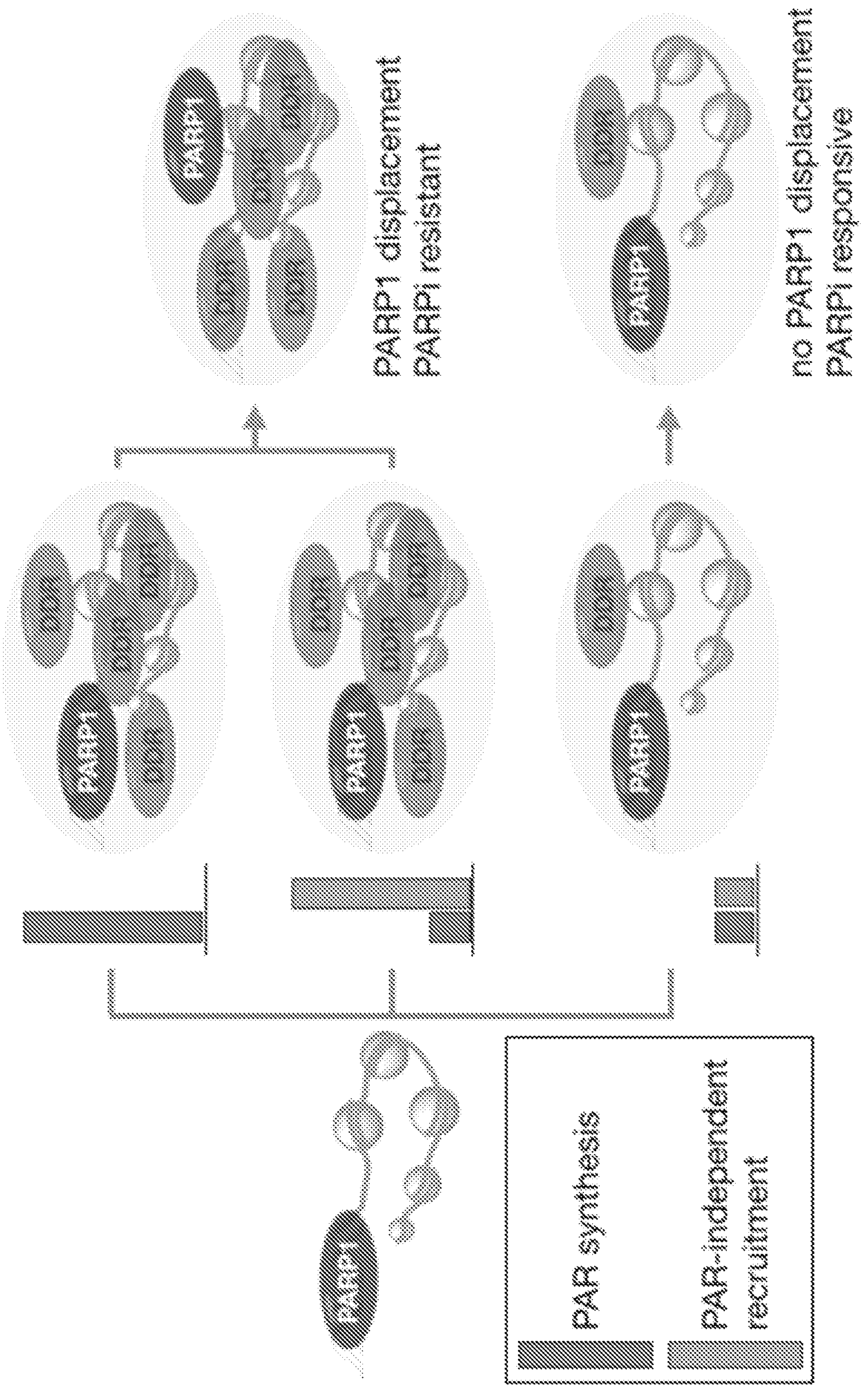

We next experimentally tested the simulation results that lack of available PAR to recruit proteins leads to trapping. Inclusion of the PARG inhibitor PDD00017273, which would be expected increase PAR levels, did not alter the veliparib or talazoparib induced $\gamma H_2AX$ DA, but it also did not impact HT1080 response to veliparib (FIGS. 27A-27E). However, a BODIPY FL labeled peptide containing the PAR-binding sequence of RNF146 (FIG. 15E) increased $\gamma H_2AX$ DA in HT1080 cells, without increasing $\gamma H_2AX$ levels (FIG. 27C), and significantly increased veliparib induced $\gamma H_2AX$ DA with a correlation to non-significant increases in chromatin trapping (FIG. 15F). Furthermore, individual HT1080 cell $\gamma H_2AX$ DA positively correlated to nuclear peptide accumulation (FIG. S11*d*), which was enhanced in the presence of veliparib (FIG. 15G). The increased $\gamma H_2AX$ DA and chromatin trapping in the presence of the PAR-binding peptide suggest that the peptide reduces the availability of PAR to recruit proteins, leading to increased trapping. These results are similar to recent findings that limited PAR production through HPF1 knockout sensitizes cells to PARPi (50).

Figure 28A:
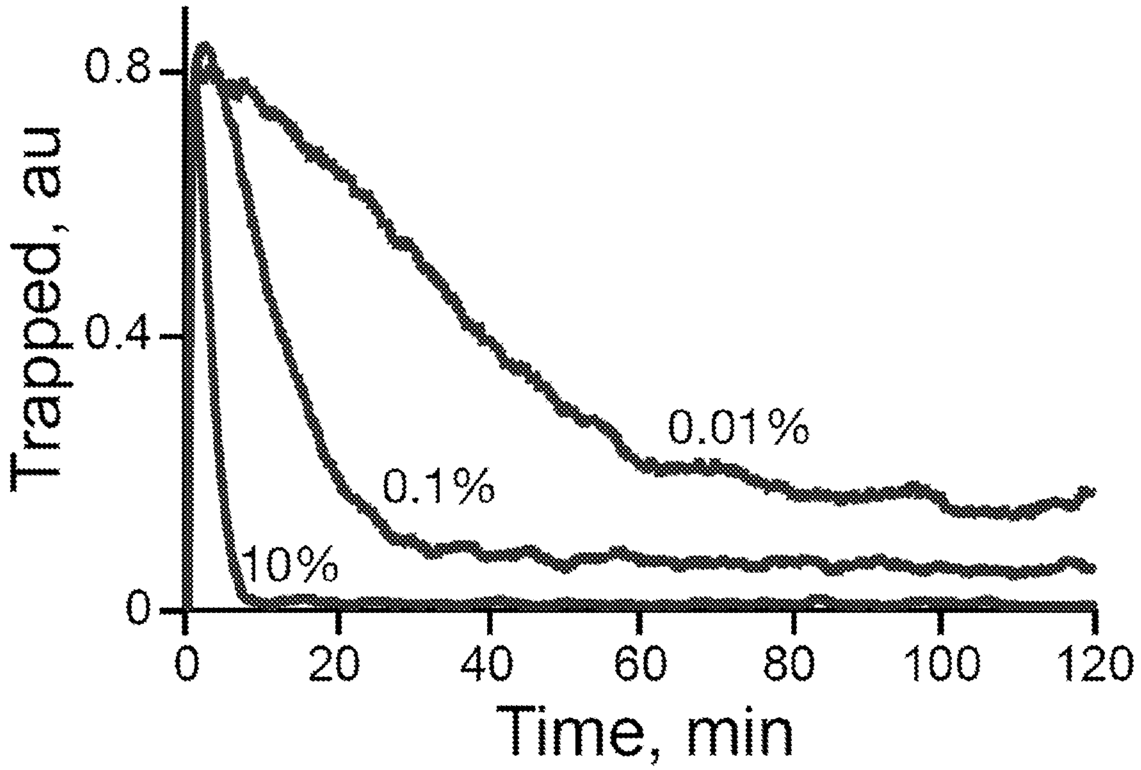
FIGS. 28A-28J: Modeling the impact of different rate constants.
Figure 28B:
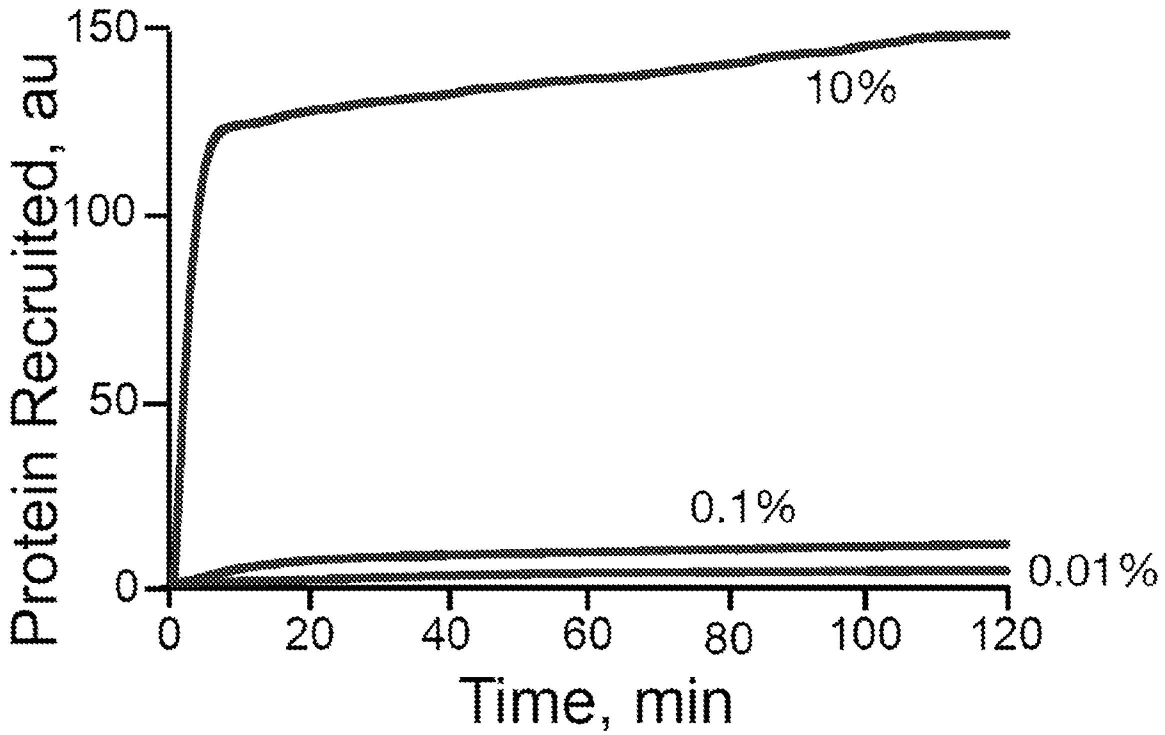
Figure 28C:
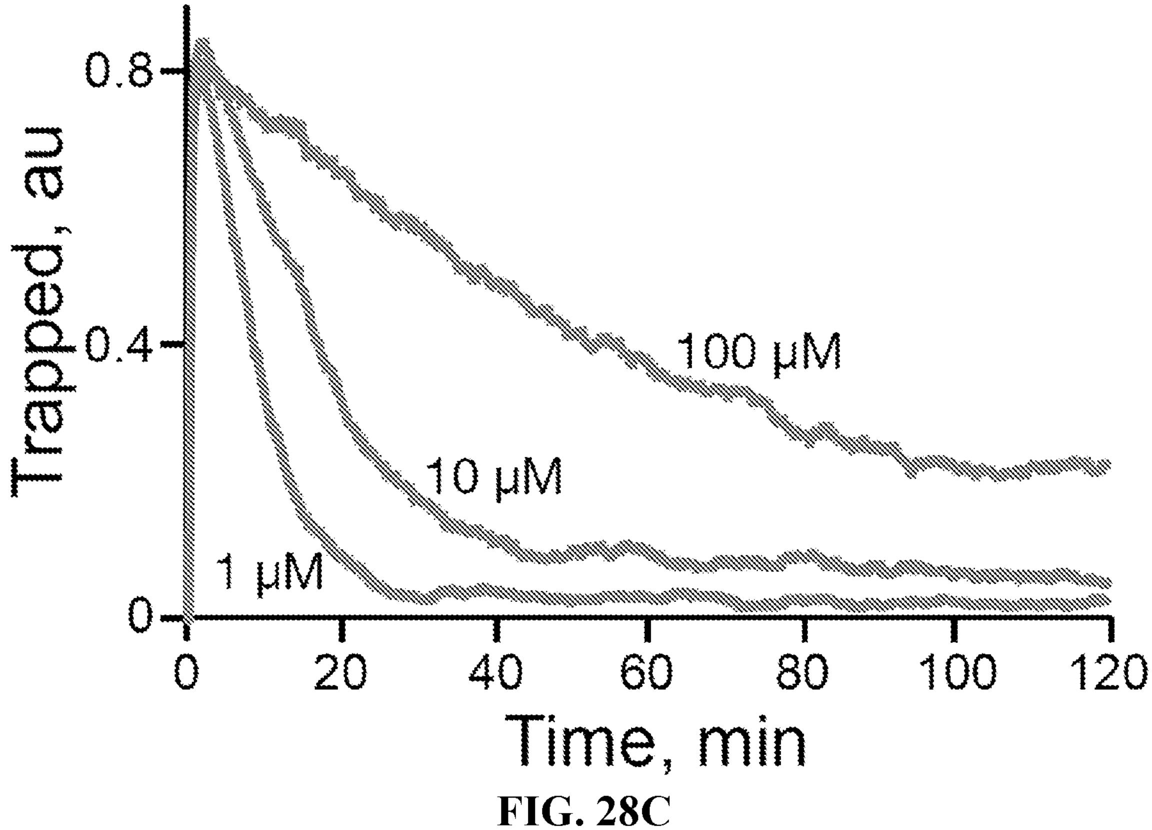
Figure 28D:
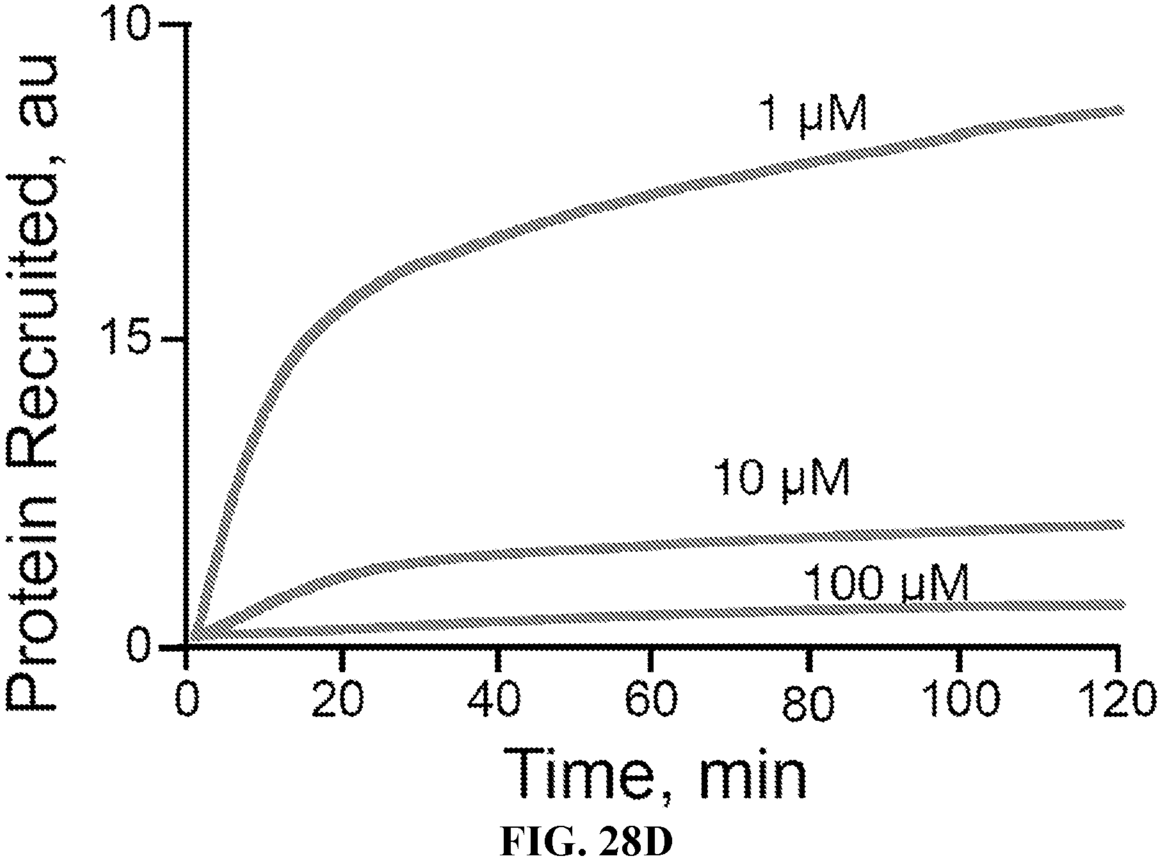
Figure 28E:
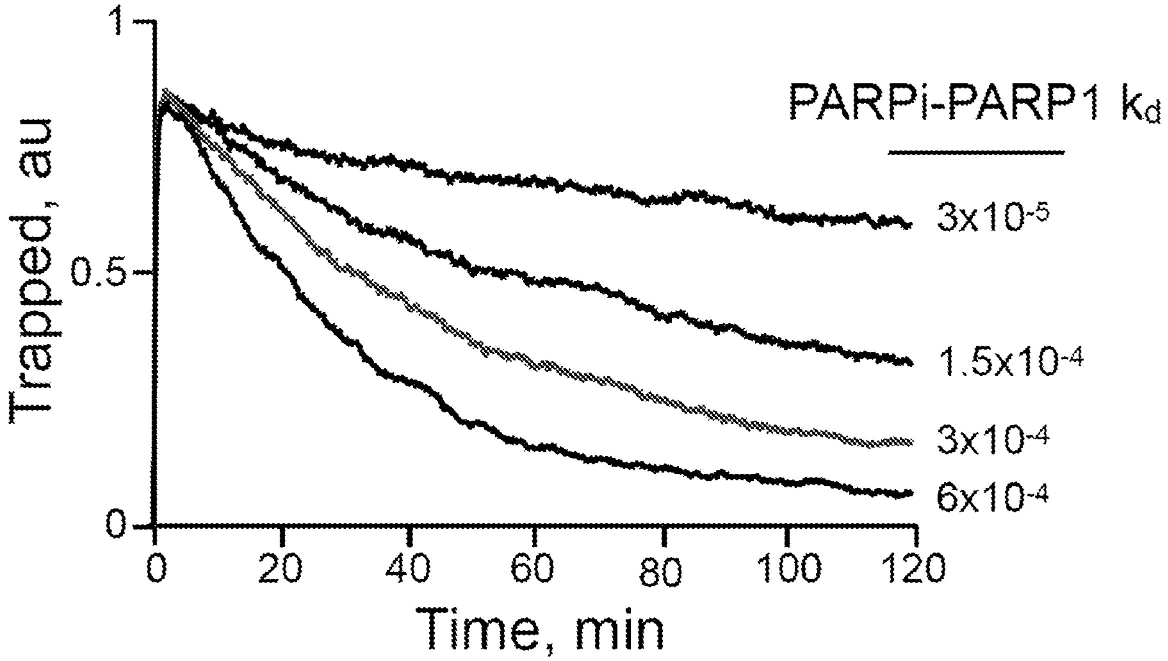
Figure 28F:
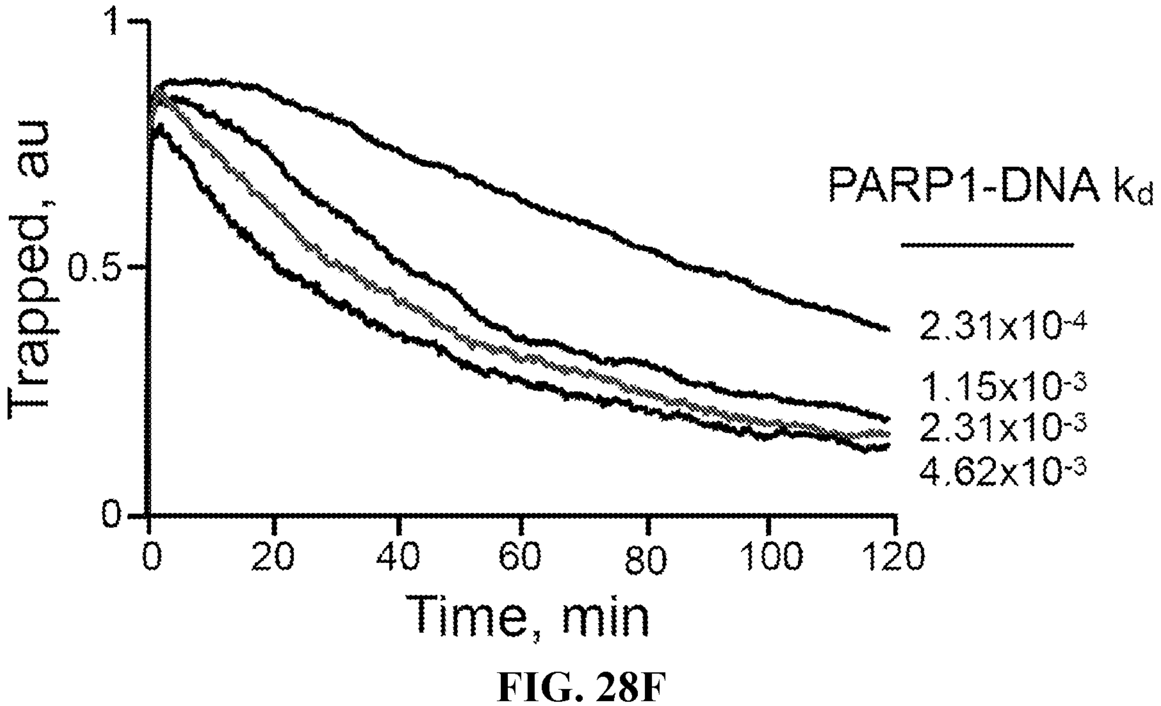
Figure 28G:
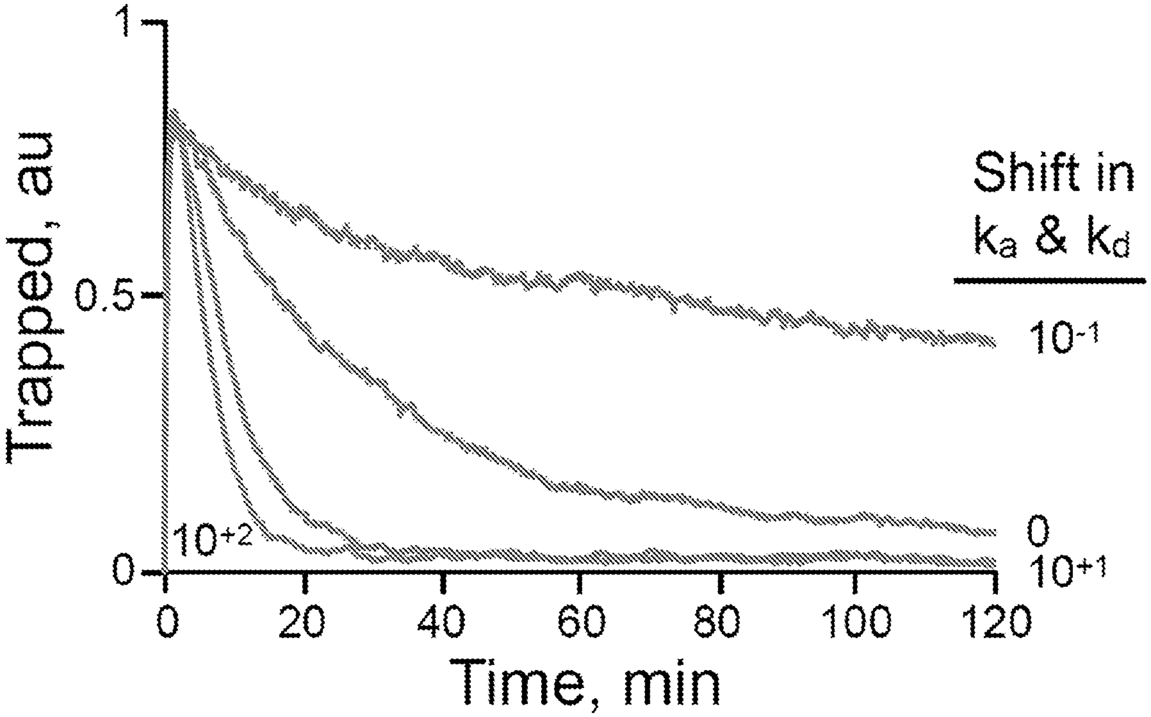
Figure 28H:
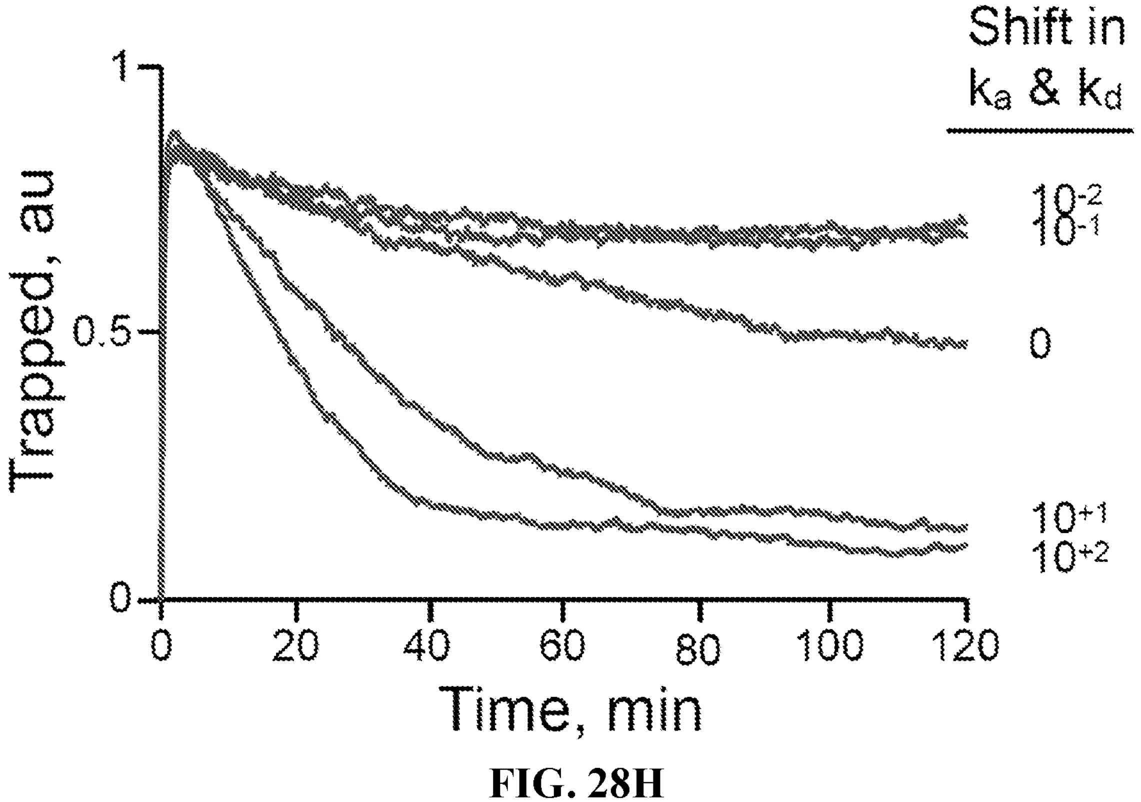
Figure 28I:
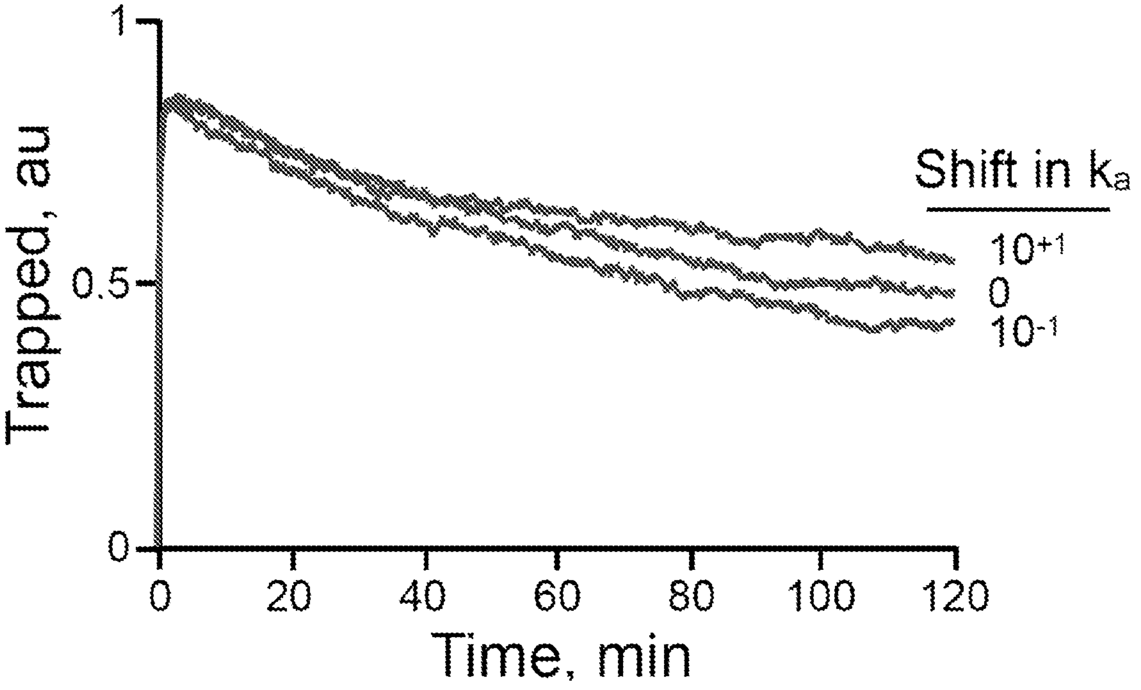
Figure 28J:
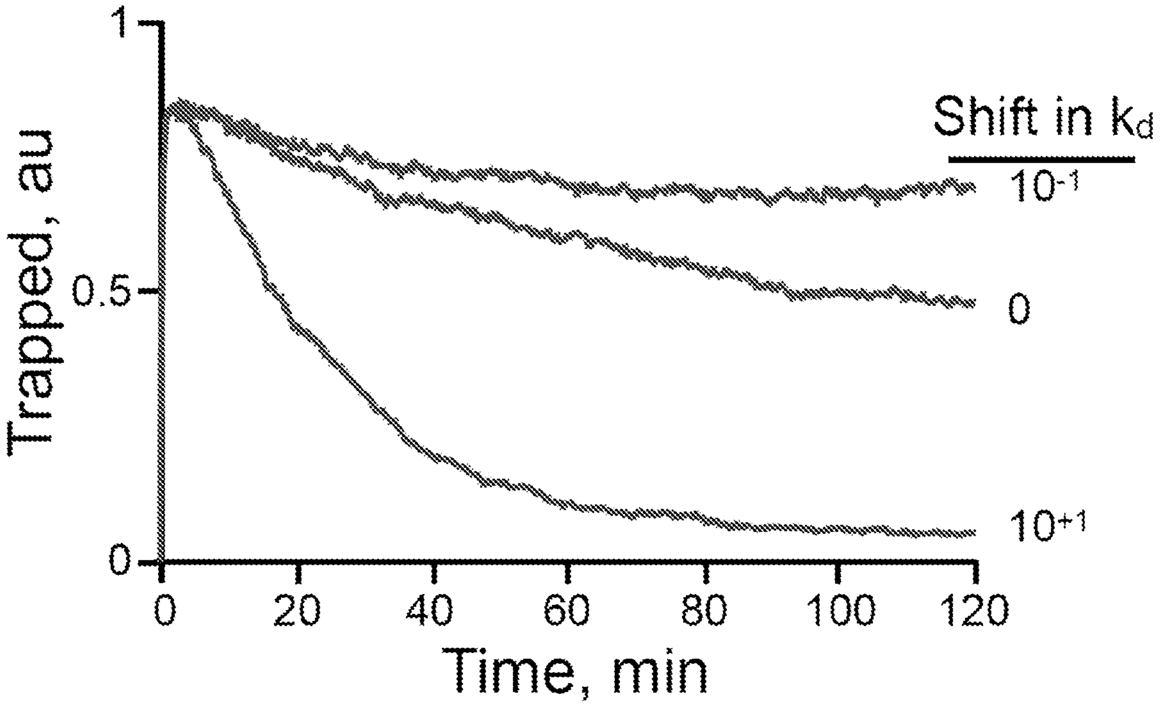
Figure 29A:
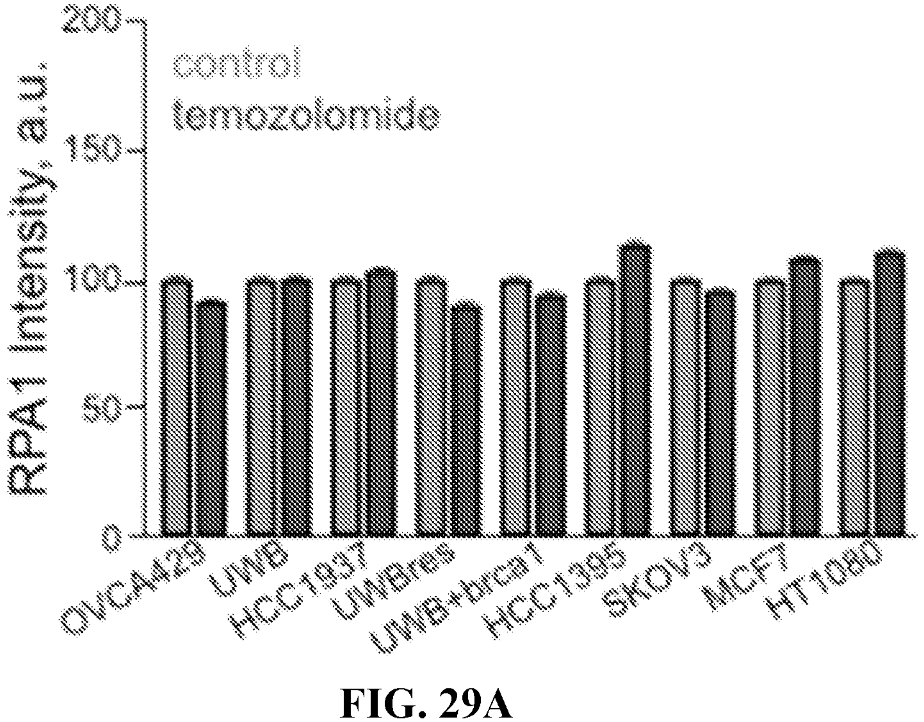
FIGS. 29A-29D: RPA1 condensate recruitment.
Figure 29B:
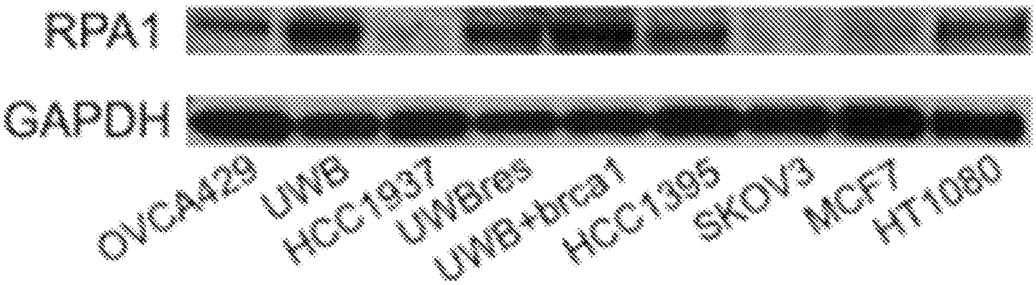
Figure 29C:
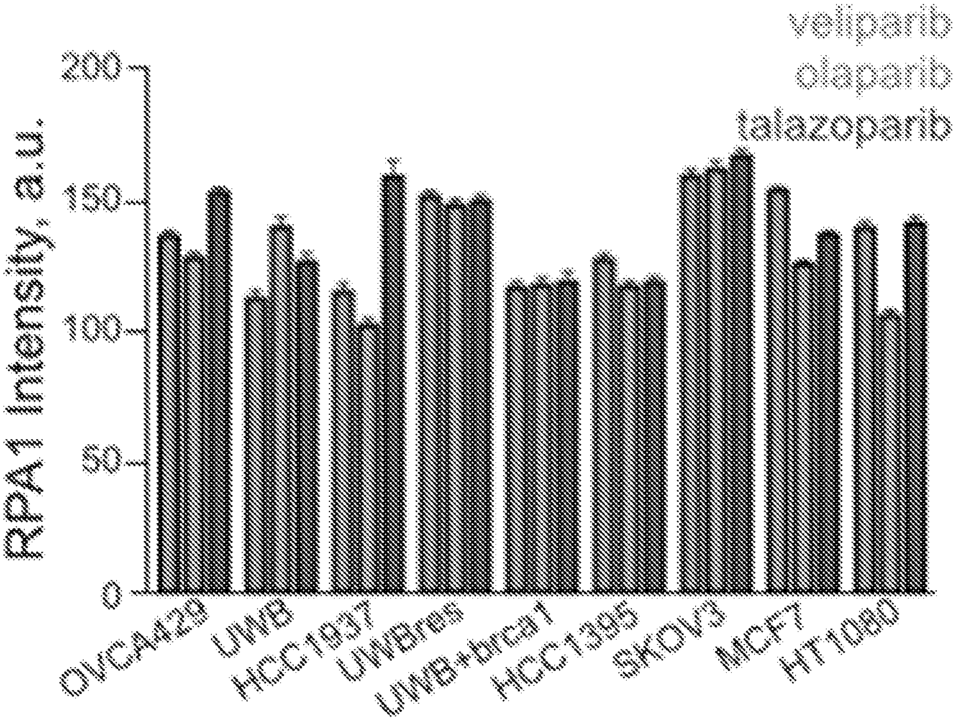
Figure 29D:
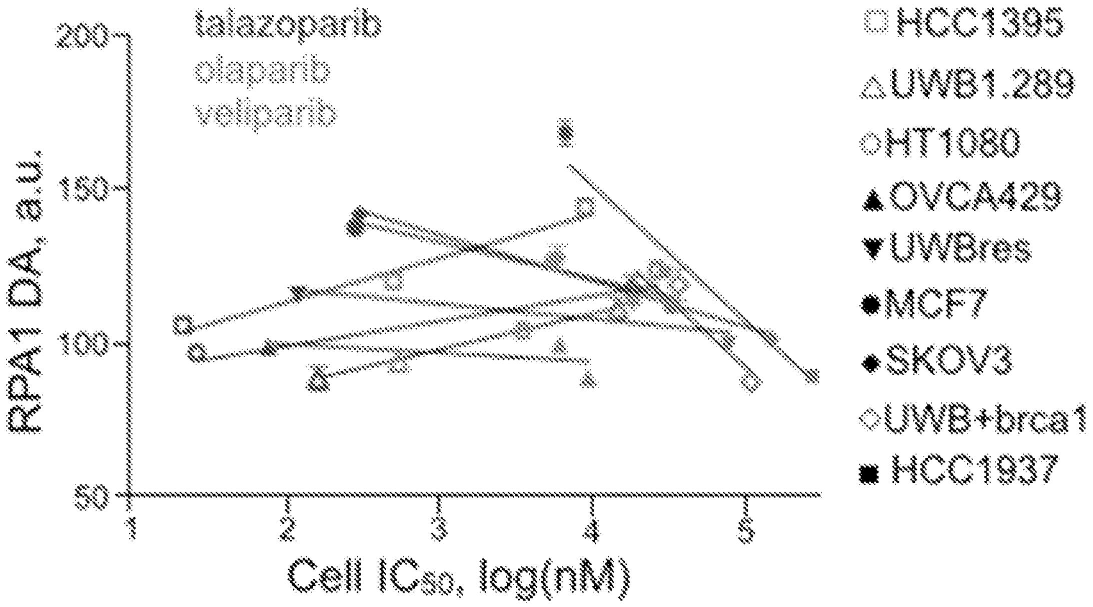

We then ran simulations with reduced NAD" concentrations and found increased trapping in a dose-dependent manner through limited protein recruitment (FIGS. 28A-28B). Simulations also showed veliparib concentration dependent trapping (FIGS. 28C-28D) similar to experimental chromatin trapping measurements. To determine which PARPi property (enzymatic inhibition of PAR production or allosteric induced PARP1 affinity for DNA) drives trapping, we ran simulations with synthetic PARPi containing a combination of veliparib and talazoparib binding constants (FIG. 15J). Here, enzymatic inhibition proved to be the key regulator of PARP trapping, while allosteric changes in PARP1 affinity for DNA showed little impact (FIGS. 28E-28F). Simulations also suggested trapping through enzymatic inhibition was driven mainly by the $k_{off}$ constant (FIGS. 28G-28J). Although clinical PARPi have comparable affinity for PARP1, their first order dissociation rate constants ($k_{off}$) are strikingly different, a potential explanation for why talazoparib is such potent trapper.

Next, we experimentally determined if PARPi-induced recruitment of DDR proteins correlates with response and focused on RPA1, a DNA single strand binding protein critical in various DDR pathways. All 9 cell lines we measured showed increased RPA1 DA upon DNA damage with TMZ (FIG. 5A), demonstrating that RPA1 is recruited to DNA damage. But, the degree of recruitment did not correlate to cellular RPA1 expression. Surprisingly, when we measured RPA1 DA induced by PARPi treatment we found different recruitment trends across PARPi for each cell line (FIG. 5B). Here, cell lines more responsive to PARPi showed a decrease in RPA1 DA with increasing PARPi potency. Yet, for more resistant cell lines, RPA1 DA shows the opposite response (FIGS. 29A-29D). Remarkably, the relationship between RPA1 DA and PARPi IC50 for each cell line correlated to overall PARPi sensitivity (FIG. 5C). And, olaparib dose dependent RPA1 DA showed similar trends in HT1080 and HCC1937 cells (FIG. 5D), confirming that the degree of PARP inhibition is driving RPA1 recruitment. These results suggest resistant cell lines are able to recruit RPA1 in a PAR-independent manner while responsive cell lines lack this mechanism.

Lastly, we found that PARP trapping was impacted by the presence of BRCA1. In isogenic UWB1.289 and UWB1.289+BRCA1 cell lines, trapping was significantly higher in the absence of BRCA1 (FIG. 5E), suggesting that either BRCA1 reduces the number of DNA damage sites where PARP1 can be trapped or BRCA1 assists in recruiting proteins that compete with PARP1 in binding DNA. Our finding that RPA1 recruitment is inverted in these cells, but not $\gamma H_2AX$ DA, by the presence of BRCA1 (FIG. 5C) indicates that recruitment does indeed play role in reduced trapping. Yet, UWB1.289 cells resistant through culture in olaparib do not express BRCA1 but have also gained the ability to recruit RPA1 in a PAR-independent manner. Therefore, our results suggest cell lines with the ability to recruit key DDR proteins in the absence PAR production are able to resist PARPi treatment (FIG. 5F). Broadly, the strong correlation of $\gamma H_2AX$ density to IC50 and RPA1 recruitment to cell line PARPi sensitivity indicates condensate properties serve as a central mechanism governing response to PARP inhibition.

Discussion

The mechanism of PARP trapping has remained elusive. The current hypothesis is that a combination of enzymatic inhibition and shifts in PARP1 affinity for DNA cause an increased duration of the PARP1-DNA interaction (24-26). Initial, ground-breaking in vitro experiments found that enzymatic activity leads to PARP1 dissociation from DNA (19, 20). But, cellular trapping measurements do not correlate well with steady-state PARPi binding affinities. Recent measurements of PARPi-specific allosteric shifts in PARP1 bound to DNA show altered binding affinities (25). However, the shifts in affinity induced by each PARPi do not align with the observed cellular PARPi trapping potency. Therefore, the hypothesis that a combination of enzymatic inhibition and allosteric shifts cause trapping arose. Yet, a simple evaluation of the measured PARP1-DNA and PARPi-PARP1 dissociation rates revealed that when the PARPi-PARP1-DNA complex ("trapped" PARP) is formed, PARP1-DNA will dissociate faster than PARPi-PARP1 for most PARPi. Therefore, there is a higher probability that PARP1 will dissociate from DNA prior to any PAR production, suggesting that PARP activity has little impact on the PARP1-DNA binding duration. Thus, for enzymatic activity to play a role in PARP trapping, trapping has to involve PARP1 dissociation from and rebinding to DNA.

Our findings here suggest an alternative "trapping" mechanism that includes PARP1 dissociation from and rebinding to DNA and agrees with the recent observation that PARP1 diffusion at sites of DNA damage is not altered by the presence of PARPi (27). We found that, unlike with topoisomerase inhibitor trapping (51), PARP trapping is not the physical stalling of PARP1 on DNA, but rather the persisting high fraction of damaged DNA bound by PARP1 in the absence of PAR-recruited competitive binding. This mechanism agrees with known cellular functions of PARP. PARP1 is one of the first proteins to bind damaged DNA not because it has the highest affinity (other proteins are known to have higher affinity (52, 53)), but because of its high abundance (54) and unique ability to locate damaged DNA (55). When bound to DNA, PARP1 activity increases the local concentration of DNA binding proteins (38-40) within growing condensates, altering the likelihood of PARP1 binding vacant DNA through increased competition. Indeed, absence of or mutations in DNA damage response proteins that are recruited to DNA damage, such as XRCC1, produce hyperactive PARP, but also increase PARP1-DNA interactions (27, 56, 57). Thus, in the absence of DNA damage response protein recruitment, once PARP1 dissociates from DNA it maintains a binding advantage to rebind DNA.

This trapping mechanism also suggests how PARPi inhibited PARP1 can be more potent in cells than the absence of PARP1. In the absence of PARP1, damaged DNA is not bound by PARP1 and is able to be bound by other DNA damage response proteins that arrive at sites of DNA damage through either random interactions or recruitment by alternative pathways. When PARP1 is present, but inhibited, it is able to outcompete the lower abundance of DNA damage response proteins at the site of DNA damage in binding DNA damage sites, stalling the DNA damage response. But, when PARP1 is present and active, the large amount of recruited DNA damage response proteins produces a damaged DNA binding advantage and outcompete PARP1 in binding DNA once it dissociates, allowing the DNA damage response to proceed.

Our stochastic simulation of PARP binding within a condensate demonstrates how binding kinetics alone can increase PARP interactions with damaged DNA. Furthermore, our finding that the PARPi dissociation constant is the essential characteristic controlling PARP trapping (FIG. 15H and FIGS. 27A-27E) reveals how trapping can be so different between the clinical inhibitors, where the dissociation rate is the most distinct difference (FIG. 12A). Our model that trapping is dependent on the limitation of DDR protein recruitment is supported experimentally. The density of $\gamma H_2AX$ in condensates correlates with PARPi efficacy across PARPi and cell lines. And, the presence of a PAR-interacting peptide increases PARP trapping.

REFERENCES

1. W. L. Kraus, J. T. Lis, PARP goes transcription. Cell 113, 677-683 (2003).
2. J. M. Pascal, The comings and goings of PARP-1 in response to DNA damage. DNA Repair (Amst) 71, 177-182 (2018).
3. M. F. Langelier, J. L. Planck, S. Roy, J. M. Pascal, Structural basis for DNA damage-dependent poly(ADP-ribosyl) ation by human PARP-1. Science 336, 728-732 (2012).
4. J. C. Ame, C. Spenlehauer, G. de Murcia, The PARP superfamily. Bioessays 26, 882-893 (2004).
5. M. O. Hottiger, P. O. Hassa, B. Luscher, H. Schuler, F. Koch-Nolte, Toward a unified nomenclature for mammalian ADP-ribosyltransferases. Trends Biochem Sci 35, 208-219 (2010).
6. S. Vyas, M. Chesarone-Cataldo, T. Todorova, Y. H. Huang, P. Chang, A systematic analysis of the PARP protein family identifies new functions critical for cell physiology. Nat Commun 4, 2240 (2013).
7. J. Menissier de Murcia et al., Functional interaction between PARP-1 and PARP-2 in chromosome stability and embryonic development in mouse. EMBO J 22, 2255-2263 (2003).
8. R. Alvarez-Gonzalez, M. K. Jacobson, Characterization of polymers of adenosine diphosphate ribose generated in vitro and in vivo. Biochemistry 26, 3218-3224 (1987).
9. V. Ayyappan et al., ADPriboDB 2.0: an updated database of ADP-ribosylated proteins. Nucleic Acids Res 49, D261-D265 (2021).
10. S. C. Larsen, I. A. Hendriks, D. Lyon, L. J. Jensen, M. L. Nielsen, Systems-wide Analysis of Serine ADP-Ribosylation Reveals Widespread Occurrence and Site-Specific Overlap with Phosphorylation. Cell Rep 24, 2493-2505 e2494 (2018).

11. A. K. L. Leung, Poly(ADP-ribose): A Dynamic Trigger for Biomolecular Condensate Formation. Trends Cell Biol 30, 370-383 (2020).
12. C. J. Lord, A. Ashworth, PARP inhibitors: Synthetic lethality in the clinic. Science 355, 1152-1158 (2017).
13. H. Farmer et al., Targeting the DNA repair defect in BRCA mutant cells as a therapeutic strategy. Nature 434, 917-921 (2005).
14. H. E. Bryant et al., Specific killing of BRCA2-deficient tumours with inhibitors of poly(ADP-ribose) polymerase. Nature 434, 913-917 (2005).
15. C. J. Lord, A. Ashworth, BRCAness revisited. Nat Rev Cancer 16, 110-120 (2016).
16. M. P. Dias, S. C. Moser, S. Ganesan, J. Jonkers, Understanding and overcoming resistance to PARP inhibitors in cancer therapy. Nat Rev Clin Oncol 18, 773-791 (2021).
17. K. Fugger, G. Hewitt, S. C. West, S. J. Boulton, Tackling PARP inhibitor resistance. Trends Cancer 7, 1102-1118 (2021).
18. E. E. Alemasova, O. I. Lavrik, Poly(ADP-ribosyl) ation by PARP1: reaction mechanism and regulatory proteins. Nucleic Acids Res 47, 3811-3827 (2019).
19. J. Murai et al., Trapping of PARP1 and PARP2 by Clinical PARP Inhibitors. Cancer Res 72, 5588-5599 (2012).
20. J. Murai et al., Stereospecific PARP trapping by BMN 673 and comparison with olaparib and rucaparib. Mol Cancer Ther 13, 433-443 (2014).
21. A. Ray Chaudhuri et al., Replication fork stability confers chemoresistance in BRCA-deficient cells. Nature 535, 382-387 (2016).
22. T. Helleday, The underlying mechanism for the PARP and BRCA synthetic lethality: clearing up the misunderstandings. Mol Oncol 5, 387-393 (2011).
23. Y. Pommier, M. J. O'Connor, J. de Bono, Laying a trap to kill cancer cells: PARP inhibitors and their mechanisms of action. Sci Transl Med 8, 362ps317 (2016).
24. T. A. Hopkins et al., Mechanistic Dissection of PARP1 Trapping and the Impact on In Vivo Tolerability and Efficacy of PARP Inhibitors. Mol Cancer Res 13, 1465-1477 (2015).
25. L. Zandarashvili et al., Structural basis for allosteric PARP-1 retention on DNA breaks. Science 368, (2020).
26. H. Xue et al., A two-step mechanism governing PARP1-DNA retention by PARP inhibitors. Sci Adv 8, eabq0414 (2022).
27. Z. Shao et al., Clinical PARP inhibitors do not abrogate PARP1 exchange at DNA damage sites in vivo. Nucleic Acids Res 48, 9694-9709 (2020).
28. M. J. Suskiewicz et al., HPF1 completes the PARP active site for DNA damage-induced ADP-ribosylation. Nature 579, 598-602 (2020).
29. J. M. Dubach et al., Quantitating drug-target engagement in single cells in vitro and in vivo. Nat Chem Biol 13, 168-173 (2017).
30. J. M. Dubach et al., In vivo imaging of specific drug-target binding at subcellular resolution. Nat Commun 5, 3946 (2014).
31. D. Fu, J. A. Calvo, L. D. Samson, Balancing repair and tolerance of DNA damage caused by alkylating agents. Nat Rev Cancer 12, 104-120 (2012).
32. F. Pessina et al., Functional transcription promoters at DNA double-strand breaks mediate RNA-driven phase separation of damage-response factors. Nat Cell Biol 21, 1286-1299 (2019)
33. A. S. Singatulina et al., PARP-1 Activation Directs FUS to DNA Damage Sites to Form PARG-Reversible Compartments Enriched in Damaged DNA. Cell Rep 27, 1809-1821 e1805 (2019).
34. R. Oshidari et al., DNA repair by Rad52 liquid droplets. Nat Commun 11, 695 (2020).
35. S. Kilic et al., Phase separation of 53BP1 determines liquid-like behavior of DNA repair compartments. EMBO J 38, e101379 (2019).
36. A. Patel et al., A Liquid-to-Solid Phase Transition of the ALS Protein FUS Accelerated by Disease Mutation. Cell 162, 1066-1077 (2015).
37. M. Altmeyer et al., Liquid demixing of intrinsically disordered proteins is seeded by poly(ADP-ribose). Nat Commun 6, 8088 (2015).
38. S. Nicolai et al., ZNF281 is recruited on DNA breaks to facilitate DNA repair by non-homologous end joining. Oncogene 39, 754-766 (2020).
39. S. Moore et al., The CHD6 chromatin remodeler is an oxidative DNA damage response factor. Nat Commun 10, 241 (2019).
40. G. Rona et al., PARP1-dependent recruitment of the FBXL10-RNF68-RNF2 ubiquitin ligase to sites of DNA damage controls H2A.Z loading. Elife 7, (2018).
41. A. A. Gopal et al., Spatially Selective Dissection of Signal Transduction in Neurons Grown on Netrin-1 Printed Nanoarrays via Segmented Fluorescence Fluctuation Analysis. ACS Nano 11, 8131-8143 (2017).
42. F. Natale et al., Identification of the elementary structural units of the DNA damage response. Nat Commun 8, 15760 (2017).
43. R. Varma, S. Mayor, GPI-anchored proteins are organized in submicron domains at the cell surface. Nature 394, 798-801 (1998).
44. N. Dimitrova, Y. C. Chen, D. L. Spector, T. de Lange, 53BP1 promotes non-homologous end joining of telomeres by increasing chromatin mobility. Nature 456, 524-528 (2008).
45. K. S. Yang, R. H. Kohler, M. Landon, R. Giedt, R. Weissleder, Single cell resolution in vivo imaging of DNA damage following PARP inhibition. Sci Rep 5, 10129 (2015).
46. M. F. Langelier, D. D. Ruhl, J. L. Planck, W. L. Kraus, J. M. Pascal, The Zn3 domain of human poly(ADP-ribose) polymerase-1 (PARP-1) functions in both DNA-dependent poly(ADP-ribose) synthesis activity and chromatin compaction. J Biol Chem 285, 18877-18887 (2010).
47. G. T. Marsischky, B. A. Wilson, R. J. Collier, Role of glutamic acid 988 of human poly-ADP-ribose polymerase in polymer formation. Evidence for active site similarities to the ADP-ribosylating toxins. J Biol Chem 270, 3247-3254 (1995).
48. J. F. Haince et al., PARP1-dependent kinetics of recruitment of MRE11 and NBS1 proteins to multiple DNA damage sites. J Biol Chem 283, 1197-1208 (2008).
49. D. T. Gillespie, Exact stochastic simulation of coupled chemical reactions. The Journal of Physical Chemistry 81, 2340-2361 (1977).
50. E. Prokhorova et al., Serine-linked PARP1 auto-modification controls PARP inhibitor response. Nat Commun 12, 4055 (2021).
51. T. K. Li, L. F. Liu, Tumor cell death induced by topoisomerase-targeting drugs. Annu 51. Rev Pharmacol Toxicol 41, 53-77 (2001).

52. T. Hey, G. Lipps, G. Krauss, Binding of XPA and RPA to damaged DNA investigated by fluorescence anisotropy. Biochemistry 40, 2901-2910 (2001).

53. J. T. Reardon et al., Comparative analysis of binding of human damaged DNA-binding protein (XPE) and *Escherichia coli* damage recognition protein (UvrA) to the major ultraviolet photoproducts: T [c,s]T, T [t,s]T, T [6-4]T, and T [Dewar]T. J Biol Chem 268, 21301-21308 (1993).

54. A. Ludwig, B. Behnke, J. Holtlund, H. Hilz, Immunoquantitation and size determination of intrinsic poly (ADP-ribose) polymerase from acid precipitates. An analysis of the in vivo status in mammalian species and in lower eukaryotes. J Biol Chem 263, 6993-6999 (1988).

55. J. Rudolph, J. Mahadevan, P. Dyer, K. Luger, Poly(ADP-ribose) polymerase 1 searches DNA via a 'monkey bar' mechanism. Elife 7, (2018).

56. N. C. Hoch et al., XRCC1 mutation is associated with PARP1 hyperactivation and cerebellar ataxia. Nature 541, 87-91 (2017).

57. A. A. Demin et al., XRCC1 prevents toxic PARP1 trapping during DNA base excision repair. Mol Cell 81, 3018-3030 e3015 (2021).

58. N. E. Sanjana, O. Shalem, F. Zhang, Improved vectors and genome-wide libraries for CRISPR screening. Nat Methods 11, 783-784 (2014).

59. P. W. Wiseman, N. O. Petersen, Image correlation spectroscopy. II. Optimization for ultrasensitive detection of preexisting platelet-derived growth factor-beta receptor oligomers on intact cells. Biophys J 76, 963-977 (1999).

60. X. A. Cambronne et al., Biosensor reveals multiple sources for mitochondrial NAD(+). Science 352, 1474-1477 (2016).

61. C. C. Fjeld, W. T. Birdsong, R. H. Goodman, Differential binding of NAD+ and NADH allows the transcriptional corepressor carboxyl-terminal binding protein to serve as a metabolic sensor. Proc Natl Acad Sci USA 100, 9202-9207 (2003).

62. M. F. Langelier, L. Zandarashvili, P. M. Aguiar, B. E. Black, J. M. Pascal, NAD (+) analog reveals PARP-1 substrate-blocking mechanism and allosteric communication from catalytic center to DNA-binding domains. Nat Commun 9, 844 (2018).

63. Y. Shen et al., BMN 673, a novel and highly potent PARP1/2 inhibitor for the treatment of human cancers with DNA repair deficiency. Clin Cancer Res 19, 5003-5015 (2013).

OTHER EMBODIMENTS

While the invention has been described in conjunction with the detailed description thereof, the forgoing description is intended to illustrate and not limit the scope of the invention, which is defined by the scope of the appended claims. Other aspects, advantages, and modifications are within the scope of the following claims.

What is claimed is:

1. A method of detecting a molecular aggregate in a biological sample, the method comprising:

directing an excitation beam to a biological sample, wherein the biological sample comprises a plurality of molecules, each of which comprises a fluorescent label, and wherein the biological sample comprises a region of interest (ROI);

acquiring an image of the biological sample, wherein the image comprises a plurality of pixels, each of which has a size that is smaller than a size of the excitation beam;

segmenting the ROI;

performing an image correlation spectroscopy (ICS) analysis of the ROI using a signal from the fluorescent label;

calculating a degree of aggregation (DA) of $$DA = \frac{\langle i \rangle}{\langle n \rangle} = c\frac{\langle n_f \rangle}{\langle n \rangle}$$

from the ICS analysis of the ROI, wherein $\langle i \rangle$ comprises an average intensity of the signal from the fluorescent label; $\langle n \rangle$ comprises a mean number of molecules in the plurality of molecules; $\langle n_f \rangle$ comprises a total number of the fluorescent label; and c comprises a constant relating signal intensity to number of signals; and determining an absence or a presence of a molecular aggregate based on the calculated DA, wherein a deviation of the calculated DA from a control value indicates the presence of the molecular aggregate.

2. The method of claim 1, wherein calculating the DA comprises calculating a spatial correlation function of $$r(\xi, \eta) = \frac{\langle \delta i(x, y) \delta i(x+\xi, y+\eta) \rangle}{\langle i \rangle^2},$$

wherein $\xi$ and $\eta$ comprise discrete pixel shifts in an x and a y direction, respectively, in the image of the biological sample.

3. The method of claim 2, wherein the spatial correlation function is calculated using a Fourier method of $$r(\xi, \eta) = \frac{F^{-1}[F(i(x, y))F^*(i(x, y))]}{\langle i \rangle^2} - 1,$$

wherein F comprises a discrete 2D spatial fast Fourier transform of the ROI, F* comprises a complex conjugate, and $F^{-1}$ comprises an inverse Fourier transform.

4. The method of claim 2, further comprising fitting the spatial correlation function to a two-dimensional (2-D) Gaussian function of $$r(\xi, \eta) = g(0, 0)\exp\left[-\frac{\xi^2 + \eta^2}{\omega_0^2}\right] + g_\infty,$$

wherein g(0, 0) comprises a zero-lags amplitude, $\omega_0$ comprises an $e^{-2}$ Gaussian correlation radius, and $g_\infty$ comprises a long spatial lag offset.

5. The method of claim 1, wherein directing the excitation beam comprises scanning the excitation beam over the biological sample or widefield illumination.

6. The method of claim 1, wherein segmenting the ROI comprises using differential interference contrast (DIC) or labeling the ROI with an second fluorescent label and detecting a signal from the second fluorescent label.

7. The method of claim 1, wherein directing the excitation beam and acquiring the image comprises using a low magnification objective with a magnification between 4× and 20×.

8. The method of claim 1, wherein the size of each pixel is between 200 to 500 nm, optionally between 300-350 nm.

9. The method of claim 1, wherein the size of the excitation beam is between 500 to 1000 nm or between 700 to 800 nm.

10. The method of claim 1, wherein the control value is a calculated DA from a control sample or a predetermined threshold value.

11. The method of claim 10, wherein the control sample is an untreated biological sample.

12. The method of claim 1, wherein the biological sample comprises a cellular sample, a tissue sample, or a whole animal.

13. The method of claim 1, wherein the fluorescent label comprises a fluorescent protein or a fluorescent dye, optionally conjugated to an antibody.

14. The method of claim 13, wherein the fluorescent protein comprises a green fluorescent protein (GFP) or a red fluorescent protein (RFP).

15. The method of claim 13, wherein the fluorescent dye comprises 4',6-diamidino-2-phenylindole (DAPI), fluorescein isothiocyanate (FITC), tetramethylrhodamine isothiocyanate (TRITC), aniline blue, an Alexa fluor dye, a Cy3 dye, or a Cy5 dye.

16. The method of claim 1, further comprising segmenting the ROI using a signal from a second fluorescent label, optionally wherein the ROI comprises a nucleus of a cell and the second fluorescent label comprises 4',6-diamidino-2-phenylindole (DAPI), or the ROI comprises an extracellular matrix of a cell and the second fluorescent label comprises aniline blue.

17. The method of claim 1, wherein the molecular aggregate is extracellular or intracellular.

18. The method of claim 1, wherein the molecular aggregate comprises proteins and/or nucleic acids, a stress granule, a DNA repair foci, a transcription complex, an immune signaling complex, a nucleolus, a P body, a chromatin complex, or a membrane signaling complex.

19. The method of claim 1, wherein the molecular aggregate comprises 53BP1, γH2AX, RPA1, RAD51, LIG3, KU80, PCGF1, VCP/P97, RPA32, TOPBP1, FEN1, RFWD3, SUMO-2, SUMO-3, APLF, or combinations thereof, or α-synuclein, FUS, TDP-43, tau, β-amyloid, huntingtin, or combinations thereof.

20. A method of detecting a molecular aggregate in a biological sample, the method comprising:

providing an image of a biological sample comprising a plurality of molecules, each of which comprises a fluorescent label, wherein the biological sample comprises a region of interest (ROI) comprising a second fluorescent label;

segmenting the ROI using a signal from the second fluorescent label;

performing an image correlation spectroscopy (ICS) analysis of the ROI using a signal from the fluorescent label;

calculating a degree of aggregation (DA) of $$DA = \frac{\langle i \rangle}{\langle n \rangle} = c\frac{\langle n_f \rangle}{\langle n \rangle}$$

from the ICS analysis of the ROI, wherein $\langle i \rangle$ comprises an average intensity of the signal from the fluorescent label; $\langle n \rangle$ comprises a mean number of molecules in the plurality of molecules; $\langle n_f \rangle$ comprises a total number of the fluorescent label; and c comprises a constant relating signal intensity to number of signals; and determining an absence or a presence of a molecular aggregate based on the calculated DA, wherein a deviation of the calculated DA from a control value indicates the presence of the molecular aggregate.

21. A method comprising:

providing a plurality of images of a biological sample; wherein each biological sample comprises a plurality of molecules, each of which comprises a fluorescent label; wherein each biological sample comprises a region of interest (ROI) comprising a second fluorescent label;

and wherein each image comprises the biological sample in a presence of a different amount of a test compound;

segmenting the ROI for each image using a signal from the second fluorescent label;

performing an image correlation spectroscopy (ICS) analysis of the ROI for each image using a signal from the fluorescent label;

calculating a degree of aggregation (DA) of $$DA = \frac{\langle i \rangle}{\langle n \rangle} = c\frac{\langle n_f \rangle}{\langle n \rangle}$$

from the ICS analysis of the ROI for each image, wherein $\langle i \rangle$ comprises an average intensity of the signal from the fluorescent label; $\langle n \rangle$ comprises a mean number of molecules in the plurality of molecules; $\langle n_f \rangle$ comprises a total number of the fluorescent label; and c comprises a constant relating signal intensity to number of signals; and determining an absence or a presence of a molecular aggregate based on the calculated DA, wherein a deviation of the calculated DA from a control value indicates the presence of the molecular aggregate.

22. The method of claim 21, further comprising plotting the calculated DA for each image against the concentration of the test compound in the image.

23. The method of claim 21, wherein the control value is a calculated DA from the biological sample in an absence of the test compound or is a predetermined threshold value.

24. The method of claim 21, wherein the test compound is an antibody or a small molecule.

* * * * *